US010081658B2

(12) United States Patent
Kalyanaraman et al.

(10) Patent No.: US 10,081,658 B2
(45) Date of Patent: Sep. 25, 2018

(54) TRUNCATED HIV ENVELOPE PROTEINS (ENV), METHODS AND COMPOSITIONS RELATED THERETO

(75) Inventors: Vaniambadi Kalyanaraman, Rockville, MD (US); Stephen Whitney, Silver Spring, MD (US); Thomas C. VanCott, Brookeville, MD (US); Victoria Polonis, Silver Spring, MD (US); Carl Alving, Bethesda, MD (US); Gary R. Matyas, Olney, MD (US); Mangala Rao, Silver Spring, MD (US); Mary Marovich, Bethesda, MD (US); Francine McCutchan, Silver Spring, MD (US); Sodsai Tovanabutra, Gaithersburg, MD (US); Eric Sanders-Buell, Vienna, VA (US)

(73) Assignees: Advanced BioScience Laboratories, Inc., Rockville, MD (US); The United States of America as Represented by the Secretary of the Army, Washington, DC (US); The Henry M. Jackson Foundation for the Advancement of Military Medicines, Inc., Bethesda, MD (US)

( * ) Notice: Subject to any disclaimer, the term of this patent is extended or adjusted under 35 U.S.C. 154(b) by 444 days.

(21) Appl. No.: 14/113,094

(22) PCT Filed: Apr. 25, 2012

(86) PCT No.: PCT/US2012/035026
§ 371 (c)(1),
(2), (4) Date: Apr. 7, 2014

(87) PCT Pub. No.: WO2012/149038
PCT Pub. Date: Nov. 1, 2012

(65) Prior Publication Data
US 2014/0220107 A1 Aug. 7, 2014

Related U.S. Application Data

(60) Provisional application No. 61/478,857, filed on Apr. 25, 2011.

(51) Int. Cl.
| | | |
|---|---|---|
| *C07K 14/005* | (2006.01) | |
| *C07K 14/16* | (2006.01) | |
| *A61K 39/12* | (2006.01) | |
| *A61K 39/21* | (2006.01) | |
| *A61K 39/00* | (2006.01) | |

(52) U.S. Cl.
CPC .......... *C07K 14/005* (2013.01); *A61K 39/12* (2013.01); *A61K 39/21* (2013.01); *A61K 2039/53* (2013.01); *C12N 2740/16122* (2013.01); *C12N 2740/16134* (2013.01)

(58) Field of Classification Search
None
See application file for complete search history.

(56) References Cited

U.S. PATENT DOCUMENTS

2003/0157135 A1* 8/2003 Tsuji ................... A61K 39/015
424/278.1
2011/0064760 A1 3/2011 Cho et al.

FOREIGN PATENT DOCUMENTS

| WO | WO 92/19742 A1 | 11/1992 |
| WO | WO 03/022869 A2 | 3/2003 |
| WO | WO 2003/022869 * | 3/2003 |
| WO | WO 03/026591 A2 | 4/2003 |
| WO | WO 07/089093 A1 | 8/2007 |

OTHER PUBLICATIONS

Brunel et al., Journal of Virology, 2006, 80(4):1680-1687.*
GenBank Accession No. ADI62314 (May 2010).*
Golden et al., Protein Expression and Purification, 1998, 14:8-12.*
Quinnan et al., Journal of Virology, Mar. 2005, 79(6):3358-3369.*
Dong et al., Journal of Virology, Mar. 2003, 77(5):3119-3130.*
Yang et al., Journal of Virology, Feb. 2001, 75(3):1165-1171.*
Buonaguro et al., Journal of Virology, Oct. 2007, 81(19):10209-10219.*
Office Action from the African Regional Intellectual Property Organization (ARIPO) for ARIPO Application No. AP/P/2013/007180, dated Apr. 20, 2016, 5 pages.
International Search Report for PCT Application No. PCT/US2012/035026, dated Mar. 9, 2012, 3 pages.
International Preliminary Report on Patentability for PCT Application No. PCT/US2012/035026, dated Oct. 29, 2013, 6 pages.
Office Communication from the European Patent Office for European Application No. 12 722 957.3-1410, dated May 30, 2016, 5 pages.
Office Communication from the European Patent Office for European Application No. 12 722 957.3-1410, dated Sep. 29, 2015, 5 pages.
First Office Action from the Chinese Patent Office for Application No. 201280031485.X (untranslated and translated versions), dated Jan. 26, 2015, 4 pages.
Second Office Action from the Chinese Patent Office for Application No. 201280031485.X (untranslated and translated versions), dated Dec. 10, 2015, 5 pages.
Third Office Action from the Chinese Patent Office for Application No. 201280031485.X (untranslated and translated versions), dated Aug. 26, 2016, 3 pages.

(Continued)

*Primary Examiner* — Nicole Kinsey White
(74) *Attorney, Agent, or Firm* — Haug Partners LLP

(57) ABSTRACT

The instant application provides methods and related compositions pertaining to novel HIV envelope proteins. In some embodiments, the invention relates to methods and compositions for the preparation, production, and administration of isolated novel HIV envelope nucleic acid and protein sequences suitable, for example, as vaccines against HIV.

25 Claims, 87 Drawing Sheets
Specification includes a Sequence Listing.

(56) References Cited

OTHER PUBLICATIONS

Fourth Office Action from the Chinese Patent Office for Application No. 201280031485.X (untranslated and translated versions), date May 18, 2017, 3 pages.
Office Action from the Japanese Patent Office (translated version) for Japanese Application No. 2014-508520, dated Feb. 28, 2016, 5 pages.
Office Action from the Japanese Patent Office (translated version) for Japanese Application No. 2014-508520, dated Jan. 1, 2017, 3 pages.
"envelope glycoprotein [Human immunodeficiency vines 1]" [Jun. 16, 2010] Retrieved from GenBank [online] Accession No. ADI62361.1 [retrieved on Mar. 18, 2016] URL: [http://www.ncbi.nlm.nih.gov/protein/298206032?sat= 18&satkey= 1930242].
"envelope glycoprotein [Human immunodeficiency virus1]" [Mar. 16, 2005] Retrieved from GenBank [online] Accession No. AAN73742.1 [retrieved on Mar. 18, 2016] URL:[http://www.ncbi.nlm.nih.gov/protein/25166967?sat=4&satkey=38832869].
"envelope glycoprotein [Human immunodeficiency virus 1]" [Mar. 16, 2005] Retrieved from GenBank [online] Accession No. AAN73661.1 [retrieved on Mar. 18, 2016] URL:[http://www.ncbi.nlm.nih.gov/protein/AAN73661.1].
"env [Human immunodeficiency virus 1]" [Sep. 5, 1995] Retrieved from GenBank [online] Accession No. AAA75116.1 [retrieved on Mar. 18, 2016] URL:[http://www.ncbi.nlm.nih.gov/protein/AAA75116.1].
"envelope glycoprotein [Human immunodeficiency virus 1]" [Jun. 16, 2010] Retrieved from GenBank [online] Accession No. ADI62314.1 [retrieved on Mar. 18, 2016] URL:[http://www.ncbi.nlm.nih.gov/protein/298205972?sat=18&satkey=1930242].
Liu, Biopolymers, (Peptide Science) 1998, vol. 47, pp. 41-62.
Cano-Sanchez, et al. "Effects of N- and C-Terminal addition of Oligolysines or Native Loop Residues on the Biophysical Properties of Transmembrane Domain Peptides from a G-protein Coupled Receptor", Journal of Peptide Science, 2006, vol. 12, pp. 808-822.
Earl, et al., "Native Oligomeric Human Immunodeficiency Virus Type 1 Envelope Glycoprotein Elicits Diverse Monoclonal Antibody Reactivities", Journal of Virology, 1994, vol. 68, No. 5, pp. 3015-3026.
Binley et al., "A Recombinant Human Immunodeficiency Virus Type 1 Envelope Glycoprotein Complex Stabilized by an Intermolecular Disulfide Bond between the gp120 and gp41 Subunits is an Antigenic Mimic of the Trimeric Virion-Associated Structure", Journal of Virology, 2000, vol. 74, No. 2, pp. 627-643.
Montero, et al., "The Membrane-Proximal External Region of the Human Immunodeficiency Virus Type 1 Envelope: Dominant Site of Antibody Neutralization and Target for Vaccine Design", Microbiology and Molecular Biology Reviews, 2008, vol. 72, No. 1, pp. 54-84.
Brunel, et al., "Structure-Function Analysis of the Epitope for 4E10, a Broadly Neutralizing Human Immunodeficiency Virus Type 1 Antibody", Journal of Virology, 2006, vol. 80, No. 4, p. 1680-1687.
Zwick, et al., "Broadly Neutralizing Antibodies Targeted to the Membrane-Proximal External Region of Human Immunodeficiency Virus Type 1 Glycoprotein gp41", Journal of Virology, 2001, vol. 75, No. 22, p. 10892-10905.
Wieczorek, et al., "Comparable Antigenicity and Immunogenicity of Oligomeric Forms of a Novel, Acute HIV-1 Subtype C gp145 Envelope for Use in Preclinical and Clinical Vaccine Research", Journal of Virology, 2015, vol. 89, No. 15, p. 7478-7493.
Frey, et al., "A Fusion-intermediate State of HIV-1 gp41 Targeted by Broadly Neutralizing Antibodies", Proceeding of the National Academy of Science (PNAS), 2008, vol. 105, No. 10, p. 3739-3744.
Database UniProt [Online] Jul. 5, 2004 (Jul. 5, 2004), "RecName: Full=Envelope glycoprotein gp160 {ECO:0000256| RuleBase:RU004292, ECO:0000256|SAAS:SAAS00139992}; AltName: Full=Endogenous retrovirus group K member 113 Env polyprotein {ECO:0000256|SAAS:SAAS00159454}; AltName: Full= Endogenous retrovirus group K member 13-1 Env polyprotein {ECO:0000256|SAAS:", retrieved from EBI accession No. UNIPROT:Q6TAP7 Database accession No. Q6TAP7.
Database UniProt [Online] Mar. 1, 2003 (Mar. 1, 2003), "RecName: Full=Envelope glycoprotein gp160 {ECO:0000256| RuleBase:RU004292, ECO:0000256|SAAS:SAAS00139992}; AltName: Full=Endogenous retrovirus group K member 113 Env polyprotein {ECO:0000256|SAAS:SAAS00159454}; AltName: Full= Endogenous retrovirus group K member 13-1 Env polyprotein {ECO:0000256|SAAS:", retrieved from EBI accession No. NIPROT:Q8ADN1 Database accession No. Q8ADN1.

\* cited by examiner

FIGURE 3

Nucleic acid sequence of HIV-1 Ba-L gp140 DC 4E10 (SEQ ID NO: 6)

ATGGATGCAATGAAGAGAGGGCTCTGCTGTGTGCTGCTGCTGTGTGGAGCAGTCTTCGTT

TCGGCTAGC GAGGAAAAGCTGTGGGTGACCGTGTACTACGGCGTGCCCGTGTGGAAAGAG

GCCACCACCACCCTGTTCTGCGCCAGCGACGCCAAGGCCTACGACACCGAGGTGCACAAC

GTGTGGGCCACCCACGCCTGCGTGCCCACCGACCCCAACCCCCAGGAAGTGGAGCTGGAA

AACGTGACCGAGAACTTCAACATGTGGAAGAACAACATGGTGGAGCAGATGCACGAGGAC

ATCATCAGCCTGTGGGACCAGAGCCTGAAGCCCTGCGTGAAGCTGACCCCCCTGTGCGTG

ACCCTGAACTGCACCGACCTGCGGAACGCCACCAACGGCAACGACACCAACACCACCTCC

AGCAGCCGGGAGATGATGGGCGGAGGGGAGATGAAGAACTGCAGCTTCAAGATCACCACC

AACATCCGGGGCAAGGTGCAGAAAGAGTACGCCCTGTTCTACGAGCTGGACATCGTGCCC

ATCGACAACAACAGCAACAACCGGTACAGGCTGATCAGCTGCAACACCAGCGTGATCACC

CAGGCCTGCCCCAAGATCAGCTTCGAGCCCATCCCCATCCACTACTGCGCCCCTGCCGGC

TTCGCCATCCTGAAGTGCAAGGACAAGAAGTTCAACGGCAAGGGCCCCTGCAGCAACGTG

AGCACCGTGCAGTGCACCCACGGCATCCGGCCCGTGGTGTCCACCCAGCTGCTGCTGAAC

GGCAGCCTGGCCGAGGAAGAGGTGGTGATCAGAAGCGAGAACTTCGCCGACAACGCCAAG

ACCATCATCGTGCAGCTGAACGAGAGCGTGGAGATCAACTGCACCCGGCCCAACAACAAC

ACCCGGAAGAGCATCCACATCGGCCCTGGCAGGGCCCTGTACACCACCGGCGAGATCATC

GGCGACATCCGGCAGGCCCACTGCAACCTGAGCCGGGCCAAGTGGAACGACACCCTGAAC

AAGATCGTGATCAAGCTGCGGGAGCAGTTCGGCAACAAGACCATCGTGTTCAAGCACAGC

AGCGGCGGAGACCCCGAGATCGTGACCCACAGCTTCAACTGTGGCGGCGAGTTCTTCTAC

TGCAACAGCACCCAGCTGTTCAACAGCACCTGGAATGTGACCGAGGAAAGCAACAACACC

GTGGAGAACAACACCATCACCCTGCCCTGCCGGATCAAGCAGATCATCAATATGTGGCAG

AAAGTGGGCAGAGCCATGTACGCCCCTCCCATCGGGGCCAGATCCGGTGCAGCAGCAAC

ATCACCGGCCTGCTGCTGACCCGGGACGGCGGACCCGAGGCCAACAAGACCGAGGTGTTC

FIGURE 3 (cont.)

CGGCCTGGCGGCGGAGATATGCGGGACAACTGGCGGAGCGAGCTGTACAAGTACAAGGTG

GTGAAGATCGAGCCCCTGGGCGTGGCCCCCACCAAGGCCAAGAGCCGGGTGGTGCAGCGG

GAGAAGAGCGCCGTGGGCATCGGCGCCGTGTTTCTGGGCTTCCTGGGAGCCGCCGGAAGC

ACCATGGGAGCCGCCAGCATGACCCTGACCGTGCAGGCCCGGCTGCTGCTGTCCGGCATC

GTGCAGCAGCAGAACAACCTGCTGCGGGCCATTGAGGCACAGCAGCATCTGCTGCAGCTG

ACCGTGTGGGGCATTAAGCAGCTGCAGGCCAGGGTGCTGGCCGTGGAGAGATACCTGCGG

GATCAGCAGCTGCTGGGGATCTGGGGCTGCAGCGGCAAGCTGATCTGCACCACCGCCGTG

CCCTGGAACGCCAGCTGGTCCAACAAGAGCCTGAACAAAATCTGGGACAACATGACCTGG

ATGGAATGGGACCGCGAGATCAACAACTACACCAGCATCATCTACAGCCTGATCGAGGAA

AGCCAGAACCAGCAGGAAAAGAACGAGCAGGAACTGCTGGAACTGGACAAGTGGGCCAGC

CTGTGGAACTGGTTCGACATCACCGAGTGGCTGTGGTACATCAAGAAGAAGAAGTGA

FIGURE 4

Amino acid sequence of HIV-1 Ba-L gp140 DC 4E10 (SEQ ID NO: 7)

MDAMKRGLCCVLLLCGAVFVSAS EEKLWVTVYYGVPVWKEATTTLFCASDAKAYDTEVHN

VWATHACVPTDPNPQEVELENVTENFNMWKNNMVEQMHEDIISLWDQSLKPCVKLTPLCV

TLNCTDLRNATNGNDTNTTSSSREMMGGGEMKNCSFKITTNIRGKVQKEYALFYELDIVP

IDNNSNNRYRLISCNTSVITQACPKISFEPIPIHYCAPAGFAILKCKDKKFNGKGPCSNV

STVQCTHGIRPVVSTQLLLNGSLAEEEVVIRSENFADNAKTIIVQLNESVEINCTRPNNN

TRKSIHIGPGRALYTTGEIIGDIRQAHCNLSRAKWNDTLNKIVIKLREQFGNKTIVFKHS

SGGDPEIVTHSFNCGGEFFYCNSTQLFNSTWNVTEESNNTVENNTITLPCRIKQIINMWQ

KVGRAMYAPPIRGQIRCSSNITGLLLTRDGGPEANKTEVFRPGGGDMRDNWRSELYKYKV

VKIEPLGVAPTKAKSRVVQREKSAVGIGAVFLGFLGAAGSTMGAASMTLTVQARLLLSGI

VQQQNNLLRAIEAQQHLLQLTVWGIKQLQARVLAVERYLRDQQLLGIWGCSGKLICTTAV

PWNASWSNKSLNKIWDNMTWMEWDREINNYTSIIYSLIEESQNQQEKNEQELLELDKWAS

LWNWFDITEWLWYIKKKK

FIGURE 5

Nucleic acid sequence of HIV-1 Ba-L gp145 (SEQ ID NO: 8)

ATGGATGCAATGAAGAGAGGGCTCTGCTGTGTGCTGCTGCTGTGTGGAGCAGTCTTCGTT
ACTACCACAGAGGCTAGC GAGGAAAAGCTGTGGGTGACCGTGTACTACGGCGTGCCCGTG
TGGAAAGAGGCCACCACCACCCTGTTCTGCGCCAGCGACGCCAAGGCCTACGACACCGAG
GTGCACAACGTGTGGGCCACCCACGCCTGCGTGCCCACCGACCCCAACCCCCAGGAAGTG
GAGCTGGAAAACGTGACCGAGAACTTCAACATGTGGAAGAACAACATGGTGGAGCAGATG
CACGAGGACATCATCAGCCTGTGGGACCAGAGCCTGAAGCCCTGCGTGAAGCTGACCCCC
CTGTGCGTGACCCTGAACTGCACCGACCTGCGGAACGCCACCAACGGCAACGACACCAAC
ACCACCTCCAGCAGCCGGGAGATGATGGGCGGAGGGGAGATGAAGAACTGCAGCTTCAAG
ATCACCACCAACATCCGGGGCAAGGTGCAGAAAGAGTACGCCCTGTTCTACGAGCTGGAC
ATCGTGCCCATCGACAACAACAGCAACAACCGGTACAGGCTGATCAGCTGCAACACCAGC
GTGATCACCCAGGCCTGCCCCAAGATCAGCTTCGAGCCCATCCCCATCCACTACTGCGCC
CCTGCCGGCTTCGCCATCCTGAAGTGCAAGGACAAGAAGTTCAACGGCAAGGGCCCCTGC
AGCAACGTGAGCACCGTGCAGTGCACCCACGGCATCCGGCCCGTGGTGTCCACCCAGCTG
CTGCTGAACGGCAGCCTGGCCGAGGAAGAGGTGGTGATCAGAAGCGAGAACTTCGCCGAC
AACGCCAAGACCATCATCGTGCAGCTGAACGAGAGCGTGGAGATCAACTGCACCCGGCCC
AACAACAACACCCGGAAGAGCATCCACATCGGCCCTGGCAGGGCCCTGTACACCACCGGC
GAGATCATCGGCGACATCCGGCAGGCCCACTGCAACCTGAGCCGGGCCAAGTGGAACGAC
ACCCTGAACAAGATCGTGATCAAGCTGCGGGAGCAGTTCGGCAACAAGACCATCGTGTTC
AAGCACAGCAGCGGCGGAGACCCCGAGATCGTGACCCACAGCTTCAACTGTGGCGGCGAG
TTCTTCTACTGCAACAGCACCCAGCTGTTCAACAGCACCTGGAATGTGACCGAGGAAAGC
AACAACACCGTGGAGAACAACACCATCACCCTGCCCTGCCGGATCAAGCAGATCATCAAT
ATGTGGCAGAAAGTGGGCAGAGCCATGTACGCCCCTCCCATCCGGGGCCAGATCCGGTGC
AGCAGCAACATCACCGGCCTGCTGCTGACCCGGGACGGCGGACCCGAGGCCAACAAGACC

FIGURE 5 (cont.)

GAGGTGTTCCGGCCTGGCGGCGGAGATATGCGGGACAACTGGCGGAGCGAGCTGTACAAG

TACAAGGTGGTGAAGATCGAGCCCCTGGGCGTGGCCCCCACCAAGGCCAAGAGCCGGGTG

GTGCAGCGGGAGAAGAGCGCCGTGGGCATCGGCGCCGTGTTTCTGGGCTTCCTGGGAGCC

GCCGGAAGCACCATGGGAGCCGCCAGCATGACCCTGACCGTGCAGGCCCGGCTGCTGCTG

TCCGGCATCGTGCAGCAGCAGAACAACCTGCTGCGGGCCATTGAGGCACAGCAGCATCTG

CTGCAGCTGACCGTGTGGGGCATTAAGCAGCTGCAGGCCAGGGTGCTGGCCGTGGAGAGA

TACCTGCGGGATCAGCAGCTGCTGGGGATCTGGGGCTGCAGCGGCAAGCTGATCTGCACC

ACCGCCGTGCCCTGGAACGCCAGCTGGTCCAACAAGAGCCTGAACAAAATCTGGGACAAC

ATGACCTGGATGGAATGGGACCGCGAGATCAACAACTACACCAGCATCATCTACAGCCTG

ATCGAGGAAAGCCAGAACCAGCAGGAAAAGAACGAGCAGGAACTGCTGGAACTGGACAAG

TGGGCCAGCCTGTGGAACTGGTTCGACATCACCGAGTGGCTGTGGTACATCAAGAAGAAG

AAGTGA

FIGURE 6

Amino acid sequence of HIV-1 Ba-L gp145 (SEQ ID NO: 9):

MDAMKRGLCCVLLLCGAVFVTTTEAS EEKLWVTVYYGVPVWKEATTTLFCASDAKAYDTE

VHNVWATHACVPTDPNPQEVELENVTENFNMWKNNMVEQMHEDIISLWDQSLKPCVKLTP

LCVTLNCTDLRNATNGNDTNTTSSSREMMGGGEMKNCSFKITTNIRGKVQKEYALFYELD

IVPIDNNSNNRYRLISCNTSVITQACPKISFEPIPIHYCAPAGFAILKCKDKKFNGKGPC

SNVSTVQCTHGIRPVVSTQLLLNGSLAEEEVVIRSENFADNAKTIIVQLNESVEINCTRP

NNNTRKSIHIGPGRALYTTGEIIGDIRQAHCNLSRAKWNDTLNKIVIKLREQFGNKTIVF

KHSSGGDPEIVTHSFNCGGEFFYCNSTQLFNSTWNVTEESNNTVENNTITLPCRIKQIIN

MWQKVGRAMYAPPIRGQIRCSSNITGLLLTRDGGPEANKTEVFRPGGGDMRDNWRSELYK

YKVVKIEPLGVAPTKAKSRVVQREKSAVGIGAVFLGFLGAAGSTMGAASMTLTVQARLLL

SGIVQQQNNLLRAIEAQQHLLQLTVWGIKQLQARVLAVERYLRDQQLLGIWGCSGKLICT

TAVPWNASWSNKSLNKIWDNMTWMEWDREINNYTSIIYSLIEESQNQQEKNEQELLELDK

WASLWNWFDITEWLWYIKKKK

FIGURE 8 pSW Clade C Env
8400 bps

- APH I
- Enhancer
- CMV Promoter
- Intron A
- Kozak Sequence
- t-Pa Signal → NheI
- puc Origin
- BGH Poly A
- Puromycin acetyl-transferase
- Clade C Env
- ECMV IRES
- IVS (synthetic intron) EcoRI

FIGURE 9

HIV-1 C3728v2c6 gp160 Codon Optimized (SEQ ID NO: 10):

tPa signal is highlighted

ATGGATGCAATGAAGAGAGGGCTCTGCTGTGTGCTGCTGCTGTGTGGAGCAGTCTTCGTT
ACTACCACAGAGGCTAGC AACCTGTGGGTGACCGTGTACTACGGCGTGCCCGTGTGGAAG
GAGGCCAAGACCACCCTGTTCTGCGCCAGCGACGCCAAGGCCTACGAGAAGGAGGTGCAC
AACGTGTGGGCCACCCACGCCTGCGTGCCCACCGACCCCAACCCCCAGGAGATGGAGCTG
CCCAACGTGACCGAGAACTTCAACATGTGGAAGAACGACATGGTGGACCAGATGCACGAG
GACATCATCAGCCTGTGGGACCAGAGCCTGAAGCCCTGCGTGAAGCTGACCCCCCTGTGC
GTGACCCTGAACTGCAACAAGGTGAACAACAACCGCAGCATCGACAACAACAGCACCGAG
GAGGAGATGAAGAACTGCACCTTCAACACCACCACCGAGATCAGGGACAAGAAGAGGACC
CAGCAGGCCCTGTTCTACAAGCTGGACATCGTGCCCCTGGGCAACAGCAACGAGAGCTAC
AGGCTGATCAACTGCAACACCAGCACCCTGACCCAGGCCTGCCCCAAGGTGACCTTCGAC
CCCATCCCCATCCACTACTGCGCCCCAGCCGGCTACGCCATCCTGAAGTGCAAGGACGAG
AAGTTCAACGGCACCGGCCCCTGCAACAACGTGTCCACCGTGCAGTGCACCCACGGCATC
AAGCCCGTGGTGTCCACCCAGCTGCTGCTGAACGGCAGCCTGGCCGAGAAGGACATCATC
ATCCGCAGCGAGAACCTGACCAACAACGTGAAGACCATCATGGTGCACCTGAACGAGAGC
GTGGAGATCAACTGTACCAGGCCCAACAACAACACCAGGAAGAGCATCAGGATCGGCCCA
GGCCAGACCTTCTACGCCACCGGCGGCATCATCGGCAACATCAGGCAGGCCTACTGCACC
ATCAGCAAGAACAAGTGGAACACCACCCTGGAGAGAGTGGCTACCAAGCTGAAGGAGTAC
TTCAAGAACACCACCATCCAGTTCGCCCCCCACTCTGGCGGCGACCTGGAGATCACCACC
CACAGCTTCAACTGCAGGGGCGAGTTCTTCTACTGCAACACAAGCCAGCTGTTCAACGGG
ACCAGCACCGGCTTCAGCAACAAGAGCACCGGCAACGAGACATTCACCCTGCCCTGCAGA
ATCAAGCAGATCATCAACATGTGGCAGGAAGTGGGCAGGGCCATGTACGCCCCACCAATC

FIGURE 9 (cont.)

GCCGGGAACATCACCTGCGTGAGCAACATCACCGGCCTGCTGCTGACCAGGGACGGCGGG

GACAACAACACAAGAACCGAGACATTCCGGCCAGGCGGCGGAGACATGAGGGACAACTGG

CGGAGCGAGCTGTACAAGTACAAGGTGGTGGAGGTGAAGCCCCTGGGCGTGGCCCCAAGC

GAAGCCAGGCGGAGAGTGGTGGAACGGGAGAAGAGGGCCGTGGGCCTGGGCGCCGTCTTT

CTGGGATTCCTGGGGGCTGCCGGATCCACCATGGGAGCCGCCAGCATCACCCTGACCGTG

CAGGCTAGGCAGCTGCTGTCCGGAATCGTGCAGCAGCAGTCCAACCTGCTGAGGGCTATC

GAGGCTCAGCAGCATATGCTCCAGCTGACCGTGTGGGGCATCAAGCAGCTGCAGACCAAG

GTGCTGGCCATCGAGAGATATCTGCAGGACCAGCAGCTGCTCGGCATCTGGGGCTGCAGC

GGCAAGCTGATCTGCACCACCAACGTGCCCTGGAACAGCAGCTGGTCCAACAAGTCCCTG

AAGGCCATCTGGGACAACATGACCTGGATGCAGTGGGACAGAGAGATCAGCAACTACACC

AACACCATCTACAGGCTGCTGGAGGACAGCCACATCCAGCAGGAGAAGAACGAGAAGGAC

CTGCTGGCCCTGAACAGCTGGAACAACCTGTGGAGCTGGTTCAACATCACCAACTGGCTG

TGGTACATCCGGATCTTCATCATGATCGTGGGCGGCCTGATCGGCCTGAGGATCATCTTC

GCCATCCTGTCCATCGTGAACAGAGTGCGCCAGGGCTACAGCCCACTGAGCTTCCAGACC

CTGACACCCAACCAGCGGGGCCCAGACAGACTGGGCAGGATCGAGGAGGAGGGCGGCGAG

CAGGACAAGGACAGATCCATCAGGCTGGTGAACGGCTTCCTGGCCCTGGCCTGGGACGAC

CTGAGAAGCCTGTGCCTGTTCAGCTACCACAGGCTGAGGGACTTCATCCTGATCGCCACC

AGGGCCGTGGAACTGCTGGGGCACTCCAGCCTGAGGGGCCTGCAGAGGGGCTGGGAGGCC

CTGAAGTACCTGGGCTCCCTGGGCCAGTATTGGGGCCAGGAGCTGAAGAAGAGCGCCATC

AGACTGCTGGACATCACCGCCATCGCCGTGGCCGAGGGCACCGACAGGATCATCGAGTTC

ATCCAGAGGATCTGCAGGGCCATCCACAACGTGCCCAACAGGATCAGGCAGGGCTTCGAG

GCCGCCCTGCTGTGATGA

FIGURE 10

HIV-1 C3728v2c6 gp160 DC codon optimized Nucleic acid seq (SEQ ID NO: 11):

tPa signal is highlighted

The gp120/gp41 cleavage site is mutated to prevent cleavage

ATGGATGCAATGAAGAGAGGGCTCTGCTGTGTGCTGCTGCTGTGTGGAGCAGTCTTCGTT
ACTACCACAGAGGCTAGC AACCTGTGGGTGACCGTGTACTACGGCGTGCCCGTGTGGAAG
GAGGCCAAGACCACCCTGTTCTGCGCCAGCGACGCCAAGGCCTACGAGAAGGAGGTGCAC
AACGTGTGGGCCACCCACGCCTGCGTGCCCACCGACCCCAACCCCCAGGAGATGGAGCTG
CCCAACGTGACCGAGAACTTCAACATGTGGAAGAACGACATGGTGGACCAGATGCACGAG
GACATCATCAGCCTGTGGGACCAGAGCCTGAAGCCCTGCGTGAAGCTGACCCCCCTGTGC
GTGACCCTGAACTGCAACAAGGTGAACAACAACCGCAGCATCGACAACAACAGCACCGAG
GAGGAGATGAAGAACTGCACCTTCAACACCACCACCGAGATCAGGGACAAGAAGAGGACC
CAGCAGGCCCTGTTCTACAAGCTGGACATCGTGCCCCTGGGCAACAGCAACGAGAGCTAC
AGGCTGATCAACTGCAACACCAGCACCCTGACCCAGGCCTGCCCCAAGGTGACCTTCGAC
CCCATCCCCATCCACTACTGCGCCCCAGCCGGCTACGCCATCCTGAAGTGCAAGGACGAG
AAGTTCAACGGCACCGGCCCCTGCAACAACGTGTCCACCGTGCAGTGCACCCACGGCATC
AAGCCCGTGGTGTCCACCCAGCTGCTGCTGAACGGCAGCCTGGCCGAGAAGGACATCATC
ATCCGCAGCGAGAACCTGACCAACAACGTGAAGACCATCATGGTGCACCTGAACGAGAGC
GTGGAGATCAACTGTACCAGGCCCAACAACAACACCAGGAAGAGCATCAGGATCGGCCCA
GGCCAGACCTTCTACGCCACCGGCGGCATCATCGGCAACATCAGGCAGGCCTACTGCACC
ATCAGCAAGAACAAGTGGAACACCACCCTGGAGAGAGTGGCTACCAAGCTGAAGGAGTAC
TTCAAGAACACCACCATCCAGTTCGCCCCCCACTCTGGCGGCGACCTGGAGATCACCACC
CACAGCTTCAACTGCAGGGGCGAGTTCTTCTACTGCAACACAAGCCAGCTGTTCAACGGG
ACCAGCACCGGCTTCAGCAACAAGAGCACCGGCAACGAGACATTCACCCTGCCCTGCAGA
ATCAAGCAGATCATCAACATGTGGCAGGAAGTGGGCAGGGCCATGTACGCCCCACCAATC

FIGURE 10 (cont.)

GCCGGGAACATCACCTGCGTGAGCAACATCACCGGCCTGCTGCTGACCAGGGACGGCGGG

GACAACAACACAAGAACCGAGACATTCCGGCCAGGCGGCGGAGACATGAGGGACAACTGG

CGGAGCGAGCTGTACAAGTACAAGGTGGTGGAGGTGAAGCCCCTGGGCGTGGCCCCAAGC

GAAGCCAGGAGCAGAGTGGTGGAACGGGAGAAGAGCGCCGTGGGCCTGGGCGCCGTCTTT

CTGGGATTCCTGGGGGCTGCCGGATCCACCATGGGAGCCGCCAGCATCACCCTGACCGTG

CAGGCTAGGCAGCTGCTGTCCGGAATCGTGCAGCAGCAGTCCAACCTGCTGAGGGCTATC

GAGGCTCAGCAGCATATGCTCCAGCTGACCGTGTGGGGCATCAAGCAGCTGCAGACCAAG

GTGCTGGCCATCGAGAGATATCTGCAGGACCAGCAGCTGCTCGGCATCTGGGGCTGCAGC

GGCAAGCTGATCTGCACCACCAACGTGCCCTGGAACAGCAGCTGGTCCAACAAGTCCCTG

AAGGCCATCTGGGACAACATGACCTGGATGCAGTGGGACAGAGAGATCAGCAACTACACC

AACACCATCTACAGGCTGCTGGAGGACAGCCACATCCAGCAGGAGAAGAACGAGAAGGAC

CTGCTGGCCCTGAACAGCTGGAACAACCTGTGGAGCTGGTTCAACATCACCAACTGGCTG

TGGTACATCCGGATCTTCATCATGATCGTGGGCGGCCTGATCGGCCTGAGGATCATCTTC

GCCATCCTGTCCATCGTGAACAGAGTGCGCCAGGGCTACAGCCCACTGAGCTTCCAGACC

CTGACACCCAACCAGCGGGGCCCAGACAGACTGGGCAGGATCGAGGAGGAGGGCGGCGAG

CAGGACAAGGACAGATCCATCAGGCTGGTGAACGGCTTCCTGGCCCTGGCCTGGGACGAC

CTGAGAAGCCTGTGCCTGTTCAGCTACCACAGGCTGAGGGACTTCATCCTGATCGCCACC

AGGGCCGTGGAACTGCTGGGGCACTCCAGCCTGAGGGGCCTGCAGAGGGGCTGGGAGGCC

CTGAAGTACCTGGGCTCCCTGGGCCAGTATTGGGGCCAGGAGCTGAAGAAGAGCGCCATC

AGACTGCTGGACATCACCGCCATCGCCGTGGCCGAGGGCACCGACAGGATCATCGAGTTC

ATCCAGAGGATCTGCAGGGCCATCCACAACGTGCCCAACAGGATCAGGCAGGGCTTCGAG

GCCGCCCTGCTGTGA

FIGURE 11

HIV-1 C06838v1c48 gp160 Codon optimized Nucleic acid seq. (SEQ ID NO: 12):

GAGACATTCAGGCCAGGCGGCGGAGACATGAGGAACAACTGGCGGAGCGAGCTGTACAAG

TACAAGGTGGTGGAGATCAAGCCCCTGGGGATCGCCCCAACCGGCGCCAAGAGAAGAGTG

GTGGAGAGAGAGAAGAGGGCCGTCGGCATGGGCGCCGTGTTTCTGGGCTTCCTGGGAGCC

GCCGGAAGCACCATGGGAGCCGCCAGCCTGACCCTGACAGTGCAGGCCAGACAGGTGCTG

TCCGGGATCGTGCAGCAGCAGAGCAACCTGCTGAGAGCTATCGAGGCTCAGCAGCACATG

CTGCAGCTGACCGTGTGGGGCATCAAGCAGCTGCAGACCAGGGTGCTGGCCATCGAGAGA

TACCTGAAAGATCAGCAGCTGCTCGGCCTCTGGGGCTGCAGCGGCAAGCTGATCTGCACC

ACAGCCGTGCCATGGAATAGCAGCTGGTCCAACAAGAGCGAGATCGACATCTGGAACAAC

ATGACCTGGATGCAGTGGGACAGAGAGATCAGCAACTACACCAACACCATCTACAGACTG

CTGGAGGACAGCCAGACCCAGCAGGAGAAGAACGAGAAGGACCTGCTGGCCCTGGACAGC

TGGAAGAACCTGTGGAACTGGTTTAACATCACCAAGTGGCTGTGGTACATCAAGATCTTC

ATCATCATCGTGGGCGGCCTGATCGGCCTGAGGATCATCTTCGCCGTGCTGTCCATCGTG

AACAGAGTGCGCCAGGGGTACAGCCCACTGAGCTTCCAGACCCTGATCCCCAGCCCCAGA

GGCCCCGACAAGCTGGGCAGGATCGAGGAGGAGGGCGGCGAGCAGGACAAGGGCAGATCC

GTGAGGCTGGTGAACGGCTTCCTGGCCCTGGCCTGGGACGACCTGAGAAGCCTGTGCCTG

TTCAGCTATCACCAGCTGAGGGACTTCATCCTGATCGTGGCCAGAGCCGTGGGCCTGCTG

GGCAGGTCCAGCCTGAGGGGCCTGCAGAGAGGCTGGGAGATCCTGAAGTACCTGGGCGGG

CTGGTGCAGTACTGGGGCCTGGAGCTGAAGAAGAGCGCCGTGAGCCTGTTCGACACAATC

GCCATCGCCGTGACCGAGGGCACCGACAGGATCATCGAGCTGATCCAGAGGTCCTGCAGA

GCCATCAGGAACGTGCCCACCAGGATCAGGCAGGGCTTCGAGGCCGCCCTGCAGTGA

FIGURE 12

HIV-1 C06838v1c48 gp160 DC codon optimized Nucleic acid seq (SEQ ID NO: 13)

tPa signal is highlighted

The gp120/gp41 cleavage site is mutated to prevent cleavage

==ATGGATGCAATGAAGAGAGGGCTCTGCTGTGTGCTGCTGCTGTGTGGAGCAGTCTTCGTT

ACTACCACAGAGGCTAGC AACCTGTGGGTGACCGTGTACTACGGCGTGCCCGTGTGGAGA

GAGGCCAAGACCACCCTGTTCTGCGCCAGCGACGCCAAGGCCTACGAAAAGGAGGTGCAC

AACGTGTGGGCCACCCACGCCTGCGTGCCCACCGACCCCGACCCCCAGGAGATGGTGCTG

AAGAACGTGACCGAGAACTTCAACATGTGGAAGAACGACATGGTGGAGCAGATGCACGAG

GACATCATCAGCCTGTGGGACCAGAGCCTGAAGCCCTGCGTGAAGCTGACCCCCCTGTGC

GTGACCCTGACCTGCACCAACGTGAACGCCACCGACAACGTGACCTACAAGGAGAAGATG

GAGGGCGAGATCAAGAACTGCAGCTTCAACATCACCACCGAGATCAGGGACAAGAAGAGG

AAGGTCCACGCCCTGTTCTACAGGCTGGACGTGGTGCAGCTGAACAACAGCAACGAGTAC

ATCCTGATCAACTGCAACACCAGCGCCATCACCCAGGCCTGCCCCAAGGTGTCCTTCGAC

CCCATCCCCATCCACTACTGCGCCCCAGCCGGCTACGCCATCCTGAAGTGCAACGACAAG

CCCTTCAACGGCACCGGCCCATGCCACAACGTGTCTACCGTGCAGTGCACCCACGGCATC

AAGCCCGTGATCAGCACCCAGCTGCTGCTGAACGGCAGCCTGGCCGAGAAGGAGGTGATC

ATCCGCTTCGAGAACCTGACCGACAACGCCAAGACCATCATCGTGCAGCTGAACCAGAGC

ATCGAGATCAAGTGCATCAGGCCCAACAACAACACCAGAGAGAGCATCAGGATCGGCCCA

GGCCAGGCCTTCTACGCCACCAGGGACATCATCGGCGACATCAGAAGGGCCTACTGCACC

ATCGAGACAGAGAGGTGGAAGGAGACACTGGGCAACGTCACAGAGAAGCTGAAGGAGTAC

TTCCCCAACACCAACATCAGCTTTGCTCCCTCCTCTGGCGGGGACCTGGAGATCACCACC

CACAGCTTCAACTGCAGGGGCGAGTTCTTCTACAGAAACACCAGCAAGCTGTTCAACAAC

AACGACACCGAGAACAACCTGACCATCACCCTGCCCTGCAGAATCAAGCAGATCGTGAAC

FIGURE 12 (cont.)

ATGTGGCAGGGCGTGGGCAGGGCCATGTACGCCCCACCCATCGAGGGCAACATCACCTGC

AAGTCCAACATCACCGGCCTGCTGCTGACCAGAGACGGCGGCAACGGCACAGAGAGGAAC

GAGACATTCAGGCCAGGCGGCGGAGACATGAGGAACAACTGGCGGAGCGAGCTGTACAAG

TACAAGGTGGTGGAGATCAAGCCCCTGGGGATCGCCCCAACCGGCGCCAAGAGCAGAGTG

GTGGAGAGAGAGAAGAGCGCCGTCGGCATGGGCGCCGTGTTTCTGGGCTTCCTGGGAGCC

GCCGGAAGCACCATGGGAGCCGCCAGCCTGACCCTGACAGTGCAGGCCAGACAGGTGCTG

TCCGGGATCGTGCAGCAGCAGAGCAACCTGCTGAGAGCTATCGAGGCTCAGCAGCACATG

CTGCAGCTGACCGTGTGGGGCATCAAGCAGCTGCAGACCAGGGTGCTGGCCATCGAGAGA

TACCTGAAAGATCAGCAGCTGCTCGGCCTCTGGGGCTGCAGCGGCAAGCTGATCTGCACC

ACAGCCGTGCCATGGAATAGCAGCTGGTCCAACAAGAGCGAGATCGACATCTGGAACAAC

ATGACCTGGATGCAGTGGGACAGAGAGATCAGCAACTACACCAACACCATCTACAGACTG

CTGGAGGACAGCCAGACCCAGCAGGAGAAGAACGAGAAGGACCTGCTGGCCCTGGACAGC

TGGAAGAACCTGTGGAACTGGTTTAACATCACCAAGTGGCTGTGGTACATCAAGATCTTC

ATCATCATCGTGGGCGGCCTGATCGGCCTGAGGATCATCTTCGCCGTGCTGTCCATCGTG

AACAGAGTGCGCCAGGGGTACAGCCCACTGAGCTTCCAGACCCTGATCCCCAGCCCCAGA

GGCCCCGACAAGCTGGGCAGGATCGAGGAGGAGGGCGGCGAGCAGGACAAGGGCAGATCC

GTGAGGCTGGTGAACGGCTTCCTGGCCCTGGCCTGGGACGACCTGAGAAGCCTGTGCCTG

TTCAGCTATCACCAGCTGAGGGACTTCATCCTGATCGTGGCCAGAGCCGTGGGCCTGCTG

GGCAGGTCCAGCCTGAGGGGCCTGCAGAGAGGCTGGGAGATCCTGAAGTACCTGGGCGGG

CTGGTGCAGTACTGGGGCCTGGAGCTGAAGAAGAGCGCCGTGAGCCTGTTCGACACAATC

GCCATCGCCGTGACCGAGGGCACCGACAGGATCATCGAGCTGATCCAGAGGTCCTGCAGA

GCCATCAGGAACGTGCCCACCAGGATCAGGCAGGGCTTCGAGGCCGCCCTGCAGTGA

FIGURE 13

HIV-1 C06980v1c3 gp160 codon optimized nucleic acid seq. (SEQ ID NO: 14):

tPa signal is highlighted

ATGGATGCAATGAAGAGAGGGCTCTGCTGTGTGCTGCTGCTGTGTGGAGCAGTCTTCGTT
ACTACCACAGAGGCTAGC AACCTGTGGGTGACCGTGTACTACGGCGTGCCCGTGTGGAGA
GAGGCCAAGACCACCCTGTTCTGCGCCAGCGACGCCAAGGCCTACGAGAGGGAGGTGCAC
AACGTGTGGGCCACCCACGCCTGCGTGCCCACCGACCCCGACCCACAGGAAATCTTTCTG
GGCAAGAACGTGACCGAGAAGTTCAACATGTGGGAGAACTACATGGTGGACCAGATGCAC
GAGGACATCATCAGCCTGTGGGACCAGAGCCTGCAGCCCTGCGTGAAGCTGACCCCCCTG
TGCATCACCCTGAACTGCACCGACTTCACCGCCCACAACGGCAGCACCGTGTACGACAAC
AACGCCACCGCCAACAGCACCAACGAGATCAAGAACTGCAGCTTCAACATCATCTCCGAG
CTGAGGGACAAGAGGAAGAAGGAGAACGCCCTGTTCAACAACCTGGACATCGTGCAGCTG
GACGGCAACTCCAGCCTGTACAGACTGATCAACTGCAACACCAGCATCATCAAGCAGGCC
TGTCCCAAGATCAGCTTCGACCCCATCCCCATCCACTACTGCGCCCCAGCCGGCTTCGTG
ATCCTGACCTGCAACAACGAGACATTCAACGGCACCGGCCCATGCAACAACGTGTCCGCT
GTGCAGTGTACCCACGGGATCAAGCCCGTGGTGTCCACCCAGCTGCTGCTGAACGGCAGC
CTGGCCAAGGGCGAGATCATGATCAGAAGCGAGAACATCACCAACAACGTGAAGACCATC
ATCGTGCACTTCAACAAGAGCGTGGAGATCGTGTGCACCAGGCCCAACAACAACACCAGG
AAGAGCATCAGGATCGGCCCAGGCCAGACCTTCTACGCCACCGGCGACATCATCGGCGAC
ATCCGGCAGGCCTACTGCAGCATCAACGAGAGCAACTGGAACATCACCCTGCAGAGGGTG
TCCAAGAAGCTGGCCGAGCACTTCCCCAACAGAACCATCCAGTTCGAGAGCCCCTCTGGC
GGCGACCTGGAGATCACCATGCACAGCTTCAACTGCAGGGGCGAGTTCTTCTACTGCAAC
ACATCCAAGCTGTTCAAGAGCACCTACCACCCCAACGGCACCTACAACCTGAACGGCACA
AACAGCACCCTGATCATCCCATGCAGGATCAAGCAGATCATCAACATGTGGCAGGGCGTG

FIGURE 13 (cont.)

GGCAAGGCCATCTACGCCAGCCCAATCGCCGGCAGCATCACCTGCAGAAGCAACATCACC

GGCCTGCTGCTGACCAGGGACGGCGGCGACACCAACGACACCGAGATCTTCAGGCCCACC

GGCGGAGACATGAGGGACAACTGGCGGAGCGAGCTGTACAAGTACAAGATCGTGGAGATC

AAGCCCCTGGGCGTGGCTCCAACCGAGGCCAAGAGAAGGGTGGTGAAGAGAGAAGAGG

GCCGTCACCATCGGCGCCGTGTTTCTGGGCTTCCTGGGAGCCGCCGGAAGCACCATGGGA

GCCGCCTCCATCACCCTGACCGTGCAGGCCAGGCAGCTGCTGTCCGGGATCGTGCAGCAG

CAGAGCAACCTGCTGCGGGCCATCGAAGCTCAGCAGCACATGCTGCAGCTGGCAGTCTGG

GGCATCAAGCAGCTGCAGGCCAGAGTGCTGGCCATCGAGAGATACCTGAAGGATCAGCAG

CTGCTCGGCATCTGGGGCTGCAGCGGCAAGCTGATCTGCACCACCGCCGTGCCCTGGAAC

AACAGCTGGTCCAACAGGACCCAGGACGAGATCTGGAAGAACCTGACCTGGATGGAGTGG

GACAGAGAGATCAGCAACTACACCAACACAATCTACGAGCTGCTGGAGGTGTCCCAGAGC

CAGCAGGAGAGGAACGAGAAGGACCTGCTGGCCCTGGACAGCTGGAACAACCTGTGGAAC

TGGTTCGACATCAGCAACTGGCTGTGGTACATCAAGATCTTCATCATGATCGTGGGCGGC

CTGATCGGCCTGAGGATCATCTTCGCCGTGCTGTCCATCGTGAACAGAGTGCGGCAGGGC

TACAGCCCCCTGAGCTTCCAGACCCTGATCCCCAACCAGAGAGAGCCCGACAGGCCCGGC

AGGATCGAGGAGGAGGGCGGCGAGCAGGACAAGGATAGATCTATCAGACTGGTGTCCGGC

TTCCTGGCCCTGGCCTGGGACGACCTGAGAAGCCTGTGCATCTTCCTGTACCACCACCTG

AGGGACCTGATCCTGATCGCCGCTAGAGCCACAGAGCTGCTGGGGAGGTCCAGCCTGAGG

GGCCTGCAGAGAGGCTGGGAGGCCCTGAAGTACCTGGGCAGCCTGGTGCAGTACTGGGGC

CTGGAGATCAAGAAGAGCGCCATCAACCTGCTGGACACAATCGCCATCGCCGTGGCCGAG

GGCACCGACAGGATCATCGAGATCGTGCAGAGGGCCTGTAGGGCCGTGCTGAACATCCTG

AGAAGGATCCGGCAGGGCCTGGAGGCTGCCCTGCAGTGA

FIGURE 14

HIV-1 C06980v1c3 gp160 DC codon optimized Nucleic acid seq (SEQ ID NO: 15):

tPa signal is highlighted

The gp120/gp41 cleavage site is mutated to prevent cleavage

ATGGATGCAATGAAGAGAGGGCTCTGCTGTGTGCTGCTGCTGTGTGGAGCAGTCTTCGTT
ACTACCACAGAGGCTAGC AACCTGTGGGTGACCGTGTACTACGGCGTGCCCGTGTGGAGA
GAGGCCAAGACCACCCTGTTCTGCGCCAGCGACGCCAAGGCCTACGAGAGGGAGGTGCAC
AACGTGTGGGCCACCCACGCCTGCGTGCCCACCGACCCCGACCCACAGGAAATCTTTCTG
GGCAAGAACGTGACCGAGAAGTTCAACATGTGGGAGAACTACATGGTGGACCAGATGCAC
GAGGACATCATCAGCCTGTGGGACCAGAGCCTGCAGCCCTGCGTGAAGCTGACCCCCCTG
TGCATCACCCTGAACTGCACCGACTTCACCGCCCACAACGGCAGCACCGTGTACGACAAC
AACGCCACCGCCAACAGCACCAACGAGATCAAGAACTGCAGCTTCAACATCATCTCCGAG
CTGAGGGACAAGAGGAAGAAGGAGAACGCCCTGTTCAACAACCTGGACATCGTGCAGCTG
GACGGCAACTCCAGCCTGTACAGACTGATCAACTGCAACACCAGCATCATCAAGCAGGCC
TGTCCCAAGATCAGCTTCGACCCCATCCCCATCCACTACTGCGCCCCAGCCGGCTTCGTG
ATCCTGACCTGCAACAACGAGACATTCAACGGCACCGGCCCATGCAACAACGTGTCCGCT
GTGCAGTGTACCCACGGGATCAAGCCCGTGGTGTCCACCCAGCTGCTGCTGAACGGCAGC
CTGGCCAAGGGCGAGATCATGATCAGAAGCGAGAACATCACCAACAACGTGAAGACCATC
ATCGTGCACTTCAACAAGAGCGTGGAGATCGTGTGCACCAGGCCCAACAACAACACCAGG
AAGAGCATCAGGATCGGCCCAGGCCAGACCTTCTACGCCACCGGCGACATCATCGGCGAC
ATCCGGCAGGCCTACTGCAGCATCAACGAGAGCAACTGGAACATCACCCTGCAGAGGGTG
TCCAAGAAGCTGGCCGAGCACTTCCCCAACAGAACCATCCAGTTCGAGAGCCCCTCTGGC
GGCGACCTGGAGATCACCATGCACAGCTTCAACTGCAGGGGCGAGTTCTTCTACTGCAAC
ACATCCAAGCTGTTCAAGAGCACCTACCACCCCAACGGCACCTACAACCTGAACGGCACA

FIGURE 14 (cont.)

AACAGCACCCTGATCATCCCATGCAGGATCAAGCAGATCATCAACATGTGGCAGGGCGTG

GGCAAGGCCATCTACGCCAGCCCAATCGCCGGCAGCATCACCTGCAGAAGCAACATCACC

GGCCTGCTGCTGACCAGGGACGGCGGCGACACCAACGACACCGAGATCTTCAGGCCCACC

GGCGGAGACATGAGGGACAACTGGCGGAGCGAGCTGTACAAGTACAAGATCGTGGAGATC

AAGCCCCTGGGCGTGGCTCCAACCGAGGCCAAGAGCAGGGTGGTGAAGAGCGAGAAGAGC

GCCGTCACCATCGGCGCCGTGTTTCTGGGCTTCCTGGGAGCCGCCGGAAGCACCATGGGA

GCCGCCTCCATCACCCTGACCGTGCAGGCCAGGCAGCTGCTGTCCGGGATCGTGCAGCAG

CAGAGCAACCTGCTGCGGGCCATCGAAGCTCAGCAGCACATGCTGCAGCTGGCAGTCTGG

GGCATCAAGCAGCTGCAGGCCAGAGTGCTGGCCATCGAGAGATACCTGAAGGATCAGCAG

CTGCTCGGCATCTGGGGCTGCAGCGGCAAGCTGATCTGCACCACCGCCGTGCCCTGGAAC

AACAGCTGGTCCAACAGGACCCAGGACGAGATCTGGAAGAACCTGACCTGGATGGAGTGG

GACAGAGAGATCAGCAACTACACCAACACAATCTACGAGCTGCTGGAGGTGTCCCAGAGC

CAGCAGGAGAGGAACGAGAAGGACCTGCTGGCCCTGGACAGCTGGAACAACCTGTGGAAC

TGGTTCGACATCAGCAACTGGCTGTGGTACATCAAGATCTTCATCATGATCGTGGGCGGC

CTGATCGGCCTGAGGATCATCTTCGCCGTGCTGTCCATCGTGAACAGAGTGCGGCAGGGC

TACAGCCCCCTGAGCTTCCAGACCCTGATCCCCAACCAGAGAGAGCCCGACAGGCCCGGC

AGGATCGAGGAGGAGGGCGGCGAGCAGGACAAGGATAGATCTATCAGACTGGTGTCCGGC

TTCCTGGCCCTGGCCTGGGACGACCTGAGAAGCCTGTGCATCTTCCTGTACCACCACCTG

AGGGACCTGATCCTGATCGCCGCTAGAGCCACAGAGCTGCTGGGGAGGTCCAGCCTGAGG

GGCCTGCAGAGAGGCTGGGAGGCCCTGAAGTACCTGGGCAGCCTGGTGCAGTACTGGGGC

CTGGAGATCAAGAAGAGCGCCATCAACCTGCTGGACACAATCGCCATCGCCGTGGCCGAG

GGCACCGACAGGATCATCGAGATCGTGCAGAGGGCCTGTAGGGCCGTGCTGAACATCCTG

AGAAGGATCCGGCAGGGCCTGGAGGCTGCCCTGCAGTGATG

FIGURE 15

HIV-1 C06980v0c22 gp160 codon optimized nucleic acid seq (SEQ ID NO: 16):

tPa signal is highlighted

ATGGATGCAATGAAGAGAGGGCTCTGCTGTGTGCTGCTGCTGTGTGGAGCAGTCTTCGTT

ACTACCACAGAGGCTAGC AACCTGTGGGTGACCGTGTACTACGGCGTGCCCGTGTGGAGA

GAGGCCAAGACCACCCTGTTCTGCGCCAGCGACGCCAAGGCCTACGAGCGGGAGGTGCAC

AACGTGTGGGCCACCCACGCCTGCGTGCCCACCGACCCCGACCCTCAGGAAATCTTCCTG

GGCAAGAACGTGACCGAGAAGTTCAACATGTGGAAGAACTACATGGTGGACCAGATGCAC

GAGGACATCATCAGCCTGTGGGACCAGAGCCTGCAGCCCTGCGTGAAGCTGACCCCCCTG

TGCATCACCCTGAACTGCACCGACGTGACCGCCCACAACGGCAGCACCGTGTACGACAAC

AACGCCACCGTGGTGAACAGCACCAACGAGATCAAGAACTGCAGCTTCAACATCACCACC

GAGCTGAGGGACAAGAGGAAGAAGGAGCACGCCCTGTTCAACAACCTGGACATCGTGCAG

CTGGACGGCAACAGCTCCCTGTACAGACTGATCAACTGCAACACCAGCATCATCAAGCAG

GCCTGCCCCAAGATCAGCTTCGACCCCATCCCCATCCACTACTGCGCCCCAGCCGGCTTC

GTGATCCTGAAGTGCAACAACGAGACATTCAACGGCACCGGCCCCTGTAACAACGTGTCC

GCTGTGCAGTGCACCCACGGCATCAAGCCCGTGGTGTCCACCCAGCTGCTGCTGAACGGC

AGCCTGGCCAAGGGCGAGATCATGATCAGAAGCGAGAACATCACCGACAACGTGAAGACC

ATCATCGTGCACCTGAACAACAGCGTGGAGATCGTGTGCACCAGGCCCAACAACAACACC

AGGAAGAGCATCAGGATCGGCCCAGGCCAGACCTTCTACGCCACCGGCGACATCATCGGC

GACATCCGGCAGGCCTACTGCAGCATCAACGAGAGCAACTGGAACGCCACCCTGCAGAGG

GTGTCCAAGAAGCTGGCCGAGCACTTCCCCAACAAGACCATCCAGTTCAAGAGCCCCTCT

GGCGGCGACCTGGAGATCACCATGCACAGCTTCAACTGCAGGGGCGAGTTCTTCTACTGC

AACACATCCAAGCTGTTTAACGGGACCTACTACCCAAACGGCACATACTACCCAAACGGG

ACCAACAGCACCCTGATCATCCCATGCAGGATCAAGCAGATCATCAACATGTGGCAGGGC

GTGGGCAAGGCCATCTACGCCAGCCCAATCGCCGGCAACATCACCTGCCGGTCCAACATC

FIGURE 15 (cont.)

ACCGGCCTGCTGCTGACCAGGGACGGCGGCGACACCAACGACACCGAGATCTTCAGGCCA

GCCGGCGGAGACATGAGGGACAACTGGCGGAGCGAGCTGTACAAGTACAAGATCGTGGAG

ATCAAGCCCCTGGGCGTGGCTCCAACCGAGGCCAAGAGAAGGGTGGTGAAGAGAGAGAAG

AGGGCCGTCACCATCGGCGCCGTGTTTCTGGGCTTCCTGGGAGCCGCCGGAAGCACCATG

GGAGCCGCCTCCATCACCCTGACCGTGCAGGCCAGGCAGCTGCTGTCCGGGATCGTGCAG

CAGCAGAGCAACCTGCTGAGAGCCATTGAGGCTCAGCAGCACATGCTGCAGCTGACAGTG

TGGGGCATCAAGCAGCTGCAGGCCAGAGTGCTGGCCATCGAGAGATACCTGAAGGATCAG

CAGCTGCTCGGCATCTGGGGCTGCAGCGGCAAGCTGATCTGCACCACCGCCGTGCCCTGG

AACAACTCCTGGTCCAACAGGACCCAGGACGAGATCTGGAAGAACCTGACCTGGATGGAG

TGGGACAGAGAGATCAGCAACTACACCAACACCATCTACGAGCTGCTGGAGGTGTCCCAG

AGCCAGCAGGAGAGGAACGAGAAGGACCTGCTGGCCCTGGATAGCTGGAACAACCTGTGG

AACTGGTTCGACATCAGCAACTGGCTGTGGTACATCAAGATCTTCATCATGATCGTGGGC

GGCCTGATCGGCCTGAGGATCATCTTCGCCGTGCTGTCCATCGTGAACAGAGTGCGGCAG

GGCTACAGCCCCCTGAGCTTCCAGACCCTGATCCCCAACCAGAGAGAGCCCGACAGGCCC

GGCAGGATCGAGGAGGAGGGCGGCGAGCAGGACAAGGACAGATCCATCAGGCTGGTGTCC

GGCTTCCTGGCCCTGGCCTGGGACGACCTGAGAAGCCTGTGCATCTTCCTGTACCACCAC

CTGAGGGACTTCATCCTGATCGCCGCCAGGGCCACAGAGCTGCTGGGGAGGTCCAGCCTG

AGGGGCCTGCAGAGAGGCTGGGAGGCCCTGAAGTACCTGGGCAGCCTGGTGCAGTACTGG

GGCCTGGAGATCAAGAAGAGCGCCATCAACCTGCTGGACACAATCGCCATCGCCGTGGCC

GAGGGCACCGACAGGATCATCGAGATCGTGCAGAGGGCCTGTAGGGCCGTGCTGAACATC

CCCAGAAGGATCAGACAGGGGCTGGAGGCTGCCCTGCAGTGA

FIGURE 16

HIV-1 C06980v0c22 gp160 DC codon optimized Nucleic acid seq (SEQ ID NO: 17):

tPa signal is highlighted

The gp120/gp41 cleavage site is mutated to prevent cleavage

<mark>ATGGATGCAATGAAGAGAGGGCTCTGCTGTGTGCTGCTGCTGTGTGGAGCAGTCTTCGTT
ACTACCACAGAGGCTAGC</mark> AACCTGTGGGTGACCGTGTACTACGGCGTGCCCGTGTGGAGA
GAGGCCAAGACCACCCTGTTCTGCGCCAGCGACGCCAAGGCCTACGAGCGGGAGGTGCAC
AACGTGTGGGCCACCCACGCCTGCGTGCCCACCGACCCCGACCCTCAGGAAATCTTCCTG
GGCAAGAACGTGACCGAGAAGTTCAACATGTGGAAGAACTACATGGTGGACCAGATGCAC
GAGGACATCATCAGCCTGTGGGACCAGAGCCTGCAGCCCTGCGTGAAGCTGACCCCCCTG
TGCATCACCCTGAACTGCACCGACGTGACCGCCCACAACGGCAGCACCGTGTACGACAAC
AACGCCACCGTGGTGAACAGCACCAACGAGATCAAGAACTGCAGCTTCAACATCACCACC
GAGCTGAGGGACAAGAGGAAGAAGGAGCACGCCCTGTTCAACAACCTGGACATCGTGCAG
CTGGACGGCAACAGCTCCCTGTACAGACTGATCAACTGCAACACCAGCATCATCAAGCAG
GCCTGCCCCAAGATCAGCTTCGACCCCATCCCCATCCACTACTGCGCCCCAGCCGGCTTC
GTGATCCTGAAGTGCAACAACGAGACATTCAACGGCACCGGCCCCTGTAACAACGTGTCC
GCTGTGCAGTGCACCCACGGCATCAAGCCCGTGGTGTCCACCCAGCTGCTGCTGAACGGC
AGCCTGGCCAAGGGCGAGATCATGATCAGAAGCGAGAACATCACCGACAACGTGAAGACC
ATCATCGTGCACCTGAACAACAGCGTGGAGATCGTGTGCACCAGGCCCAACAACAACACC
AGGAAGAGCATCAGGATCGGCCCAGGCCAGACCTTCTACGCCACCGGCGACATCATCGGC
GACATCCGGCAGGCCTACTGCAGCATCAACGAGAGCAACTGGAACGCCACCCTGCAGAGG
GTGTCCAAGAAGCTGGCCGAGCACTTCCCCAACAAGACCATCCAGTTCAAGAGCCCCTCT
GGCGGCGACCTGGAGATCACCATGCACAGCTTCAACTGCAGGGGCGAGTTCTTCTACTGC FIGURE 16 (cont.)

AACACATCCAAGCTGTTTAACGGGACCTACTACCCAAACGGCACATACTACCCAAACGGG

ACCAACAGCACCCTGATCATCCCATGCAGGATCAAGCAGATCATCAACATGTGGCAGGGC

GTGGGCAAGGCCATCTACGCCAGCCCAATCGCCGGCAACATCACCTGCCGGTCCAACATC

ACCGGCCTGCTGCTGACCAGGGACGGCGGCGACACCAACGACACCGAGATCTTCAGGCCA

GCCGGCGGAGACATGAGGGACAACTGGCGGAGCGAGCTGTACAAGTACAAGATCGTGGAG

ATCAAGCCCCTGGGCGTGGCTCCAACCGAGGCCAAGAGCAGGGTGGTGAAGAGCGAGAAG

AGCGCCGTCACCATCGGCGCCGTGTTTCTGGGCTTCCTGGGAGCCGCCGGAAGCACCATG

GGAGCCGCCTCCATCACCCTGACCGTGCAGGCCAGGCAGCTGCTGTCCGGGATCGTGCAG

CAGCAGAGCAACCTGCTGAGAGCCATTGAGGCTCAGCAGCACATGCTGCAGCTGACAGTG

TGGGGCATCAAGCAGCTGCAGGCCAGAGTGCTGGCCATCGAGAGATACCTGAAGGATCAG

CAGCTGCTCGGCATCTGGGGCTGCAGCGGCAAGCTGATCTGCACCACCGCCGTGCCCTGG

AACAACTCCTGGTCCAACAGGACCCAGGACGAGATCTGGAAGAACCTGACCTGGATGGAG

TGGGACAGAGAGATCAGCAACTACACCAACACCATCTACGAGCTGCTGGAGGTGTCCCAG

AGCCAGCAGGAGAGGAACGAGAAGGACCTGCTGGCCCTGGATAGCTGGAACAACCTGTGG

AACTGGTTCGACATCAGCAACTGGCTGTGGTACATCAAGATCTTCATCATGATCGTGGGC

GGCCTGATCGGCCTGAGGATCATCTTCGCCGTGCTGTCCATCGTGAACAGAGTGCGGCAG

GGCTACAGCCCCCTGAGCTTCCAGACCCTGATCCCCAACCAGAGAGAGCCCGACAGGCCC

GGCAGGATCGAGGAGGAGGGCGGCGAGCAGGACAAGGACAGATCCATCAGGCTGGTGTCC

GGCTTCCTGGCCCTGGCCTGGGACGACCTGAGAAGCCTGTGCATCTTCCTGTACCACCAC

CTGAGGGACTTCATCCTGATCGCCGCCAGGGCCACAGAGCTGCTGGGGAGGTCCAGCCTG

AGGGGCCTGCAGAGAGGCTGGGAGGCCCTGAAGTACCTGGGCAGCCTGGTGCAGTACTGG

GGCCTGGAGATCAAGAAGAGCGCCATCAACCTGCTGGACACAATCGCCATCGCCGTGGCC

GAGGGCACCGACAGGATCATCGAGATCGTGCAGAGGGCCTGTAGGGCCGTGCTGAACATC

CCCAGAAGGATCAGACAGGGGCTGGAGGCTGCCCTGCAGTGA

FIGURE 18 pSWTIPK3 sequence (SEQ ID NO: 18):

TGGCACATGGCCAATGCATATCGATCTATACATTGAATCAATATTGGCAATTAGCCATAT

TAGTCATTGGTTATATAGCATAAATCAATATTGGCTATTGGCCATTGCATACGTTGTATC

TATATCATAATATGTACATTTATATTGGCTCATGTCCAATATGACCGCCATGTTGACATT

GATTATTGACTAGTTATTAATAGTAATCAATTACGGGGTCATTAGTTCATAGCCCATATA

TGGAGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTTTCC

ATTGACGTCAATGGGTGGAGTATTTACGGTAAACTGCCCACTTGGCAGTACATCAAGTGT

ATCATATGCCAAGTCCGCCCCCTATTGACGTCAATGACGGTAAATGGCCCGCCTGGCATT

ATGCCCAGTACATGACCTTACGGGACTTTCCTACTTGGCAGTACATCTACGTATTAGTCA

TCGCTATTACCATGGTGATGCGGTTTTGGCAGTACACCAATGGGCGTGGATAGCGGTTTG

ACTCACGGGGATTTCCAAGTCTCCACCCCATTGACGTCAATGGGAGTTTGTTTTGGCACC

AAAATCAACGGGACTTTCCAAAATGTCGTAATAACCCCGCCCCGTTGACGCAAATGGGCG

GTAGGCGTGTACGGTGGGAGGTCTATATAAGCAGAGCTCGTTTAGTGAACCGTCAGATCG

CCTGGAGACGCCATCCACGCTGTTTTGACCTCCATAGAAGACACCGGGACCGATCCAGCC

TCCGCGGCCGGGAACGGTGCATTGGAACGCGGATTCCCCGTGCCAAGAGTGACGTAAGTA

CCGCCTATAGACTCTATAGGCACACCCCTTTGGCTCTTATGCATGCTATACTGTTTTTGG

CTTGGGGCCTATACACCCCCGCTTCCTTATGCTATAGGTGATGGTATAGCTTAGCCTATA

GGTGTGGGTTATTGACCATTATTGACCACTCCCCTATTGGTGACGATACTTTCCATTACT

AATCCATAACATGGCTCTTTGCCACAACTATCTCTATTGGCTATATGCCAATACTCTGTC

CTTCAGAGACTGACACGGACTCTGTATTTTTACAGGATGGGGTCCCATTTATTATTTACA

AATTCACATATACAACAACGCCGTCCCCCGTGCCCGCAGTTTTTATTAAACATAGCGTGG

GATCTCCACGCGAATCTCGGGTACGTGTTCCGGACATGGGCTCTTCTCCGGTAGCGGCGG

FIGURE 18 (cont. - 1)

AGCTTCCACATCCGAGCCCTGGTCCCATGCCTCCAGCGGCTCATGGTCGCTCGGCAGCTC

CTTGCTCCTAACAGTGGAGGCCAGACTTAGGCACAGCACAATGCCCACCACCACCAGTGT

GCCGCACAAGGCCGTGGCGGTAGGGTATGTGTCTGAAAATGAGCTCGGAGATTGGGCTCG

CACCGCTGACGCAGATGGAAGACTTAAGGCAGCGGCAGAAGAAGATGCAGGCAGCTGAGT

TGTTGTATTCTGATAAGAGTCAGAGGTAACTCCCGTTGCGGTGCTGTTAACGGTGGAGGG

CAGTGTAGTCTGAGCAGTACTCGTTGCTGCCGCGCGCGCCACCAGACATAATAGCTGACA

GACTAACAGACTGTTCCTTTCCATGGGTCTTTTCTGCAGTCACCGTCCATTTAAATACGC

GTGCCACCATGGATGCAATGAAGAGAGGGCTCTGCTGTGTGCTGCTGCTGTGTGGAGCAG

TCTTCGTTACTACCACAGAGGCTAGCGGGGATATCGGCGCCGAATTCGGATCCACTAGTA

GATCTCTCGAGAACGGCCGCCAGTGTGCTGGAATTAATTCGCTGTCTGCGAGGGCCAGCT

GTTGGGGTGAGTACTCCCTCTCAAAAGCGGGCATGACTTCTGCGCTAAGATTGTCAGTTT

CCAAAAACGAGGAGGATTTGATATTCACCTGGCCCGCGGTGATGCCTTTGAGGGTGGCCG

CGTCCATCTGGTCAGAAAAGACAATCTTTTTGTTGTCAAGCTTGAGGTGTGGCAGGCTTG

AGATCTGGCCATACACTTGAGTGACAATGACATCCACTTTGCCTTTCTCTCCACAGGTGT

CCACTCCCAGGTCCAACTGCAGGTCGAGCATGCATCTAGGGCGGCCAATTCCGCCCCTCT

CCCTCCCCCCCCCCTAACGTTACTGGCCGAAGCCGCTTGGAATAAGGCCGGTGTGCGTTT

GTCTATATGTTATTTTCCACCATATTGCCGTCTTTTGGCAATGTGAGGGCCCGGAAACCT

GGCCCTGTCTTCTTGACGAGCATTCCTAGGGGTCTTTCCCCTCTCGCCAAAGGAATGCAA

GGTCTGTTGAATGTCGTGAAGGAAGCAGTTCCTCTGGAAGCTTCTTGAAGACAAACAACG

TCTGTAGCGACCCTTTGCAGGCAGCGGAACCCCCCACCTGGCGACAGGTGCCTCTGCGGC

CAAAAGCCACGTGTATAAGATACACCTGCAAAGGCGGCACAACCCCAGTGCCACGTTGTG

AGTTGGATAGTTGTGGAAAGAGTCAAATGGCTCTCCTCAAGCGTATTCAACAAGGGGCTG

AAGGATGCCCAGAAGGTACCCCATTGTATGGGATCTGATCTGGGGCCTCGGTGCACATGC

TTTACATGTGTTTAGTCGAGGTTAAAAAAACGTCTAGGCCCCCCGAACCACGGGGACGTG

FIGURE 18 (cont. - 2)

GTTTTCCTTTGAAAAACACGATGATAAGCTTGCCACAACCCACAAGGAGACGACCTTCCA

TGACCGAGTACAAGCCCACGGTGCGCCTCGCCACCCGCGACGACGTCCCCCGGGCCGTAC

GCACCCTCGCCGCCGCGTTCGCCGACTACCCCGCCACGCGCCACACCGTGGACCCGGACC

GCCACATCGAGCGGGTCACCGAGCTGCAAGAACTCTTCCTCACGCGCGTCGGGCTCGACA

TCGGCAAGGTGTGGGTCGCGGACGACGGCGCTGCGGTGGCGGTCTGGACCACGCCGGAGA

GCGTCGAAGCGGGGGCGGTGTTCGCCGAGATCGGCCCGCGCATGGCCGAGTTGAGCGGTT

CCCGGCTGGCCGCGCAGCAACAGATGGAAGGCCTCCTGGCTCCGCACCGGCCCAAGGAGC

CCGCGTGGTTCCTGGCCACCGTCGGCGTCTCGCCCGACCACCAGGGCAAGGGTCTGGGCA

GCGCCGTCGTGCTCCCCGGAGTGGAGGCGGCCGAGCGCGCCGGGGTGCCCGCCTTCCTGG

AGACCTCCGCGCCCCGCAACCTCCCCTTCTACGAGCGGCTCGGCTTCACCGTCACCGCCG

ACGTCGAGGTGCCCGAAGGACCGCGCACCTGGTGCATGACCCGCAAGCCCGGTGCCTGAC

GCCCGCCCCACGACCCGCAGCGCCCGACCGAAAGGAGCGCACGACCCCATGGCTCCGACC

GAAGCCACCCGGGGCGGCCCCGCCGACCCCGCACCCGCCCCCGAGGCCCACCGACGTCGA

CCTCGAGGGCGCGCCGCTGATCAGCCTCGACTGTGCCTTCTAGTTGCCAGCCATCTGTTG

TTTGCCCCTCCCCCGTGCCTTCCTTGACCCTGGAAGGTGCCACTCCCACTGTCCTTTCCT

AATAAAATGAGGAAATTGCATCGCATTGTCTGAGTAGGTGTCATTCTATTCTGGGGGGTG

GGGTGGGGCAGGACAGCAAGGGGGAGGATTGGGAAGACAATAGCAGGCATGCTGGGGATG

CGGTGGGCTCTATGGCTTCTGCGGCCGCAGCTTGGCGTAATCATGGTCATAGCTGTTTCC

TGTGTGAAATTGTTATCCGCTCACAATTCCACACAACATACGAGCCGGAAGCATAAAGTG

TAAAGCCTGGGGTGCCTAATGAGTGAGCTAACTCACATTAATTGCGTTGCGCTCACTGCC

CGCTTTCCAGTCGGGAAACCTGTCGTGCCAGCTGCATTAATGAATCGGCCAACGCGCGGG

GAGAGGCGGTTTGCGTATTGGGCGCTCTTCCGCTTCCTCGCTCACTGACTCGCTGCGCTC

GGTCGTTCGGCTGCGGCGAGCGGTATCAGCTCACTCAAAGGCGGTAATACGGTTATCCAC

FIGURE 18 (cont. - 3)

AGAATCAGGGGATAACGCAGGAAAGAACATGTGAGCAAAAGGCCAGCAAAAGGCCAGGAA

CCGTAAAAAGGCCGCGTTGCTGGCGTTTTTCCATAGGCTCCGCCCCCCTGACGAGCATCA

CAAAAATCGACGCTCAAGTCAGAGGTGGCGAAACCCGACAGGACTATAAAGATACCAGGC

GTTTCCCCCTGGAAGCTCCCTCGTGCGCTCTCCTGTTCCGACCCTGCCGCTTACCGGATA

CCTGTCCGCCTTTCTCCCTTCGGGAAGCGTGGCGCTTTCTCATAGCTCACGCTGTAGGTA

TCTCAGTTCGGTGTAGGTCGTTCGCTCCAAGCTGGGCTGTGTGCACGAACCCCCCGTTCA

GCCCGACCGCTGCGCCTTATCCGGTAACTATCGTCTTGAGTCCAACCCGGTAAGACACGA

CTTATCGCCACTGGCAGCAGCCACTGGTAACAGGATTAGCAGAGCGAGGTATGTAGGCGG

TGCTACAGAGTTCTTGAAGTGGTGGCCTAACTACGGCTACACTAGAAGAACAGTATTTGG

TATCTGCGCTCTGCTGAAGCCAGTTACCTTCGGAAAAAGAGTTGGTAGCTCTTGATCCGG

CAAACAAACCACCGCTGGTAGCGGTGGTTTTTTTGTTTGCAAGCAGCAGATTACGCGCAG

AAAAAAAGGATCTCAAGAAGATCCTTTGATCTTTTCTACGGGGTCTGACGCTCAGTGGAA

CGAAAACTCACGTTAAGGGATTTTGGTCATGAGATTATCAAAAAGGATCTTCACCTAGAT

CCTTTTAAATTAAAAATGAAGTTTTAAATCAATCTAAAGTATATATGAGTAAACTTGGTC

TGACAGTTAGAAAAACTCATCGAGCATCAAATGAAACTGCAATTTATTCATATCAGGATT

ATCAATACCATATTTTTGAAAAAGCCGTTTCTGTAATGAAGGAGAAAACTCACCGAGGCA

GTTCCATAGGATGGCAAGATCCTGGTATCGGTCTGCGATTCCGACTCGTCCAACATCAAT

ACAACCTATTAATTTCCCCTCGTCAAAAATAAGGTTATCAAGTGAGAAATCACCATGAGT

GACGACTGAATCCGGTGAGAATGGCAAAAGCTTATGCATTTCTTTCCAGACTTGTTCAAC

AGGCCAGCCATTACGCTCGTCATCAAAATCACTCGCATCAACCAAACCGTTATTCATTCG

TGATTGCGCCTGAGCGAGACGAAATACGCGATCGCTGTTAAAAGGACAATTACAAACAGG

AATCGAATGCAACCGGCGCAGGAACACTGCCAGCGCATCAACAATATTTTCACCTGAATC

AGGATATTCTTCTAATACCTGGAATGCTGTTTTCCCGGGGATCGCAGTGGTGAGTAACCA

FIGURE 18 (cont. - 4)

TGCATCATCAGGAGTACGGATAAAATGCTTGATGGTCGGAAGAGGCATAAATTCCGTCAG

CCAGTTTAGTCTGACCATCTCATCTGTAACATCATTGGCAACGCTACCTTTGCCATGTTT

CAGAAACAACTCTGGCGCATCGGGCTTCCCATACAATCGATAGATTGTCGCACCTGATTG

CCCGACATTATCGCGAGCCCATTTATACCCATATAAATCAGCATCCATGTTGGAATTTAA

TCGCGGCCTTGAGCAAGACGTTTCCCGTTGAATATGGCTCATACTCTTCCTTTTTCAATA

TTATTGAAGCATTTATCAGGGTTATTGTCTCATGAGCGGATACATATTTGAATGTATTTA

GAAAAATAAACAAATAGGGGTTCCGCGCACATTTCCCCGAAAAGTGCCAC

FIGURE 22 pSWC06980v0c22 gp145 sequence (SEQ ID NO: 19):

TGGCACATGGCCAATGCATATCGATCTATACATTGAATCAATATTGGCAATTAGCCATAT

TAGTCATTGGTTATATAGCATAAATCAATATTGGCTATTGGCCATTGCATACGTTGTATC

TATATCATAATATGTACATTTATATTGGCTCATGTCCAATATGACCGCCATGTTGACATT

GATTATTGACTAGTTATTAATAGTAATCAATTACGGGGTCATTAGTTCATAGCCCATATA

TGGAGTTCCGCGTTACATAACTTACGGTAAATGGCCCGCCTGGCTGACCGCCCAACGACC

CCCGCCCATTGACGTCAATAATGACGTATGTTCCCATAGTAACGCCAATAGGGACTTTCC

ATTGACGTCAATGGGTGGAGTATTTACGGTAAACTGCCCACTTGGCAGTACATCAAGTGT

ATCATATGCCAAGTCCGCCCCCTATTGACGTCAATGACGGTAAATGGCCCGCCTGGCATT

ATGCCCAGTACATGACCTTACGGGACTTTCCTACTTGGCAGTACATCTACGTATTAGTCA

TCGCTATTACCATGGTGATGCGGTTTTGGCAGTACACCAATGGGCGTGGATAGCGGTTTG

ACTCACGGGGATTTCCAAGTCTCCACCCCATTGACGTCAATGGGAGTTTGTTTTGGCACC

AAAATCAACGGGACTTTCCAAAATGTCGTAATAACCCCGCCCCGTTGACGCAAATGGGCG

GTAGGCGTGTACGGTGGGAGGTCTATATAAGCAGAGCTCGTTTAGTGAACCGTCAGATCG

CCTGGAGACGCCATCCACGCTGTTTTGACCTCCATAGAAGACACCGGGACCGATCCAGCC

TCCGCGGCCGGGAACGGTGCATTGGAACGCGGATTCCCCGTGCCAAGAGTGACGTAAGTA

CCGCCTATAGACTCTATAGGCACACCCCTTTGGCTCTTATGCATGCTATACTGTTTTTGG

CTTGGGGCCTATACACCCCGCTTCCTTATGCTATAGGTGATGGTATAGCTTAGCCTATA

GGTGTGGGTTATTGACCATTATTGACCACTCCCCTATTGGTGACGATACTTTCCATTACT

AATCCATAACATGGCTCTTTGCCACAACTATCTCTATTGGCTATATGCCAATACTCTGTC

CTTCAGAGACTGACACGGACTCTGTATTTTTACAGGATGGGGTCCCATTTATTATTTACA

AATTCACATATACAACAACGCCGTCCCCCGTGCCCGCAGTTTTTATTAAACATAGCGTGG

GATCTCCACGCGAATCTCGGGTACGTGTTCCGGACATGGGCTCTTCTCCGGTAGCGGCGG

FIGURE 22 (cont.-1)

AGCTTCCACATCCGAGCCCTGGTCCCATGCCTCCAGCGGCTCATGGTCGCTCGGCAGCTC

CTTGCTCCTAACAGTGGAGGCCAGACTTAGGCACAGCACAATGCCCACCACCACCAGTGT

GCCGCACAAGGCCGTGGCGGTAGGGTATGTGTCTGAAAATGAGCTCGGAGATTGGGCTCG

CACCGCTGACGCAGATGGAAGACTTAAGGCAGCGGCAGAAGAAGATGCAGGCAGCTGAGT

TGTTGTATTCTGATAAGAGTCAGAGGTAACTCCCGTTGCGGTGCTGTTAACGGTGGAGGG

CAGTGTAGTCTGAGCAGTACTCGTTGCTGCCGCGCGCCACCAGACATAATAGCTGACA

GACTAACAGACTGTTCCTTTCCATGGGTCTTTTCTGCAGTCACCGTCCATTTAAATACGC

GTGCCACCATGGATGCAATGAAGAGAGGGCTCTGCTGTGTGCTGCTGCTGTGTGGAGCAG

TCTTCGTTACTACCACAGAGGCTAGCAACCTGTGGGTGACCGTGTACTACGGCGTGCCCG

TGTGGAGAGAGGCCAAGACCACCCTGTTCTGCGCCAGCGACGCCAAGGCCTACGAGCGGG

AGGTGCACAACGTGTGGGCCACCCACGCCTGCGTGCCCACCGACCCCGACCCTCAGGAAA

TCTTCCTGGGCAAGAACGTGACCGAGAAGTTCAACATGTGGAAGAACTACATGGTGGACC

AGATGCACGAGGACATCATCAGCCTGTGGGACCAGAGCCTGCAGCCCTGCGTGAAGCTGA

CCCCCCTGTGCATCACCCTGAACTGCACCGACGTGACCGCCCACAACGGCAGCACCGTGT

ACGACAACAACGCCACCGTGGTGAACAGCACCAACGAGATCAAGAACTGCAGCTTCAACA

TCACCACCGAGCTGAGGGACAAGAGGAAGAAGGAGCACGCCCTGTTCAACAACCTGGACA

TCGTGCAGCTGGACGGCAACAGCTCCCTGTACAGACTGATCAACTGCAACACCAGCATCA

TCAAGCAGGCCTGCCCCAAGATCAGCTTCGACCCCATCCCCATCCACTACTGCGCCCCAG

CCGGCTTCGTGATCCTGAAGTGCAACAACGAGACATTCAACGGCACCGGCCCCTGTAACA

ACGTGTCCGCTGTGCAGTGCACCCACGGCATCAAGCCCGTGGTGTCCACCCAGCTGCTGC

TGAACGGCAGCCTGGCCAAGGGCGAGATCATGATCAGAAGCGAGAACATCACCGACAACG

TGAAGACCATCATCGTGCACCTGAACAACAGCGTGGAGATCGTGTGCACCAGGCCCAACA

ACAACACCAGGAAGAGCATCAGGATCGGCCCAGGCCAGACCTTCTACGCCACCGGCGACA

TCATCGGCGACATCCGGCAGGCCTACTGCAGCATCAACGAGAGCAACTGGAACGCCACCC

FIGURE 22 (cont.-2)

TGCAGAGGGTGTCCAAGAAGCTGGCCGAGCACTTCCCCAACAAGACCATCCAGTTCAAGA

GCCCCTCTGGCGGCGACCTGGAGATCACCATGCACAGCTTCAACTGCAGGGGCGAGTTCT

TCTACTGCAACACATCCAAGCTGTTTAACGGGACCTACTACCCAAACGGCACATACTACC

CAAACGGGACCAACAGCACCCTGATCATCCCATGCAGGATCAAGCAGATCATCAACATGT

GGCAGGGCGTGGGCAAGGCCATCTACGCCAGCCCAATCGCCGGCAACATCACCTGCCGGT

CCAACATCACCGGCCTGCTGCTGACCAGGGACGGCGGCGACACCAACGACACCGAGATCT

TCAGGCCAGCCGGCGGAGACATGAGGGACAACTGGCGGAGCGAGCTGTACAAGTACAAGA

TCGTGGAGATCAAGCCCCTGGGCGTGGCTCCAACCGAGGCCAAGAGCAGGGTGGTGAAGA

GCGAGAAGAGCGCCGTCACCATCGGCGCCGTGTTTCTGGGCTTCCTGGGAGCCGCCGGAA

GCACCATGGGAGCCGCCTCCATCACCCTGACCGTGCAGGCCAGGCAGCTGCTGTCCGGGA

TCGTGCAGCAGCAGAGCAACCTGCTGAGAGCCATTGAGGCTCAGCAGCACATGCTGCAGC

TGACAGTGTGGGGCATCAAGCAGCTGCAGGCCAGAGTGCTGGCCATCGAGAGATACCTGA

AGGATCAGCAGCTGCTCGGCATCTGGGGCTGCAGCGGCAAGCTGATCTGCACCACCGCCG

TGCCCTGGAACAACTCCTGGTCCAACAGGACCCAGGACGAGATCTGGAAGAACCTGACCT

GGATGGAGTGGGACAGAGAGATCAGCAACTACACCAACACCATCTACGAGCTGCTGGAGG

TGTCCCAGAGCCAGCAGGAGAGGAACGAGAAGGACCTGCTGGCCCTGGATAGCTGGAACA

ACCTGTGGAACTGGTTCGACATCAGCAACTGGCTGTGGTACATCAAGAAGAAGAAGTGAA

TTCGGATCCACTAGTAGATCTCTCGAGAACGGCCGCCAGTGTGCTGGAATTAATTCGCTG

TCTGCGAGGGCCAGCTGTTGGGGTGAGTACTCCCTCTCAAAAGCGGGCATGACTTCTGCG

CTAAGATTGTCAGTTTCCAAAAACGAGGAGGATTTGATATTCACCTGGCCCGCGGTGATG

CCTTTGAGGGTGGCCGCGTCCATCTGGTCAGAAAAGACAATCTTTTTGTTGTCAAGCTTG

AGGTGTGGCAGGCTTGAGATCTGGCCATACACTTGAGTGACAATGACATCCACTTTGCCT

TTCTCTCCACAGGTGTCCACTCCCAGGTCCAACTGCAGGTCGAGCATGCATCTAGGGCGG

FIGURE 22 (cont.-3)

CCAATTCCGCCCCTCTCCCTCCCCCCCCCCTAACGTTACTGGCCGAAGCCGCTTGGAATA

AGGCCGGTGTGCGTTTGTCTATATGTTATTTTCCACCATATTGCCGTCTTTTGGCAATGT

GAGGGCCCGGAAACCTGGCCCTGTCTTCTTGACGAGCATTCCTAGGGGTCTTTCCCCTCT

CGCCAAAGGAATGCAAGGTCTGTTGAATGTCGTGAAGGAAGCAGTTCCTCTGGAAGCTTC

TTGAAGACAAACAACGTCTGTAGCGACCCTTTGCAGGCAGCGGAACCCCCCACCTGGCGA

CAGGTGCCTCTGCGGCCAAAAGCCACGTGTATAAGATACACCTGCAAAGGCGGCACAACC

CCAGTGCCACGTTGTGAGTTGGATAGTTGTGGAAAGAGTCAAATGGCTCTCCTCAAGCGT

ATTCAACAAGGGGCTGAAGGATGCCCAGAAGGTACCCCATTGTATGGGATCTGATCTGGG

GCCTCGGTGCACATGCTTTACATGTGTTTAGTCGAGGTTAAAAAAACGTCTAGGCCCCCC

GAACCACGGGGACGTGGTTTTCCTTTGAAAAACACGATGATAAGCTTGCCACAACCCACA

AGGAGACGACCTTCCATGACCGAGTACAAGCCCACGGTGCGCCTCGCCACCCGCGACGAC

GTCCCCCGGGCCGTACGCACCCTCGCCGCCGCGTTCGCCGACTACCCCGCCACGCGCCAC

ACCGTGGACCCGGACCGCCACATCGAGCGGGTCACCGAGCTGCAAGAACTCTTCCTCACG

CGCGTCGGGCTCGACATCGGCAAGGTGTGGGTCGCGGACGACGGCGCTGCGGTGGCGGTC

TGGACCACGCCGGAGAGCGTCGAAGCGGGGGCGGTGTTCGCCGAGATCGGCCCGCGCATG

GCCGAGTTGAGCGGTTCCCGGCTGGCCGCGCAGCAACAGATGGAAGGCCTCCTGGCTCCG

CACCGGCCCAAGGAGCCCGCGTGGTTCCTGGCCACCGTCGGCGTCTCGCCCGACCACCAG

GGCAAGGGTCTGGGCAGCGCCGTCGTGCTCCCCGGAGTGGAGGCGGCCGAGCGCGCCGGG

GTGCCCGCCTTCCTGGAGACCTCCGCGCCCCGCAACCTCCCCTTCTACGAGCGGCTCGGC

TTCACCGTCACCGCCGACGTCGAGGTGCCCGAAGGACCGCGCACCTGGTGCATGACCCGC

AAGCCCGGTGCCTGACGCCCGCCCCACGACCCGCAGCGCCCGACCGAAAGGAGCGCACGA

CCCCATGGCTCCGACCGAAGCCACCCGGGGCGGCCCCGCCGACCCCGCACCCGCCCCGA

GGCCCACCGACGTCGACCTCGAGGGCGCGCCGCTGATCAGCCTCGACTGTGCCTTCTAGT

FIGURE 22 (cont.-4)

TGCCAGCCATCTGTTGTTTGCCCCTCCCCCGTGCCTTCCTTGACCCTGGAAGGTGCCACT

CCCACTGTCCTTTCCTAATAAAATGAGGAAATTGCATCGCATTGTCTGAGTAGGTGTCAT

TCTATTCTGGGGGGTGGGGTGGGGCAGGACAGCAAGGGGGAGGATTGGGAAGACAATAGC

AGGCATGCTGGGGATGCGGTGGGCTCTATGGCTTCTGCGGCCGCAGCTTGGCGTAATCAT

GGTCATAGCTGTTTCCTGTGTGAAATTGTTATCCGCTCACAATTCCACACAACATACGAG

CCGGAAGCATAAAGTGTAAAGCCTGGGGTGCCTAATGAGTGAGCTAACTCACATTAATTG

CGTTGCGCTCACTGCCCGCTTTCCAGTCGGGAAACCTGTCGTGCCAGCTGCATTAATGAA

TCGGCCAACGCGCGGGGAGAGGCGGTTTGCGTATTGGGCGCTCTTCCGCTTCCTCGCTCA

CTGACTCGCTGCGCTCGGTCGTTCGGCTGCGGCGAGCGGTATCAGCTCACTCAAAGGCGG

TAATACGGTTATCCACAGAATCAGGGGATAACGCAGGAAAGAACATGTGAGCAAAAGGCC

AGCAAAAGGCCAGGAACCGTAAAAAGGCCGCGTTGCTGGCGTTTTTCCATAGGCTCCGCC

CCCCTGACGAGCATCACAAAAATCGACGCTCAAGTCAGAGGTGGCGAAACCCGACAGGAC

TATAAAGATACCAGGCGTTTCCCCCTGGAAGCTCCCTCGTGCGCTCTCCTGTTCCGACCC

TGCCGCTTACCGGATACCTGTCCGCCTTTCTCCCTTCGGGAAGCGTGGCGCTTTCTCATA

GCTCACGCTGTAGGTATCTCAGTTCGGTGTAGGTCGTTCGCTCCAAGCTGGGCTGTGTGC

ACGAACCCCCCGTTCAGCCCGACCGCTGCGCCTTATCCGGTAACTATCGTCTTGAGTCCA

ACCCGGTAAGACACGACTTATCGCCACTGGCAGCAGCCACTGGTAACAGGATTAGCAGAG

CGAGGTATGTAGGCGGTGCTACAGAGTTCTTGAAGTGGTGGCCTAACTACGGCTACACTA

GAAGAACAGTATTTGGTATCTGCGCTCTGCTGAAGCCAGTTACCTTCGGAAAAAGAGTTG

GTAGCTCTTGATCCGGCAAACAAACCACCGCTGGTAGCGGTGGTTTTTTTGTTTGCAAGC

AGCAGATTACGCGCAGAAAAAAAGGATCTCAAGAAGATCCTTTGATCTTTTCTACGGGGT

CTGACGCTCAGTGGAACGAAAACTCACGTTAAGGGATTTTGGTCATGAGATTATCAAAAA

GGATCTTCACCTAGATCCTTTTAAATTAAAAATGAAGTTTTAAATCAATCTAAAGTATAT

FIGURE 22 (cont.-5)

ATGAGTAAACTTGGTCTGACAGTTAGAAAAACTCATCGAGCATCAAATGAAACTGCAATT
TATTCATATCAGGATTATCAATACCATATTTTTGAAAAAGCCGTTTCTGTAATGAAGGAG
AAAACTCACCGAGGCAGTTCCATAGGATGGCAAGATCCTGGTATCGGTCTGCGATTCCGA
CTCGTCCAACATCAATACAACCTATTAATTTCCCCTCGTCAAAAATAAGGTTATCAAGTG
AGAAATCACCATGAGTGACGACTGAATCCGGTGAGAATGGCAAAAGCTTATGCATTTCTT
TCCAGACTTGTTCAACAGGCCAGCCATTACGCTCGTCATCAAAATCACTCGCATCAACCA
AACCGTTATTCATTCGTGATTGCGCCTGAGCGAGACGAAATACGCGATCGCTGTTAAAAG
GACAATTACAAACAGGAATCGAATGCAACCGGCGCAGGAACACTGCCAGCGCATCAACAA
TATTTTCACCTGAATCAGGATATTCTTCTAATACCTGGAATGCTGTTTTCCCGGGGATCG
CAGTGGTGAGTAACCATGCATCATCAGGAGTACGGATAAAATGCTTGATGGTCGGAAGAG
GCATAAATTCCGTCAGCCAGTTTAGTCTGACCATCTCATCTGTAACATCATTGGCAACGC
TACCTTTGCCATGTTTCAGAAACAACTCTGGCGCATCGGGCTTCCCATACAATCGATAGA
TTGTCGCACCTGATTGCCCGACATTATCGCGAGCCCATTTATACCCATATAAATCAGCAT
CCATGTTGGAATTTAATCGCGGCCTTGAGCAAGACGTTTCCCGTTGAATATGGCTCATAC
TCTTCCTTTTTCAATATTATTGAAGCATTTATCAGGGTTATTGTCTCATGAGCGGATACA
TATTTGAATGTATTTAGAAAAATAAACAAATAGGGGTTCCGCGCACATTTCCCCGAAAAG
TGCCAC

FIGURE 23

HIV-1 C06980v0c22 gp145 codon optimized nucleic acid seq. (SEQ ID NO: 20):

GTGGGCAAGGCCATCTACGCCAGCCCAATCGCCGGCAACATCACCTGCCGGTCCAACATC

ACCGGCCTGCTGCTGACCAGGGACGGCGGCGACACCAACGACACCGAGATCTTCAGGCCA

GCCGGCGGAGACATGAGGGACAACTGGCGGAGCGAGCTGTACAAGTACAAGATCGTGGAG

ATCAAGCCCCTGGGCGTGGCTCCAACCGAGGCCAAGAGCAGGGTGGTGAAGAGCGAGAAG

AGCGCCGTCACCATCGGCGCCGTGTTTCTGGGCTTCCTGGGAGCCGCCGGAAGCACCATG

GGAGCCGCCTCCATCACCCTGACCGTGCAGGCCAGGCAGCTGCTGTCCGGGATCGTGCAG

CAGCAGAGCAACCTGCTGAGAGCCATTGAGGCTCAGCAGCACATGCTGCAGCTGACAGTG

TGGGGCATCAAGCAGCTGCAGGCCAGAGTGCTGGCCATCGAGAGATACCTGAAGGATCAG

CAGCTGCTCGGCATCTGGGGCTGCAGCGGCAAGCTGATCTGCACCACCGCCGTGCCCTGG

AACAACTCCTGGTCCAACAGGACCCAGGACGAGATCTGGAAGAACCTGACCTGGATGGAG

TGGGACAGAGAGATCAGCAACTACACCAACACCATCTACGAGCTGCTGGAGGTGTCCCAG

AGCCAGCAGGAGAGGAACGAGAAGGACCTGCTGGCCCTGGATAGCTGGAACAACCTGTGG

AACTGGTTCGACATCAGCAACTGGCTGTGGTACATCAAGAAGAAGAAGTGA

FIGURE 24

HIV-1 C06980v0c22 gp145 protein (SEQ ID NO: 32):

tPa signal is highlighted

MDAMKRGLCCVLLLCGAVFVTTTEAS NLWVTVYYGVPVWREAKTTLFCASDAKAYEREVH

NVWATHACVPTDPDPQEIFLGKNVTEKFNMWKNYMVDQMHEDIISLWDQSLQPCVKLTPL

CITLNCTDVTAHNGSTVYDNNATVVNSTNEIKNCSFNITTELRDKRKKEHALFNNLDIVQ

LDGNSSLYRLINCNTSIIKQACPKISFDPIPIHYCAPAGFVILKCNNETFNGTGPCNNVS

AVQCTHGIKPVVSTQLLLNGSLAKGEIMIRSENITDNVKTIIVHLNNSVEIVCTRPNNNT

RKSIRIGPGQTFYATGDIIGDIRQAYCSINESNWNATLQRVSKKLAEHFPNKTIQFKSPS

GGDLEITMHSFNCRGEFFYCNTSKLFNGTYYPNGTYYPNGTNSTLIIPCRIKQIINMWQG

VGKAIYASPIAGNITCRSNITGLLLTRDGGDTNDTEIFRPAGGDMRDNWRSELYKYKIVE

IKPLGVAPTEAKSRVVKSEKSAVTIGAVFLGFLGAAGSTMGAASITLTVQARQLLSGIVQ

QQSNLLRAIEAQQHMLQLTVWGIKQLQARVLAIERYLKDQQLLGIWGCSGKLICTTAVPW

NNSWSNRTQDEIWKNLTWMEWDREISNYTNTIYELLEVSQSQQERNEKDLLALDSWNNLW

NWFDISNWLWYIKKKK

FIGURE 25

(A) tPa signal (SEQ ID NOS: 33 and 21)

Highlighted regions are from the Nhe1 cloning site. This is not part of a native tPa gene, but is incorporated for cloning purposes. Cleavage occurs between the A and S.

Nucleic acid

ATGGATGCAATGAAGAGAGGGCTCTGCTGTGTGCTGCTGCTGTGTGGAGCAGTCTTCGTT TCG GCTAGC (SEQ ID NO: 33)

Protein

MDAMKRGLCCVLLLCGAVFVS AS (SEQ ID NO: 21)

(B) tPa signal (SEQ ID NOS: 34 and 22)

Highlighted regions are from the Nhe1 cloning site. This is not part of a native tPa gene, but is incorporated for cloning purposes. Cleavage occurs between the A and S.

Nucleic acid

ATGGATGCAATGAAGAGAGGGCTCTGCTGTGTGCTGCTGCTGTGTGGAGCAGTCTTCGTT ACTACCACAGAG GCTAGC (SEQ ID NO: 34)

Protein

MDAMKRGLCCVLLLCGAVFVTTTE AS (SEQ ID NO: 22)

FIGURE 35

```
C3728v2c6 WT      SNLWVTVYYGVPVWKEAKTTLFCASDAKAYEKEVHNVWATHACVPTDPNP
C3728v2c6 DC      SNLWVTVYYGVPVWKEAKTTLFCASDAKAYEKEVHNVWATHACVPTDPNP
C06838v1c48 WT    SNLWVTVYYGVPVWREAKTTLFCASDAKAYEKEVHNVWATHACVPTDPDP
C06838v1C48 DC    SNLWVTVYYGVPVWREAKTTLFCASDAKAYEKEVHNVWATHACVPTDPDP
C06980v1c3 WT     SNLWVTVYYGVPVWREAKTTLFCASDAKAYEREVHNVWATHACVPTDPDP
C06980v1c3 DC     SNLWVTVYYGVPVWREAKTTLFCASDAKAYEREVHNVWATHACVPTDPDP
C06980v0c22 WT    SNLWVTVYYGVPVWREAKTTLFCASDAKAYEREVHNVWATHACVPTDPDP
C06980v0c22 DC    SNLWVTVYYGVPVWREAKTTLFCASDAKAYEREVHNVWATHACVPTDPDP

C3728v2c6 WT      QEMEL-PNVTENFNMWKNDMVDQMHEDIISLWDQSLKPCVKLTPLCVTLN
C3728v2c6 DC      QEMEL-PNVTENFNMWKNDMVDQMHEDIISLWDQSLKPCVKLTPLCVTLN
C06838v1c48 WT    QEMVL-KNVTENFNMWKNDMVEQMHEDIISLWDQSLKPCVKLTPLCVTLT
C06838v1C48 DC    QEMVL-KNVTENFNMWKNDMVEQMHEDIISLWDQSLKPCVKLTPLCVTLT
C06980v1c3 WT     QEIFLGKNVTEKFNMWENYMVDQMHEDIISLWDQSLQPCVKLTPLCITLN
C06980v1c3 DC     QEIFLGKNVTEKFNMWENYMVDQMHEDIISLWDQSLQPCVKLTPLCITLN
C06980v0c22 WT    QEIFLGKNVTEKFNMWKNYMVDQMHEDIISLWDQSLQPCVKLTPLCITLN
C06980v0c22 DC    QEIFLGKNVTEKFNMWKNYMVDQMHEDIISLWDQSLQPCVKLTPLCITLN

C3728v2c6 WT      CNKVNNN------RSID-NNSTEEEMKNCTFNTTTEIRDKKRTQQALFYK
C3728v2c6 DC      CNKVNNN------RSID-NNSTEEEMKNCTFNTTTEIRDKKRTQQALFYK
C06838v1c48 WT    CTNVNAT------DNVTYKEKMEGEIKNCSFNITTEIRDKKRKVHALFYR
C06838v1C48 DC    CTNVNAT------DNVTYKEKMEGEIKNCSFNITTEIRDKKRKVHALFYR
C06980v1c3 WT     CTDFTAHNGSTVYDNNATA-NSTNEIKNCSFNIISELRDKRKKENALFNN
C06980v1c3 DC     CTDFTAHNGSTVYDNNATA-NSTNEIKNCSFNIISELRDKRKKENALFNN
C06980v0c22 WT    CTDVTAHNGSTVYDNNATVVNSTNEIKNCSFNITTELRDKRKKEHALFNN
C06980v0c22 DC    CTDVTAHNGSTVYDNNATVVNSTNEIKNCSFNITTELRDKRKKEHALFNN

C3728v2c6 WT      LDIVPLGNSNESYRLINCNTSTLTQACPKVTFDPIPIHYCAPAGYAILKC
C3728v2c6 DC      LDIVPLGNSNESYRLINCNTSTLTQACPKVTFDPIPIHYCAPAGYAILKC
C06838v1c48 WT    LDVVQLNNSNE-YILINCNTSAITQACPKVSFDPIPIHYCAPAGYAILKC
C06838v1C48 DC    LDVVQLNNSNE-YILINCNTSAITQACPKVSFDPIPIHYCAPAGYAILKC
C06980v1c3 WT     LDIVQLDGNSSLYRLINCNTSIIKQACPKISFDPIPIHYCAPAGFVILTC
C06980v1c3 DC     LDIVQLDGNSSLYRLINCNTSIIKQACPKISFDPIPIHYCAPAGFVILTC
C06980v0c22 WT    LDIVQLDGNSSLYRLINCNTSIIKQACPKISFDPIPIHYCAPAGFVILKC
C06980v0c22 DC    LDIVQLDGNSSLYRLINCNTSIIKQACPKISFDPIPIHYCAPAGFVILKC

C3728v2c6 WT      KDEKFNGTGPCNNVSTVQCTHGIKPVVSTQLLLNGSLAEKDIIIRSENLT
C3728v2c6 DC      KDEKFNGTGPCNNVSTVQCTHGIKPVVSTQLLLNGSLAEKDIIIRSENLT
C06838v1c48 WT    NDKPFNGTGPCHNVSTVQCTHGIKPVISTQLLLNGSLAEKEVIIRFENLT
C06838v1C48 DC    NDKPFNGTGPCHNVSTVQCTHGIKPVISTQLLLNGSLAEKEVIIRFENLT
C06980v1c3 WT     NNETFNGTGPCNNVSAVQCTHGIKPVVSTQLLLNGSLAKGEIMIRSENIT
C06980v1c3 DC     NNETFNGTGPCNNVSAVQCTHGIKPVVSTQLLLNGSLAKGEIMIRSENIT
C06980v0c22 WT    NNETFNGTGPCNNVSAVQCTHGIKPVVSTQLLLNGSLAKGEIMIRSENIT
C06980v0c22 DC    NNETFNGTGPCNNVSAVQCTHGIKPVVSTQLLLNGSLAKGEIMIRSENIT

C3728v2c6 WT      NNVKTIMVHLNESVEINCTRPNNNTRKSIRIGPGQTFYATGGIIGNIRQA
C3728v2c6 DC      NNVKTIMVHLNESVEINCTRPNNNTRKSIRIGPGQTFYATGGIIGNIRQA
C06838v1c48 WT    DNAKTIIVQLNQSIEIKCIRPNNNTRESIRIGPGQAFYATRDIIGDIRRA
C06838v1C48 DC    DNAKTIIVQLNQSIEIKCIRPNNNTRESIRIGPGQAFYATRDIIGDIRRA
C06980v1c3 WT     NNVKTIIVHFNKSVEIVCTRPNNNTRKSIRIGPGQTFYATGDIIGDIRQA
C06980v1c3 DC     NNVKTIIVHFNKSVEIVCTRPNNNTRKSIRIGPGQTFYATGDIIGDIRQA
C06980v0c22 WT    DNVKTIIVHLNNSVEIVCTRPNNNTRKSIRIGPGQTFYATGDIIGDIRQA
C06980v0c22 DC    DNVKTIIVHLNNSVEIVCTRPNNNTRKSIRIGPGQTFYATGDIIGDIRQA
```

FIGURE 35 (cont.-1)

```
C3728v2c6 WT        YCTISKNKWNTTLERVATKLKEYFKNTTIQFAPHSGGDLEITTHSFNCRG
C3728v2c6 DC        YCTISKNKWNTTLERVATKLKEYFKNTTIQFAPHSGGDLEITTHSFNCRG
C06838v1c48 WT      YCTIETERWKETLGNVTEKLKEYFPNTNISFAPSSGGDLEITTHSFNCRG
C06838v1C48 DC      YCTIETERWKETLGNVTEKLKEYFPNTNISFAPSSGGDLEITTHSFNCRG
C06980v1c3 WT       YCSINESNWNITLQRVSKKLAEHFPNRTIQFESPSGGDLEITMHSFNCRG
C06980v1c3 DC       YCSINESNWNITLQRVSKKLAEHFPNRTIQFESPSGGDLEITMHSFNCRG
C06980v0c22 WT      YCSINESNWNATLQRVSKKLAEHFPNKTIQFKSPSGGDLEITMHSFNCRG
C06980v0c22 DC      YCSINESNWNATLQRVSKKLAEHFPNKTIQFKSPSGGDLEITMHSFNCRG

C3728v2c6 WT        EFFYCNTSQLFNGT--STGFSNKSTGNETFTLPCRIKQIINMWQEVGRAM
C3728v2c6 DC        EFFYCNTSQLFNGT--STGFSNKSTGNETFTLPCRIKQIINMWQEVGRAM
C06838v1c48 WT      EFFYRNTSKLFN--------NNDTENNLTITLPCRIKQIVNMWQGVGRAM
C06838v1C48 DC      EFFYRNTSKLFN--------NNDTENNLTITLPCRIKQIVNMWQGVGRAM
C06980v1c3 WT       EFFYCNTSKLFKSTYHPNGTYNLNGTNSTLIIPCRIKQIINMWQGVGKAI
C06980v1c3 DC       EFFYCNTSKLFKSTYHPNGTYNLNGTNSTLIIPCRIKQIINMWQGVGKAI
C06980v0c22 WT      EFFYCNTSKLFNGTYYPNGTYYPNGTNSTLIIPCRIKQIINMWQGVGKAI
C06980v0c22 DC      EFFYCNTSKLFNGTYYPNGTYYPNGTNSTLIIPCRIKQIINMWQGVGKAI

C3728v2c6 WT        YAPPIAGNITCVSNITGLLLTRDGGDNNTRTETFRPGGGDMRDNWRSELY
C3728v2c6 DC        YAPPIAGNITCVSNITGLLLTRDGGDNNTRTETFRPGGGDMRDNWRSELY
C06838v1c48 WT      YAPPIEGNITCKSNITGLLLTRDGGNGTERNETFRPGGGDMRNNWRSELY
C06838v1C48 DC      YAPPIEGNITCKSNITGLLLTRDGGNGTERNETFRPGGGDMRNNWRSELY
C06980v1c3 WT       YASPIAGSITCRSNITGLLLTRDGGDTND-TEIFRPTGGDMRDNWRSELY
C06980v1c3 DC       YASPIAGSITCRSNITGLLLTRDGGDTND-TEIFRPTGGDMRDNWRSELY
C06980v0c22 WT      YASPIAGNITCRSNITGLLLTRDGGDTND-TEIFRPAGGDMRDNWRSELY
C06980v0c22 DC      YASPIAGNITCRSNITGLLLTRDGGDTND-TEIFRPAGGDMRDNWRSELY

C3728v2c6 WT        KYKVVEVKPLGVAPSEARRRVVEREKRAVGLGAVFLGFLGAAGSTMGAAS
C3728v2c6 DC        KYKVVEVKPLGVAPSEARSRVVEREKSAVGLGAVFLGFLGAAGSTMGAAS
C06838v1c48 WT      KYKVVEIKPLGIAPTGAKRRVVEREKRAVGMGAVFLGFLGAAGSTMGAAS
C06838v1C48 DC      KYKVVEIKPLGIAPTGAKSRVVEREKSAVGMGAVFLGFLGAAGSTMGAAS
C06980v1c3 WT       KYKIVEIKPLGVAPTEAKRRVVKREKRAVTIGAVFLGFLGAAGSTMGAAS
C06980v1c3 DC       KYKIVEIKPLGVAPTEAKSRVVKSEKSAVTIGAVFLGFLGAAGSTMGAAS
C06980v0c22 WT      KYKIVEIKPLGVAPTEAKRRVVKREKRAVTIGAVFLGFLGAAGSTMGAAS
C06980v0c22 DC      KYKIVEIKPLGVAPTEAKSRVVKSEKSAVTIGAVFLGFLGAAGSTMGAAS

C3728v2c6 WT        ITLTVQARQLLSGIVQQQSNLLRAIEAQQHMLQLTVWGIKQLQTKVLAIE
C3728v2c6 DC        ITLTVQARQLLSGIVQQQSNLLRAIEAQQHMLQLTVWGIKQLQTKVLAIE
C06838v1c48 WT      LTLTVQARQVLSGIVQQQSNLLRAIEAQQHMLQLTVWGIKQLQTRVLAIE
C06838v1C48 DC      LTLTVQARQVLSGIVQQQSNLLRAIEAQQHMLQLTVWGIKQLQTRVLAIE
C06980v1c3 WT       ITLTVQARQLLSGIVQQQSNLLRAIEAQQHMLQLAVWGIKQLQARVLAIE
C06980v1c3 DC       ITLTVQARQLLSGIVQQQSNLLRAIEAQQHMLQLAVWGIKQLQARVLAIE
C06980v0c22 WT      ITLTVQARQLLSGIVQQQSNLLRAIEAQQHMLQLTVWGIKQLQARVLAIE
C06980v0c22 DC      ITLTVQARQLLSGIVQQQSNLLRAIEAQQHMLQLTVWGIKQLQARVLAIE

C3728v2c6 WT        RYLQDQQLLGIWGCSGKLICTTNVPWNSSWSNKSLKAIWDNMTWMQWDRE
C3728v2c6 DC        RYLQDQQLLGIWGCSGKLICTTNVPWNSSWSNKSLKAIWDNMTWMQWDRE
C06838v1c48 WT      RYLKDQQLLGLWGCSGKLICTTAVPWNSSWSNKSEIDIWNNMTWMQWDRE
C06838v1C48 DC      RYLKDQQLLGLWGCSGKLICTTAVPWNSSWSNKSEIDIWNNMTWMQWDRE
C06980v1c3 WT       RYLKDQQLLGIWGCSGKLICTTAVPWNNSWSNRTQDEIWKNLTWMEWDRE
C06980v1c3 DC       RYLKDQQLLGIWGCSGKLICTTAVPWNNSWSNRTQDEIWKNLTWMEWDRE
C06980v0c22 WT      RYLKDQQLLGIWGCSGKLICTTAVPWNNSWSNRTQDEIWKNLTWMEWDRE
C06980v0c22 DC      RYLKDQQLLGIWGCSGKLICTTAVPWNNSWSNRTQDEIWKNLTWMEWDRE
```

FIGURE 35 (cont.-2)

```
C3728v2c6 WT        ISNYTNTIYRLLEDSHIQQEKNEKDLLALNSWNNLWSWFNITNWLWYIRI
C3728v2c6 DC        ISNYTNTIYRLLEDSHIQQEKNEKDLLALNSWNNLWSWFNITNWLWYIRI
C06838v1c48 WT      ISNYTNTIYRLLEDSQTQQEKNEKDLLALDSWKNLWNWFNITKWLWYIKI
C06838v1C48 DC      ISNYTNTIYRLLEDSQTQQEKNEKDLLALDSWKNLWNWFNITKWLWYIKI
C06980v1c3 WT       ISNYTNTIYELLEVSQSQQERNEKDLLALDSWNNLWNWFDISNWLWYIKI
C06980v1c3 DC       ISNYTNTIYELLEVSQSQQERNEKDLLALDSWNNLWNWFDISNWLWYIKI
C06980v0c22 WT      ISNYTNTIYELLEVSQSQQERNEKDLLALDSWNNLWNWFDISNWLWYIKI
C06980v0c22 DC      ISNYTNTIYELLEVSQSQQERNEKDLLALDSWNNLWNWFDISNWLWYIKI

C3728v2c6 WT        FIMIVGGLIGLRIIFAILSIVNRVRQGYSPLSFQTLTPNQRGPDRLGRIE
C3728v2c6 DC        FIMIVGGLIGLRIIFAILSIVNRVRQGYSPLSFQTLTPNQRGPDRLGRIE
C06838v1c48 WT      FIIIVGGLIGLRIIFAVLSIVNRVRQGYSPLSFQTLIPSPRGPDKLGRIE
C06838v1C48 DC      FIIIVGGLIGLRIIFAVLSIVNRVRQGYSPLSFQTLIPSPRGPDKLGRIE
C06980v1c3 WT       FIMIVGGLIGLRIIFAVLSIVNRVRQGYSPLSFQTLIPNQREPDRPGRIE
C06980v1c3 DC       FIMIVGGLIGLRIIFAVLSIVNRVRQGYSPLSFQTLIPNQREPDRPGRIE
C06980v0c22 WT      FIMIVGGLIGLRIIFAVLSIVNRVRQGYSPLSFQTLIPNQREPDRPGRIE
C06980v0c22 DC      FIMIVGGLIGLRIIFAVLSIVNRVRQGYSPLSFQTLIPNQREPDRPGRIE

C3728v2c6 WT        EEGGEQDKDRSIRLVNGFLALAWDDLRSLCLFSYHRLRDFILIATRAVEL
C3728v2c6 DC        EEGGEQDKDRSIRLVNGFLALAWDDLRSLCLFSYHRLRDFILIATRAVEL
C06838v1c48 WT      EEGGEQDKGRSVRLVNGFLALAWDDLRSLCLFSYHQLRDFILIVARAVGL
C06838v1C48 DC      EEGGEQDKGRSVRLVNGFLALAWDDLRSLCLFSYHQLRDFILIVARAVGL
C06980v1c3 WT       EEGGEQDKDRSIRLVSGFLALAWDDLRSLCIFLYHHLRDLILIAARATEL
C06980v1c3 DC       EEGGEQDKDRSIRLVSGFLALAWDDLRSLCIFLYHHLRDLILIAARATEL
C06980v0c22 WT      EEGGEQDKDRSIRLVSGFLALAWDDLRSLCIFLYHHLRDFILIAARATEL
C06980v0c22 DC      EEGGEQDKDRSIRLVSGFLALAWDDLRSLCIFLYHHLRDFILIAARATEL

C3728v2c6 WT        LGHSSLRGLQRGWEALKYLGSLGQYWGQELKKSAIRLLDITAIAVAEGTD
C3728v2c6 DC        LGHSSLRGLQRGWEALKYLGSLGQYWGQELKKSAIRLLDITAIAVAEGTD
C06838v1c48 WT      LGRSSLRGLQRGWEILKYLGGLVQYWGLELKKSAVSLFDTIAIAVTEGTD
C06838v1C48 DC      LGRSSLRGLQRGWEILKYLGGLVQYWGLELKKSAVSLFDTIAIAVTEGTD
C06980v1c3 WT       LGRSSLRGLQRGWEALKYLGSLVQYWGLEIKKSAINLLDTIAIAVAEGTD
C06980v1c3 DC       LGRSSLRGLQRGWEALKYLGSLVQYWGLEIKKSAINLLDTIAIAVAEGTD
C06980v0c22 WT      LGRSSLRGLQRGWEALKYLGSLVQYWGLEIKKSAINLLDTIAIAVAEGTD
C06980v0c22 DC      LGRSSLRGLQRGWEALKYLGSLVQYWGLEIKKSAINLLDTIAIAVAEGTD

C3728v2c6 WT        RIIEFIQRICRAIHNVPNRIRQGFEAALL*    (SEQ ID NO. 35)
C3728v2c6 DC        RIIEFIQRICRAIHNVPNRIRQGFEAALL*    (SEQ ID NO. 36)
C06838v1c48 WT      RIIELIQRSCRAIRNVPTRIRQGFEAALQ*    (SEQ ID NO. 37)
C06838v1C48 DC      RIIELIQRSCRAIRNVPTRIRQGFEAALQ*    (SEQ ID NO. 38)
C06980v1c3 WT       RIIEIVQRACRAVLNILRRIRQGLEAALQ*    (SEQ ID NO. 39)
C06980v1c3 DC       RIIEIVQRACRAVLNILRRIRQGLEAALQ*    (SEQ ID NO. 40)
C06980v0c22 WT      RIIEIVQRACRAVLNIPRRIRQGLEAALQ*    (SEQ ID NO. 41)
C06980v0c22 DC      RIIEIVQRACRAVLNIPRRIRQGLEAALQ*    (SEQ ID NO. 42)
```

FIGURE 36

C06980v0c22 gp145 amino acid sequence (SEQ ID NO: 32):

```
  1   mdamkrglcc vlllcgavfv tttea snlwv tvyygvpvwr eakttlfcas dakayerevh
              t-Pa Signal 61   nvwathacvp tdpdpqeifl gknvtekfnm wknymvdqmh ediislwdqs lqpcvkltpl 121   citlnctdvt ahngstvydn natvvnstne ikncsfnitt elrdkrkkeh alfnnldivq 181   ldgnsslyrl incntsiikq acpkisfdpi pihycapagf vilkcnnetf ngtgpcnnvs 241   avqcthgikp vvstqlllng slakgeimir senitdnvkt iivhlnnsve ivctrpnnnt 301   rksirigpgq tfyatgdiig dirqaycsin esnwnatlqr vskklaehfp nktiqfksps 361   ggdleitmhs fncrgeffyc ntsklfngty ypngtyypng tnstliipcr ikqiinmwqg 421   vgkaiyaspi agnitcrsni tglllltrdgg dtndteifrp aggdmrdnwr selykykive 481   ikplgvapte ak srvvk sek s avtigavfl gflgaagstm gaasitltvq arqllsgivq
                    Cleavage site R to S mutation
541   qqsnllraie aqqhmlqltv wgikqlqarv laieryl kdq qllgiwgcsg klicttavpw 601   nnswsnrtqd eiwknltwme wdreisnytn tiyellevsq sqqernekdl laldswnnlw 661   nwfdisnwlw yik kkk
                  Triple lysine
```

FIGURE 37

C06980v0c22 gp145 nucleotide sequence (SEQ ID NO: 20) and translation (SEQ ID NO: 32):

```
  1   atggatgcaa tgaagagagg gctctgctgt gtgctgctgc tgtgtggagc agtcttcgtt
      >>........................t-Pa leader..........................>
        m  d  a  m  k  r  g  l  c  c  v  l  l  l  c  g  a  v  f  v NheI
                    -+----
 61   actaccacag aggctagcaa cctgtgggtg accgtgtact acggcgtgcc cgtgtggaga
      >...t-Pa leader..>>
        t  t  t  e  a  s
                        >>......................gp145.....................>
                            s  n  l  w  v  t  v  y  y  g  v  p  v  w  r 121   gaggccaaga ccaccctgtt ctgcgccagc gacgccaagg cctacgagcg ggaggtgcac
      >............................gp145.............................>
        e  a  k  t  t  l  f  c  a  s  d  a  k  a  y  e  r  e  v  h 181   aacgtgtggg ccacccacgc ctgcgtgccc accgacccg accctcagga aatcttcctg
      >............................gp145.............................>
        n  v  w  a  t  h  a  c  v  p  t  d  p  d  p  q  e  i  f  l 241   ggcaagaacg tgaccgagaa gttcaacatg tggaagaact acatggtgga ccagatgcac
      >............................gp145.............................>
        g  k  n  v  t  e  k  f  n  m  w  k  n  y  m  v  d  q  m  h 301   gaggacatca tcagcctgtg ggaccagagc ctgcagccct gcgtgaagct gacccccctg
      >............................gp145.............................>
        e  d  i  i  s  l  w  d  q  s  l  q  p  c  v  k  l  t  p  l 361   tgcatcaccc tgaactgcac cgacgtgacc gcccacaacg gcagcaccgt gtacgacaac
      >............................gp145.............................>
        c  i  t  l  n  c  t  d  v  t  a  h  n  g  s  t  v  y  d  n 421   aacgccaccg tggtgaacag caccaacgag atcaagaact gcagcttcaa catcaccacc
      >............................gp145.............................>
        n  a  t  v  v  n  s  t  n  e  i  k  n  c  s  f  n  i  t  t 481   gagctgaggg acaagaggaa gaaggagcac gccctgttca acaacctgga catcgtgcag
      >............................gp145.............................>
        e  l  r  d  k  r  k  k  e  h  a  l  f  n  n  l  d  i  v  q 541   ctggacggca acagctccct gtacagactg atcaactgca acaccagcat catcaagcag
      >............................gp145.............................>
        l  d  g  n  s  s  l  y  r  l  i  n  c  n  t  s  i  i  k  q 601   gcctgcccca agatcagctt cgacccatc cccatccact actgcgcccc agccggcttc
      >............................gp145.............................>
        a  c  p  k  i  s  f  d  p  i  p  i  h  y  c  a  p  a  g  f 661   gtgatcctga agtgcaacaa cgagacattc aacggcaccg gcccctgtaa caacgtgtcc
      >............................gp145.............................>
        v  i  l  k  c  n  n  e  t  f  n  g  t  g  p  c  n  n  v  s
```

FIGURE 37 (cont.-1)

```
 721   gctgtgcagt gcacccacgg catcaagccc gtggtgtcca cccagctgct gctgaacggc
       >..................gp145..................>
         a  v  q  c  t  h  g  i  k  p  v  v  s  t  q  l  l  l  n  g 781   agcctggcca agggcgagat catgatcaga agcgagaaca tcaccgacaa cgtgaagacc
       >..................gp145..................>
         s  l  a  k  g  e  i  m  i  r  s  e  n  i  t  d  n  v  k  t 841   atcatcgtgc acctgaacaa cagcgtggag atcgtgtgca ccaggcccaa caacaacacc
       >..................gp145..................>
         i  i  v  h  l  n  n  s  v  e  i  v  c  t  r  p  n  n  n  t 901   aggaagagca tcaggatcgg cccaggccag accttctacg ccaccggcga catcatcggc
       >..................gp145..................>
         r  k  s  i  r  i  g  p  g  q  t  f  y  a  t  g  d  i  i  g 961   gacatccggc aggcctactg cagcatcaac gagagcaact ggaacgccac cctgcagagg
       >..................gp145..................>
         d  i  r  q  a  y  c  s  i  n  e  s  n  w  n  a  t  l  q  r 1021   gtgtccaaga agctggccga gcacttcccc aacaagacca tccagttcaa gagcccctct
       >..................gp145..................>
         v  s  k  k  l  a  e  h  f  p  n  k  t  i  q  f  k  s  p  s 1081   ggcggcgacc tggagatcac catgcacagc ttcaactgca ggggcgagtt cttctactgc
       >..................gp145..................>
         g  g  d  l  e  i  t  m  h  s  f  n  c  r  g  e  f  f  y  c 1141   aacacatcca agctgtttaa cgggacctac tacccaaacg gcacatacta cccaaacggg
       >..................gp145..................>
         n  t  s  k  l  f  n  g  t  y  y  p  n  g  t  y  y  p  n  g 1201   accaacagca ccctgatcat cccatgcagg atcaagcaga tcatcaacat gtggcagggc
       >..................gp145..................>
         t  n  s  t  l  i  i  p  c  r  i  k  q  i  i  n  m  w  q  g 1261   gtgggcaagg ccatctacgc cagcccaatc gccggcaaca tcacctgccg gtccaacatc
       >..................gp145..................>
         v  g  k  a  i  y  a  s  p  i  a  g  n  i  t  c  r  s  n  i 1321   accggcctgc tgctgaccag ggacggcggc gacaccaacg acaccgagat cttcaggcca
       >..................gp145..................>
         t  g  l  l  l  t  r  d  g  g  d  t  n  d  t  e  i  f  r  p 1381   gccggcggag acatgaggga caactggcgg agcgagctgt acaagtacaa gatcgtggag
       >..................gp145..................>
         a  g  g  d  m  r  d  n  w  r  s  e  l  y  k  y  k  i  v  e 1441   atcaagcccc tgggcgtggc tccaaccgag gccaag agca gggtggtgaa g agc gagaag
       >..................gp145..................>
         i  k  p  l  g  v  a  p  t  e  a  k  s   r  v  v  k  s  e  k
                                                                    Cleavage site R to S mutations
1501   agc gccgtca ccatcggcgc cgtgtttctg ggcttcctgg gagccgccgg aagcaccatg
       >..................gp145..................>
         s  a  v  t  i  g  a  v  f  l  g  f  l  g  a  a  g  s  t  m
       Cleavage site R to S mutation
```

FIGURE 37 (cont.-2)

```
1561  ggagccgcct ccatcaccct gaccgtgcag gccaggcagc tgctgtccgg gatcgtgcag
      >............................gp145..............................>
        g   a   a   s   i   t   l   t   v   q   a   r   q   l   l   s   g   i   v   q 1621  cagcagagca acctgctgag agccattgag gctcagcagc acatgctgca gctgacagtg
      >............................gp145..............................>
        q   q   s   n   l   l   r   a   i   e   a   q   q   h   m   l   q   l   t   v 1681  tggggcatca agcagctgca ggccagagtg ctggccatcg agagatacct gaaggatcag
      >............................gp145..............................>
        w   g   i   k   q   l   q   a   r   v   l   a   i   e   r   y   l   k   d   q 1741  cagctgctcg gcatctgggg ctgcagcggc aagctgatct gcaccaccgc cgtgccctgg
      >............................gp145..............................>
        q   l   l   g   i   w   g   c   s   g   k   l   i   c   t   t   a   v   p   w 1801  aacaactcct ggtccaacag gacccaggac gagatctgga agaacctgac ctggatggag
      >............................gp145..............................>
        n   n   s   w   s   n   r   t   q   d   e   i   w   k   n   l   t   w   m   e 1861  tgggacagag agatcagcaa ctacaccaac accatctacg agctgctgga ggtgtcccag
      >............................gp145..............................>
        w   d   r   e   i   s   n   y   t   n   t   i   y   e   l   l   e   v   s   q 1921  agccagcagg agaggaacga gaaggacctg ctggccctgg atagctggaa caacctgtgg
      >............................gp145..............................>
        s   q   q   e   r   n   e   k   d   l   l   a   l   d   s   w   n   n   l   w EcoRI
                                                                       --+----
1981  aactggttcg acatcagcaa ctggctgtgg tacatcaaga agaagaagtg aattc
      >............................gp145..................>>
        n   w   f   d   i   s   n   w   l   w   y   i   k   k   k   k    -
                                                            Lysine terminus
```

FIGURE 39

| Envelope | Antigen | Clade | Year | Antigen Binding Titers (ug/ml) | | | | |
|---|---|---|---|---|---|---|---|---|
| | | | | 2F5 | 4E10 | 2G12 | b12 | VRC01 |
| C06980 | gp145 | C | 2008 | >25 | 1.0 | >25 | 20.0 | 0.01 |
| 57128 | gp140 | D | 1998 | >25 | >25 | 0.1 | 6.7 | >25 |
| A07412 | gp120 | D | 1999 | >25 | >25 | >25 | >25 | 0.1 |
| | gp140 | | | >25 | >25 | 22.9 | >25 | 4.3 |
| 57140 | gp120 | D | 1998 | >25 | >25 | 20.0 | >25 | 0.02 |
| | gp140 | | | >25 | >25 | >25 | >25 | 0.02 |

| |
|---|
| >25 |
| 10-25 |
| 2-10 |
| <2 |

FIGURE 40

| Clade/CoR. | Envelope | PV Neutralization Sensitivity (ug/ml) | | | | |
|---|---|---|---|---|---|---|
| | | 2F5 | 4E10 | 2G12 | b12 | VRC01 |
| C/R5 | C06980 | >25 | 4.7 | >25 | >25 | 0.7 |
| D/R5 | 57128 | >25 | 11.7 | 10.5 | 24.4 | >25 |
| D/R5 | A07412 | 1.4 | 2.2 | >25 | 3.0 | 0.3 |
| C/R5 | 20635-4 | >25 | 0.3 | >25 | 0.1 | NT |
| C/R5 | 93/MW/965 | >25 | 10.3 | >25 | 3.2 | NT |
| C/R5 | PBL 288 | >25 | 4.5 | >25 | >25 | NT |
| D/R5 | E13613M4 | 3.2 | 12.8 | >25 | 1.1 | NT |
| D/R5 | NKU3006 | 2.1 | 2.7 | >25 | >25 | NT |
| D/R5 | A03349M1 | >25 | 2.4 | >25 | 1.8 | NT |

| |
|---|
| >25 |
| 10-25 |
| 2-10 |
| <2 |

FIGURE 41

6 Groups of 4 New Zealand White females

| Group | Antigen | Adjuvant/Vehicle |
|---|---|---|
| 1 | gp145 | Alhydrogel |
| 2 | gp145 | Liposome formulation 1 containing lipid A, preformed and mixed with gp145 |
| 3 | gp145 | Liposome formulation 1 containing lipid A with encapsulated gp145 |
| 4 | gp145 | Liposome formulation 2 containing lipid A and PIP with encapsulated gp145 |
| 5 | None | Liposome formulation 1 containing lipid A |
| 6 | mper23, clade B | Liposome formulation 2 containing lipid A and PIP with encapsulated mper23 |

→ 25 ug dose at weeks 0, 4 and 8
→ Bleeds at weeks -2, 0, 4, 8, 10, 12 (terminal)
→ Binding titers of $10^4$-$10^5$ to:
  6980 gp145, CN54 gp140, ZA 1157 gp120

Geometric mean titers, all groups (SEM)

(C gp120 = ZA.1197MB, S Africa)

I.P. Western Blot of Protein-free media adapted CHO C06980v0c22 gp145 cell line

Lane
1. 4E10 Human anti-gp41
2. 2F5 Human anti-gp41
3. NHS
4. HIV-1(+) Plasma
5. Standards The gp145 is precipitated from the conditioned media using human antibodies, resolved on 4-15% SDS-PAGE, transferred to PVDF and detected using rabbit antisera to gp120 and gp160.

FIGURE 50

| Potential N-glycosylation sites |
|---|
| 29 |
| 31 |
| 29 |
| 28 |
| 28 |

% Sequence Identity:

| | ConC | C06980 | A07412 | 57140 | 57128 |
|---|---|---|---|---|---|
| ConC | 100 | NA | NA | NA | NA |
| C06980 | 82.9 | 100 | NA | NA | NA |
| A07412 | 77.2 | 71.4 | 100 | NA | NA |
| 57140 | 75.7 | 71 | 78.9 | 100 | NA |
| 57128 | 75.7 | 70.2 | 77.8 | 77.8 | 100 |

FIGURE 51

```
C06980  SNLWYTVYYGVPVWREAKTTLFCASDAKAYEREVHNVWATHACVPTDPDPQEIFLGKNVTEKFNMWKNYMVDQMHEDIISLWDQSLQ
ConC    G...........K.............................MV.E-....M......D....................X
A07412  -S...........K..T..........HKA.A..I.........N.R.MI..-....M......N..E............K
57140   -S...........K..T.........S.A.A..I..........N.R..K.E-....M......N..E............K
57128   -S...........K..T..........KA.A..I..........M....V..-....M......D..E........E...K

C06980  PCVKLTPLCITLNCTOVAHNGSTVYDNNATVVNSTHEIXNCSFNITTELRDKRKKEHALFNNLDIVQLDGN--------SSLYRLINC
ConC    ...........V......NN.TNATNST.N...................K..VY...YR.....P.NE........E....
A07412  ...........V......TYWNGTLQGNETKGKN---RSD.NT........I...K.Q.T....YK..V.P.EDKDSNKTTNYSS......
57140   ...........VI.D.N---NTHYVNASYVNAT.TEET.M..........--....KQ.V..F.DR..V.PI.K.------NKS......
57128   ...........V.......---NAKIEQNVTV.G------MR.....M....K..K.Q.Y...YK..V..I.NSST----NTD......

C06980  NTSIIKQACPKISFDPIPIHYCAFAGFVILKCNNETFNGTGPCNNVSAVQCTHGIKPVVSTQLLLNGSLAKGEIHIRSENITDHVKT
ConC    ...A.T.....V...........YA......K.............T................EE..I......L.N.A..
A07412  ...VVT.....VT.E...........A......K.........K..T.......R..............EE..I........N.A..
57140   ...A.T......T.E...........A....DKK..........K..T.......R..............EE..I......L.N.A..
57128   ...A.T......T.E..........YA......K....M...K..T.......R..............EE..V......L.N.A.I

C06980  IIVHLNNSVEIVCTRPNNNTRKSIRIGPGQTFYATGDIIGDIRQAYCSINESNWNATLQRVSXKLAEHFP-NKTIQPKSPSGGDLEI
ConC    ...........E.......................N.S.DK..K.............K......*.....K.EDS.......
A07412  ...Q..E...T.D.I............AL.T.-....N....H.NVSKVK.GRM.K..AE..KDLLNQT.N.T..PS....P..
57140   ...Q..E..P.T.I.......Q.THL...RALFT.-N.V......H.N.SGEK...K...Q.A...RGL.NGST.MI..PS....P.V
57128   ...Q..K....N.....S.....GVH.....AI.S..Q......K.H.N.SRKE..S...Q.T...GSL.N-TTK.I.NAS....P..

C06980  TMHSFNCRGEFFYCHTSKLFNGTYYPNGTY--------YPNGTNSTLIIPCRIKQIIDMWQGVGKAIYASPIAGNITCRSNITGLLLT
ConC    .T...........S..NN.------------TNS...ITK........K..R.N..PP........K........T
A07412  .T.....G.........G...SLLNEQ----------FNETS.D.ITLQ.................M..PP...P.S.S........T
57140   EH.....G.........G...NSVWS.D.SSSND---TSSSS...ITL........L..E....M..PP...I.K.S.........Q
57128   .T.....N.........AG..-STWHRTNSENINSKMTNKTEDVNITLQ........T.......M..PPVS.I.R.S.........T

C06980  RDGGDTND----TEIFRPAGGDMRDHNRSELYXYXIVEIKPLGVAPTEAXSRVVKSEKSAVTIGAVPLGFLGAAGSTMGAASITLTV
ConC    ....KK.T---.......G.................V...........K.......ER..R..G..................
A07412  ....N.GN---DS.....G.................V.R.E.M.L...R......ER....IGL..M...............L....
57140   ....NHDSRTNTN.....G.................V.RLE...I...R......ER....IGL..M...............SM....
57128   ....GADN-NRQN.....G.................V.R.E...I...K.R....ER....IGL..L......T...P...VSM....

C06980  QARQLLSGIVQQQSNLLRAIEAQQHMLQLTVWGIKQLQARVLAIERYLXDQQLLGIWGCSGKLICTTAVPWNNSWSNRTQOEIWKNL
ConC    ................................T...............................S....KS.ED..D.M
A07412  ............N........L...........M.S...............M....T....ST....SVE...N.M
57140   ...L.......N........L............V.S..R.............RH....S....S....KSL.K..N.M
57128   ....V.......N........L........I..V.S..............M....N....S....KSL.Y....M

C06980  TWMEMDREISHYTNTIYELLEVSQSQQERNEKDLLALDSWNNLWNMFDISHNNLWYIXXXX    (SEQ ID NO. 1)
ConC    ...Q......D...R..D..N...X.............K.......T.......        (SEQ ID NO. 2)
A07412  ...Q.E....E...GL..T.I.E..T...K..QE..Q..K.AS.....S.TK           (SEQ ID NO. 3)
57140   .....EK..E...GL..S.I.E...T......QE..Q..QMAS.....S...           (SEQ ID NO. 4)
57128   .....EK..D...EL..S.I....I...K..QE..K....AS.....S.TK            (SEQ ID NO. 5)
```

TRUNCATED HIV ENVELOPE PROTEINS (ENV), METHODS AND COMPOSITIONS RELATED THERETO

CROSS-REFERENCE TO RELATED APPLICATIONS

This application is the National Stage entry under U.S.C. § 371 of International Application No. PCT/US2012/035026, filed Apr. 25, 2012, which claims the benefit of priority under 35 U.S.C. § 119 of U.S. Provisional Application Ser. No. 61/478,857, filed Apr. 25, 2011, which is incorporated herein by reference in its entirety.

FEDERAL FUNDING

This invention was made with government support under Cooperative Agreement Number W81XWH-07-2-0067 awarded by the U.S. Army Medical Research and Materiel Command. The government has certain rights in the invention.

FIELD OF THE INVENTION

The invention relates generally to novel HIV envelope proteins and to methods and compositions related thereto. More particularly, the invention relates to methods and compositions for the preparation, production, and administration of isolated novel HIV envelope nucleic acid and protein sequences suitable, for example, in certain embodiments, as vaccines against HIV.

BACKGROUND OF THE INVENTION

AIDS, or Acquired Immunodeficiency Syndrome, is caused by human immunodeficiency virus (HIV) and is characterized by several clinical features including wasting syndromes, central nervous system degeneration and profound immunosuppression that results in opportunistic infections and malignancies. HIV is a member of the lentivirus family of animal retroviruses, which include the visna virus of sheep and the bovine, feline, and simian immunodeficiency viruses (SIV). Two closely related types of HIV, designated HIV-1 and HIV-2, have been identified thus far, of which HIV-1 is by far the most common cause of AIDS. However, HIV-2, which differs in genomic structure and antigenicity, causes a similar clinical syndrome.

The form of HIV-1 that dominates the global epidemic is called the major group of HIV-1. There are three HIV-1 groups, the major group (M group), the outlier group (O group), and the non-M/non-O group (N group). There is also the P group. The M group is further divided into nine distinct genetic subtypes, which are commonly referred to as clades and circulating recombinant forms (CRFs). HIV-1 M group subtypes/clades are labelled A, B, C, D, F, G, H, J, and K. Clade B is the most prevalent in the United States, while clade C is the most prevalent worldwide. CRF01_AE or former clade E and CRF02_AG are the most prevalent inter-subtype recombinant strains in the HIV-1 epidemic. Geographic distribution of genetic subtypes and inter-subtype recombinant forms is continually changing, and current data offers incomplete estimates.

An infectious HIV particle consists of two identical strands of RNA, each approximately 9.2 kb long, packaged within a core of viral proteins. This core structure is surrounded by a phospholipid bilayer envelope derived from the host cell membrane that also includes virally-encoded membrane proteins (Abbas et al., Cellular and Molecular Immunology, 4th edition, W.B. Saunders Company, 2000, p. 454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural proteins. The gag gene encodes structural proteins of the nucleocapsid core and matrix. The pol gene encodes reverse transcriptase (RT), integrase (IN), and viral protease (PR) enzymes required for viral replication. The tat gene encodes a protein that is required for elongation of viral transcripts. The rev gene encodes a protein that promotes the nuclear export of incompletely spliced or unspliced viral RNAs. The vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The env gene encodes the viral envelope glycoprotein that is translated as a 160-kilodalton (kDa) precursor (gp160) and cleaved by a cellular protease to yield the external 120-kDa envelope glycoprotein (gp120) and the transmembrane 41-kDa envelope glycoprotein (gp41), which are required for the infection of cells (Abbas et al., Cellular and Molecular Immunology, 4th edition, W.B. Saunders Company, 2000, pp. 454-456). gp140 is a modified form of the Env glycoprotein, which contains the external 120-kDa envelope glycoprotein portion and the extracellular part of the gp41 portion of Env and has characteristics of both gp120 and gp41. The nef gene is conserved among primate lentiviruses and is one of the first viral genes that is transcribed following infection. In vitro, several functions have been described, including downregulation of CD4 and MHC class I surface expression, altered T-cell signaling and activation, and enhanced viral infectivity.

HIV infection initiates with gp120 on the viral particle binding to the CD4 and chemokine receptor molecules (e.g., CXCR4, CCR5) on the cell membrane of target cells such as CD4$^+$ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp120 expressed on the surface of infected cells. In this case, the uninfected cells bind, via the CD4 receptor-gp120 interaction, to infected cells and fuse to form a syncytium, which cannot survive. Destruction of CD4$^+$ T-lymphocytes, which are important to immune defense, is a major cause of the progressive immune dysfunction that is the hallmark of AIDS disease progression. The loss of CD4$^+$ T cells seriously impairs the body's ability to fight most invaders, but it has a particularly severe impact on the defenses against viruses, fungi, parasites and certain bacteria, including mycobacteria.

Research on the Env glycoprotein has shown that the virus has many effective protective mechanisms with few vulnerabilities (Wyatt & Sodroski, Science. 1998 Jun. 19; 280(5371):1884-8). For fusion with its target cells, HIV-1 uses a trimeric Env complex containing gp120 and gp41 subunits (Burton et al., Nat. Immunol. 2004 March; 5(3):

233-6). The fusion potential of the Env complex is triggered by engagement of the CD4 receptor and a coreceptor, usually CCR5 or CXCR4. Neutralizing antibodies seem to work either by binding to the mature trimer on the virion surface and preventing initial receptor engagement events, or by binding after virion attachment and inhibiting the fusion process (Parren & Burton, Adv Immunol. 2001; 77:195-262). In the latter case, neutralizing antibodies may bind to epitopes whose exposure is enhanced or triggered by receptor binding. However, given the potential antiviral effects of neutralizing antibodies, it is not unexpected that HIV-1 has evolved multiple mechanisms to protect it from antibody binding (Johnson & Desrosiers, Annu Rev Med. 2002; 53:499-518).

Most experimental HIV-1 vaccines tested in human and/or non-human primate suggests that a successful vaccine will incorporate immunogens that elicit broad neutralizing antibodies (bNabs) and robust cell-mediated immunity. HIV-1 envelope glycoprotein (Env) is the main viral protein involved in the entry of the virus and is also the primary target for neutralizing antibodies, but due to immune evasion strategies and extreme sequence variability of Envs, generation of bNabs has been a daunting task (Phogat S, Wyatt R. Curr_Pharm Des. 2007, 13:213-27; Phogat S, et al. J Intern Med. 2007 262:26-43, Karlsson Hedestam G B, et al Nat Rev Microbiol. 2008, 6:143-55).

Developing effective vaccines to prevent HIV infection or neutralize HIV infection has been difficult. The ability to elicit broad and potent neutralizing antibodies is a major challenge in the development of an HIV-1 vaccine. It is a primary goal to develop an HIV vaccine that can effectively elicit specific anti-viral neutralizing antibodies as well as cell-mediated immune responses to prevent infection and control the spread of HIV, with a potential for considerable breadth of reactivity across genetic clades. The extraordinary degree of genetic diversity of HIV has been problematic for vaccine development.

Citation or identification of any document in this application is not an admission that such document is available as prior art to the present invention.

SUMMARY OF THE INVENTION

In certain embodiments, the instant application provides an isolated peptide comprising a truncated HIV Env protein, wherein the HIV Env protein is mutated in the native gp120/gp41 cleavage site to prevent protease cleavage, comprises the MPER of gp41, and is truncated prior to the transmembrane domain.

In some embodiments, the HIV Env protein comprises about 1-10 hydrophilic amino acids at its C-terminus. in certain embodiments, the about 1-10 hydrophilic amino acids are three lysines.

In some embodiments, the MPER of gp41 comprises the 4E10 epitope. In certain embodiments, the MPER of gp41 comprises the amino acid sequence: LWYIK (SEQ ID NO: 24) at its C-terminus. In further embodiments, the HIV Env protein comprises about 1-10 non-native hydrophilic amino acids C-terminal to and contiguous with the LWYIK (SEQ ID NO: 24) amino acid sequence. In certain embodiments, the HIV Env protein binds integrin $\alpha 4\beta 7$.

In some embodiments, the HIV Env protein is derived from an HIV-1 strain classified in a group selected the group consisting of: M, O, N, and P. In certain embodiments, the HIV-1 strain is isolated from an individual with an acute HIV-1 infection. In other embodiments, the HIV-1 strain is isolated from an individual with a chronic HIV-1 infection.

In certain embodiments, the HIV Env protein is derived from an HIV-1 group M strain. In further embodiments, the HIV-1 group M strain is a subtype (clade) selected from the group consisting of: A, B, C, D, F, G, H, J, and K. In a particular embodiment, the subtype (clade) is clade B. In another embodiment, the subtype (clade) is clade D. In yet another embodiment, the subtype (clade) is clade C.

In certain embodiments, the HIV Env protein comprises an amino acid sequence having 85% or greater identity to the amino acid sequence depicted in SEQ ID NO: 1. In further embodiments, the HIV Env protein comprises 90% or greater identity to the amino acid sequence depicted in SEQ ID NO: 1. In yet other embodiments, the peptide comprises an amino acid sequence having 95% or greater identity to the amino acid sequence depicted in SEQ ID NO: 1. In certain embodiments, the peptide comprises an amino acid sequence having 98% or greater identity to the amino acid sequence depicted in SEQ ID NO: 1. In other embodiments, the peptide comprises an amino acid sequence having 99% or greater identity to the amino acid sequence depicted in SEQ ID NO: 1. In a particular embodiment, the peptide comprises the amino acid sequence depicted in SEQ ID NO: 1.

In some embodiments, the application pertains to an isolated nucleic acid comprising a nucleic acid sequence encoding an amino acid sequence having 85%, 90%, 95%, 98%, 99%, or greater identity to the amino acid sequence depicted in SEQ ID NO: 1. In certain embodiments, the nucleic acid sequence encodes the amino acid sequence depicted in SEQ ID NO: 1. In a particular embodiment, the isolated nucleic acid comprises the nucleic acid sequence depicted in SEQ ID NO: 20.

In yet other embodiments, the instant application pertains to a vector comprising nucleic acid encoding an amino acid sequence having 85%, 90%, 95%, 98%, 99%, or greater identity to the amino acid sequence depicted in SEQ ID NO: 1. In certain embodiments, the application relates to a host cell comprising the vector comprising nucleic acid encoding an amino acid sequence having 85%, 90%, 95%, 98%, 99%, or greater identity to the amino acid sequence depicted in SEQ ID NO: 1. In a particular embodiment, the host cell is a CHO cell.

In yet other embodiments, the instant application relates to a method of making a peptide comprising an amino acid sequence having at least 85% or greater identity to the amino acid sequence depicted in SEQ ID NO: 1, comprising culturing a host cell comprising a vector comprising nucleic acid encoding an amino acid sequence having 85%, 90%, 95%, 98%, 99%, or greater identity to the amino acid sequence depicted in SEQ ID NO: 1 under conditions suitable for protein expression and isolating the peptide.

In certain embodiments, the instant application provides a composition comprising an isolated HIV Env protein, such as an isolated HIV Env protein comprising an amino acid sequence having 85%, 90%, 95%, 98%, 99%, or greater identity to the amino acid sequence depicted in SEQ ID NO: 1 and pharmaceutically acceptable carrier.

In yet other embodiments, the instant application relates to a method of generating antibodies against HIV in a mammal, comprising administering to the mammal a composition comprising an isolated HIV Env protein, such as an isolated HIV Env protein comprising an amino acid sequence having 85%, 90%, 95%, 98%, 99%, or greater identity to the amino acid sequence depicted in SEQ ID NO: 1 and a pharmaceutically acceptable carrier. In certain embodiments, the composition further comprises an adjuvant. In certain embodiments, the adjuvant comprises a liposome formulation. In further embodiments, the liposome formulation comprises one or more of: dimyristoyl phosphatidylcholine, dimyristoyl phosphatidylglycerol, cholesterol, and phospholipid. In a particular embodiment, the liposome formulation comprises phospholipid A. In certain embodiments, the antibodies generated in the mammal are antibodies that compete with the peptide comprising the truncated HIV Env protein for binding integrin α4β7.

In some embodiments, the instant application relates to a method of conferring immunity against HIV in a mammal, comprising administering to the mammal a composition comprising an isolated HIV Env protein, such as an isolated HIV Env protein comprising an amino acid sequence having 85%, 90%, 95%, 98%, 99%, or greater identity to the amino acid sequence depicted in SEQ ID NO: 1 and a pharmaceutically acceptable carrier. In certain embodiments, the composition further comprises an adjuvant. In certain embodiments, the adjuvant comprises a liposome formulation. In further embodiments, the liposome formulation comprises one or more of: dimyristoyl phosphatidylcholine, dimyristoyl phosphatidylglycerol, cholesterol, and phospholipid. In a particular embodiment, the liposome formulation comprises phospholipid A. In further embodiments, the method comprises administering the composition to the mammal by injection.

Examples of mammals to which the compositions of the invention can be administered include human, non-human primates, dogs, rabbits, guinea pigs, and mice.

In yet other embodiments, the instant application relates to a subunit vaccine comprising an HIV Env protein of the invention, such as an isolated peptide comprising a truncated HIV Env protein, wherein the HIV Env protein is mutated in the native gp120/gp41 cleavage site to prevent protease cleavage, comprises the MPER of gp41, and is truncated prior to the transmembrane domain. In some embodiments, the HIV Env protein comprises about 1-10 hydrophilic amino acids at its C-terminus. In certain embodiments, the about 1-10 hydrophilic amino acids are three lysines. In other embodiments, the subunit vaccine comprises an isolated HIV Env protein, such as an isolated HIV Env protein comprising an amino acid sequence having 85%, 90%, 95%, 98%, 99%, or greater identity to the amino acid sequence depicted in SEQ ID NO: 1

In some embodiments, the instant application relates to a nucleic acid vaccine comprising an isolated nucleic acid comprising a nucleic acid sequence encoding an amino acid sequence having 85%, 90%, 95%, 98%, 99%, or greater identity to the amino acid sequence depicted in SEQ ID NO: 1. In certain embodiments, the nucleic acid sequence encodes the amino acid sequence depicted in SEQ ID NO: 1.

In yet other embodiments, the instant application pertains to an isolated peptide comprising an amino acid sequence having 90% or greater identity to the amino acid sequence depicted in SEQ ID NO: 3, SEQ ID NO: 4, or SEQ ID NO: 5. In certain embodiments, the peptide comprises an amino acid sequence having 98% or greater identity to an amino acid sequence depicted in SEQ ID NO: 3, SEQ ID NO: 4, or SEQ ID NO: 5. In further embodiments, the peptide comprises an amino acid sequence having 99% or greater identity to an amino acid sequence depicted in SEQ ID NO: 3, SEQ ID NO: 4, or SEQ ID NO: 5. In a particular embodiment, the peptide comprises the amino acid sequence depicted in SEQ ID NO: 3, SEQ ID NO: 4, or SEQ ID NO: 5.

In another embodiment, the application relates to an isolated nucleic acid sequence comprising a nucleic acid sequence encoding an amino acid sequence having 90%, 95%, 98%, 99%, or greater identity to the amino acid sequence depicted in SEQ ID NO: 3, SEQ ID NO: 4, or SEQ ID NO: 5. In certain embodiments, the nucleic acid sequence encodes the amino acid sequence depicted in SEQ ID NO: 3, SEQ ID NO: 4, or SEQ ID NO: 5.

In some embodiments, the instant application relates to a kit comprising (a) a composition comprising an isolated peptide comprising a truncated HIV Env protein, wherein the HIV Env protein is mutated in the native gp120/gp41 cleavage site to prevent protease cleavage, comprises the MPER of gp41, and is truncated prior to the transmembrane domain and a pharmaceutically acceptable carrier and (b) instructions for administration of the composition to a mammal. In some embodiments, the HIV Env protein comprises about 1-10 hydrophilic amino acids at its C-terminus. In certain embodiments, the about 1-10 hydrophilic amino acids are three lysines.

In some embodiments, the application relates to a kit comprising (a) a composition comprising an isolated HIV Env protein, such as an isolated HIV Env protein comprising an amino acid sequence having 85%, 90%, 95%, 98%, 99%, or greater identity to the amino acid sequence depicted in SEQ ID NO: 1 and (b) instructions for administration of the composition to a mammal.

In other embodiments, the application relates to a kit comprising (a) a composition comprising an isolated nucleic acid comprising a nucleic acid sequence encoding an amino acid sequence having 85%, 90%, 95%, 98%, 99%, or greater identity to the amino acid sequence depicted in SEQ ID NO: 1 and a pharmaceutically acceptable carrier and (b) instructions for administration of the composition to a mammal. In certain embodiments, the nucleic acid sequence encodes the amino acid sequence depicted in SEQ ID NO: 1

In certain embodiments, the application relates to an isolated peptide comprising a truncated HIV Env protein, wherein the HIV Env protein is mutated in the native gp120/gp41 cleavage site to prevent protease cleavage, comprises the MPER of gp41, and is truncated prior to the transmembrane domain, wherein the HIV Env protein is mutated in the leader sequence. In some embodiments, the native signal peptide is replaced with a tPA signal peptide. In certain embodiments, the tPA signal peptide comprises a sequence selected from the group consisting of: SEQ ID NO: 21 and SEQ ID NO: 22.

In yet other embodiments, the instant application provides an isolated peptide comprising an amino acid sequence having 90% or greater identity to the amino acid sequence depicted in SEQ ID NO: 7 or SEQ ID NO: 9. In further embodiments, the peptide comprises an amino acid sequence having 98% or greater identity to an amino acid sequence depicted in SEQ ID NO: 7 or SEQ ID NO: 9. In still further embodiments, the peptide comprises an amino acid sequence having 99% or greater identity to an amino acid sequence depicted in SEQ ID NO: 7 or SEQ ID NO: 9. In a particular embodiment, the peptide comprises the amino acid sequence depicted in SEQ ID NO: 7 or SEQ ID NO: 9.

In some embodiments, the application relates to an isolated nucleic acid sequence comprising a nucleic acid sequence encoding an amino acid sequence having 85%, 90%, 95%, 98%, 99%, or greater identity to the amino acid sequence depicted in SEQ ID NO: 7 or SEQ ID NO: 9. In certain embodiments, the isolated nucleic acid sequence comprises a nucleic acid sequence depicted in SEQ ID NO: 3 or SEQ ID NO: 5.

These and other embodiments are disclosed or are obvious from and encompassed by, the following Detailed Description.

BRIEF DESCRIPTION OF THE DRAWINGS

FIG. 3 depicts the nucleic acid sequence of HIV-1 Ba-L gp140 DC 4E10 (SEQ ID NO: 6). The tPa signal is highlighted.

FIG. 4 depicts the amino acid sequence of Ba-L gp140 DC 4E10 protein (SEQ ID NO: 7). The tPa signal is highlighted.

FIG. 5 depicts the nucleic acid sequence of HIV-1 Ba-L gp145 (SEQ ID NO: 8). Highlighted is the tPa signal peptide. This sequence is identical in the gp145 region to FIG. 3, differing only in the tPa signal sequence.

FIG. 6 depicts the amino acid sequence of HIV-1 Ba-L gp145 protein (SEQ ID NO: 9). The tPa signal is highlighted.

FIG. 8: HIV-1 subtype C gp160 expression plasmid. HIV-1 gp160 genes are ligated into pSWTIPK3 at the NheI and EcoRI sites in frame with the t-Pa signal peptide.

FIG. 9 depicts the nucleic acid sequence for Clade C, C3728v2c6 gp160 (SEQ ID NO: 10). The HIV-1 C3728v2c6 gp160 nucleic acid sequence is codon optimized. The tPa signal is highlighted FIG. 10 depicts the nucleic acid sequence for Clade C, C3728v2c6 gp160 DC (SEQ ID NO: 11). The HIV-1 C3728v2c6 gp160 DC nucleic acid sequence is codon optimized. The tPa signal is highlighted. The gp120/gp41 cleavage site is mutated to prevent cleavage.

FIG. 11 depicts the nucleic acid sequence for Clade C, C06838v1c48 gp160 (SEQ ID NO: 12). The HIV-1 C06838v1c48 gp160 nucleic acid sequence is codon optimized. The tPa signal is highlighted.

FIG. 12 depicts the nucleic acid sequence for Clade C, C06838v1c48 gp160 DC (SEQ ID NO: 13). The HIV-1 C06838v1c48 gp160 DC nucleic acid sequence is codon optimized. The tPa signal is highlighted. The gp120/gp41 cleavage site is mutated to prevent cleavage.

FIG. 13 depicts the nucleic acid sequence for Clade C, C06980v1c3 gp160 (SEQ ID NO: 14). The HIV-1 C06980v1c3 gp160 nucleic acid sequence is codon optimized. The tPa signal is highlighted.

FIG. 14 depicts the nucleic acid sequence for Clade C, C06980v1c3 gp160 DC (SEQ ID NO: 15). The HIV-1 C06980v1c3 gp160 DC nucleic acid sequence is codon optimized. The tPa signal is highlighted. The gp120/gp41 cleavage site is mutated to prevent cleavage.

FIG. 15 depicts the nucleic acid sequence for Clade C, C06980v0c22 gp160 (SEQ ID NO: 16). The HIV-1 C06980v0c22 gp160 nucleic acid sequence is codon optimized. The tPa signal is highlighted.

FIG. 16 depicts the nucleic acid sequence for Clade C, C06980v0c22 gp160 DC (SEQ ID NO: 17). The HIV-1 C06980v0c22 gp160 DC nucleic acid sequence is codon optimized. The tPa signal is highlighted. The gp120/gp41 cleavage site is mutated to prevent cleavage.

FIG. 18 depicts the nucleic acid sequence for pSWTIPK3 (SEQ ID NO: 18).

FIG. 22 depicts the nucleic acid sequence for pSWC06980v0c22 gp145 (SEQ ID NO: 19).

FIG. 23 depicts the codon optimized nucleic acid sequence for HIV-1 C06980v0c22 gp145 (SEQ ID NO: 20). The tPa signal is highlighted.

FIG. 24 is the protein sequence of HIV-1 C06980v0c22 gp145 (SEQ ID NO: 32). The tPa signal is highlighted.

FIG. 25A (SEQ ID NO: 21) and B (SEQ ID NO: 22) depicts tPA sequences employed in the Env proteins of the invention.

DETAILED DESCRIPTION

Figure 1:
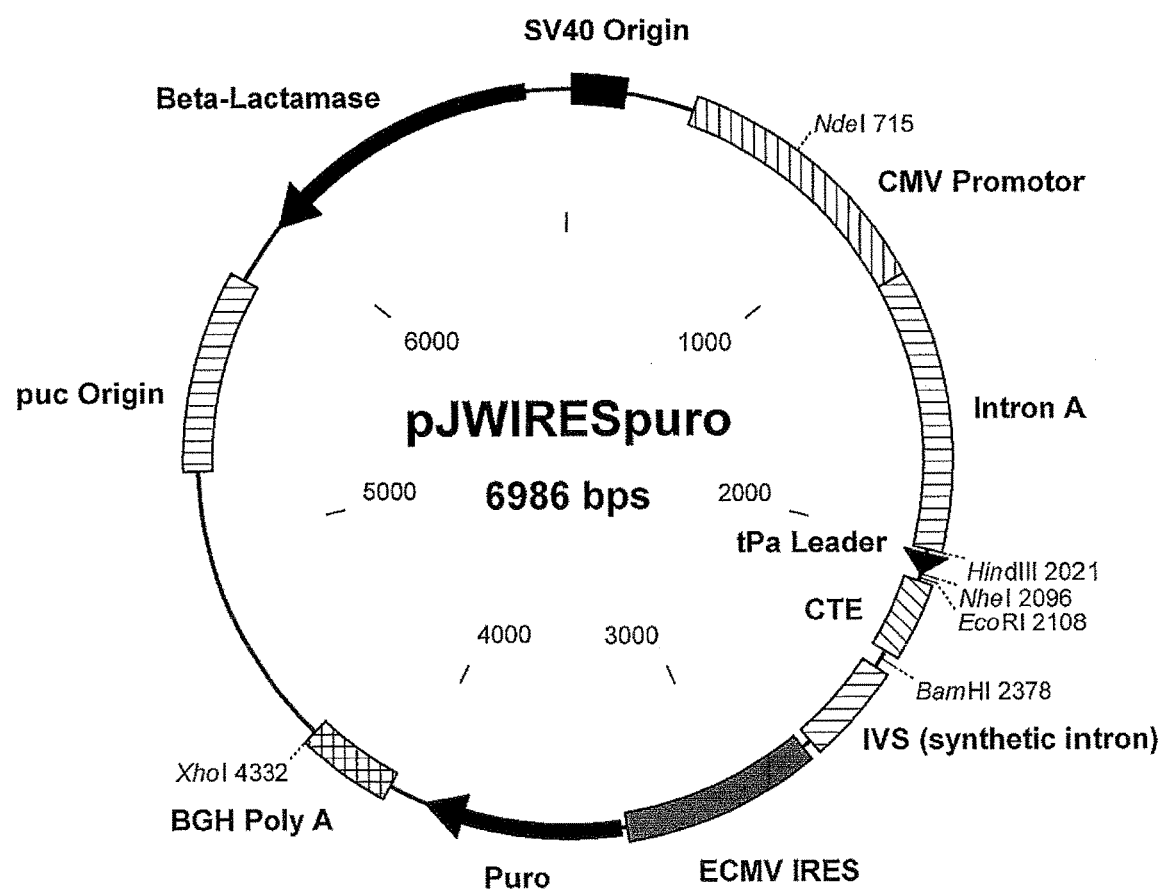
FIG. 1 is a schematic of the vector, pJWIRESpuro.

Many candidate HIV vaccines do not interact with the natural neutralizing antibodies in humans. As described herein, Applicants have demonstrated that the HIV-1 Env can be modified to bind broadly reactive antibodies. Accordingly, the instant invention provides methods and related compositions pertaining to novel HIV Env proteins.

The novel HIV Env proteins of the invention comprise the entire ectodomain of an HIV Env protein, including the membrane proximal external region (MPER) of gp41. The gp41 protein consists of three main domains, namely, the ectodomain, the transmembrane domain, and the cytoplasmic tail. The ectodomain consists of the fusion peptide, N-terminal heptad repeat, C-terminal heptad repeat, and the MPER.

The MPER of gp41 typically comprises the last 24-28 C-terminal amino acids of the gp41 ectodomain. The MPER is a highly conserved region of the HIV Env protein and contains epitopes for broadly neutralizing human monoclonal antibodies, in particular, the 2F5, Z13, and 4E10 monoclonal antibodies.

The inventive HIV Env proteins described herein are truncated HIV Env proteins that are mutated in the gp120/gp41 cleavage site to prevent protease cleavage, comprise the MPER of gp41, and are truncated prior to the transmembrane domain. The HIV Env proteins of the invention may comprise any native MPER of the gp41 of an HIV Env protein.

In certain embodiments, the HIV Env proteins of the invention comprise an MPER sequence comprising the amino acid sequence, ALDSWNNLWNWFDIS (SEQ ID NO: 23). In certain embodiments, the HIV Env proteins of the invention comprise an MPER sequence comprising the amino acid sequence, LWYIK (SEQ ID NO: 24). In some embodiments, the MPER sequence comprises the amino acid sequence, ELLALDSWNNLWNWFDISNWLWYIK (SEQ ID NO: 25). In other embodiments, the MPER sequence comprises the amino acid sequence, DLLALDSWKNLWNWFDITNWLWYIK (SEQ ID NO:26).

Typically, an HIV Env protein of the invention will comprise at least one of the epitopes for the monoclonal antibodies, 2F5, Z13, and 4E10. Examples of 2F5 epitopes include ALDSWN (SEQ ID NO: 27) as disclosed herein, ELDKWA (SEQ ID NO: 28), and EKNEQELLELDKWASLW (SEQ ID NO: 29) (see, e.g., Montero, M, et al., Microbiology and Molecular Biology Reviews (2008) 72(1):54-84 and references cited therein). Examples of 4E10 epitopes include NWFDIS (SEQ ID NO: 30) as disclosed herein and NWFDIT (SEQ ID NO: 31). Id.

The HIV Env proteins of the instant invention lack the transmembrane domain and cytoplasmic tail but comprise the entire ectodomain of gp41. In certain embodiments, the ectodomain is modified to comprise about 1-10 hydrophilic amino acids at its C-terminus. The hydrophilic amino acid residues are typically added to the ectodomain of a truncated HIV Env protein of the invention in order to, in certain embodiments, improve exposure of this region by making it more hydrophilic. In embodiments wherein the HIV Env protein comprises about 1-10 hydrophilic amino acids at its C-terminus, the hydrophilic amino acids are typically contiguous with the final amino acid residue of the native MPER sequence. Thus, the 1-10 hydrophilic amino acids typically comprise the final amino acid residues at the C-terminus of the HIV Env protein. In certain embodiments, the 1-10 hydrophilic amino acids are one or more lysine residues.

In certain embodiments, the HIV Env proteins of the instant invention are derived from an HIV strain isolated from an individual with an acute HIV infection. In other embodiments, the HIV infection is chronic. In certain embodiments, the HIV Env protein is derived from an HIV-1 strain classified in a group that is M, O, N, or P. In a particular embodiment, the HIV Env protein is derived from an HIV-1 group M strain. In further embodiments, the HIV-1 group M strain is a subtype (clade) selected from A, B, C, D, F, G, H, J, K, and hybrids thereof. In further embodiments, the HIV Env proteins are derived from an HIV-1 Group M strain that is a Clade B, Clade C, or Clade D strain. In some embodiments, the Clade B, C, or D strain is isolated from an individual with an acute infection. In other embodiments, the Clade B, C, or D strain is isolated from an individual with a chronic infection. Examples of suitable parent HIV strains from which the Env proteins of the instant invention can be derived include the HIV-1 Clade D sequences depicted in GenBank under Accession Nos. AF484477, AF484511, and AF484502 and the HIV-1 Clade C sequences depicted in GenBank under Accession Nos. HM215344 and HM215345.

In certain embodiments, the HIV Env proteins described herein are useful as immunogens in different forms to use as HIV vaccine components to elicit bNabs, e.g., against HIV-1. The different forms of the HIV Env can be used in a prime, as DNA/vector expressing the protein/protein and/or as a boost as protein. For example, in some embodiments, an HIV Env protein of the invention is administered to a mammal as a DNA vaccine, followed by administration of a boost as protein. In further embodiments, the HIV Env protein is administered as nucleic acid in a plasmid, followed by administration in a viral vector (e.g., as nucleic acid in an MVA), followed by administration as a protein. In some embodiments, the inventive HIV Env proteins could also be used as particulate immunogens by crosslinking to virus particles like Qbeta, cow pea mosaic virus, CRM, HPV, HBsAg, etc.

In certain embodiments, HIV Env proteins of the instant invention are utilized as reagents for screening of new broad neutralizing antibodies and/or mapping of human sera with broad neutralizing serum activity and animal sera following immunization studies. In other embodiments, HIV Env proteins of the instant invention are utilized for screening of small molecules that compete for binding of broad neutralizing antibodies. The identified small molecules could be used as immunogens or anti-viral compounds.

As described herein, Applicants have generated recombinant Env proteins with unique sequences in which Applicants have modified the leader, modified the cleavage site for gp120/gp41, added a hydrophilic amino acid-tail and terminated the sequence before the transmembrane domain such that it comprises the full ectodomain of gp41. The DNA sequences are unique as they are codon optimized.

Figure 38:
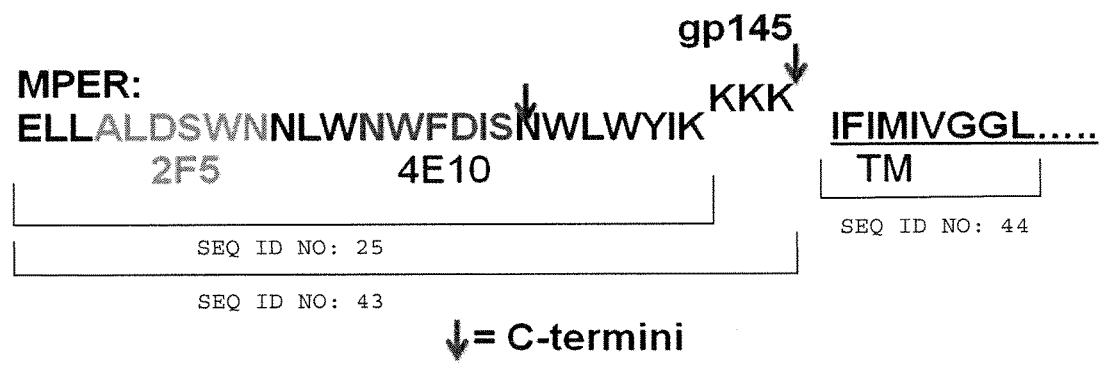
Figure 42:
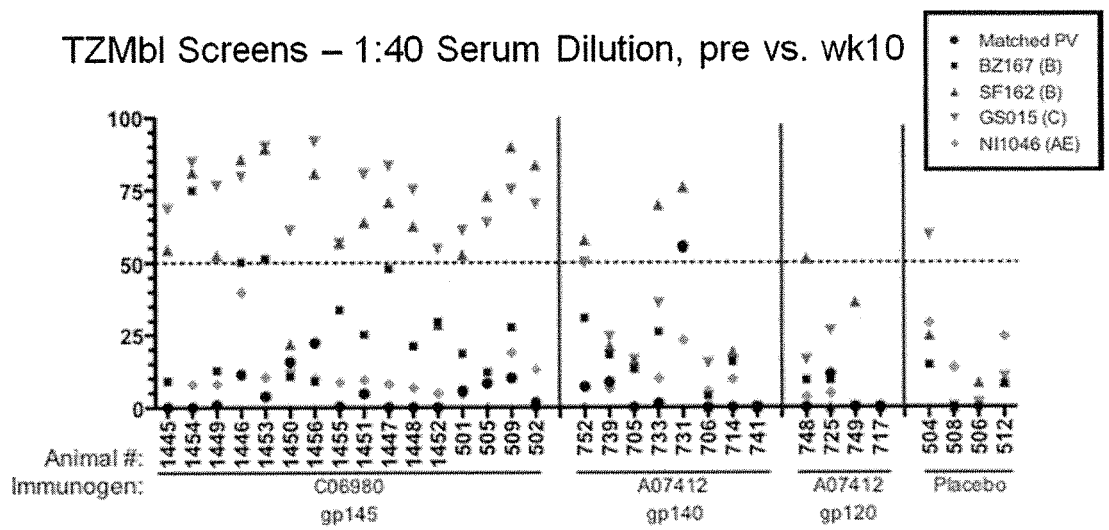
Figure 43:
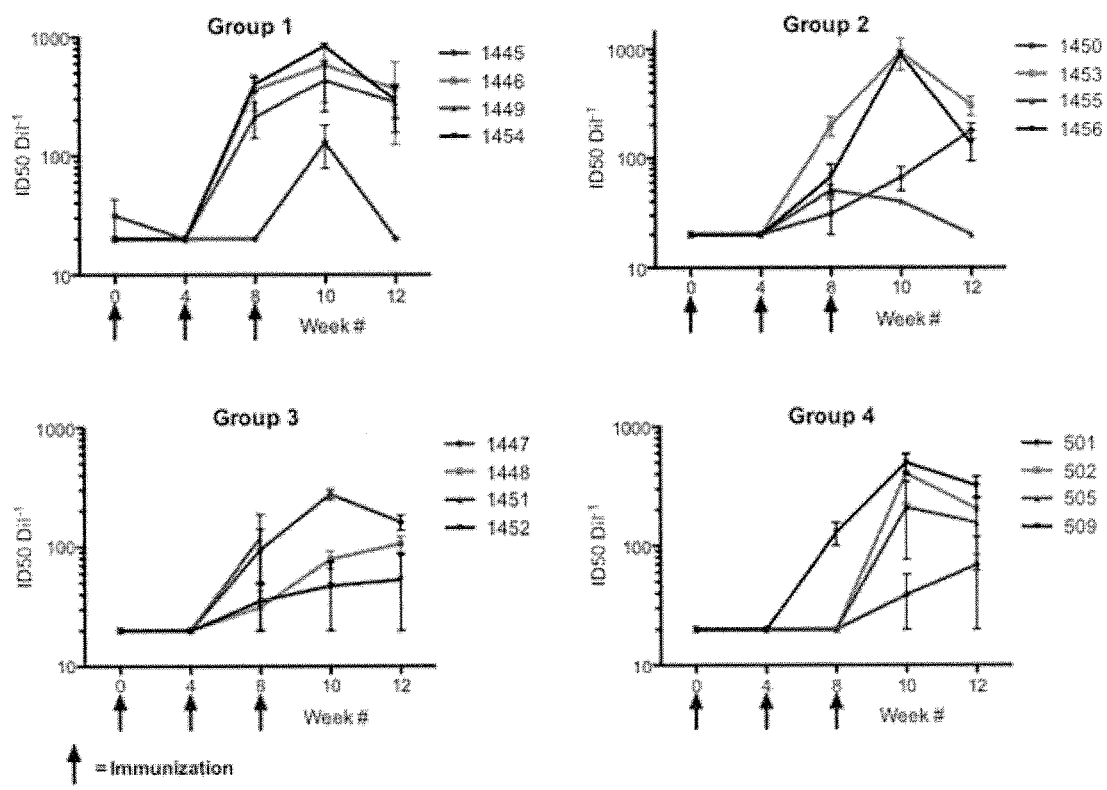
Figure 44:
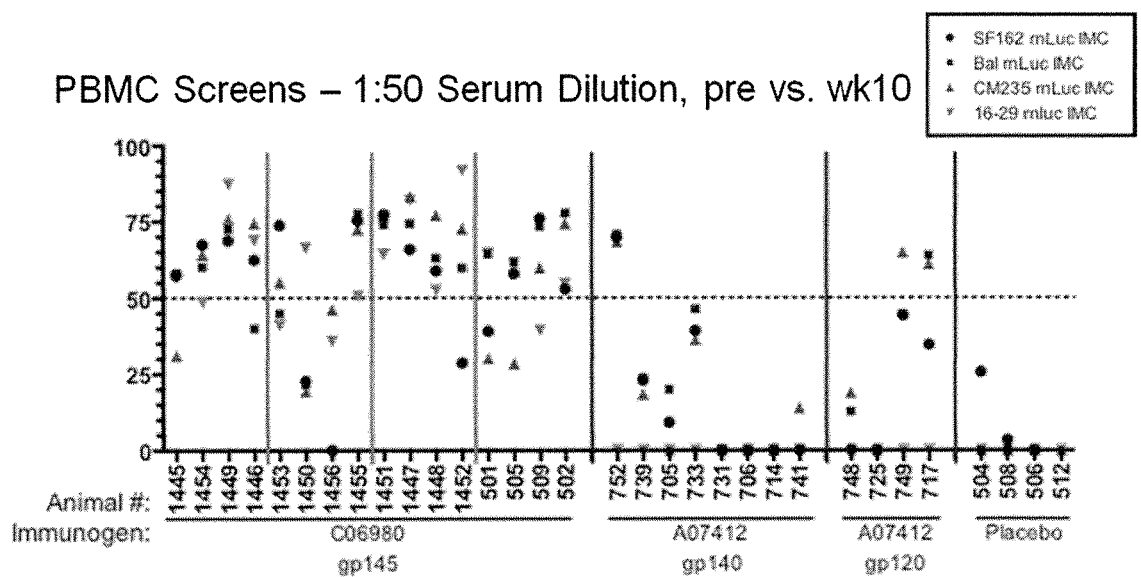
Figure 45:
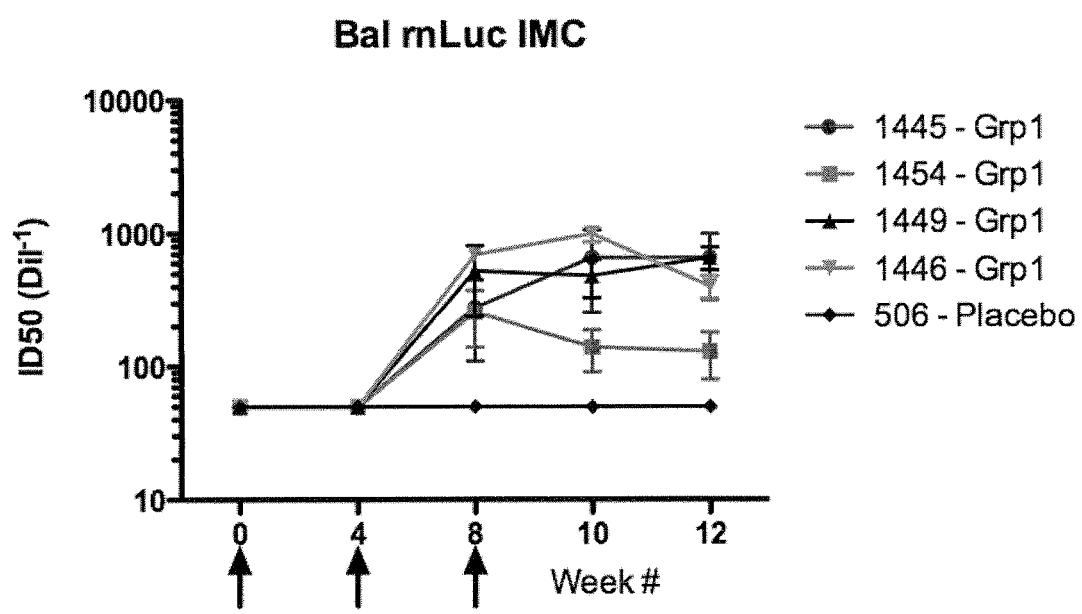
Figure 46:
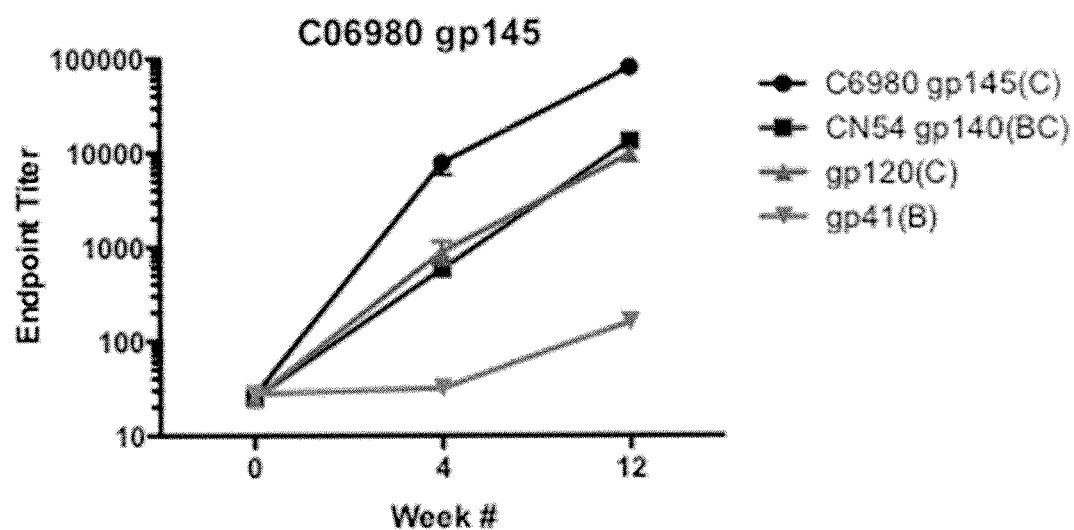
Figure 47:
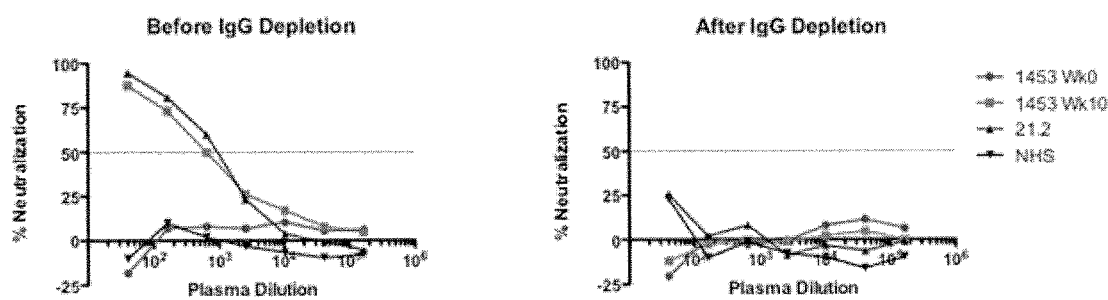
Figure 48:
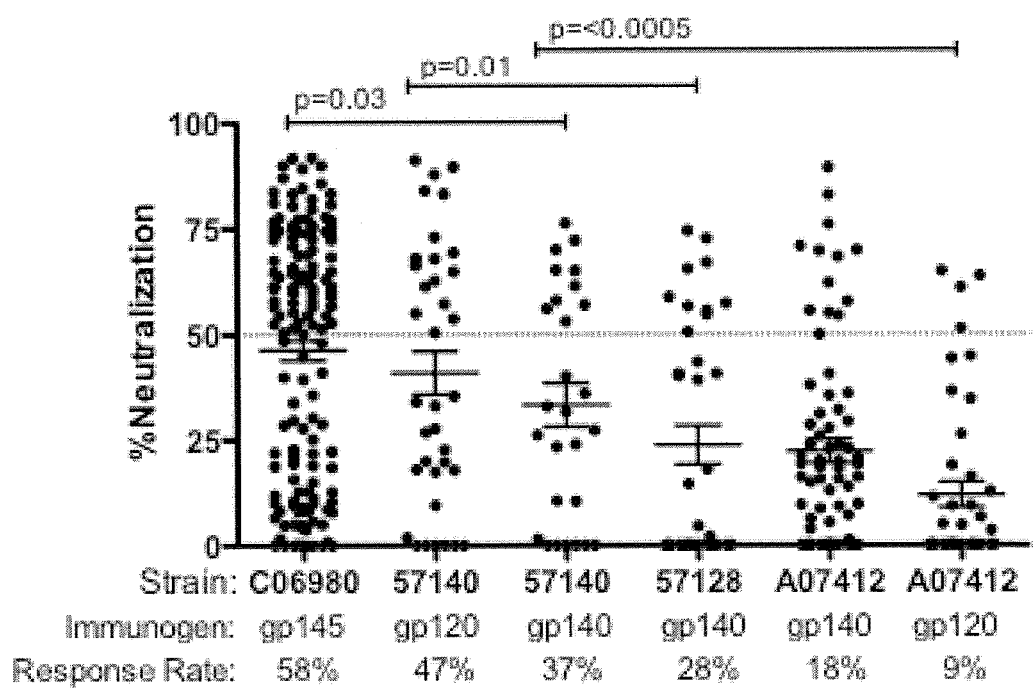
Figure 49:
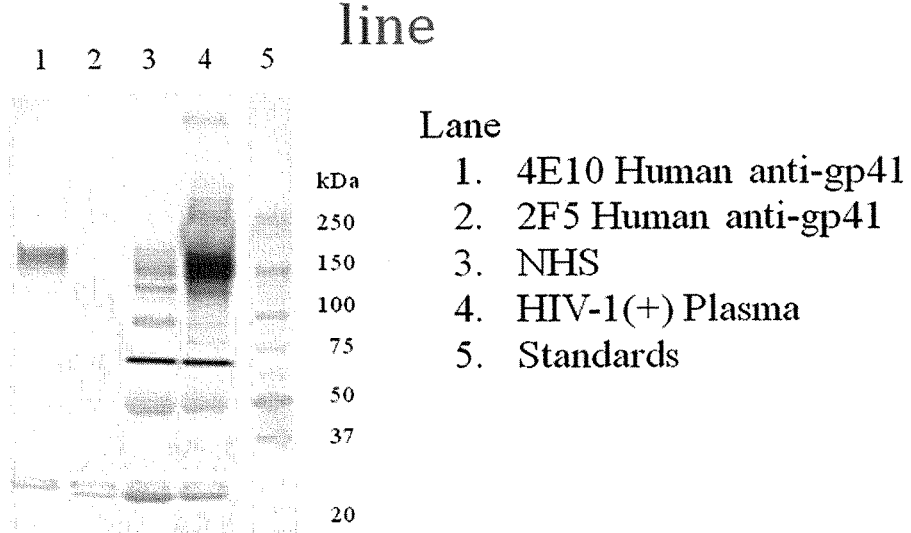
Figure 52:
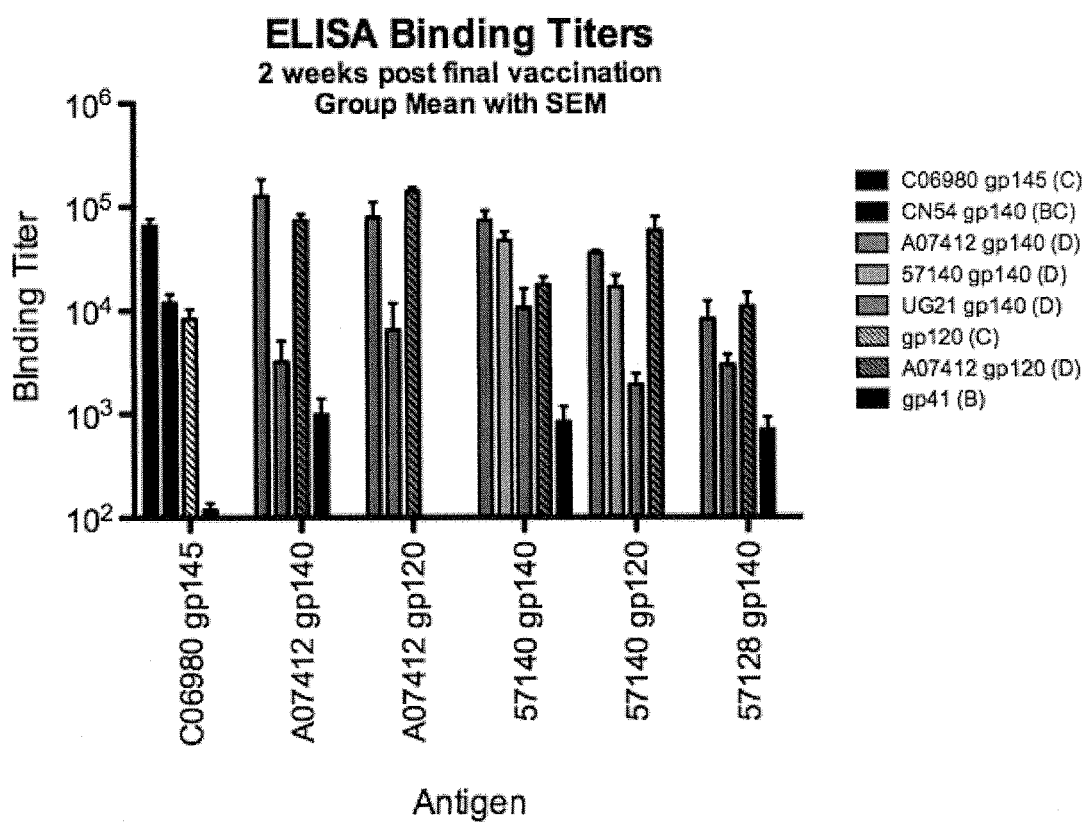
Figure 53:
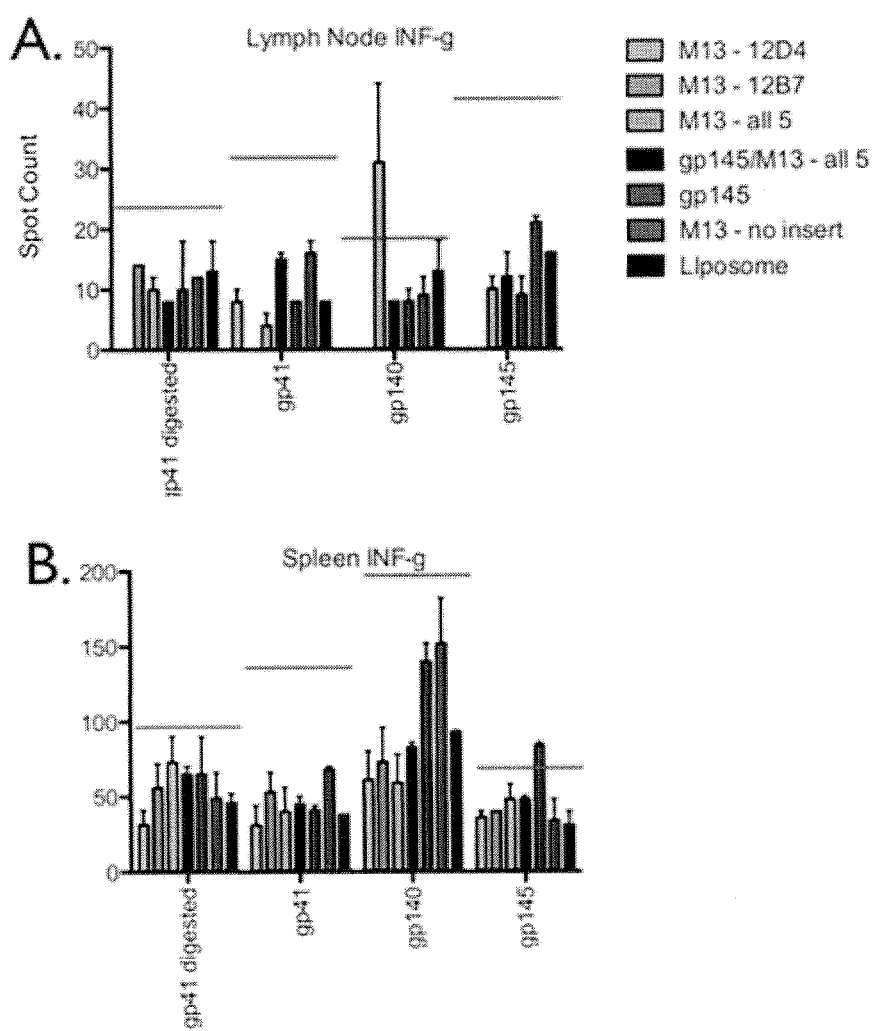
Figure 54:
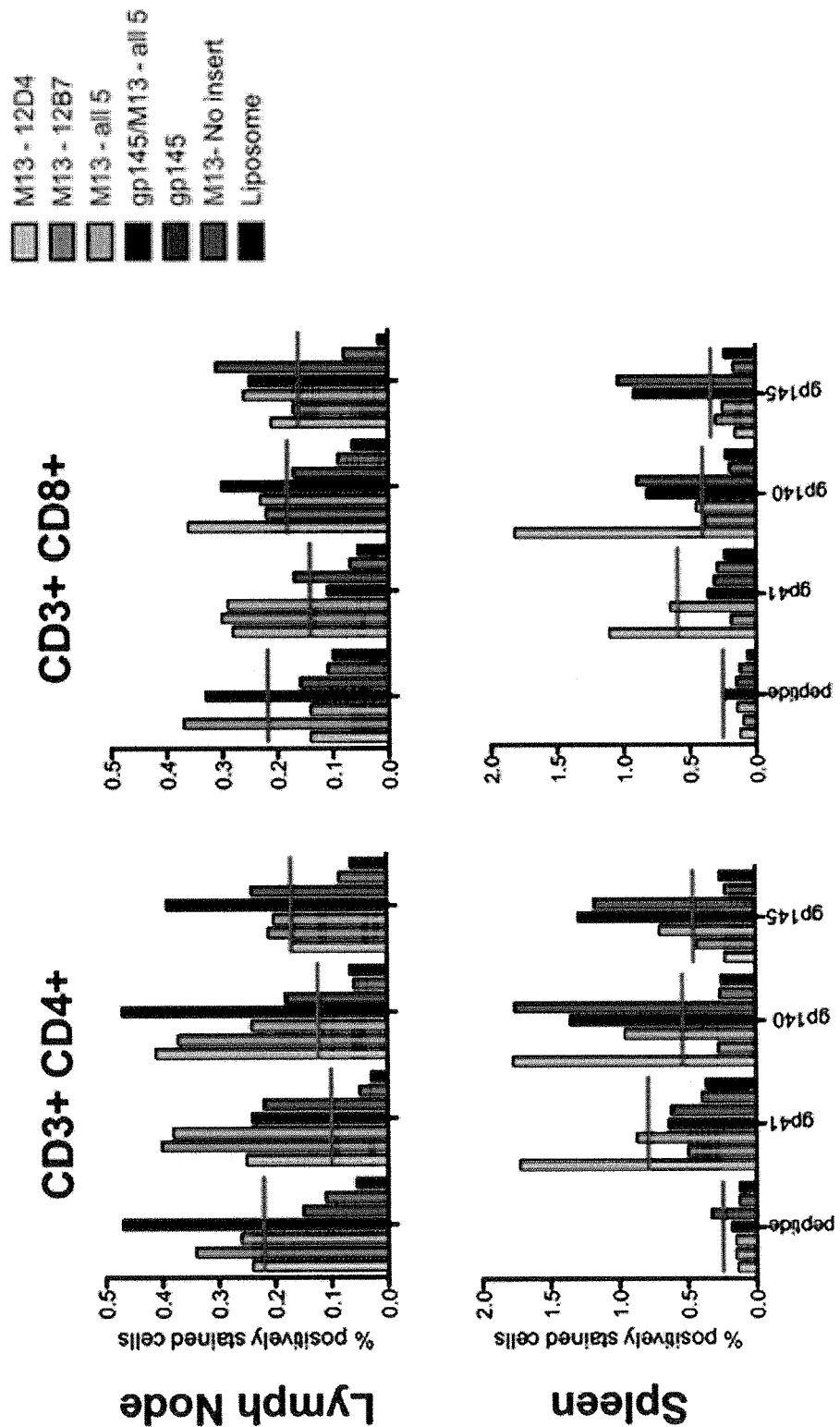
Figure 55:
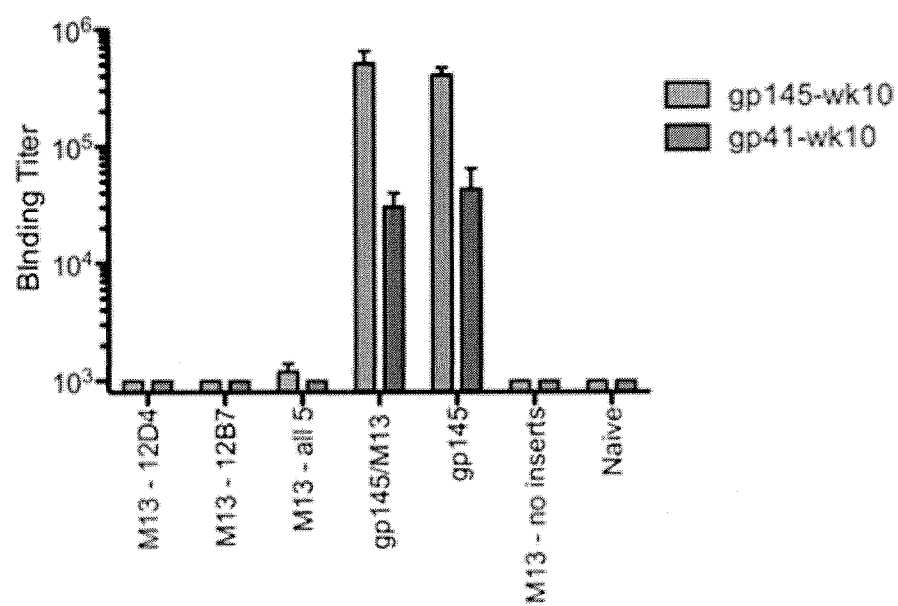

In another advantageous embodiment, the HIV Env proteins have substantially similar sequences to the HIV Env protein sequences depicted in FIGS. 4, 6, 24, 35, 36, and/or 37. In another particularly advantageous embodiment, the HIV Env proteins have a substantially similar MPER sequence to the MPER sequence depicted in FIG. 38.

In a particularly advantageous embodiment, the HIV Env proteins of the present invention have about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% sequence identity to SEQ ID NO: 1 or any of the HIV Env protein sequences depicted in FIGS. 3-6, 23, 24, and 35-37.

In one embodiment, the HIV Env proteins of the present invention may be used as reagants to screen for and identify new broadly neutralizing antibodies. Assays for screening for neutralizing antibodies are known in the art. A neutralization assay approach has been described previously (Binley J M, et al., (2004). Comprehensive Cross-Clade Neutralization Analysis of a Panel of Anti-Human Immunodeficiency Virus Type 1 Monoclonal Antibodies. *J. Virol.* 78: 13232-13252). Pseudotyped viruses may be generated by co-transfecting cells with at least two plasmids encoding the soluble Env cDNA of the present invention and the rest of the HIV genome separately. In the HIV genome encoding vector, the Env gene may be replaced by the firefly luciferase gene. Transfectant supernatants containing pseudotyped virus may be co-incubated overnight with B cell supernatants derived from activation of an infected donor's primary peripheral blood mononuclear cells (PBMCs) or with monoclonal or polyclonal (serum) antibodies. Cells stably transfected with and expressing CD4 plus the CCR5 and CXCR4 coreceptors may be added to the mixture and incubated for 3 days at 37° C. Infected cells may be quantified by luminometry.

In some embodiments, for the screening of broad neutralizing antibodies, an envelope-enzyme fusion protein may be constructed by attaching an enzyme to the C-terminal end of an envelope protein. Virus particles comprising of the fusion protein and wild type and/or soluble envelope glycoprotein may be generated and used to infect target cells in the presence of a patients' sera. Activities of enzyme measured in such infected cells are measures of virus binding and entry to the target cells that are mediated by the wild type viral envelope protein. Examples of enzymes that can be used to generate the fusion protein include, but are not limited to, luciferase, bacterial or placental alkaline phosphatase, β-galactosidase, and fluorescent proteins such as Green fluorescent protein or toxins. The assay, in general, can also be carried out in 96-well plate. Decreased enzyme activities in the presence of the sera indicate that there are neutralizing antibodies in the sera.

As used herein, the terms "drug," "agent," and "compound" encompass any composition of matter or mixture which provides some pharmacologic effect that can be demonstrated in-vivo or in vitro. This includes small molecules, antibodies, microbiologicals, vaccines, vitamins, and other beneficial agents. As used herein, the terms further include any physiologically or pharmacologically active substance that produces a localized or systemic effect in a patient.

Nucleic Acids, Proteins, and Recombinant Technology

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

The term "nucleic acid" encompasses DNA, RNA (e.g., mRNA, tRNA), heteroduplexes, and synthetic molecules capable of encoding a polypeptide and includes all analogs and backbone substitutes such as PNA that one of ordinary skill in the art would recognize as capable of substituting for naturally occurring nucleotides and backbones thereof. Nucleic acids may be single stranded or double stranded, and may be chemical modifications. The terms "nucleic acid" and "polynucleotide" are used interchangeably. Because the genetic code is degenerate, more than one codon may be used to encode a particular amino acid, and the present compositions and methods encompass nucleotide sequences which encode a particular amino acid sequence.

Unless otherwise indicated, nucleic acids are written left to right in 5' to 3' orientation; amino acid sequences are written left to right in amino to carboxy orientation, respectively.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling or bioactive component. The conventional one-letter or three-letter code for amino acid residues are used herein.

As used herein, a "synthetic" molecule is produced by in vitro chemical or enzymatic synthesis rather than by an organism.

As used herein, the term "expression" refers to the process by which a polypeptide is produced based on the nucleic acid sequence of a gene. The process includes both transcription and translation.

A "gene" refers to the DNA segment encoding a polypeptide or RNA.

An "isolated" polynucleotide or polypeptide is one that is substantially free of the materials with which it is associated in its native environment. By substantially free, is meant at least 50%, advantageously at least 70%, more advantageously at least 80%, and even more advantageously at least 90% free of these materials.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences in association therewith.

"Native" proteins or polypeptides refer to proteins or polypeptides isolated from the source in which the proteins naturally occur. "Recombinant" polypeptides refer to polypeptides produced by recombinant DNA techniques; e.g., produced from cells transformed by an exogenous DNA construct encoding the desired polypeptide. "Synthetic" polypeptides include those prepared by chemical synthesis as well as the synthetic antigens described above.

By "homolog" is meant an entity having a certain degree of identity with the subject amino acid sequences and the subject nucleotide sequences. As used herein, the term "homolog" covers identity with respect to structure and/or function, for example, the expression product of the resultant nucleotide sequence has the enzymatic activity of a subject amino acid sequence. With respect to sequence identity, preferably there is at least 70%, 75%, 80%, 81%, 82%, 83%, 84%, 85%, 86%, 87%, 88%, 89%, 90%, 91%, 92%, 93%, 94%, 95%, 96%, 97%, 98%, or even 99% sequence identity. These terms also encompass allelic variations of the sequences. The term, homolog, may apply to the relationship between genes separated by the event of speciation or to the relationship between genes separated by the event of genetic duplication.

Relative sequence identity can be determined by commercially available computer programs that can calculate % identity between two or more sequences using any suitable algorithm for determining identity, using, for example, default parameters. A typical example of such a computer program is CLUSTAL. Advantageously, the BLAST algorithm is employed, with parameters set to default values. The BLAST algorithm is described in detail on the National Center for Biotechnology Information (NCBI) website.

The homologs of the peptides as provided herein typically have structural similarity with such peptides. A homolog of a polypeptide includes one or more conservative amino acid substitutions, which may be selected from the same or different members of the class to which the amino acid belongs.

In one embodiment, the sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

The present invention also encompasses conservative substitution (substitution and replacement are both used herein to mean the interchange of an existing amino acid residue with an alternative residue) that may occur e.g., like-for-like substitution such as basic for basic, acidic for acidic, polar for polar, etc. Non-conservative substitution may also occur e.g., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyridylalanine, thienylalanine, naphthylalanine and phenylglycine. Conservative substitutions that may be made are, for example, within the groups of basic amino acids (Arginine, Lysine and Histidine), acidic amino acids (glutamic acid and aspartic acid), aliphatic amino acids (Alanine, Valine, Leucine, Isoleucine), polar amino acids (Glutamine, Asparagine, Serine, Threonine), aromatic amino acids (Phenylalanine, Tryptophan and Tyrosine), hydroxylamino acids (Serine, Threonine), large amino acids (Phenylalanine and Tryptophan) and small amino acids (Glycine, Alanine).

Many methods of amplifying DNA are known in the art, and any such method can be used, see for example Sambrook et al., Molecular Cloning; A Laboratory Manual 2 d ed. (1989). For example, a DNA fragment of interest can be amplified using the polymerase chain reaction or some other cyclic polymerase mediated amplification reaction.

The amplified region of DNA can then be sequenced using any method known in the art. Advantageously, the nucleic acid sequencing is by automated methods (reviewed by Meldrum, Genome Res. September 2000; 10(9):1288-303, the disclosure of which is incorporated by reference in its entirety), for example using a Beckman CEQ 8000 Genetic Analysis System (Beckman Coulter Instruments, Inc.). Methods for sequencing nucleic acids include, but are not limited to, automated fluorescent DNA sequencing (see, e.g., Watts & MacBeath, Methods Mol. Biol. 2001; 167: 153-70 and MacBeath et al., Methods Mol. Biol. 2001; 167:119-52), capillary electrophoresis (see, e.g., Bosserhoff et al., Comb Chem High Throughput Screen. December 2000; 3(6):455-66), DNA sequencing chips (see, e.g., Jain, Pharmacogenomics. August 2000; 1(3):289-307), mass spectrometry (see, e.g., Yates, Trends Genet. January 2000; 16(1):5-8), pyrosequencing (see, e.g., Ronaghi, Genome Res. January 2001; 11(1):3-11), and ultrathin-layer gel electrophoresis (see, e.g., Guttman & Ronai, Electrophoresis. December 2000; 21 (18):3952-64), the disclosures of which are hereby incorporated by reference in their entireties. The sequencing can also be done by any commercial company. Examples of such companies include, but are not limited to, the University of Georgia Molecular Genetics Instrumentation Facility (Athens, Ga.) or SeqWright DNA Technologies Services (Houston, Tex.).

Any one of the methods known in the art for amplification of DNA may be used, such as for example, the polymerase chain reaction (PCR), the ligase chain reaction (LCR) (Barany, F., Proc. Natl. Acad. Sci. (U.S.A.) 88:189-193 (1991)), the strand displacement assay (SDA), or the oligonucleotide ligation assay ("OLA") (Landegren, U. et al., Science 241: 1077-1080 (1988)). Nickerson, D. A. et al. have described a nucleic acid detection assay that combines attributes of PCR and OLA (Nickerson, D. A. et al., Proc. Natl. Acad. Sci. (U.S.A.) 87:8923-8927 (1990)). Other known nucleic acid amplification procedures, such as transcription-based amplification systems (Malek, L. T. et al., U.S. Pat. No. 5,130,238; Davey, C. et al., European Patent Application 329,822; Schuster et al., U.S. Pat. No. 5,169,766; Miller, H. I. et al., PCT Application WO89/06700; Kwoh, D. et al., Proc. Natl. Acad. Sci. (U.S.A.) 86:1173 (1989); Gingeras, T. R. et al., PCT Application WO88/10315)), or isothermal amplification methods (Walker, G. T. et al., Proc. Natl. Acad. Sci. (U.S.A.) 89:392-396 (1992)) may also be used.

To perform a cyclic polymerase mediated amplification reaction according to the present invention, the primers are hybridized or annealed to opposite strands of the target DNA, the temperature is then raised to permit the thermostable DNA polymerase to extend the primers and thus replicate the specific segment of DNA spanning the region between the two primers. Then the reaction is thermocycled so that at each cycle the amount of DNA representing the sequences between the two primers is doubled, and specific amplification of gene DNA sequences, if present, results.

Any of a variety of polymerases can be used in the present invention. For thermocyclic reactions, the polymerases are thermostable polymerases such as Taq, KlenTaq, Stoffel Fragment, Deep Vent, Tth, Pfu, Vent, and UlTma, each of which are readily available from commercial sources. For non-thermocyclic reactions, and in certain thermocyclic reactions, the polymerase will often be one of many polymerases commonly used in the field, and commercially available, such as DNA pol 1, Klenow fragment, T7 DNA polymerase, and T4 DNA polymerase. Guidance for the use of such polymerases can readily be found in product literature and in general molecular biology guides.

Typically, the annealing of the primers to the target DNA sequence is carried out for about 2 minutes at about 37-55° C., extension of the primer sequence by the polymerase enzyme (such as Taq polymerase) in the presence of nucleoside triphosphates is carried out for about 3 minutes at about 70-75° C., and the denaturing step to release the extended primer is carried out for about 1 minute at about 90-95° C. However, these parameters can be varied, and one of skill in the art would readily know how to adjust the temperature and time parameters of the reaction to achieve the desired results. For example, cycles may be as short as 10, 8, 6, 5, 4.5, 4, 2, 1, 0.5 minutes or less.

Also, "two temperature" techniques can be used where the annealing and extension steps may both be carried out at the same temperature, typically between about 60-65° C., thus reducing the length of each amplification cycle and resulting in a shorter assay time.

Typically, the reactions described herein are repeated until a detectable amount of product is generated. Often, such detectable amounts of product are between about 10 ng and about 100 ng, although larger quantities, e.g. 200 ng, 500 ng, 1 mg or more can also, of course, be detected. In terms of concentration, the amount of detectable product can be from about 0.01 pmol, 0.1 pmol, 1 pmol, 10 pmol, or more. Thus, the number of cycles of the reaction that are performed can be varied, the more cycles are performed, the more amplified product is produced. In certain embodiments, the reaction comprises 2, 5, 10, 15, 20, 30, 40, 50, or more cycles.

For example, the PCR reaction may be carried out using about 25-50 µl samples containing about 0.01 to 1.0 ng of template amplification sequence, about 10 to 100 pmol of each generic primer, about 1.5 units of Taq DNA polymerase (Promega Corp.), about 0.2 mM dDATP, about 0.2 mM dCTP, about 0.2 mM dGTP, about 0.2 mM dTTP, about 15 mM $MgCl_2$, about 10 mM Tris-HCl (pH 9.0), about 50 mM KCl, about 1 µg/ml gelatin, and about 10 µl/ml Triton X-100 (Saiki, 1988).

Those of ordinary skill in the art are aware of the variety of nucleotides available for use in the cyclic polymerase mediated reactions. Typically, the nucleotides will consist at least in part of deoxynucleotide triphosphates (dNTPs), which are readily commercially available. Parameters for optimal use of dNTPs are also known to those of skill, and are described in the literature. In addition, a large number of nucleotide derivatives are known to those of skill and can be used in the present reaction. Such derivatives include fluorescently labeled nucleotides, allowing the detection of the product including such labeled nucleotides, as described below. Also included in this group are nucleotides that allow the sequencing of nucleic acids including such nucleotides, such as chain-terminating nucleotides, dideoxynucleotides and boronated nuclease-resistant nucleotides. Commercial kits containing the reagents most typically used for these methods of DNA sequencing are available and widely used. Other nucleotide analogs include nucleotides with bromo-, iodo-, or other modifying groups, which affect numerous properties of resulting nucleic acids including their antigenicity, their replicatability, their melting temperatures, their binding properties, etc. In addition, certain nucleotides include reactive side groups, such as sulfhydryl groups, amino groups, N-hydroxysuccinimidyl groups, that allow the further modification of nucleic acids comprising them.

The term "oligonucleotide" is defined as a molecule comprised of two or more deoxyribonucleotides, preferably more than three. Its exact size will depend upon many factors which, in turn, depend upon the ultimate function and use of the oligonucleotide. The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use for the method. In certain embodiments, oligonucleotides that can be used as primers to amplify specific nucleic acid sequences of a gene in cyclic polymerase-mediated amplification reactions, such as PCR reactions, consist of oligonucleotide fragments. Such fragments should be of sufficient length to enable specific annealing or hybridization to the nucleic acid sample. The sequences typically will be about 8 to about 44 nucleotides in length, but may be longer. Longer sequences, e.g., from about 14 to about 50, are advantageous for certain embodiments.

In embodiments where it is desired to amplify a fragment of DNA, primers having contiguous stretches of about 8, 9, 10, 11, 12, 13, 14, 15, 16, 17, 18, 19, 20, 21, 22, 23, or 24 nucleotides from a gene sequence are contemplated.

As used herein, "hybridization" refers to the process by which one strand of nucleic acid base pairs with a complementary strand, as occurs during blot hybridization techniques and PCR techniques.

Whichever probe sequences and hybridization methods are used, one ordinarily skilled in the art can readily determine suitable hybridization conditions, such as temperature and chemical conditions. Such hybridization methods are well known in the art. For example, for applications requiring high selectivity, one will typically desire to employ relatively stringent conditions for the hybridization reactions, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand. It is generally appreciated that conditions can be rendered more stringent by the addition of increasing amounts of formamide. Other variations in hybridization reaction conditions are well known in the art (see for example, Sambrook et al., Molecular Cloning; A Laboratory Manual 2 d ed. (1989)).

Hybridization conditions are based on the melting temperature (Tm) of the nucleic acid binding complex, as taught, e.g., in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of ordinary skill in the art, a maximum stringency hybridization can be used to identify or detect identical nucleotide sequences while an intermediate (or low) stringency hybridization can be used to identify or detect similar or related polynucleotide sequences.

In one aspect, the present invention employs nucleotide sequences that can hybridize to another nucleotide sequence under stringent conditions (e.g., 65° C. and 0.1×SSC {1×SSC=0.15 M NaCl, 0.015 M Na3 Citrate pH 7.0). Where the nucleotide sequence is double-stranded, both strands of the duplex, either individually or in combination, may be employed by the present invention. Where the nucleotide sequence is single-stranded, it is to be understood that the complementary sequence of that nucleotide sequence is also included within the scope of the present invention.

Stringency of hybridization refers to conditions under which polynucleic acid hybrids are stable. Such conditions are evident to those of ordinary skill in the field. As known to those of ordinary skill in the art, the stability of hybrids is reflected in the melting temperature (Tm) of the hybrid which decreases approximately 1 to 1.5° C. with every 1% decrease in sequence homology. In general, the stability of a hybrid is a function of sodium ion concentration and temperature. Typically, the hybridization reaction is performed under conditions of higher stringency, followed by washes of varying stringency.

As used herein, high stringency includes conditions that permit hybridization of only those nucleic acid sequences that form stable hybrids in 1 M Na+ at 65-68° C. High stringency conditions can be provided, for example, by hybridization in an aqueous solution containing 6×SSC, 5×Denhardt's, 1% SDS (sodium dodecyl sulphate), 0.1 Na+ pyrophosphate and 0.1 mg/ml denatured salmon sperm DNA as non-specific competitor. Following hybridization, high stringency washing may be done in several steps, with a final wash (about 30 minutes) at the hybridization temperature in 0.2-0.1×SSC, 0.1% SDS.

It is understood that these conditions may be adapted and duplicated using a variety of buffers, e.g., formamide-based buffers, and temperatures. Denhardt's solution and SSC are well known to those of ordinary skill in the art as are other suitable hybridization buffers (see, e.g., Sambrook, et al., eds. (1989) Molecular Cloning: A Laboratory Manual, Cold Spring Harbor Laboratory Press, New York or Ausubel, et al., eds. (1990) Current Protocols in Molecular Biology, John Wiley & Sons, Inc.). Optimal hybridization conditions are typically determined empirically, as the length and the GC content of the hybridizing pair also play a role.

Nucleic acid molecules that differ from the sequences of the primers and probes disclosed herein, are intended to be within the scope of the invention. Nucleic acid sequences that are complementary to these sequences, or that are hybridizable to the sequences described herein under conditions of standard or stringent hybridization, and also analogs and derivatives are also intended to be within the scope of the invention. Advantageously, such variations will differ from the sequences described herein by only a small number of nucleotides, for example by 1, 2, or 3 nucleotides.

Nucleic acid molecules corresponding to natural allelic variants, homologues (i.e., nucleic acids derived from other species), or other related sequences (e.g., paralogs) of the sequences described herein can be isolated based on their homology to the nucleic acids disclosed herein, for example by performing standard or stringent hybridization reactions using all or a portion of the known sequences as probes. Such methods for nucleic acid hybridization and cloning are well known in the art.

Similarly, a nucleic acid molecule detected in the methods of the invention may include only a fragment of the specific sequences described. Fragments provided herein are defined as sequences of at least 6 (contiguous) nucleic acids, a length sufficient to allow for specific hybridization of nucleic acid primers or probes, and are at most some portion less than a full-length sequence. Fragments may be derived from any contiguous portion of a nucleic acid sequence of choice. Derivatives and analogs may be full length or other than full length, if the derivative or analog contains a modified nucleic acid or amino acid, as described below.

Derivatives, analogs, homologues, and variants of the nucleic acids of the invention include, but are not limited to, molecules comprising regions that are substantially homologous to the nucleic acids of the invention, in various embodiments, by at least about 70%, 80%, 85%, 90%, 95%, 96%, 97%, 98%, or even 99% identity over a nucleic acid sequence of identical size or when compared to an aligned sequence in which the alignment is done by a computer homology program known in the art.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

In all search programs in the suite the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Alternatively or additionally, the term "homology" or "identity", for instance, with respect to a nucleotide or amino acid sequence, can indicate a quantitative measure of homology between two sequences. The percent sequence homology can be calculated as $(N_{ref}-N_{dif})*100/-N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC(N $N_{ref}=8$; N $N_{dif}=2$). "Homology" or "identity" can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur & Lipman, Proc Natl Acad Sci USA 1983; 80:726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences. Without undue experimentation, the skilled artisan can consult with many other programs or references for determining percent homology.

As regards codon optimization, the nucleic acid molecules of the invention have a nucleotide sequence that encodes the antigens of the invention and can be designed to employ codons that are used in the genes of the subject in which the antigen is to be produced. Such methods, and the selection of such methods, are well known to those of skill in the art. In addition, there are several companies that will optimize codons of sequences, such as Geneart (geneart(dot) com). Thus, the nucleotide sequences of the invention can readily be codon optimized.

As used herein, the term "probe" refers to a molecule (e.g., an oligonucleotide, whether occurring naturally as in a purified restriction digest or produced synthetically, recombinantly or by PCR amplification), that is capable of hybridizing to another molecule of interest (e.g., another oligonucleotide). When probes are oligonucleotides they may be single-stranded or double-stranded. Probes are useful in the detection, identification and isolation of particular targets (e.g., gene sequences). As described herein, it is contemplated that probes used in the present invention may be labelled with a label so that is detectable in any detection system, including, but not limited to enzyme (e.g., ELISA, as well as enzyme-based histochemical assays), fluorescent, radioactive, and luminescent systems.

The primers and probes described herein may be readily prepared by, for example, directly synthesizing the fragment by chemical means or by introducing selected sequences into recombinant vectors for recombinant production. Methods for making a vector or recombinants or plasmid for amplification of the fragment either in vivo or in vitro can be any desired method, e.g., a method which is by or analogous to the methods disclosed in, or disclosed in documents cited in: U.S. Pat. Nos. 4,603,112; 4,769,330; 4,394,448; 4,722,848; 4,745,051; 4,769,331; 4,945,050; 5,494,807; 5,514,375; 5,744,140; 5,744,141; 5,756,103; 5,762,938; 5,766,599; 5,990,091; 5,174,993; 5,505,941; 5,338,683; 5,494,807; 5,591,639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450 and 6,312,683; U.S. patent application Ser. No. 920,197, filed Oct. 16, 1986; WO 90/01543; WO91/11525; WO 94/16716; WO 96/39491; WO 98/33510; EP 265785; EP 0 370 573; Andreansky et al., Proc. Natl. Acad. Sci. USA 1996; 93:11313-11318; Ballay et al., EMBO J. 1993; 4:3861-65; Feigner et al., J. Biol. Chem. 1994; 269:2550-2561; Frolov et al., Proc. Natl. Acad. Sci. USA 1996; 93:11371-11377; Graham, Tibtech 1990; 8:85-87; Grunhaus et al., Sem. Virol. 1992; 3:237-52; Ju et al., Diabetologia 1998; 41:736-739; Kitson et al., J. Virol. 1991; 65:3068-3075; McClements et al., Proc. Natl. Acad. Sci. USA 1996; 93:11414-11420; Moss, Proc. Natl. Acad. Sci. USA 1996; 93:11341-11348; Paoletti, Proc. Natl. Acad. Sci. USA 1996; 93:11349-11353; Pennock et al., Mol. Cell. Biol. 1984; 4:399-406; Richardson (Ed), Methods in Molecular Biology 1995; 39, "Baculovirus Expression Protocols," Humana Press Inc.; Smith et al. (1983) Mol. Cell. Biol. 1983; 3:2156-2165; Robertson et al., Proc. Natl. Acad. Sci. USA 1996; 93:11334-11340; Robinson et al., Sem. Immunol. 1997; 9:271; and Roizman, Proc. Natl. Acad. Sci. USA 1996; 93:11307-11312. Strategies for probe design are described in WO95/11995, EP 717,113 and WO97/29212.

The present invention further contemplates direct and indirect labelling techniques. For example, direct labelling incorporates fluorescent dyes directly into the nucleotide sequences that hybridize to the array-associated probes (e.g., dyes are incorporated into nucleotide sequence by enzymatic synthesis in the presence of labelled nucleotides or PCR primers). Direct labelling schemes yield strong hybridization signals, typically using families of fluorescent dyes with similar chemical structures and characteristics, and are simple to implement. In some embodiments comprising direct labelling of nucleic acids, cyanine or alexa analogs are utilized in multiple-fluor comparative array analyses. In other embodiments, indirect labelling schemes can be utilized to incorporate epitopes into the nucleic acids either prior to or after hybridization to the microarray probes. One or more staining procedures and reagents are used to label the hybridized complex (e.g., a fluorescent molecule that binds to the epitopes, thereby providing a fluorescent signal by virtue of the conjugation of dye molecule to the epitope of the hybridised species).

Oligonucleotide sequences used as probes according to the present invention may be labeled with a detectable moiety. Various labeling moieties are known in the art. Said moiety may be, for example, a radiolabel (e.g., 3H, 125I, 35S, 14C, 32P, etc.), detectable enzyme (e.g. horse radish peroxidase (HRP), alkaline phosphatase etc.), a fluorescent dye (e.g., fluorescein isothiocyanate, Texas red, rhodamine, Cy3, Cy5, Bodipy, Bodipy Far Red, Lucifer Yellow, Bodipy 630/650-X, Bodipy R6G-X and 5-CR 6G, and the like), a colorimetric label such as colloidal gold or colored glass or plastic (e.g. polystyrene, polypropylene, latex, etc.), beads, or any other moiety capable of generating a detectable signal such as a colorimetric, fluorescent, chemiluminescent or electrochemiluminescent (ECL) signal.

Probes may be labeled directly or indirectly with a detectable moiety, or synthesized to incorporate the detectable moiety. In one embodiment, a detectable label is incorporated into a nucleic acid during at least one cycle of a cyclic polymerase-mediated amplification reaction. For example, polymerases can be used to incorporate fluorescent nucleotides during the course of polymerase-mediated amplification reactions. Alternatively, fluorescent nucleotides may be incorporated during synthesis of nucleic acid primers or probes. To label an oligonucleotide with the fluorescent dye, one of conventionally-known labeling methods can be used (Nature Biotechnology, 14, 303-308, 1996; Applied and Environmental Microbiology, 63, 1143-1147, 1997; Nucleic Acids Research, 24, 4532-4535, 1996). An advantageous probe is one labeled with a fluorescent dye at the 3' or 5' end and containing G or C as the base at the labeled end. If the 5' end is labeled and the 3' end is not labeled, the OH group on the C atom at the 3'-position of the 3' end ribose or deoxyribose may be modified with a phosphate group or the like although no limitation is imposed in this respect.

Spectroscopic, photochemical, biochemical, immunochemical, electrical, optical or chemical means can be used to detect such labels. The detection device and method may include, but is not limited to, optical imaging, electronic imaging, imaging with a CCD camera, integrated optical imaging, and mass spectrometry. Further, the amount of labeled or unlabeled probe bound to the target may be quantified. Such quantification may include statistical analysis. In other embodiments the detection may be via conductivity differences between concordant and discordant sites, by quenching, by fluorescence perturbation analysis, or by electron transport between donor and acceptor molecules.

In yet another embodiment, detection may be via energy transfer between molecules in the hybridization complexes in PCR or hybridization reactions, such as by fluorescence energy transfer (FET) or fluorescence resonance energy transfer (FRET). In FET and FRET methods, one or more nucleic acid probes are labeled with fluorescent molecules, one of which is able to act as an energy donor and the other of which is an energy acceptor molecule. These are sometimes known as a reporter molecule and a quencher molecule respectively. The donor molecule is excited with a specific wavelength of light for which it will normally exhibit a fluorescence emission wavelength. The acceptor molecule is also excited at this wavelength such that it can accept the emission energy of the donor molecule by a variety of distance-dependent energy transfer mechanisms. Generally the acceptor molecule accepts the emission energy of the donor molecule when they are in close proximity (e.g., on the same, or a neighboring molecule). FET and FRET techniques are well known in the art. See for example U.S. Pat. Nos. 5,668,648, 5,707,804, 5,728,528, 5,853,992, and 5,869,255 (for a description of FRET dyes), Tyagi et al. Nature Biotech. vol. 14, p 303-8 (1996), and Tyagi et al., Nature Biotech. vol 16, p 49-53 (1998) (for a description of molecular beacons for FET), and Mergny et al. Nucleic Acid Res. vol 22, p 920-928, (1994) and Wolf et al. PNAS vol 85, p 8790-94 (1988) (for general descriptions and methods fir FET and FRET), each of which is hereby incorporated by reference.

The nucleotide sequences of the present invention may be inserted into vectors. The term "vector" is widely used and understood by those of ordinary skill in the art, and as used herein the term "vector" is used consistent with its meaning to those of ordinary skill in the art. For example, the term "vector" is commonly used by those ordinarily skilled in the art to refer to a vehicle that allows or facilitates the transfer of nucleic acid molecules from one environment to another or that allows or facilitates the manipulation of a nucleic acid molecule.

For example, a vector is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo; i.e., capable of replication under its own control. An "origin of replication" refers to those DNA sequences that participate in DNA synthesis. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences which facilitate the efficient transcription and translation of the inserted DNA fragment are used in connection with the host. The expression vector typically contains an origin of replication, promoter(s), terminator(s), as well as specific genes which are capable of providing phenotypic selection in transformed cells. When the polynucleotide encodes a polyprotein fragment, advantageously, in the vector, an initiation codon (ATG) is placed at 5' of the reading frame and a stop codon is placed at 3'. Other elements for controlling expression may be present, such as enhancer sequences, stabilizing sequences and signal sequences permitting the secretion of the protein. The transformed hosts can be fermented and cultured according to means known in the art to achieve optimal cell growth.

Any vector that allows expression of the immunogens of the present invention may be used in accordance with the present invention. In certain embodiments, the immunogens of the present invention may be used in vitro (such as using cell-free expression systems) and/or in cultured cells grown in vitro. For such applications, any vector that allows expression of the immunogens in vitro and/or in cultured cells may be used.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. A "cDNA" is defined as copy-DNA or complementary-DNA, and is a product of a reverse transcription reaction from an mRNA transcript.

Transcriptional and translational control sequences are DNA regulatory sequences, such as promoters, enhancers, ribosome binding sites, upstream regulatory domains, polyadenylation signals, terminators, and the like, that provide for the expression of a coding sequence in a host cell. A "cis-element" is a nucleotide sequence, also termed a "consensus sequence" or "motif", that interacts with other proteins which can upregulate or downregulate expression of a specific gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes. Not all of these control sequences need always be present in a recombinant vector so long as the desired gene is capable of being transcribed and translated.

A "promoter sequence" is a DNA regulatory region capable of binding RNA polymerase in a cell and initiating transcription of a downstream (3' direction) coding sequence. The promoter sequence is typically bounded at its 3' terminus by the transcription initiation site and extends upstream (5' direction) to include the minimum number of bases or elements necessary to initiate transcription at levels detectable above background. Within the promoter sequence is a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

As used herein, the terms "restriction endonucleases" and "restriction enzymes" refer to enzymes which cut double-stranded DNA at or near a specific nucleotide sequence.

"Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant" or "recombinant molecule".

A cell has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

As used herein, the term "host" is meant to include not only prokaryotes but also eukaryotes such as yeast, plant and animal cells. Prokaryotic hosts may include *E. coli, S. tymphimurium, Serratia marcescens* and *Bacillus subtilis*. Eukaryotic hosts include yeasts such as *Pichia pastoris*, mammalian cells and insect cells and plant cells, such as *Arabidopsis thaliana* and *Tobaccum nicotiana*. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Mandin-Darby bovine kidney ("MDBK") cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insert hosts useful in the present invention include, but are not limited to, *Spodoptera frugiperda* cells.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, the coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. For example, a polynucleotide, may be placed by genetic engineering techniques into a plasmid or vector derived from a different source, and is a heterologous polynucleotide. A promoter removed from its native coding sequence and operatively linked to a coding sequence other than the native sequence is a heterologous promoter.

As used herein, "fragment" or "portion" as applied to a gene or a polypeptide, will ordinarily be at least 10 residues, more typically at least 20 residues, and preferably at least 30 (e.g., 50) residues in length, but less than the entire, intact sequence. Fragments of these genes can be generated by methods known to those skilled in the art, e.g., by restriction digestion of naturally occurring or recombinant fiber or fibritin genes, by recombinant DNA techniques using a vector that encodes a defined fragment of the fiber or fibritin gene, or by chemical synthesis.

Methods for making and/or administering a vector or recombinants or plasmid for expression of gene products of genes of the invention either in vivo or in vitro can be any desired method, e.g., a method which is by or analogous to the methods disclosed in, or disclosed in documents cited in: U.S. Pat. Nos. 4,603,112; 4,769,330; 4,394,448; 4,722,848; 4,745,051; 4,769,331; 4,945,050; 5,494,807; 5,514,375; 5,744,140; 5,744,141; 5,756,103; 5,762,938; 5,766,599; 5,990,091; 5,174,993; 5,505,941; 5,338,683; 5,494,807; 5,591,639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450 and 6; 312,683;

U.S. patent application Ser. No. 920,197, filed Oct. 16, 1986; WO 90/01543; WO91/11525; WO 94/16716; WO 96/39491; WO 98/33510; EP 265785; EP 0 370 573; Andreansky et al., Proc. Natl. Acad. Sci. USA 1996; 93:11313-11318; Ballay et al., EMBO J. 1993; 4:3861-65; Feigner et al., J. Biol. Chem. 1994; 269:2550-2561; Frolov et al., Proc. Natl. Acad. Sci. USA 1996; 93:11371-11377; Graham, Tibtech 1990; 8:85-87; Grunhaus et al., Sem. Virol. 1992; 3:237-52; Ju et al., Diabetologia 1998; 41:736-739; Kitson et al., J. Virol. 1991; 65:3068-3075; McClements et al., Proc. Natl. Acad. Sci. USA 1996; 93:11414-11420; Moss, Proc. Natl. Acad. Sci. USA 1996; 93:11341-11348; Paoletti, Proc. Natl. Acad. Sci. USA 1996; 93:11349-11353; Pennock et al., Mol. Cell. Biol. 1984; 4:399-406; Richardson (Ed), Methods in Molecular Biology 1995; 39, "Baculovirus Expression Protocols," Humana Press Inc.; Smith et al. (1983) Mol. Cell. Biol. 1983; 3:2156-2165; Robertson et al., Proc. Natl. Acad. Sci. USA 1996; 93:11334-11340; Robinson et al. Sem. Immunol. 1997; 9:271; and Roizman, Proc. Natl. Acad. Sci. USA 1996; 93:11307-11312.

The invention also provides for transformed host cells comprising a vector of the invention. In one embodiment, the vector is introduced into the cell by transfection, electroporation or infection. The invention also provides for a method for preparing a transformed cell expressing an immunogen of the present invention comprising transfecting, electroporating or infecting a cell with an expression vector (e.g., a DNA vaccine) to produce an infected producing cell and maintaining the host cell under biological conditions sufficient for expression of the immunogen in the host cell.

According to another embodiment of the invention, the expression vectors are expression vectors used for the in vitro expression of proteins in an appropriate cell system. The expressed proteins can be harvested in or from the culture supernatant after, or not after secretion (if there is no secretion a cell lysis typically occurs or is performed), optionally concentrated by concentration methods such as ultrafiltration and/or purified by purification means, such as affinity, ion exchange or gel filtration-type chromatography methods.

It is understood to one of skill in the art that conditions for culturing a host cell varies according to the particular gene and that routine experimentation is necessary at times to determine the optimal conditions for culturing the vector depending on the host cell. A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means as described above, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

For applications where it is desired that the immunogens be expressed in vivo, for example when the immunogens of the invention are used in DNA or DNA-containing vaccines, any vector that allows for the expression of the immunogens of the present invention and is safe for use in vivo may be used. In preferred embodiments the vectors used are safe for use in humans, mammals and/or laboratory animals.

The vectors used in accordance with the present invention should typically be chosen such that they contain a suitable gene regulatory region, such as a promoter or enhancer, such that the immunogens of the invention can be expressed.

For example, when the aim is to express the immunogens of the invention in vitro, or in cultured cells, or in any prokaryotic or eukaryotic system for the purpose of producing the protein(s) encoded by that immunogen, then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the immunogens under the identified circumstances.

When the aim is to express the immunogens of the invention in vivo in a subject, for example in order to generate an immune response against an HIV antigen and/or protective or therapeutic immunity against HIV, expression vectors that are suitable for expression on that subject, and that are safe for use in vivo, should be chosen. For example, in some embodiments it may be desired to express the immunogens of the invention in a laboratory animal, such as for pre-clinical testing of HIV immunogenic compositions and vaccines of the invention. In other embodiments, it will be desirable to express the immunogens of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications be attenuated to prevent vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

Any vector suitable for administration as a vaccine may be employed in the instant invention. In certain embodiments of the instant invention, vectors suitable for use as DNA vaccines are used, such as pVAX and pcDNA vectors (Invitrogen).

In other embodiments of the present invention, viral vectors are used. Viral expression vectors are well known to those skilled in the art and include, for example, viruses such as adenoviruses (e.g., adenovirus subtypes Ad5, Ad11, Ad26, Ad35, Ad48 and Ad49), adeno-associated viruses (AAV), alphaviruses, retroviruses and poxviruses, including avipox viruses, attenuated poxviruses, and vaccinia viruses, such as the modified vaccinia Ankara virus (MVA). In certain embodiments, a vaccine of the invention comprises an adenovirus selected from Ad5, Ad11, Ad26, Ad35, Ad48 and Ad49. Such viruses, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors.

Following expression, the antigens of the invention can be isolated and/or purified or concentrated using any suitable technique known in the art. For example, anion or cation exchange chromatography, phosphocellulose chromatography, hydrophobic interaction chromatography, affinity chromatography, immuno-affinity chromatography, hydroxyapatite chromatography, lectin chromatography, molecular sieve chromatography, isoelectric focusing, gel electrophoresis, or any other suitable method or combination of methods can be used.

In certain embodiments, the nucleotide sequences and/or antigens of the invention are administered in vivo, for example where the aim is to produce an immunogenic response in a subject. A "subject" in the context of the present invention may be any animal. For example, in some embodiments it may be desired to express the immunogens of the invention in a laboratory animal, such as for pre-clinical testing of HIV immunogenic compositions and vaccines of the invention. In other embodiments, it will be desirable to express the immunogens of the invention in human subjects, such as in clinical trials and for actual clinical use of the immunogenic compositions and vaccine of the invention. In certain embodiments the subject is a human, for example a human that is infected with, or is at risk of infection with, an HIV.

For such in vivo applications the nucleotide sequences and/or antigens of the invention are preferably administered as a component of an immunogenic composition comprising the nucleotide sequences and/or antigens of the invention in admixture with a pharmaceutically acceptable carrier. The immunogenic compositions of the invention are useful to stimulate an immune response against HIV and may be used as one or more components of a prophylactic or therapeutic vaccine against HIV for the prevention, amelioration or treatment of HIV. The nucleic acids and vectors of the invention are useful for providing genetic vaccines, i.e., vaccines for delivering the nucleic acids encoding the antigens of the invention to a subject, such as a human, such that the antigens are then expressed in the subject to elicit an immune response.

Immunogenic Compositions

The term "immunogenic protein or peptide" as used herein also includes peptides and polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises at least one epitope or antigenic determinant. The term epitope relates to a protein site able to induce an immune reaction of the humoral type (B cells) and/or cellular type (T cells).

The term "immunogenic protein or peptide" further contemplates deletions, additions and substitutions to the sequence, so long as the polypeptide functions to produce an immunological response as defined herein.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, suppressor-T cells, and/or cytotoxic T cells and/or γδ T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

Generation of an immunological response may involve antigen presenting cells (APCs). APCs may be "professional" antigen presenting cells or may be another cell that may be induced to present antigen to T cells. APCs include dendritic cells (DCs) such as interdigitating DCs or follicular DCs, Langerhans cells, PBMCs, macrophages, B-lymphocytes, or other cell types such as epithelial cells, fibroblasts or endothelial cells, activated or engineered by transfection to express a MHC molecule (Class I or II) on their surfaces. APCs also include hybridomas, lymphomas, and synthetic APCs such as lipid membranes. Precursors of APCs include CD34+ cells, monocytes, fibroblasts and endothelial cells. Cytokine genes which may promote immune potentiation include IL-2, IL-12, IFN-γ, TNF-α, IL-18, etc. Such proteins include MHC molecules (Class I or Class II), CD80, CD86, or CD40. Examples of T cells include helper T cells (CD4+) and CD8+ cells.

The terms "immunogenic" protein or polypeptide as used herein also refers to an amino acid sequence which elicits an immunological response as described above. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996) J. Immunol. 157:3242-3249; Suhrbier, A. (1997) Immunol. and Cell Biol. 75:402-408; Gardner et al. (1998) 12th World AIDS Conference, Geneva, Switzerland, Jun. 28-Jul. 3, 1998. Immunogenic fragments, for purposes of the present invention, will usually include at least about 3 amino acids, at least about 5 amino acids, at least about 10-15 amino acids, or at least about 25 or more amino acids, of the molecule. There is no critical upper limit to the length of the fragment, which could comprise nearly the full-length of the protein sequence, or even a fusion protein comprising at least one epitope of the protein.

As mentioned earlier, epitope determination procedures, such as, generating overlapping peptide libraries (Hemmer B. et al., Immunology Today, 1998, 19 (4), 163-168), Pepscan (Geysen et al., (1984) Proc. Nat. Acad. Sci. USA, 81, 3998-4002; Geysen et al., (1985) Proc. Nat. Acad. Sci. USA, 82, 178-182; Van der Zee R. et al., (1989) Eur. J. Immunol., 19, 43-47; Geysen H. M., (1990) Southeast Asian J. Trop. Med. Public Health, 21, 523-533; Multipin® Peptide Synthesis Kits de Chiron) and algorithms (De Groot A. et al., (1999) Nature Biotechnology, 17, 533-561), and in PCT Application Serial No. PCT/US2004/022605 all of which are incorporated herein by reference in their entireties, can be used in the practice of the invention, without undue experimentation. Other documents cited and incorporated herein may also be consulted for methods for determining epitopes of an immunogen or antigen and thus nucleic acid molecules that encode such epitopes.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, F(ab')$_2$, Fv and scFv which are capable of binding the epitope determinant. These antibody fragments retain some ability to selectively bind with its antigen or receptor and include, for example:

(i) Fab, the fragment which contains a monovalent antigen-binding fragment of an antibody molecule can be produced by digestion of whole antibody with the enzyme papain to yield an intact light chain and a portion of one heavy chain;

(ii) Fab', the fragment of an antibody molecule can be obtained by treating whole antibody with pepsin, followed by reduction, to yield an intact light chain and a portion of the heavy chain; two Fab' fragments are obtained per antibody molecule;

(iii) F(ab')$_2$, the fragment of the antibody that can be obtained by treating whole antibody with the enzyme pepsin without subsequent reduction; F(ab')2 is a dimer of two Fab' fragments held together by two disulfide bonds;

(iv) scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

A "neutralizing antibody" is one that can neutralize the ability of that pathogen to initiate and/or perpetuate an infection in a host and/or in target cells in vitro. A neutralizing antibody may inhibit the entry of HIV-1 virus with a neutralization index >1.5 or >2.0. Broad and potent neutralizing antibodies may neutralize greater than about 50% of HIV-1 viruses (from diverse clades and different strains within a clade) in a neutralization assay. The inhibitory concentration of the monoclonal antibody may be less than about 25 mg/ml to neutralize about 50% of the input virus in the neutralization assay.

An "isolated antibody" or "non-naturally occurring antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

An "antibody fragment" comprises a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

It should be understood that the proteins, including the antibodies of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated or non-naturally occurring replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

According to the invention, in certain embodiments, administration of a vaccine of the invention can be combined with other vaccinations within the framework of vaccination programs, in the form of immunization or vaccination kits or methods, or in the form of multivalent immunogenic compositions and multivalent vaccines, e.g., comprising at least one vaccine component against a target pathogenic agent, such as HIV, and at least one vaccine component against at least one other pathogenic agent. This also includes the expression by the same expression vector of genes of at least two pathogenic agents.

The invention thus also relates to a multivalent or "cocktail" immunogenic composition or a multivalent or "cocktail" vaccine against a target pathogenic agent, such as HIV, and against at least one other pathogen of the target species, using the same in vivo expression vector containing and expressing at least one polynucleotide of the target pathogenic agent, such as HIV, according to the invention and at least one polynucleotide expressing an immunogen of another pathogen As discussed herein, these multivalent compositions or vaccines can also comprise a pharmaceutically acceptable carrier or vehicle or excipient, and optionally an adjuvant.

The immunogenic compositions or vaccines as discussed herein can also be combined with at least one conventional vaccine (e.g., inactivated, live attenuated, or subunit) directed against the same pathogen or at least one other pathogen of the species to which the composition or vaccines is directed. The immunogenic compositions or vaccines discussed herein can be administered prior to or after the conventional vaccine, e.g., in a "prime-boost" regimen.

Formulations

The compositions of the invention can include any pharmaceutically acceptable carrier known in the art.

To facilitate the administration of a vaccine of the invention, the vaccine can be formulated into suitable pharmaceutical compositions. Generally, such compositions include the active ingredient (e.g., a DNA vaccine) and a pharmacologically acceptable carrier. Such compositions can be suitable for delivery of the active ingredient to a patient for medical application, and can be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention can be formulated in a conventional manner using one or more pharmacologically or physiologically acceptable carriers comprising excipients, as well as optional auxiliaries, which facilitate processing of the active compounds into preparations, which can be used pharmaceutically. Proper formulation is dependent upon the route of administration chosen. Thus, for injection, the active ingredient can be formulated in aqueous solutions, preferably in physiologically compatible buffers. For transmucosal administration, penetrants appropriate to the barrier to be permeated are used in the formulation. Such penetrants are generally known in the art. For oral administration, the active ingredient can be combined with carriers suitable for inclusion into tablets, pills, dragees, capsules, liquids, gels, syrups, slurries, suspensions and the like. For administration by inhalation, the active ingredient is conveniently delivered in the form of an aerosol spray presentation from pressurized packs or a nebuliser, with the use of a suitable propellant. The active ingredient can be formulated for parenteral administration by injection, e.g., by bolus injection or continuous infusion. Such compositions can take such forms as suspensions, solutions or emulsions in oily or aqueous vehicles, and can contain formulatory agents such as suspending, stabilizing and/or dispersing agents. Other pharmacological excipients are known in the art.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/ or non-ionic surfactants such as TWEEN™, PLURONICS™ or polyethylene glycol (PEG).

An immunogenic or immunological composition of the invention, e.g., a DNA vaccine, can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri(caprylate/ caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the PLURONIC® products, e.g., L121. The adjuvant can be a mixture of emulsifier(s), micelle-forming agent, and oil such as that which is commercially available under the name PROVAX® (IDEC Pharmaceuticals, San Diego, Calif.).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

The term "adjuvant" encompasses vaccine adjuvants. A vaccine adjuvant is a component that potentiates the immune responses to an antigen and/or modulates it towards the desired immune responses. See The European Medicines Agency (EMEA) Evaluation of Medicines for Human Use, Guideline on Adjuvants in Vaccines, (2005), page 6. Examples of suitable adjuvants include mineral salts, such as aluminum hydroxide and aluminum or calcium phosphate gels; oil emulsions and surfactant based formulations, e.g., MF59 (microfluidized detergent stabilized oil-in-water emulsion), QS21 (purified saponin), AS02 [SBAS2] (oil-in-water+MPL+QS-21), Montanide ISA-51 and ISA-720 (stabilized water-in-oil emulsion); particulate adjuvants, e.g., virosomes (unilamellar liposomal vehicles incorporating influenze hemagglutinin), AS04 ([SBAS4] Al salt with MPL), ISCOMS (structured complex of saponins and lipids), polylactide co-glycolide (PLG); microbial derivatives (natural and synthetic), e.g., monophosphoryl lipid A (MPL), Detox (MPL+$M.$ $Phlei$ cell wall skeleton), AGP [RC-529] (synthetic acylated monosaccharide), DC_Chol (lipoidal immunostimulators able to self-organize into liposomes), OM-174 (lipid A derivative), CpG motifs (synthetic oligonucleotides containing immunostimulatory CpG motifs), modified LT and CT (genetically modified bacterial toxins to provide non-toxic adjuvant effects); endogenous human immunomodulators, e.g., hGM-CSF or hIL-12 (cytokines that can be administered either as protein or plasmid encoded), Immudaptin (C3d tandem array); and inert vehicles, such as gold particles. Id.

Adjuvants that enhance the effectiveness of the vaccine may also be added to the formulation. Further to the above, adjuvants include, but are not limited to, mineral salts (e.g., $AlK(SO_4)_2$, $AlNa(SO_4)_2$, $AlNH(SO_4)_2$, silica, alum, $Al(OH)_3$, $Ca_3(PO_4)_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et at (2002) Eur. J. Immunol. 32(7): 1958-68; poly IC or poly AU acids, polyarginine with or without CpG (also known in the art as IC31; see Schellack, C. et al (2003) Proceedings of the 34$^{th}$ Annual Meeting of the German Society of Immunology; Lingnau, K. et at (2002) Vaccine 20(29-30): 3498-508), JuvaVax™ (U.S. Pat. No. 6,693,086), certain natural substances (e.g., wax D from $Mycobacterium$ $tuberculosis$, substances found in $Cornyebacterium$ $parvum$, $Bordetella$ $pertussis$, or members of the genus $Brucella$), flagellin (Toll-like receptor 5 ligand; see McSorley, S. J. et at (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, A. K. et al (2004) 22(13-14): 1791-8), and the CCR5 inhibitor CMPD167 (see Veazey, R. S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA1-DD/ISCOMs (see Mowat, A. M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IGF-1, IFN-α, IFN-β, and IFN-γ (Boyer et al., (2002) J. Liposome Res. 121:137-142; WO01/095919), immunoregulatory proteins such as CD40L (ADX40; see, for example, WO03/063899), and the CDIa ligand of natural killer cells (also known as CRONY or α-galactosyl ceramide; see Green, T. D. et al, (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the antigens of the invention or on separate expression vectors.

The oil in water emulsion, which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters. The oil is used in combination with emulsifiers to form an emulsion. The emulsifiers may be nonionic surfactants, such as: esters of on the one hand sorbitan, mannide (e.g., anhydromannitol oleate), glycerol, polyglycerol or propylene glycol and on the other hand oleic, isostearic, ricinoleic or hydroxystearic acids, said esters being optionally ethoxylated, polyoxypropylene-polyoxyethylene copolymer blocks, such as Pluronic, e.g., L121.

For maleic anhydride-alkenyl derivative copolymers, EMA (Monsanto) may be used, which are straight-chain or crosslinked ethylene-maleic anhydride copolymers and they are, for example, crosslinked by divinyl ether. Reference is also made to J. Fields et al., Nature 186: 778-780, Jun. 4, 1960. With regard to structure, the acrylic or methacrylic acid polymers and EMA are preferably formed by basic units having the following formula in which: R1 and R2, which can be the same or different, represent H or CH3, x=0 or 1, preferably x=1, y=1 or 2, with x+y=2. For EMA, x=0 and y=2 and for carbomers x=y=1. These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 (incorporated herein by reference) which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL® (BF Goodrich, Ohio, USA) are particularly appropriate. They are cross-linked with an allyl sucrose or with allyl pentaerythritol. Among then, there may be mentioned CARBOPOL® 974P, 934P and 971P. Among the copolymers of maleic anhydride and alkenyl derivative, the copolymers EMA® (Monsanto) which are copolymers of maleic anhydride and ethylene, linear or cross-linked, for example cross-linked with divinyl ether, are preferred. Reference may be made to J. Fields et al., Nature, 186: 778-780, 4 Jun. 1960, incorporated herein by reference.

The term "liposome" as used herein encompasses smectic mesophases, which may comprise either phospholipid or nonphospholipid smectic mesophases. See, for example, "smectic mesophase" in Small, D. M., in "The Physical Chemistry of Lipids, From Alkanes to Phospholipids" Handbook of Lipid Research, Vol, 4, Plenum, N.Y., 1986, pp. 49-50, which states that "[w]hen a given molecule is heated, instead of melting directly into an isotropic liquid, it may instead pass through intermediate states called mesophases or liquid crystals, characterized by residual order in some directions but by lack of order in others . . . . In general, the molecules of liquid crystals are somewhat longer than they are wide and have a polar or aromatic part somewhere along the length of the molecule. The molecular shape and the polar-polar, or aromatic, interaction permit the molecules to align in partially ordered arrays . . . . These structures characteristically occur in molecules that possess a polar group at one end. Liquid crystals with long-range order in the direction of the long axis of the molecule are called smectic, layered, or lamellar liquid crystals . . . . In the smectic states the molecules may be in single or double layers, normal or tilted to the plane of the layer, and with frozed or melted aliphatic chains." See also FIGS. 3-4 of Small.

Advantageously, the immunogenic compositions and vaccines according to the invention comprise an effective quantity to elicit an immunological response and/or a protective immunological response of one or more expression vectors and/or polypeptides as discussed herein; and, an effective quantity can be determined from this disclosure, including the documents incorporated herein, and the knowledge in the art, without undue experimentation. The immunogenic compositions can be designed to introduce the antigens, nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Administration

Suitable dosages of the antigens, nucleic acids and expression vectors of the invention (collectively, the immunogens) in an immunogenic composition of the invention can be readily determined by those of skill in the art. For example, the dosage of the immunogens can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

Assays for assessing the cellular response to HIV vaccines of the instant invention include intracellular staining (e.g., flow cytometry) and ELISPOT (an enzyme-linked immunosorbent assay format), which allow detecting and counting cells producing cytokines (e.g., TNFα and IFN-γ) in response to antigens. For example, isolation of splenocytes or peripheral blood monocyte cells (PBMCs) from animals or human patients followed by in vitro challenge with an HIV epitope such as 2F5 or 4E10, and finally testing by ELISPOT and/or intracellular cytokine staining (ICS), can determine the potential for a cell-mediated immune response in vaccine recipients. Flow cytometry using tetramers (e.g., molecules consisting of four copies of a given class I molecule bound to their cognate peptide and alkaline phosphatase) allows the enumeration of antigen-specific T cells (e.g., detection of T cells that recognize specific peptides bound to major histocompatibility complex (MHC) class I molecules). A standard chromium release assay can be used to assess cytotoxicity. To assess a cell-mediated immune response to a DNA vaccine, the more traditional approaches of measuring T cell proliferation in response to antigen and CTL-mediated killing of autologous cells expressing HIV epitopes can also be used.

ELISA assays and Western blots can be used to assess humoral immune responses. In particular, ELISA and Western blots can be used to assess antibody binding, antibody neutralizing capability, antibody-mediated fusion inhibition, and antibody-dependent cytotoxicity.

An MT-2 assay can be performed to measure neutralizing antibody responses. Antibody-mediated neutralization can be measured in an MT-2 cell-killing assay as described previously (Montefiori et al., 1988, J. Clin. Microbiol., 26:231-237). The inhibition of the formation of syncytia by the sera shows the activity of neutralizing antibodies present within the sera, induced by vaccination. Briefly, vaccinated test and control sera can be exposed to virally infected cells (e.g., MT-2 T cell line). Neutralization can be measured by staining viable cells (e.g., with Finter's neutral red when cytopathic effects in control wells are about >70% but less than 100%). Percentage protection can be determined by calculating the difference in absorption ($A_{540}$) between test wells (cells+virus) and dividing this result by the difference in absorption between cell control wells (cells only) and virus control wells (virus only). Neutralizing titers are then expressed as the reciprocal of the plasma dilution required to protect at least 50% of cells from virus-induced killing.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions can serve to provide protective immunity of a subject against HIV infection or to prevent or attenuate the progression of AIDS in a subject already infected with HIV. When provided therapeutically, the immunogenic compositions can serve to ameliorate and treat AIDS symptoms and are advantageously used as soon after infection as possible, preferably before appearance of any symptoms of AIDS but may also be used at (or after) the onset of the disease symptoms.

Suitable doses of nucleic acid compositions for humans can range from 1 μg/kg to 1 mg/kg of total nucleic acid, e.g., from 5 μg/kg-500 mg/kg of total DNA, 10 μg/kg-250 μg/kg of total DNA, or 10 μg/kg-170 μg/kg of total DNA. In one embodiment, a human subject (18-50 years of age, 45-75 kg) is administered 1.2 mg-7.2 mg of DNA. DNA vaccines can be administered multiple times, e.g., between two-six times, e.g., three times. In a particular embodiment, 100 μg of a DNA composition is administered to a human subject at 0, 4, and 12 weeks (100.mu.g per administration).

An example of range for an immunogenic amount of protein composition is 5 μg/kg-500 μg/kg, e.g., 10-100 μg/kg of total protein, with adjuvant. In one embodiment, a dose of 325 μg of a protein composition is administered to a human (18-55 years of age, 45-75 kg).

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Additional methods of delivery of DNA to animal tissue include electroporation, jet injection, sonoporation, microneedle-assisted delivery, etc. Alternatively, delivery routes can be oral, intranasal or by any other suitable route. Delivery also be accomplished via a mucosal surface such as the anal, vaginal or oral mucosa.

Immunization schedules (or regimens) are well known for animals (including humans) and can be readily determined for the particular subject and immunogenic composition. Hence, the immunogens can be administered one or more times to the subject. In certain embodiments, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks and up to 6 months or more. With DNA tatooing, the interval is typically only 3 days (e.g., 0, 3, and 6 days). The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector).

The immunogenic compositions of the invention can be administered alone, or can be co-administered, or sequentially administered, with other immunogens and/or immunogenic compositions, e.g., with "other" immunological, antigenic or vaccine or therapeutic compositions thereby providing multivalent or "cocktail" or combination compositions of the invention and methods of employing them. For example, in some embodiments, an HIV Env protein of the instant invention is administered in a viral vector, such as an MVA, which also comprises genes encoding one or more other HIV proteins, such as, e.g., gag and pol. Again, the ingredients and manner (e.g., sequential or co-administration) of administration, as well as dosages can be determined taking into consideration such factors as the age, sex, weight, species and condition of the particular subject, and the route of administration.

In certain embodiments, the immunogenic compositions of the invention are administered to a mammal. In further embodiments, the mammal is a human, a non-human primate, a dog, a rabbit, a guinea pig, or a mouse.

Those of ordinary skill in the art can easily make a determination of the proper dosage of a protein subunit and/or DNA vaccine. Generally, certain factors will impact the dosage that is administered; although the proper dosage is such that, in one context, in embodiments where a DNA vaccine is administered, the exogenous gene is expressed and the gene product is produced in the particular cell of the mammal. Preferably, the dosage is sufficient to have a therapeutic and/or prophylactic effect on the animal.

Combination Therapies

The methods of treating subjects infected with HIV with the compositions of the instant invention can include combination therapies, in which other HIV treatments are administered. For example, a subject undergoing HIV Env protein subunit vaccination according to the instant invention can be administered anti-retroviral drugs individually, or in combination, for example, with various combinations of nucleoside reverse transcriptase inhibitors, non-nucleoside reverse transcriptase inhibitors, and HIV protease inhibitors.

Nucleoside reverse transcriptase inhibitors include, e.g., zidovudine (AZT); didanosine (ddI); zalcitabine (ddC); stavudine (d4T); lamivudine (3TC); abacavir (1592U89);

adefovir dipivoxil [bis(POM)-PMEA]; lobucavir (BMS-180194); and lodenosine (FddA), 9-(2,3-dideoxy-2-fluoro-b-D-threo-pentofuranosyl)adenine.

Non-nucleoside reverse transcriptase inhibitors include nevirapine (BI-RG-587); delaviradine (BHAP, U-90152); and efavirenz (DMP-266).

Protease inhibitors include saquinavir (Ro 31-8959); ritonavir (ABT-538); indinavir (MK-639); nelfnavir (AG-1343) available under the VIRACEPT™ tradename from Agouron Pharmaceuticals, Inc.; amprenavir (141W94), a non-peptide protease inhibitor, tradename AGENERASE™; and lasinavir (BMS-234475).

Kits

The compositions of the instant invention and their methods of use are ideally suited for preparation of kits. HIV Env nucleic acid and/or protein may be provided in containers that can be in any form, e.g., lyophilized, or in solution (e.g., a distilled water or buffered solution), etc. In the kits of the invention, a set of instructions will typically be included.

The kits can include one or more other elements including: other reagents, e.g., a diluent, devices or other materials for preparing the composition for administration; pharmaceutically acceptable carriers; and devices or other materials for administration to a subject. Instructions for use can include instructions for therapeutic application including suggested dosages and/or modes of administration, e.g., in a human subject, as described herein.

The kit can further contain at least one additional reagent, such as a diagnostic or therapeutic agent, e.g., a diagnostic agent to monitor a response to immune response to the compositions in the subject, or an additional therapeutic agent as described herein.

In one embodiment, the kit includes a vial (or other suitable container) containing one or more recombinant HIV Env proteins of the instant invention. In certain embodiments, the kit further includes an adjuvant and an excipient. The adjuvant and the excipient are formulated with the protein, and can be included in the formulation or packaged separately within the kit.

The invention will now be further described by way of the following non-limiting examples.

Example 1

Ba-L gp140 DC 4E10

The HIV-1 Ba-L gp160 gene, minus the signal peptide was codon optimized and synthesiszed at Geneart. The gp120/gp41 cleavage site was altered to prevent cleavage: Arg 501 and Arg 509 were changed to Serines. The gp140 DC 4E10 sequence was amplified by PCR and inserted into the pJWIRES expression plasmid in frame with the tPa signal. The amino terminus begins with E(30) and the carboxyl terminus ends at . . . WLWYIK(681) (SEQ ID NO: 45) with an additional KKK added to help solubility. The pJWIRES includes the following:

Expression of the inserted gene is driven by the CMV promotor and Bovine Growth Hormone (BGH) Poly A. It has puromycin acetyl transferase gene linked to the inserted gene through IRES sequence for Puromycin resistance.

The resulting construct is referred to as pJW Ba-L gp140 DC 4E10 Puro (FIG. 1).

Figure 2:
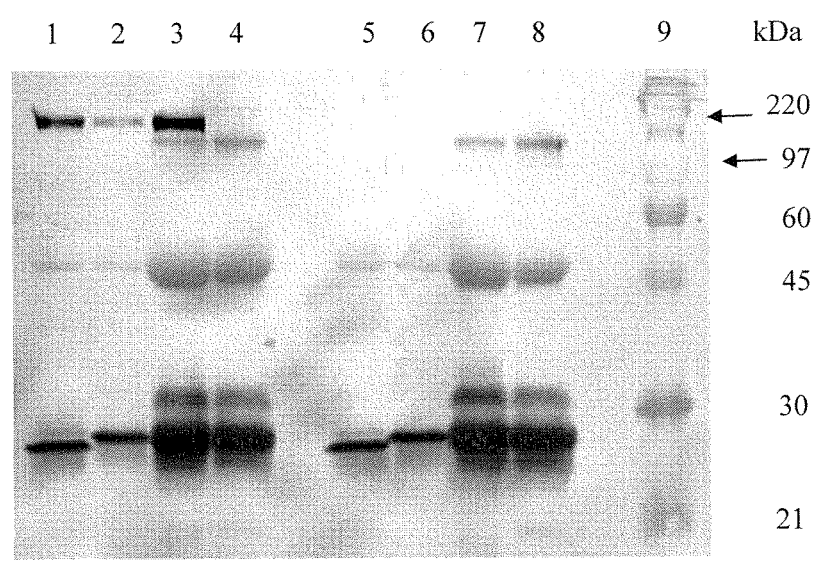
FIG. 2: Immunoprecipitation Western Blot of 293/pJW Ba-L gp140 DC 4E10 Puro transfection. Conditioned media of 293 cells transfected with pJW Ba-L gp140 DC 4E10 Puro and naïve cells are immunoprecipitated with Human monoclonal antibodies to the MPER region (2F5 and 4E10), HIV-1 (+) human serum and normal human serum. Precipitated proteins are resolved on 12.5% SDS-PAGE and transferred to PVDF. Ba-L gp140 DC 4E10 proteins are detected with MoAb to gp41 (M25) followed by Goat anti-mouse IgG AP conjugate, and BCIP/NBT substrate. Ba-L gp140 DC 4E10 is detected with 4E10 (lane 1), 2F5 (lane 2) and HIV-1(+) human serum (lane 3), and not detected with normal human serum (lane 4). No band corresponding to Ba-L gp140 DC 4E10 is detected in the naïve sample with 4E10 (lane 5), 2F5 (lane 6) and HIV-1(+) human serum (lane 7) or normal human serum (lane 8).

Transfection studies were performed using HEK 293 cells using lipofectamine 2000. IP western blot of the conditioned media using 4E10 and 2F5 Human MPER antibodies (Polymun Scientific GmbH, Klosterneuburg, Austria) showed reactivity with the gp140 DC 4E10 as shown in FIG. 2.

See also FIGS. 3-4 for the nucleic acid and protein sequences of the Clade B sequence, Ba-L gp140 DC 4E10.

FIGS. 5-6 depict the nucleic acid and protein sequences for a second modified Clade B sequence, Ba-L gp145.

Example 2

Clade D gp140 Methods

Cell Line Development and Molecular Cloning

Chinese Hamster Ovary (CHO) cell lines stably expressing the extracellular domains of gp160 (gp140) for 3 HIV-1 clade D isolates were developed. The goal was to develop cell lines that secrete high levels of gp140 that can be purified and be used in HIV-1 vaccine development. The isolates chosen for gp140 expression are A07412 (parent sequence, GenBank Accession No. AF484477; see also GenBank Accession No. AY736828), 57128 (parent sequence, GenBank Accession No. AF484502; see also GenBank Accession No. AY736829) and 57140 (parent sequence, GenBank Accession No. AF484511). In order to maximize expression in this system, the gp140 codes were created synthetically at GENEART. Through this process, the genes were codon optimized for expression in human cells by designing the genes using codons that correspond to the most abundant tRNAs present in human cells. Human codon optimization is ideal for any DNA vaccine component to be used in humans, but is also quite effective in yielding high levels of expression in CHO. In addition to codon optimization, the synthetic genes were also designed to eliminate various cis-acting elements that can reduce transcription/translation efficiency (such as splice sites, poly A sites, adenine-rich elements, the Rev Responsive Elements (RRE), and other mRNA secondary structures) as well as other motifs (such as GC-rich stretches, internal TATA boxes, Qui site) that may destabilize mRNA.

For each isolate, the gp140 genes were mutated at the primary and secondary gp120/gp41 cleavage sites using a PCR-based process. This was done to prevent gp120/gp41 cleavage, resulting in stable gp140 molecules upon secretion. In addition, the native signal peptide for each was removed so that the efficient Tissue Plasminogen Activator (tPA) signal in the expression vector can be used as the secretory signal. The gp140 codes each have a stop codon inserted just prior to the Transmembrane (TM) Domain to prevent the gp140 from being bound to the cell membrane upon secretion. The gp140 genes were ligated into the mammalian expression vector pJWTCDE-N at the NheI and EcoRI sites for stable expression in CHO cells.

A07412

The amino acid sequence of the amino terminus is SL(30) WVT . . . (SEQ ID NO: 46), and the carboxyl terminus is . . . FSITK(673)-Stop (SEQ ID NO: 47). The amino terminal serine is a foreign residue from the NheI cloning site at the end of the tPa signal. The gp120/gp41 cleavage site was altered from RAKRRVVEREKR(507) (SEQ ID NO: 48) to RAKSRVVEREKS (SEQ ID NO: 49). See also FIG. 51, SEQ ID NO: 3.

57140

The amino acid sequence of the amino terminus is SL(33) WVT . . . (SEQ ID NO: 46), and the carboxyl terminus is . . . FSISN(673)-Stop (SEQ ID NO: 50). The amino terminal serine is a foreign residue from the NheI cloning site at the end of the tPa signal. The gp120/gp41 cleavage site was altered from RAKRRVVEREKR(507) (SEQ ID NO: 48) to RAKSRVVEREKS (SEQ ID NO: 49). See also FIG. 51, SEQ ID NO: 4.

57128

The amino acid sequence of the amino terminus is SL(33) WVT . . . (SEQ ID NO: 46), and the carboxyl terminus is . . . FSITK(671)-Stop (SEQ ID NO: 47). The amino terminal serine is a foreign residue from the NheI cloning site at the end of the tPa signal. The gp120/gp41 cleavage site was altered from KARRRVVEREKR(507) (SEQ ID NO: 51) to KARSRVVEREKS (SEQ ID NO: 52). See also FIG. 51, SEQ ID NO: 5.

Figure 7:
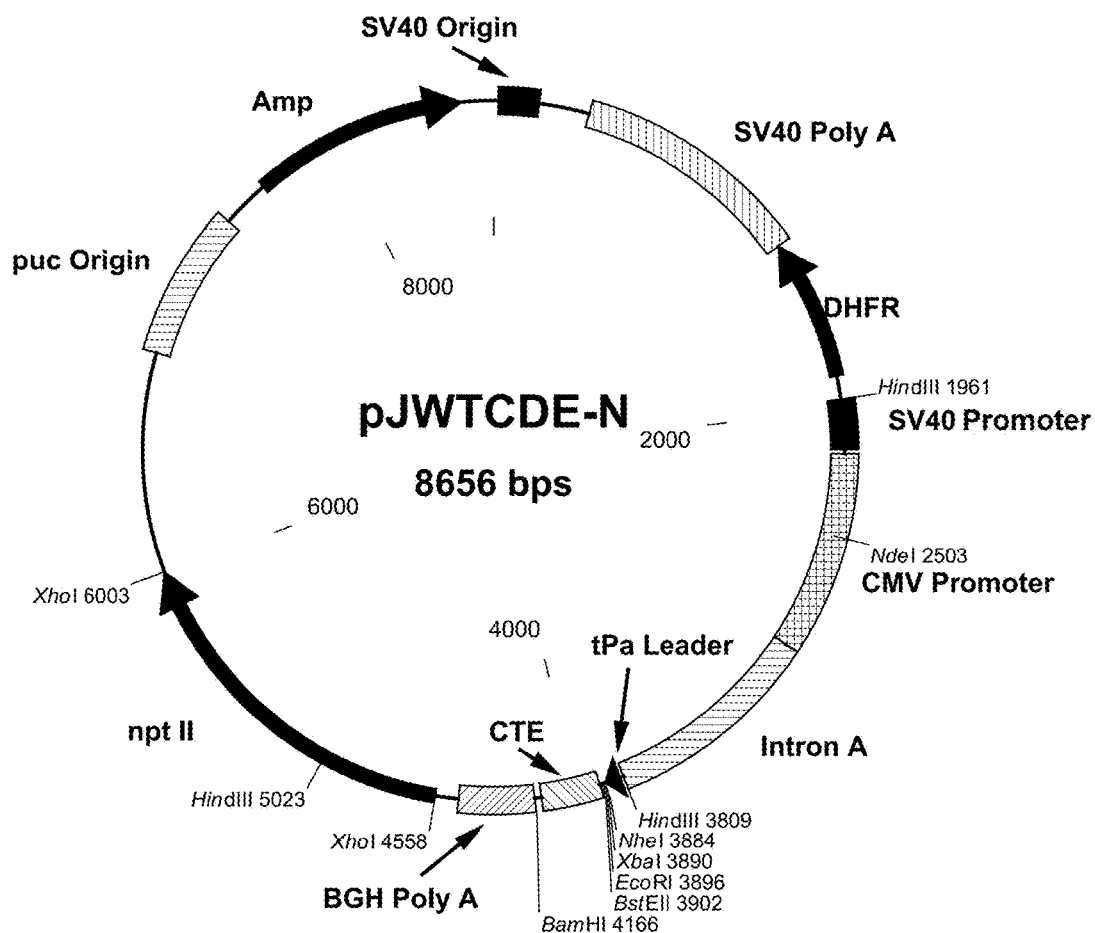
FIG. 7: Mammalian expression plasmid pJWTCDE-N.
Figure 17:
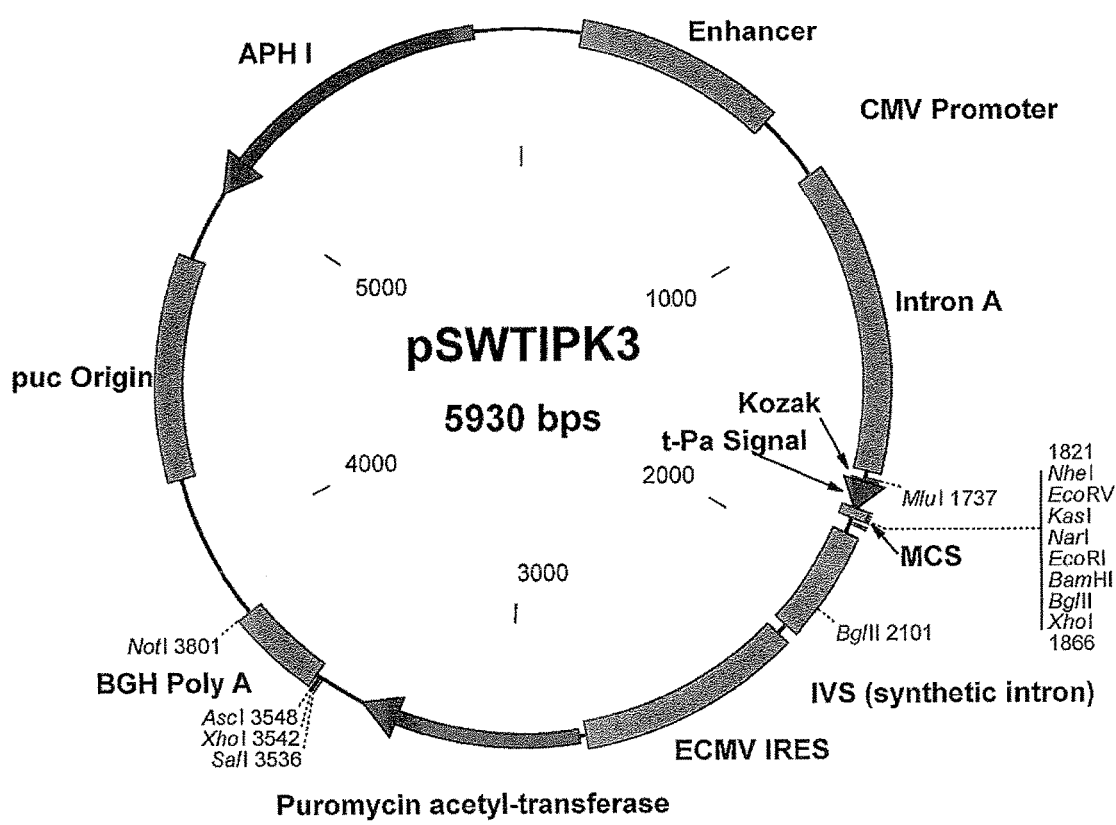
FIG. 17 is a schematic of the pSWTIPK3 vector.

The pJWTCDE-N contains the following elements for efficient expression of foreign genes in CHO cells (FIG. 7):

(1) Transcription of the gp140 genes are driven by the CMV promoter/intron A and Bovine Growth Hormone (BGH) Poly A
(2) Neomycin Phosphotransferase II (NPT II) gene, driven by the SV40 promoter and a synthetic poly A for the selection of stably transfected cells under G418 Sulfate selection.
(3) Dihydrofolate Reductase (DHFR) gene, driven by a partially crippled SV40 promoter and SV40 poly A for fairly weak expression of DHFR in transfected Cells. This facilitates selection in nucleoside-free media as well as inducing gene amplification of the foreign DNA through treatment with the DHFR inhibitor Methotrexate (MTX). This gene amplification can greatly increase the level gp140 production along with the increase in DHFR production needed to sustain life in MTX-containing media.

After cloning the expression vectors for each, sequencing of the inserted gp140 genes are performed to ensure proper construction.

To Establish Stable CHO Cell Lines Secreting gp140, CHO Cells Deficient in DHFR (CHO-dhfr-) were transfected using Lipofectamine 2000 (Gibco). Transfected cells were analyzed in a gp120 antigen capture assay and in radioimmunoprecipitation (RIP) with HIV-1 (+) human serum to detect the presence and quality of gp140 production. Transfected cells were plated into 96-well plates for selection in alpha MEM with 10% dialyzed Fetal Bovine Serum and 550 µg/mlG418 Sulfate. Surviving cells were screened with a gp120 antigen capture assay, and fairly high gp140 producers were selected for expansion and single-cell cloning.

The gp120 antigen capture assay is an ELISA-based assay for the detection and quantification of gp120 protein. Molecules, such as gp140 and the later described gp140 DC 4E10 and gp145 proteins, which contain the gp120 sequence, can also be detected with this assay. The microtiter wells in a 96-well plate are coated with two murine monoclonal antibodies that react with unique epitopes on HIV-1 gp120. When gp120 standard solutions or tissue culture test samples are added to the wells, an immune complex forms with the plate-bound antibodies and the gp120 in solution. Unbound materials are then thoroughly washed away. The conjugate solution, containing peroxidase-conjugated human anti-gp120 polyclonal antibodies is then added. The conjugated antibodies complex with other epitopes on the captured gp120. After washing away the unbound conjugate solution, the peroxidase substrate is added. The enzyme-substrate reaction results in the substrate's blue color change. Upon adding the stop solution (2 N sulfuric acid), the blue changes to yellow, which can be quantitatively measured by reading the absorbance at 450 nm. The amount of gp120 in the gp120 standards and test samples is relative to the absorbance. The concentration of gp120 in a test sample can be calculated based on the standard curve.

True clones were compared to find a few strong producers using a gp120 antigen capture assay and RIP. The best were treated with 0.02 µM MTX to facilitate gene amplification of the foreign DNA. Once cells were able to grow at normal rates in MTX, they were cloned again to find higher producers. Cell lines were cloned by limiting dilution, analyzed for optimum expression and adapted for growth in the protein-free media HyQPFCHO Liquid Soy (HyClone; Logan, Utah).

Protein Purification

Conditioned media from CHO cultures were harvested by centrifugation and concentrated with tangential flow 100 kDa molecular weight cutoff filters to about 2 L. Media was buffered with phosphate buffer, and pH was adjusted to 7.2. Sodium chloride concentration was adjusted to 300 mM, and media was filtered with 0.22 micron filter. Media was passed through a GNL agarose (Vector Laboratories; Burlingame, Calif.) column, and Env proteins were eluted in PBS containing 500 mM methyl α-D-mannopoyranoside. Media was passed on the GNL agarose column 3-4 additional times to remove all of the Env protein from the conditioned media. Additional procedures were performed to further purify the Env proteins. The sodium chloride concentration of the GNL agarose eluates were adjusted to 212 mM and passed through a column of Q-sepharose (Amersham Biosciences; Piscataway, N.J.). The high molecular weight impurities bind Q-sepharose, but Env does not under these conditions. To disrupt any abnormal multimers formed through air oxidation, the Q sepharose treated Env proteins were concentrated to about 3 ml and treated with 50 mM DTT for 15 hours at 4° C., followed by 1 hour at 21° C. DTT treated preparations were then run on a Superdex 200 26/60 (Amersham Biosciences) gel filtration column to remove additional high and low molecular weight impurities, as well as to reduce the amount of Env breakdown products. The column was run at 0.5 ml/min. in PBS containing 1 mM DTT. Fractions containing the purest Env proteins, as analyzed on SDS-PAGE, were pooled. Proteins were then buffer exchanged on 10 ml PD-10 columns (Amersham Biosciences) equilibrated with PBS. Finally, proteins were filtered with 0.22 µm filters, aliquoted and stored at −70° C.

Example 3

Introduction

Plasmid DNA constructs expressing the Env proteins of four subtype C isolates isolated from patients at the acute and early seroconversion stages of infection were developed and tested to downselect the best candidate for gp145 expression. Isolate C06980v0c22 was selected, stable cell lines expressing C06980v0c22 gp145 were developed, and research cell banks were produced. Purified gp145 protein was produced and supplied for study in preclinical immunogenicity studies.

As described above, Applicants collaborated on the development of a subtype D HIV-1 subunit vaccine. Sequences for 4 subtype D HIV-1 isolates were provided and several gp140 and gp120-secreting CHO cell lines were prepared. Cell lines were adapted to serum-free media and the Env proteins purified for preclinical immunogenicity studies. Small animals were immunized and gp140 and gp120-specific serum antibody binding titers evaluated by ELISA and neutralizing antibody titers against the homologous primary isolate evaluated using the pseudotype assay. While all gp120 and gp140 proteins were immunogenic, none elicited detectable neutralizing antibody against the homologous pseudotyped isolate.

HIV Env subunit vaccine efforts were pursued using subtype C Env sequences with the goal of eliciting more potent and broadly neutralizing antibody responses. As discussed above, a DNA construct had been developed encoding modifications of the HIV-1 Ba-L (Subtype B) Env. This construct coded for a truncated gp160 molecule referred to as gp145. This gp145 protein includes a modified tissue plasminogen activator (t-Pa) signal peptide upstream of a cleavage deficient gp160 that is truncated at the end of the membrane proximal external region (MPER). At the C terminus, three additional lysine residues were included, theoretically to increase the hydrophilicity of the C tail in order to present potentially neutralizing MPER epitopes to the immune system. Unlike the previous gp140 molecules discussed above, this gp145 molecule reacted to the neutralizing anti-MPER huMAb 4E10 in ELISA and western blot.

Subtype C is known to be the most common international subtype, and since preliminary data suggested subtype C infections may induce the most broadly cross-reactive HIV-1 neutralizing response in natural infection, subtype C sequences were investigated. A gp145 construct was proposed to be created using a primary CCR5-dependant subtype C Env sequence. Stable CHO cell lines expressing this Env protein were developed.

Envelope Downselection

The env sequences from 4 subtype C strains were provided for codon optimization and synthesis. Transient expression studies were performed to select which isolate would be used for further gp145 development.

An electronic copy was provided of four. South African subtype C R5 HIV-1 envelope sequences from three acute (C06838v1c48, C06980v0c22 and C3728v2c6) and one early seroconverted (C06980v1c3) HIV-1 infections. Two of the sequences are from the same individual, one during acute infection (C06980v0c22) and the other after seroconversion (C06980v1c3).

In order to maximize expression in Chinese Hamster Ovary (CHO) cells, the env genes were synthesized incorporating C. griseus (Chinese Hamster) codon bias by Geneart AG (Regensberg, Germany). To further optimize expression, cis-acting motifs that can reduce translational efficiency were eliminated (e.g., internal TATA boxes, chi-sites, ribosomal entry sites, RNA secondary structure, repeat sequences, etc.). Two versions of each env gene were synthesized: a) gp160, full-length gp160 minus the native signal peptide and b) gp160 DC, full-length gp160 minus the native signal peptide and with mutations in the gp120/gp41 primary and secondary cleavage sites to prevent protease cleavage.

The translations of the four gp160 (WT) and gp160 DC (cleavage mutant) genes are compared (FIG. 35). Molecules are shown as the sequences following the t-Pa signal peptide cleavage in the expressed proteins. The shaded regions are areas of variability. The boxed region highlights the gp120/gp41 cleavage sites; arginine to serine mutations in the gp160DC genes prevent the proteolytic cleavage. The gp160 genes were cloned into pSWTIPK3, a proprietary mammalian expression plasmid (Advanced BioSciences Laboratories, Inc.), at the NheI and EcoRI sites, in frame with the tPa signal peptide (FIG. 8). The native leader sequences are replaced by the tPa signal peptide, which provides a more efficient secretion signal, enhancing gp160 production and transport to the cell membrane. The expression plasmids contain the Cytomegalovirus (CMV) promoter to control expression. The plasmids were expanded and purified from transformed *Escherichia coli*, and the gp160 coding regions were sequenced to confirm sequence identity.

Chinese hamster ovary cells (CHO-K1) and Human embryonic kidney cells (HEK293; clone 293H) cells were transfected and analyzed for gp160 production in western blot and antigen capture ELISA. Based on production quality and quantity of gp160 molecules, a decision was made which isolate will be used to develop CHO cell lines producing the gp145 protein. Cells were transfected with the four gp160 and gp160DC plasmid constructs using lipofection (Lipofectamine 2000; Invitrogen, Carlsbad, Calif.). Cultures transfected with HIV-1Ba-L gp145, HIV-1Ba-L gp160 or HIV-1 subtype C gp140 expression constructs served as positive controls. Naïve CHO-K1 and HEK293 served as negative controls. Media and cell lysates were harvested 48 hours post-transfection for analysis.

Figure 19:
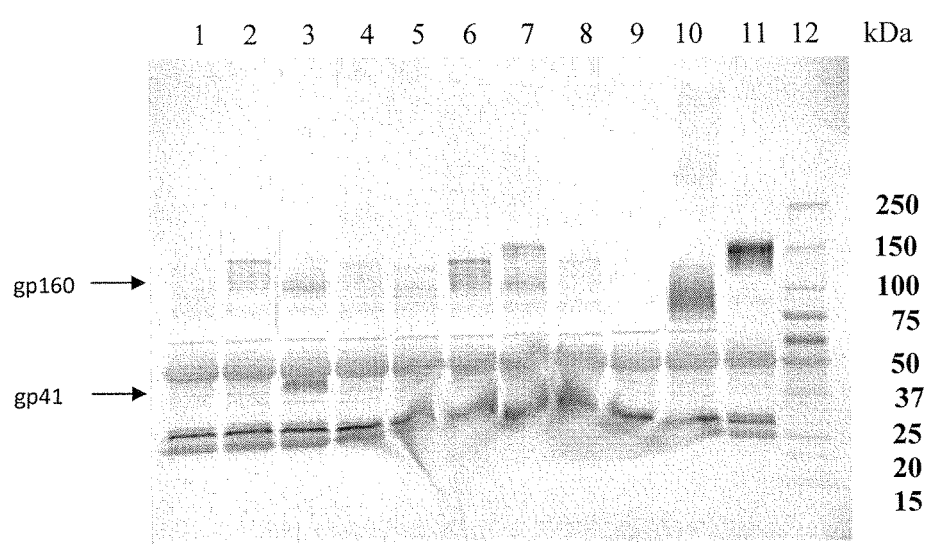
FIG. 19: IP western blot of CHO-K1 cells transfected with HIV-1 subtype C gp160 and gp160 DC expression plasmids. Env proteins are immunoprecipitated from the 48 hr. post-transfection cell lysates using HIV-1 (+) human serum, resolved on 4-15% SDS-PAGE and transferred to PVDF. Proteins from the following constructs were detected using rabbit antibodies to HIV-1 subtype B gp160: C06838v1c48 gp160 (lane 1), C06980v1c3 gp160 (lane 2), C06980v0c22 gp160 (lane 3), C3728v2c6 gp160 (lane 4), C06838v1c48 gp160DC (lane 5), C06980v1c3 gp160DC (lane 6), C06980v0c22 gp160DC (lane 7), C3728v2c6 gp160DC (lane 8), naïve CHO-K1 (−) control (lane 9), Ba-L gp145 (+) control (lane 10) and subtype C 96ZM651 gp140 (+) control (lane 11). Molecular weight protein markers are run in lane 12.

Media and cell lysate samples from CHO-K1 transfections were evaluated for gp41/gp120/gp160 content via IP western blot using an HIV-1 positive human serum for immunoprecipitation and an HIV-1Ba-L gp160 immunized rabbit's serum for detection. No Env expression was detected in the media for any construct except the Ba-L gp145 control (data not shown). If gp160 is processed into gp41 and gp120, the gp120 could shed into the media; the amount of shed gp120 is below the assay detection limit. From the cell lysates, Env expression is evident with each of the subtype C gp160 and gp160DC constructs (FIG. 19). Each construct produces gp160; each isolate runs at a different size, likely due to different glycosylation patterns. Only pSWC06980v0c22 gp160 shows gp160 processing into gp120 and gp41.

Figure 20:
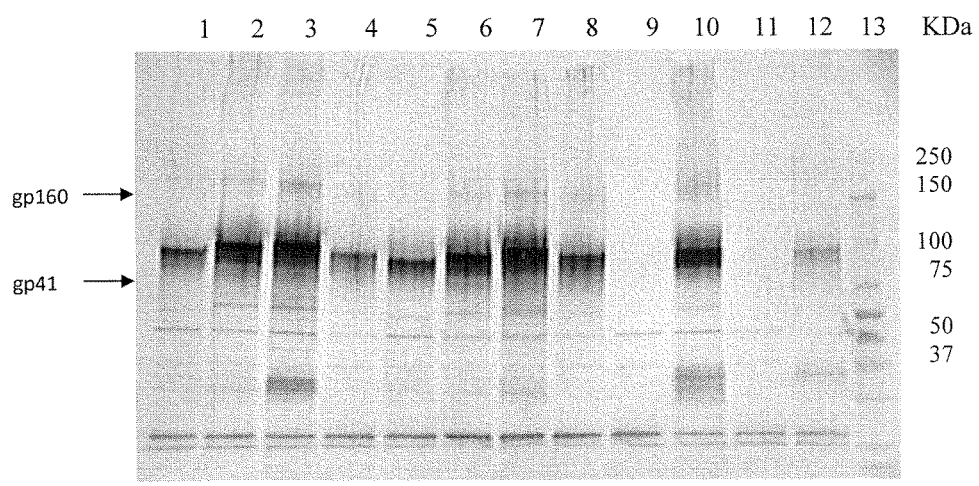
FIG. 20: IP western blot of HEK293 cells transfected with HIV-1 subtype C gp160 and gp160 DC expression plasmids. Env proteins are immunoprecipitated from the 48 hr. post-transfection cell lysates using huMAb to gp41 (4E10), resolved on 4-15% SDS-PAGE and transferred to PVDF. Proteins from the following constructs were detected using rabbit antibodies to HIV-1 subtype B gp160: C06838v1c48 gp160 (lane 1), C06980v1c3 gp160 (lane 2), C06980v0c22 gp160 (lane 3), C3728v2c6 gp160 (lane 4), C06838v1c48 gp160DC (lane 5), C06980v1c3 gp160DC (lane 6), C06980v0c22 gp160DC (lane 7), C3728v2c6 gp160DC (lane 8), naïve HEK293 (−) control (lane 9), Ba-L gp160 (+) control (lane 10), naïve CHO-K1 (−) control (lane 11) and CHO-K1/Ba-L gp160 (+) control (lane 12). Molecular weight protein markers are run in lane 13.

Because expression levels in CHO-K1 were quite low, transfection and analysis using HEK293 cells was performed to further evaluate each construct. Cell lysate samples from HEK293 transfections were evaluated for gp41/gp160 content via IP western blot using huMAb to gp41 (4E10) for immunoprecipitation and HIV-1Ba-L gp160 immunized rabbit's serum for detection. Env expression is strongly evident with each of the subtype C gp160 and gp160DC constructs (FIG. 20). Each construct produces gp160; each isolate runs at a different size, likely due to different glycosylation patterns. Again, only pSWC06980v0c22 gp160 shows gp160 processing into gp120 and gp41.

To quantify gp120/gp160 production levels, media and cell lysates from transfected CHO-K1 and HEK293 were analyzed in an HIV-1 gp120 antigen capture assay (Table 1). In the CHO-K1 transfections, Env expression was detected with each construct except C06838v1c48 gp160DC. Expression levels were quite low overall, compared to the Ba-L gp145 control. This was due to very low expression levels and difficulty in the detection of the Env proteins from these isolates. Level of the Ba-L gp145 expression was also quite low due to the low efficiency in transfecting CHO cells. The highest producing subtype C constructs were the C06980v0c22 and C3728v2c6 gp160s. It should be noted that concentration values are based on relative reactivities to a subtype C gp120 standard from a different isolate. Exact concentrations may differ than as reported due to possible differences in each isolates' affinities to the antibodies used in the assays.

TABLE 1

HIV-1 gp120 Antigen Capture Assay of CHO-K1 cells transfected with HIV-1 subtype C gp160 and gp160 DC expression plasmids. Quantities of gp120 and gp160 are detected at 48 hrs post-transfection in media and cell lysates.

| Construct | gp120/gp160 (ng/ml) | |
|---|---|---|
| | Media | Cell Lysate |
| pSWC06838v1c48 gp160 | 0.6 | 0.0 |
| pSWC06980v1c3 gp160 | 1.0 | 0.7 |
| pSWC06980v0c22 gp160 | 3.2 | 5.7 |
| pSWC3728v2c6 gp160 | 7.2 | 6.7 |
| pSWC06838v1c48 gp160DC | 0.0 | 0.0 |
| pSWC06980v1c3 gp160DC | 0.4 | 0.7 |
| pSWC06980v0c22 gp160DC | 1.6 | 1.2 |
| pSWC3728v2c6 gp160DC | 2.5 | 3.4 |
| (−) Control | 0.0 | 0.0 |
| (+) Control: Ba-L gp145 | 25.0 | 3.0 |

Since detection of Env proteins was so weak in CHO-K1, analysis of HEK293 transfections was performed to verify results. In HEK293, Env expression was detected using antigen capture with each construct (Table 2). In HEK293, 06838v1c48 gp160DC was now detected, but very weakly. Expression levels were much higher than with the CHO-K1. The highest producing subtype C constructs were again the C06980v0c22 and C3728v2c6 gp160s.

TABLE 2

HIV-1 gp120 Antigen Capture Assay of HEK293 cells transfected with HIV-1 subtype C gp160 and gp160 DC expression plasmids. Quantities of gp120 and gp160 are detected at 48 hrs post-transfection in media and cell lysates.

| Construct | Cell Type | gp120/gp160 (ng/ml) | |
|---|---|---|---|
| | | Media | Cell Lysate |
| pSWC06838v1c48 gp160 | 293H | 0.0 | 0.9 |
| pSWC06980v1c3 gp160 | 293H | 28.2 | 11.6 |
| pSWC06980v0c22 gp160 | 293H | 94.1 | 94.6 |
| pSWC3728v2c6 gp160 | 293H | 198.2 | 87.7 |
| pSWC06838v1c48 gp160DC | 293H | 0.0 | 0.8 |
| pSWC06980v1c3 gp160DC | 293H | 2.7 | 8.8 |
| pSWC06980v0c22 gp160DC | 293H | 13.9 | 37.7 |
| pSWC3728v2c6 gp160DC | 293H | 59.3 | 92.1 |
| (−) Control | 293H | 0.0 | 0.0 |
| (+) Control: Ba-L gp145 | 293H | 237.0 | 61.0 |
| (+) Control: Ba-L gp160 | 293H | 79.0 | 62.0 |
| (−) Control | CHO-K1 | 0.0 | 0.0 |
| (+) Control: Ba-L gp145 | CHO-K1 | 41.0 | 3.0 |
| (+) Control: Ba-L gp160 | CHO-K1 | 21.0 | 29.0 |

Further evaluation of gp160 production was performed using two gp160 antigen capture assays utilizing the human monoclonal antibodies 4E10 (Table 3) and 2F5 (Table 4). The gp160 from each isolate reacted strongly with the 4E10-based assay. Even the C06838v1c48 isolate reacted strongly, indicating that the gp120 assay gives artificially low results for this isolate. The gp160 from each isolate reacted with the 2F5-based assay, although weaker than the 4E10-based assay. The C06980v1c22 isolate reacted the strongest. The weaker 2F5 reactivity is explained by the fact that the 2F5 epitope is quite different in the subtype C isolates from that in the subtype β isolates from which the antibody was developed. Without being bound to theory, Applicants think reactivity to 2F5 may possibly be through interactions with gp160-bound lipids rather than the amino acid backbone. These assays demonstrate that the MPER is exposed on each construct.

TABLE 3

HIV-1 gp160 Antigen Capture Assay using of HEK293 cells transfected with HIV-1 subtype C gp160 and gp160 DC expression plasmids. 4E10 huMAb to gp41 MPER is used as the capture antibody. Relative quantities of gp160 are detected at 48 hrs post-transfection in media and cell lysates.

| Construct | OD 450 nm | |
|---|---|---|
| | Media | Cell Lysate |
| pSWC06838v1c48 gp160 | 0.146 | 2.655 |
| pSWC06980v1c3 gp160 | 0.926 | 2.718 |
| pSWC06980v0c22 gp160 | 2.534 | 2.736 |
| pSWC3728v2c6 gp160 | 0.589 | 2.779 |
| pSWC06838v1c48 gp160DC | 0.162 | 2.703 |
| pSWC06980v1c3 gp160DC | 1.105 | 2.588 |
| pSWC06980v0c22 gp160DC | 2.608 | 2.616 |
| pSWC3728v2c6 gp160DC | 0.681 | 2.652 |
| (−) Control | 0.123 | 0.156 |
| (+) Control: Ba-L gp145 | 2.417 | 2.553 |

TABLE 4

HIV-1 gp160 Antigen Capture Assay using of HEK293 cells transfected with HIV-1 subtype C gp160 and gp160 DC expression plasmids. 2F5 huMAb to gp41 MPER is used as the capture antibody. Relative quantities of gp160 are detected at 48 hrs post-transfectionin media and cell lysates.

| Construct | OD 450 nm | |
|---|---|---|
| | Media | Cell Lysate |
| pSWC06838v1c48 gp160 | 0.146 | 0.530 |
| pSWC06980v1c3 gp160 | 0.200 | 0.399 |
| pSWC06980v0c22 gp160 | 0.344 | 1.458 |
| pSWC3728v2c6 gp160 | 0.198 | 0.781 |
| pSWC06838v1c48 gp160DC | 0.155 | 0.506 |
| pSWC06980v1c3 gp160DC | 0.179 | 0.446 |
| pSWC06980v0c22 gp160DC | 0.298 | 1.210 |
| pSWC3728v2c6 gp160DC | 0.219 | 0.829 |
| (−) Control | 0.135 | 0.150 |
| (+) Control: Ba-L gp145 | 2.268 | 2.638 |

Applicants concluded that the isolate C06980v0c22 would be used to establish CHO cell lines producing gp145. The decision to use this isolate was based on several factors:
- Its relatively strong expression, as compared to isolates C06838v1c48 and C06980v1c2
- Processing of gp160 into gp120 and gp41 was most pronounced with this isolate
- This strain was isolated early from the patient during acute infection
- Its strong reactivity with the MPER antibody 4E10
- This virus was infection competent CHO-K1/C06980v0c22 gp145 Cell Line Development The C06980v0c22 gp145 DNA expression plasmid was constructed and used to establish stably transfected CHO-K1 cells producing gp145. These cell lines were adapted for growth in protein-free media, and cell banks were established. The clone H-73-9-2-8 was selected for gp145 protein production.

Figure 21:
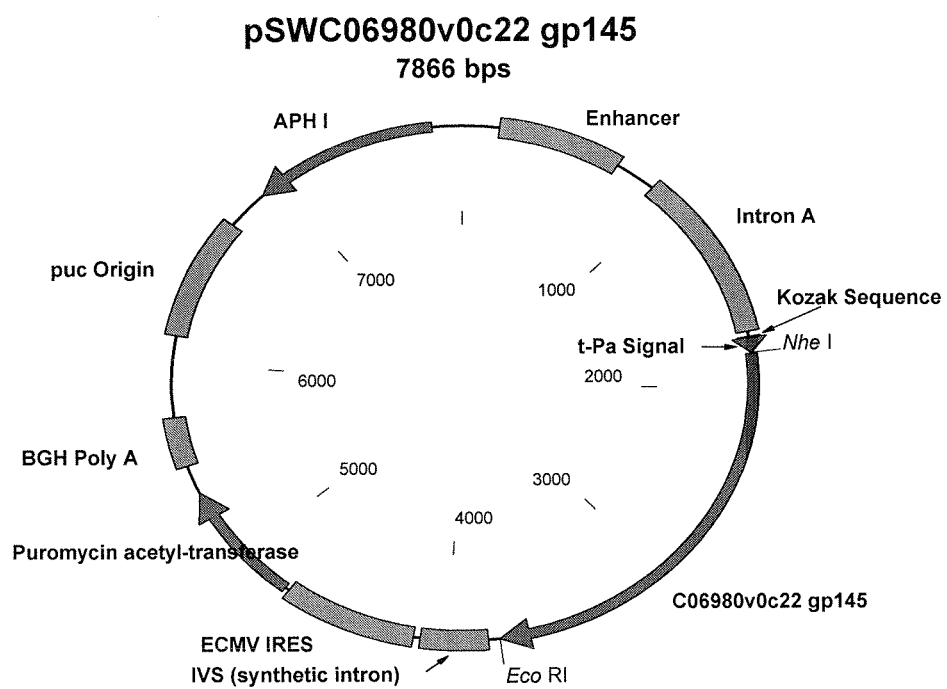
FIG. 21: HIV-1 C06980v0c22 gp145 expression plasmid. The HIV-1 gp145 gene is ligated into pSWTIPK3 at the NheI and EcoRI sites in frame with the t-Pa signal peptide.

The C06980v0c22 gp145 DNA construct was developed by modifying the gp160DC gene using a PCR-based technique. The gp145 gene is composed of residues N30, directly downstream of the native signal peptide cleavage site, through K676 just prior to the transmembrane domain. Following K676, the gp145 terminates with three additional lysines (FIG. 36 and FIG. 37). These are included to theoretically increase the hydrophilicity of the C terminus, thus increasing exposure of the MPER for presentation to the immune system. Upon signal peptide cleavage, it is predicted that a foreign serine from the modified t-Pa signal will be present at the amino terminus. The gp145 gene was ligated at the NheI and EcoRI sites in the mammalian expression plasmid pSWTIPK3 and named pSWC06980v0c22 gp145 (FIG. 21). The plasmid was amplified in the *E. coli* (Invitrogen) strain DH5α and purified using an Endofree Plasmid Maxi kit (Qiagen, Valencia, Calif.). The plasmids were analyzed by restriction digest, and the sequence of the gp145 coding region was confirmed by DNA bidirectional sequencing. The plasmid contains the puromycin acetyl-transferase gene for selection of stable colonies under puromycin selection. It is driven by an internal ribosomal entry site (IRES) and the CMV promoter. This facilitates a high level of expression of the gp145 gene by linking its expression with that of the puromycin resistance marker.

A summary of important features of the mammalian expression vector can be described as follows:

The vector contains an antibiotic resistance gene that can be used as a selectable marker in bacteria during construction. Therapeutic products derived from such vectors should avoid use of penicillin or related antibiotics during their construction. Therefore, kanamycin is used instead of ampicillin.

The gp145 gene to be expressed is codon optimized for enhanced expression of the product. The gene is synthesized using CHO codon bias, using codons that correspond to the most abundant tRNAs present in CHO cells. The synthetic gene is also designed to eliminate any cis-acting elements that can reduce transcription/translation efficiency as well as other motifs that may destabilize mRNA.

The gp145 gene is introduced into the vector in frame with a modified t-Pa signal peptide to allow for efficient transport to the cell membrane.

The gene is expressed under control of a strong promoter and efficient poly-A signal. The powerful CMV promoter and the efficient Bovine Growth Hormone (BGH) poly-A are used.

For the selection of stable protein-expressing cell clones, the vector contains a selectable marker: puromycin acetyl-transferase gene for puromycin resistance driven by an internal ribosomal entry site (IRES) and the CMV promoter.

In developing cell lines, care was taken to perform tasks, keep records and use materials that would be acceptable with the FDA should the need arise to use these cell lines in the clinical setting. The CHO-K1 (cat# CCL.61) cells were obtained from ATCC (Manassas, Va.). To establish stable CHO-K1 cell lines, the preferred method of transfection is electroporation. A benefit of this method is in its avoidance of uncharacterized animal-derived components. In addition, animal derived products were avoided unless necessary. Recombinant trypsin was used instead of porcine trypsin and the fetal bovine serum (FBS) was well defined from a New Zealand source to reduce the chances of BSE contamination. FBS was irradiated, heat inactivated and sterile filtered.

CHO-K1 cells were separately electroporated with supercoiled and linearized pSWC06980v0c22 gp145 DNA (linearized with the single cutter: NruI). Both forms of DNA were used, as both have their benefits and drawbacks when establishing cell lines. Supercoiled DNA typically transfects with higher efficiency, which may be beneficial, as CHO-K1 cells transfect poorly. Linear DNA transfects with less efficiency, but incorporates into host genome with better efficiency than supercoiled DNA. Briefly, 5×106 CHO-K1 cells were suspended in 0.5 ml electroporation buffer (Bio-Rad, Hercules, Calif.), mixed with 100 µl Electroporation Buffer containing 100 µg plasmid DNA in 0.4 cm electrode cuvettes. Cells were pulsed using a Gene Pulser apparatus (BioRad) at 350V with 125 µFD, set on ice for 30 minutes, pooled and cultured in 5.5 ml complete F-12 K medium (F12-K (Invitrogen, Inc.), containing 10% heat inactivated FBS (Hyclone Laboratories, Logan Utah), 10 µg/ml gentamicin (Invitrogen, Inc.) and 2 mM l-glutamine (Quality Biologicals, Inc., Columbia, Md.)).

Figure 26:
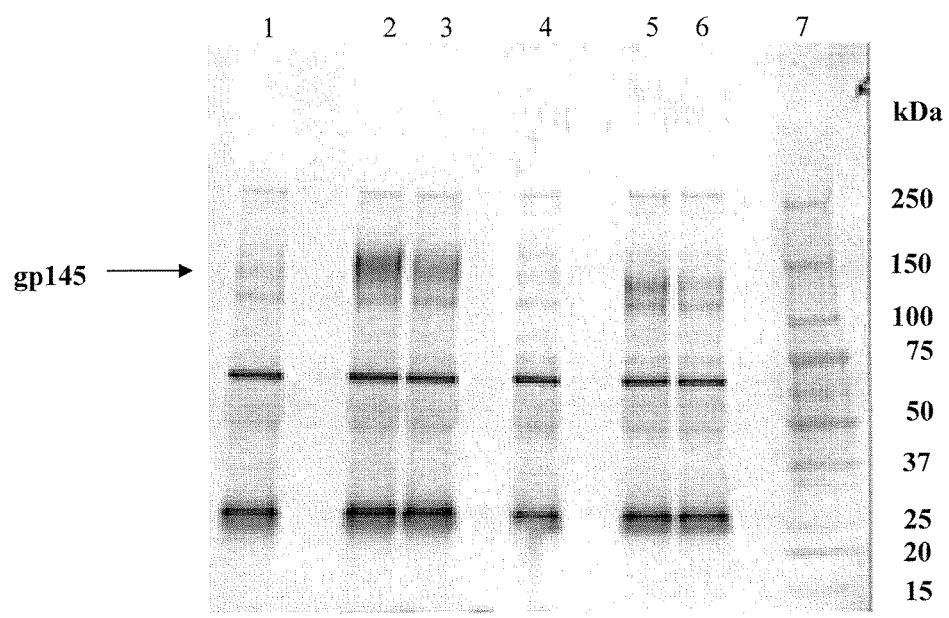
FIG. 26: IP western blot of CHO-K1 cells transfected with pSWC06980v0c22 gp145. Env proteins are immunoprecipitated from the 48 hr. post-transfection conditioned media and cell lysates using HIV-1 (+) human serum, resolved on 4-15% SDS-PAGE and transferred to PVDF. The gp145 was detected using rabbit antibodies to HIV-1 subtype B gp160 and Subtype C gp120: naïve CHO-K1 (−) control media (lane 1), supercoiled pSWC06980v0c22 gp145 media (lane 2), linearized pSWC06980v0c22 gp145 media (lane 3), naïve CHO-K1 (−) control cell lysate (lane 4), supercoiled pSWC06980v0c22 gp145 cell lysate (lane 5), linearized pSWC06980v0c22 gp145 cell lysate (lane 6). Molecular weight protein markers are run in lane 7.

Forty-eight hours post-electroporation, conditioned media and cell lysate samples were taken for analyses in a gp120 antigen capture assay and IP western blot. The gp120 antigen capture assay results confirm the secretion of gp145 into the conditioned media. Production was quite low at only four and nine ng/ml from the linear and supercoiled DNA, respectively. Production from the supercoiled DNA is higher than that from the linearized DNA, as expected. Env proteins from Media and cell lysate samples were analyzed in IP western blot (FIG. 26). The presence of gp145 in the conditioned media from both the supercoiled and linearized DNA electroporated cells is evident at about 140 KDa, as expected. A slightly lower molecular weight species of gp145 is evident in the cell lysates, as expected. This likely represents incompletely processed gp145.

Forty-eight hours post-electroporation, cells were plated at about 4500 cells/well in 96-well plates for selection in cF12-K. After 24 hours, cells were put under puromycin selection in cF12K containing 10 µg/ml puromycin (Sigma-Aldrich, St. Louis, Mo.). Media was changed twice a week until puromycin-resistant colonies reached about 50% confluency. Conditioned media was analyzed for gp145 production using the gp120 antigen capture assay. Twenty cultures with the highest production were expanded, frozen and cloned by limiting dilution to isolate true clones that stably express gp145. The best production levels of uncloned cultures reached 2 µg/ml.

From the original 20 cultures initially selected and cloned, >100 clones were analyzed by gp120 antigen capture assay. Based on gp145 production levels, 17 cell lines, representing 12 of the original cultures were determined to be potential candidates for gp145 production. Frozen stocks for each cell line were made. Studies to compare production levels of each of the selected clones were performed. Briefly, cells were seeded in a 24-well plate at 1×105 cells in 1 ml tissue culture media and incubated at 37° C. for 64 hours. Media was harvested and analyzed by gp120 antigen capture assay and I.P. western blot. Based on their antigen capture and I.P. western blot results, clones H-73-9, H-84-1 and H-94-10 were selected for adaptation to protein-free media required for protein production. A five vial cell bank was frozen for each. Each clone produced between 1 and 2 mg gp145/L. In I.P. western blot, each of the selected clones has strong gp145 reactivity at about 140 kDa as expected.

It was observed that CHO-K1 cells electroporated with supercoiled DNA yielded higher transient gp145 production than those cells electroporated with linearized DNA: 9 ng/ml verses 4 ng/ml, respectively. However, both supercoiled and linearized DNA yielded about 100 stable cell lines following puromycin selection. Interestingly, 16 of the 17 best gp145 producing cell lines were derived from the linearized DNA. This supports Applicants' prediction that supercoiled DNA is more efficiently taken up by cells, but linearized DNA is more efficiently integrated and results in higher protein yields in stable cell lines.

The three selected cell lines were adapted for growth in protein-free media. As adaptation for growth in protein-free media can be difficult for certain clones, three were selected to increase the likelihood that an adaptable clone is selected. In addition, each clone was adapted to three different media (PowerCHO-1 CD, PowerCHO-2 CD and PowerCHO-3 CD, Lonza, Walkersville, Md.), each containing 5 µg/ml puromycin and 4 mM l-glutamine. After several passages in protein-free media, clone H-73-9 grown in PowerCHO-1 CD, PowerCHO-2 CD and PowerCHO-3 CD adapted and were named H-73-9-1, H-73-9-2, and H-73-9-3, respectively. Clone H-84-1 grown in PowerCHO-2 CD also adapted well and was named H-84-1-2. A two vial cell bank was frozen for each.

Figure 27:
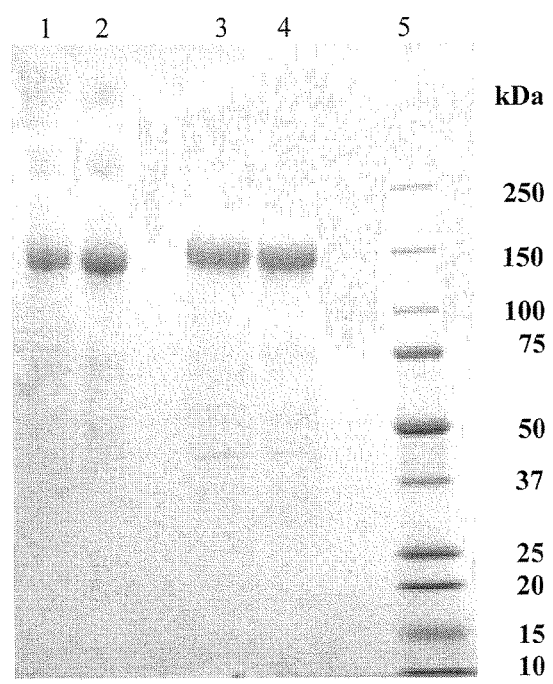
FIG. 27: 4-15% SDS-PAGE of C06980v0c22 gp145 purified from the conditioned media of CHO cell lines H-73-9-2-8 and H-73-9-3-9. 5 μg protein is resolved under reducing and nonreducing conditions and stained with coomassie blue 8250: H-73-9-2-8 nonreduced (lane 1), H-73-9-3-9 nonreduced (lane 2), H-73-9-2-8 reduced (lane 3) and H-73-9-3-9 reduced (lane 4). A molecular weight protein marker is run in lane 5.
Figure 28:
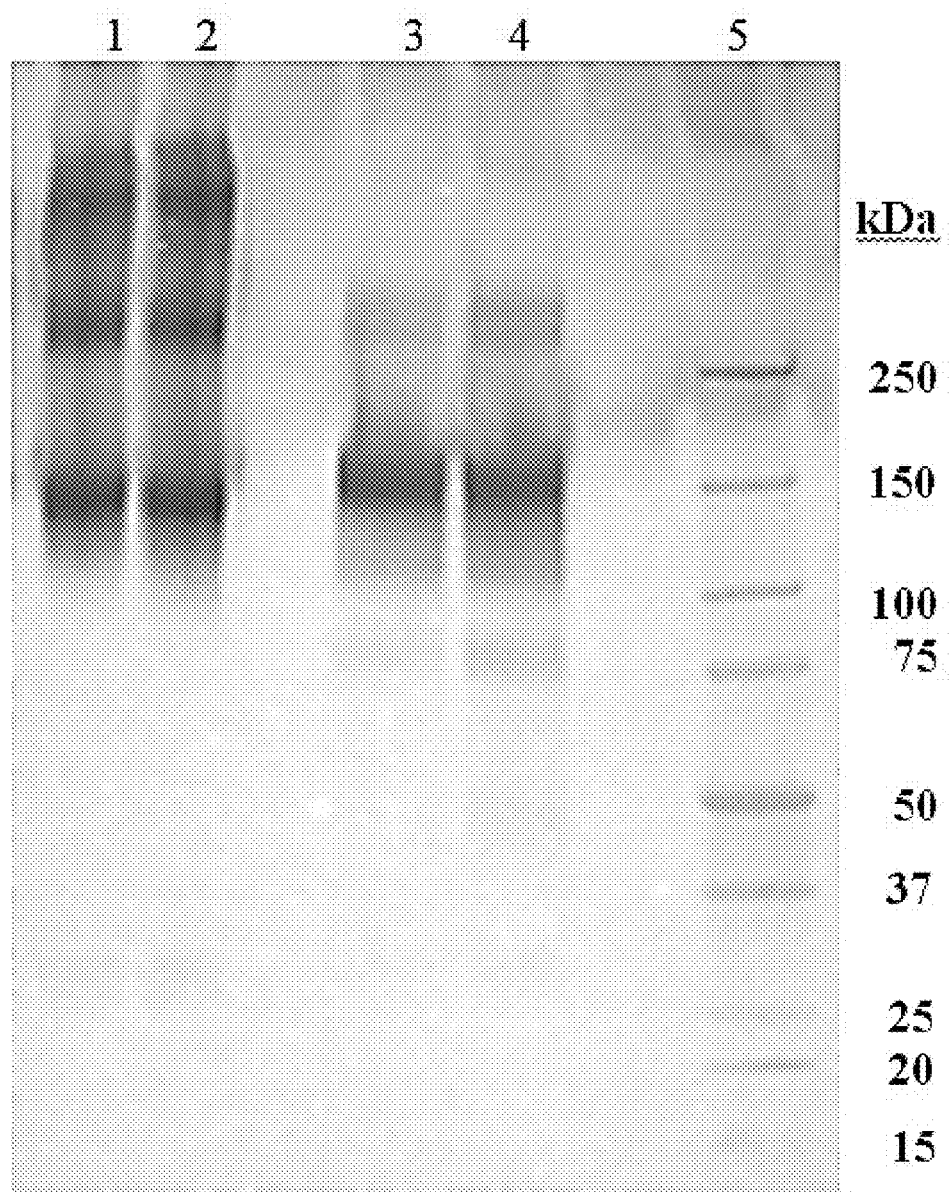
FIG. 28: Western blot of C06980v0c22 gp145 purified from the conditioned media of CHO cell lines H-73-9-2-8 and H-73-9-3-9. 0.5 μg protein is resolved under reducing and nonreducing conditions on 4-15% SDS-PAGE, transferred to PVDF and detected with an HIV-1 (+) serum: H-73-9-2-8 nonreduced (lane 1), H-73-9-3-9 nonreduced (lane 2), H-73-9-2-8 reduced (lane 3) and H-73-9-3-9 reduced (lane 4). A molecular weight protein marker is run in lane 5.
Figure 29:
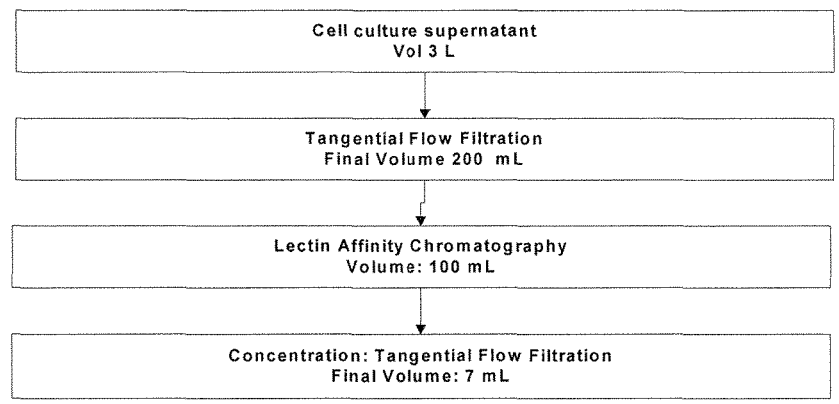
FIG. 29: Flow chart of downstream purification methods for gp145
Figure 30:
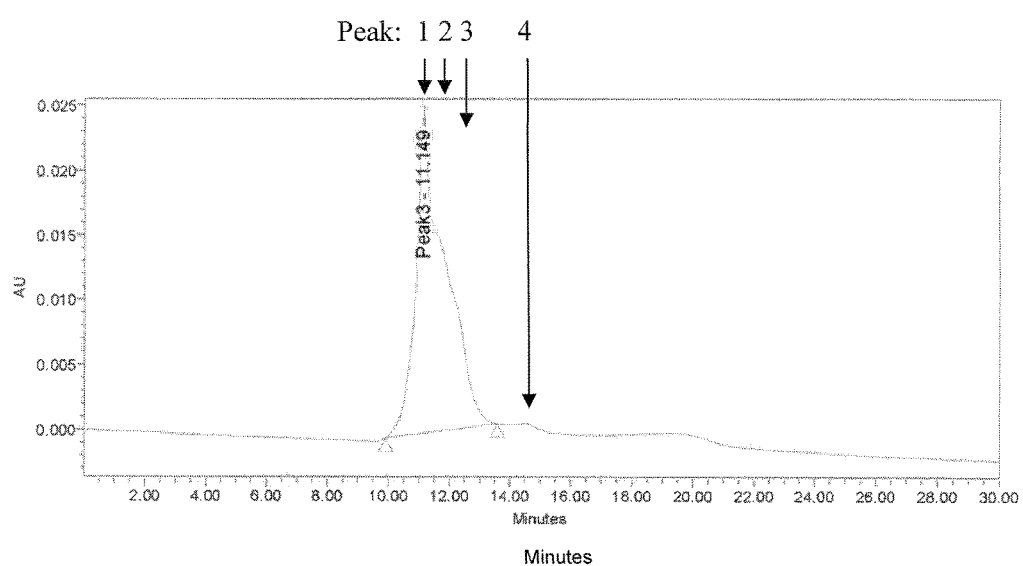
FIG. 30. SE-HPLC analysis of purified Recombinant HIV-1C06980v0c22 gp145 (lot 112009). 1:10 dilution of purified protein was prepared in 1×PBS and 20 μL was loaded on the TSK-GEL 3000SWXL Column (TOSOH BIOSEP). The column was eluted with isocratic gradient of 1×PBS at flow rate of 1.0 mL/min, resulting in the identification of in lane 4. For each lot of gp145, 3 multimeric species (A, B and C) are evident. Multimer B is predominant.

The four adapted cultures were again cloned by limiting dilution and the best producing clone for each culture was identified by the gp120 antigen capture assay. Of these, two cultures were identified as being the best producers; H-73-9-2-8 and H-73-9-3-9. Two vial cell banks were frozen for each, and cultures were expanded to about 500 ml for small-scale protein purification. Conditioned media was harvested, buffered with 20 mM Tris, pH 8, 0.5% Triton-X-100 and 500 mM sodium chloride. Buffered media was run through 2 ml columns of Galanthus nivalis lectin (GNL) agarose (Vector Laboratories, Inc., Burlingame, Calif.). The columns were washed with Tris, pH 8, 0.5% Triton-X-100 and 500 mM sodium chloride, followed by PBS. The bound gp145 was eluted with 400 mM methyl α-D-mannopyranoside. Purified gp145 was analyzed in SDS-PAGE and western blot (FIG. 27 and FIG. 28). Both clones produce an approximately 145 kDa protein that reacts well in western blot. Under nonreducing conditions, some dimer and high order multimers are evident, also. Both cell lines produced >1.2 mg/L according to Comassie Plus Protein Assay (Pierce). Clone H-73-9-2-8 had better growth characteristics (slightly healthier and faster growth), thus was selected gp145 production.

A 10 vial research cell bank (RCB) for H-73-9-2-8 (lot Apr. 17, 2008) was made and stored in liquid nitrogen freezer. 2×106 cells were frozen in 10 vials of 1 ml protein-free freezing medium (7.5% DMSO (Sigma-Aldrich), 50% fresh growth media, 42.5% Profreeze CDM (Lonza)). The genomic DNA was isolated from 5×106 cells using Qiamp Blood Mini Kit (Qiagen), and the integrated gp145 gene region was amplified by PCR and sequenced in both directions. There was a 100% sequence match in the gp145 coding region. Two weeks after cell banking, cells were tested for mycoplasma contamination using MycoAlert *Mycoplasma* detection Kit (Lonza) and were found to be negative. One vial was thawed and put into culture to test for viability. After 3 days of culture, cells were 77% viable and tested positive for gp145 production in gp120 antigen capture assay. Culture was tested for bacterial contamination, and showed no bacterial growth in inoculated SOC broth after incubation at 37° C. for 24 hours.

A culture grown from the H-73-9-2-8 RCB lot Apr. 17, 2008 was used to makes 25 vial RCB (lot F1144) and stored in liquid nitrogen freezer. 10×106 cells were frozen in 25 vials of 1 ml protein-free freezing medium (7.5% DMSO (Sigma-Aldrich), 50% PowerCHO-2 CD, 42.5% Profreeze CDM (Lonza)). At the time of cell banking, the culture was tested for mycoplasma contamination and was found to be negative. The culture was tested for bacterial and fungal contamination, and showed no bacterial growth in thioglycollate broth or fungal growth in soybean-Casein digest broth. One vial from the cell bank was thawed and cultured in the media previously described to check for viability and to confirm production of gp145 in these cells. Upon thawing, viability was acceptable at 87%. Growth characteristics were as expected and gp145 production was confirmed by antigen capture assay.

C06980v0c22 gp145 Protein Production

Three lots of gp145 were produced and delivered for further studies (Table 5).

TABLE 5

| HIV-1$_{C06980v0c22}$ gp145 Lots provided | | |
|---|---|---|
| Lot Number | Concentration (mg/ml) | Total Delivered (mg) |
| 112009 | 1.1 | 7 |
| 120710A | 1.0 | 18 |
| 120710B | 0.975 | 5 |

Lot 112009

H-73-9-2-8 culture was expanded to 3 L in PowerCHO-2 CD supplemented with 4 mM 1-gluatmine and 5 μg/ml puromycin using roller bottles. The conditioned media was clarified by centrifugation. Media samples from the 3 L harvest were analyzed in antigen capture. Results predicted nearly 4 mg gp145/L media in gross. Quality and yield was determined to be acceptable for production using the 3 L harvest. The gp145 protein was purified as described below and as outlined in FIG. 29.

Harvested media was concentrated at room temperature using a 0.1 m2 Pellicon filtration unit with molecular weight cut off of 30 kDa. The system was flushed with 1.0 M NaOH followed by WFI water then by 1×PBS buffer. The CHO cell culture supernatant (3 L) was introduced and the system was operated in a recirculation mode. The concentration was performed at a permeate flux of −1 L per hr/0.1 m2 and a cross flow of 0.5 L/min. At the end of concentration, the sample was concentrated to 200 mL. The concentrated cell culture supernatant was stored at −70° C. until further processing.

The gp145 was purified using Lectin Affinity Chromatography. Concentrated media was adjusted to 500 mM sodium chloride and was run over 25 ml column of GNL agarose. The column was washed with PBS and the bound gp145 was eluted with 500 mM methyl α-D-mannopyranoside. The purification was performed at a flow rate of 10 ml/min. The eluate (100 mL) was concentrated and diafiltered into PBS using a tangential flow filtration. A 50 cm2 Pellicon filtration unit with molecular weight cut off of 30 kDa was used for this step. The system was flushed with 1.0 M NaOH, followed by WFI water then by PBS. The eluate was then introduced, and the system was operated in recirculation mode. The ultra filtration was performed at a permeate flux of 2.0 mL/min., and the cross flow was ~40 ml/min. The volume of the GNL-Eluate was reduced to 8 mL in PBS.

Protein content was estimated by Bradford assay and found to be 1.1 mg/mL. Endotoxin in the purified gp145 was estimated using colorimetric LAL assay (Lonza) and found to be 31.8 EU/mg protein. SDS-PAGE analysis in reduced and non-reduced condition showed the molecular weight of ~145 kD for the purified protein.

As can be seen from SE-HPLC analysis (FIG. 30), lot 112009 gp145 was eluted in four multimeric forms, referred to as A, B, C, and D. Based on the mobility of protein standards, the apparent molecular weight of each gp145 species is calculated (Table 6). The major peak calculates as >669 kDa (estimated to about 895 kDa), corresponding to form A. Two shoulders are evident at >669 (estimated to about 680 kDa) and 571 kDa, corresponding to forms B and C, respectively. A fourth, but minor peak of 417 kDa corresponds to a form D.

TABLE 6

Retention time and molecular weight of protein standards and purified gp145 (lot 112009) multimer species

| Protein | Retention Time (Min) | Molecular Weight (kDa) | Multimeric form |
|---|---|---|---|
| Thyroglobulin | 11.81 | 669 | N/A |
| Ferritin | 13.74 | 440 | N/A |
| Catalase | 16.18 | 232 | N/A |
| Bovine Gamma Globulin | 16.52 | 150 | N/A |
| Bovine Serum Albumin | 16.75 | 66 | N/A |
| gp145 peak 1 | 11.15 | Approx. 895 | A |
| gp145 peak 2 | 11.77 | Approx. 680 | B |
| gp145 peak 3 | 12.25 | 571 | C |
| gp145 peak 4 | 14.64 | 417 | D |

The purity of the gp145 was 96.1% by SDS-PAGE followed by laser densitometry.

Lot 120710A

Figure 31:
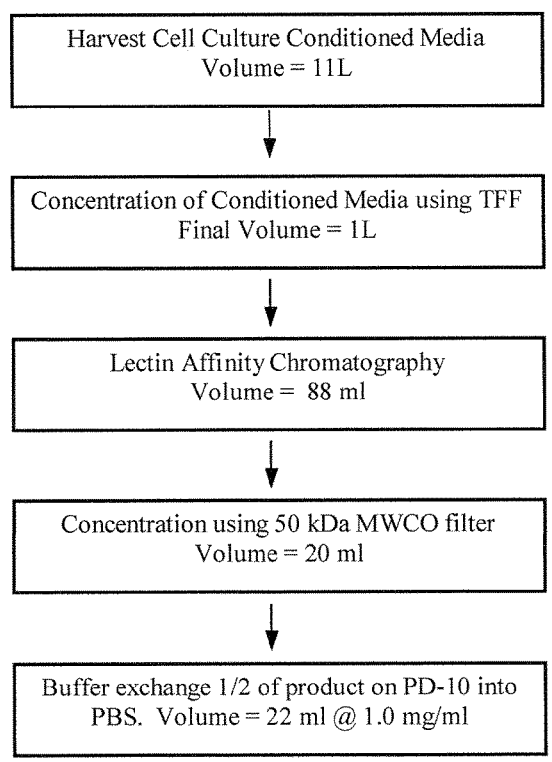

H-73-9-2-8 culture was expanded to 11 L in PowerCHO-2 CD supplemented with 4 mM 1-gluatmine and 5 µg/ml puromycin using roller bottles. The conditioned media was clarified by centrifugation. Media samples from the 11 L harvest were analyzed in antigen capture. Results predict nearly 8 mg gp145/L media in gross. Quality and yield was determined to be acceptable for production using the 11 L harvest. The gp145 protein was purified as described below and as outlined in FIG. 31.

Harvested media was concentrated at room temperature using a 0.1 m2 Pellicon filtration unit with molecular weight cut off of 30 kDa operating in a recirculation mode as described for lot 112009. The 11 L conditioned media was concentrated to 1 L.

The concentrated conditioned media was buffered with 20 mM Tris, pH8, 500 mM sodium chloride and 0.5% Triton-X-100, and then clarified with 0.22 µm filter. Conditioned media was passed over 20 ml GNL-Agarose resin at 4° C. at about 1 ml/min. The resin was washed with 20 mM Tris, pH8, 500 mM sodium chloride and 0.5% Triton-X-100 buffer, and then equilibrated with PBS. The gp145 was eluted in PBS containing 0.5M Methyl-∝-D manopyranoside. GNL-Eluate (88 mL) was concentrated to 20 ml with 50 kDa MWCO filter. 10 ml was set aside for use in preparing lot 120710B. The remaining 10 ml was run on PD10 buffer exchange resin into PBS. Eluted material was sterile filtered with 0.22 µm filter, aliquoted and stored at −70° C. Lot 120710A final product has a volume of 22 ml.

Protein content was estimated by Bradford assay and found to be 1.0 mg/mL. Endotoxin in the purified gp145 was estimated using colorimetric LAL assay and found to be <0.313 EU/mg protein. SDS-PAGE analysis in reduced and non-reduced condition shows the molecular weight of 142 kD for the purified protein. Under non-reducing conditions, multimers are also evident. This represents multimers held together with disulfide bonds.

Figure 32:
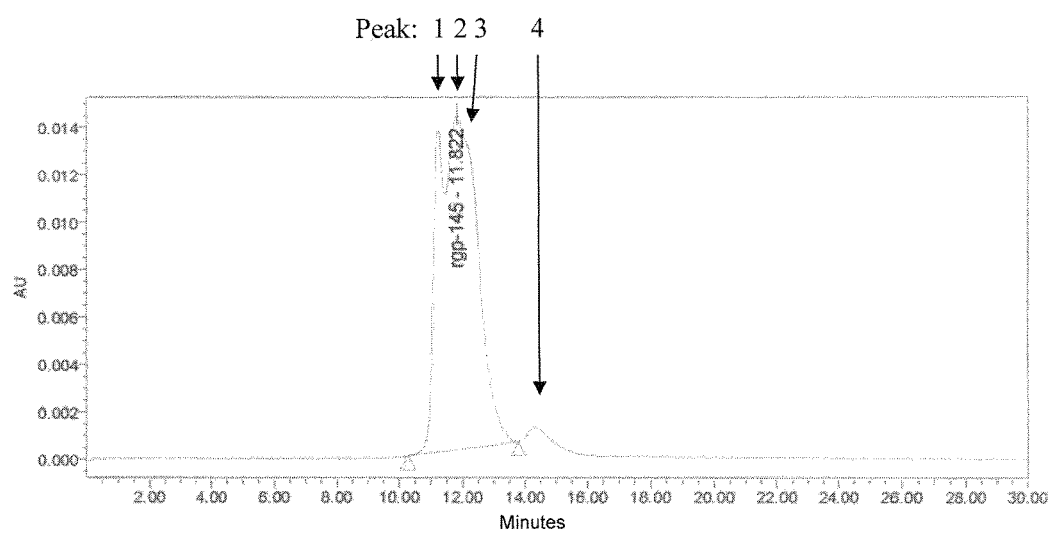

As can be seen from SE-HPLC analysis (FIG. 32), gp145 lot 120710A was eluted in four multimeric forms as with lot 112009. Based on the mobility of protein standards, the molecular weight of each gp145 species is calculated (Table 7). The major peak calculates as 666 kDa, corresponding to a form B. A second peak and a shoulder calculate to >669 kDa (estimated to about 845 kDa) and 584 kDa, corresponding to forms A and C, respectively. A fourth, but minor peak of 411 kDa corresponds to a form D.

TABLE 7

Retention time and molecular weight of protein standards and purified HIV-1C06980v0c22 gp145 lot 120710A multimer species

| Protein | Retention Time (Min) | Molecular Weight (kDa) | Multimeric form |
|---|---|---|---|
| Thyroglobulin | 11.813 | 669 | N/A |
| Ferritin | 13.677 | 440 | N/A |
| Catalase | 16.114 | 232 | N/A |
| Bovine Gamma Globulin | 16.400 | 150 | N/A |
| Bovine Serum Albumin | 16.737 | 66 | N/A |
| gp145 peak 1 | 11.226 | Approx. 845 | A |
| gp145 peak 2 | 11.824 | 666 | B |
| gp145 peak 3 | 12.217 | 584 | C |
| gp145 peak 4 | 14.343 | 411 | D |

The purity of HIV-1$C_{06980v0c22}$ gp145 lot 120710A was 94.2% by SDS-PAGE followed by laser densitometry.

Lot 120710B

Lot 120710B is made from the same gp145 eluted during lectin affinity chromatography as lot 120710A. For lot 120710B, an additional step for the purpose of reducing intermolecular disulfide bonds is employed. The rationale for this is based on the observation that the previous lot of gp145 (lot 112009) is in the form of high order multimers. Without being bound to theory, Applicants believe that many of these multimers are due to oxidation, resulting in intermolecular disulfide bridges. Reduction of these bonds is attempted to produce protein in the form of lower order multimers, preferably trimer.

Figure 33:
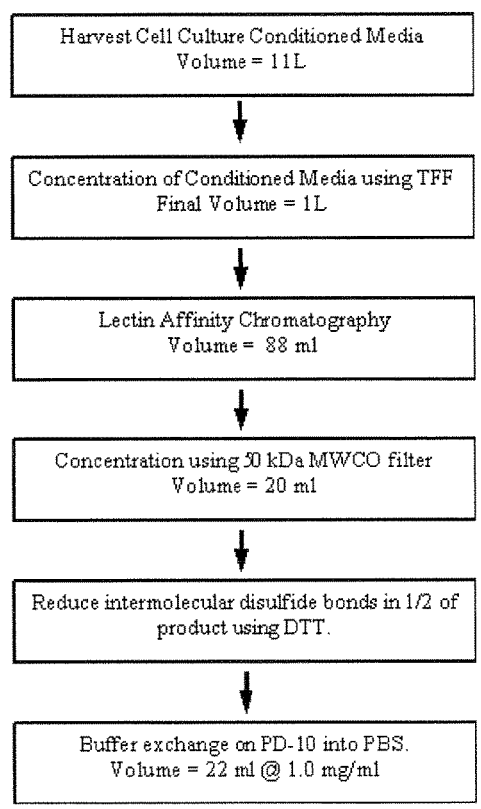

The gp145 protein was purified as described below and as outlined in FIG. 33.

10 ml of the concentrated GNL eluate described for lot 120710A had been set aside for use in preparing lot 120710B. This 10 ml was treated with 50 mM DTT at 37° C. for 30 minutes, then run on PD10 buffer exchange resin into PBS. Eluted material was sterile filtered with 0.22 µm filter, aliquoted and stored at −70° C. Lot 120710B final product has a volume of 22 ml.

Protein content was estimated by Bradford assay and found to be 0.975 mg/mL. Endotoxin in the purified gp145 was estimated using colorimetric LAL assay and found to be <0.321 EU/mg protein. SDS-PAGE analysis in reduced and non-reduced condition shows the molecular weight of 143 kD for the purified protein. Under non-reducing conditions, only trace amount of multimers are also evident. This represents multimers held together with disulfide bonds. Treatment with DTT reduced many of these bonds compared to the non-DTT treated lot 120710A.

Western blot shows the major band at about 143 kDa under reducing and non-reducing conditions. Several multimeric forms of gp145 are evident under non-reducing conditions, but fewer than seen with the non-DTT treated lot 120710A. Under reducing conditions, these multimers have mainly been reduced to monomer.

Figure 34:
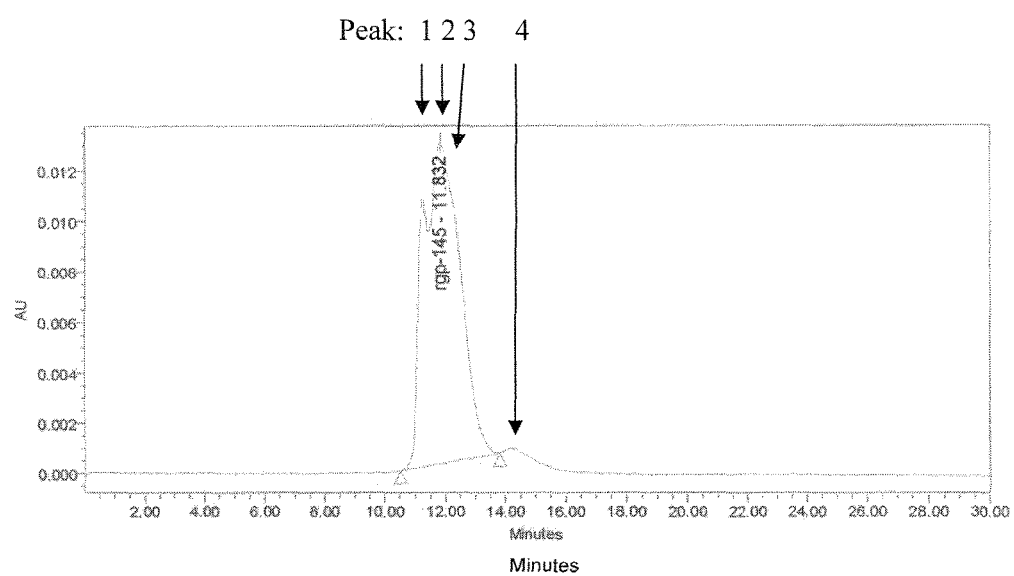

As can be seen from SE-HPLC analysis (FIG. 34), gp145 was eluted in four multimeric forms as with lots 120710A and 112009. Based on the mobility of protein standards, the molecular weight of each gp145 species is calculated (Table 8). The major peak calculates as 665 kDa, corresponding to a form B. A second peak and a shoulder calculate to >669 kDa (estimated to about 844 kDa) and 572 kDa, corresponding to forms A and C, respectively. A fourth, but minor peak of 412 kDa corresponds to form D.

TABLE 8

Retention time and molecular weight of protein standards and purified HIV-1C06980v0c22 gp145 lot 120710B multimer species.

| Protein | Retention Time (Min) | Molecular Weight (kDa) | Multimeric form |
|---|---|---|---|
| Thyroglobulin | 11.813 | 669 | N/A |
| Ferritin | 13.677 | 440 | N/A |
| Catalase | 16.114 | 232 | N/A |
| Bovine Gamma Globulin | 16.400 | 150 | N/A |
| Bovine Serum Albumin | 16.737 | 66 | N/A |
| gp145 peak 1 | 11.23 | Approx. 844 | A |
| gp145 peak 2 | 11.83 | 665 | B |
| gp145 peak 3 | 12.289 | 572 | C |
| gp145 peak 4 | 14.327 | 412 | D |

The purity of the gp145 is 94.2% by SDS-PAGE followed by laser densitometry.

DTT reduction of intermolecular disulfide bonds had some effect on the multimeric form of gp145. In SDS-PAGE, it is clear that most intermolecular disulfide bonds were reduced with DTT treatment, if compared to non-DTT treated. SE-HPLC shows only a modest increase in form C, perhaps due to a modest reduction of form A.

Further investigation of the nature of the multimeric forms is included below in Example 7.

Example 4

Induction of Neutralizing Antibodies to HIV-1 by Immunization with CHO-Expressed Recombinant gp145 Derived from Acute Clade C HIV-1

Animals:
24 New Zealand White female rabbits, 1.8-2 kg
The rabbits are divided into 6 groups of 4 animals each. The individual animals are identified by cage cards and ear tags.

| Group | Antigen | Adjuvant/Vehicle |
|---|---|---|
| 1 | gp145 | Alhydrogel |
| 2 | gp145 | Liposome formulation 1 containing lipid A, preformed and mixed with gp145 |
| 3 | gp145 | Liposome formulation 1 containing lipid A with encapsulated gp145 |
| 4 | gp145 | Liposome formulation 2 containing lipid A and PIP with encapsulated gp145 |
| 5 | None | Liposome formulation 1 containing lipid A |
| 6 | mper23, clade B | Liposome formulation 2 containing lipid A and PIP with encapsulated mper23 |

Antigen:
25 μg/rabbit/dose
gp145 as described above expressed in CHO cell (acute clade C, C0698v0c22) in PBS, pH 7.4
mper23 (NK-4): LELDKWASLWNWFDITNWLWYIK (SEQ ID NO: 53), (HBX2 variant; Swiss-Prot accession number P04578 except that the N at position 674 was replaced with D.)
Adjuvants:
Alhydrogel (0.6 mg Al3+/dose) formulated at 0.6 mg Al3+ in 0.125 ml of PBS, ph 7.4; Mixed with equal volume of antigen
Liposome formulation 1—DMPC:cholesterol:DMPG (9:7.5:1); 50 mM phospholipids containing 100 μg of lipid A/0.25 ml dose; PBS, pH 7.4. DPMC refers to dimyristoyl phosphotidylcholine, and DMPG refers to dimyristoyl phosphotidylglycerol.

Liposome formulation 2—DMPC:cholesterol:PIP (1:1.5:1); 50 mM phospholipids containing 100 μg of lipid A/0.25 ml dose; PBS, pH 7.4. PIP refers to phosphotidyl inositol-4-phosphate.

Bleeding:
The animals are bled at weeks −2, 0, 4, 8, and 10 from an ear artery using a 20-24 gauge butterfly catheter. Approximately, 5 ml of blood is taken during each phlebotomy. The blood is incubated at room temperature for 2-3 hr and then refrigerated overnight at 4 C prior to centrifugation to remove the serum from the clot. The serum is aliquoted: 1×1 ml and 3×0.5 ml in plastic vials and frozen at −80 C.

At week 12, the rabbits are terminally bled by cardiac puncture after anesthesia with atamine/Xylanine with a 60 cc syringe and an 18 gauge needle. The serum is aliquoted: 5×1 ml and 5×5 ml in plastic vials and frozen at −80° C.
Immunization:
Weeks 0, 4 and 8 by the intramuscular route in alternating caudal thigh muscles. Inject 0.25 ml with a 23-27 gauge needle.
Schedule:

| Week | Procedure Receive rabbits |
|---|---|
| Week −2 | Release from quarantine |
| Week −2 | Pre-bleed |
| Week 0 | Pre-bleed |
| Week 0 | Immunize IM, 0.25 ml |
| Week 4 | Bleed |
| Week 4 | Immunize IM, 0.25 ml |
| Week 8 | Bleed |
| Week 8 | Immunize IM, 0.25 ml |
| Week 10 | Bleed |
| Week 12 | Terminal Bleed |

See also FIG. 41. Results are presented in FIGS. 42-48, 52.

Example 5

The following methods detailed below for the mouse studies incorporate the immunogenicity/antigenicity methods used in the rabbit studies depicted in the Figures (see FIGS. 41-48, 52), except rabbits received 25 ug of gp145 or placebo in liposomes as described.
Gp145 Mouse Immununogenicity Study: Antigeniciy/Immunogoenicity Methods Antigens The gp145 protein was produced from an envelope sequence isolated from an acute, subtype C infected individual from Tanzania. The entire ecto-domain of the protein is present, including the MPER of gp41. The protein was designed to include two mutations (R508S, R511S) in the gp120/gp41 cleavage site to prevent protease cleavage and a multi-lysine C-terminal to facilitate production and MPER epitope presentation. The protein was produced in CHO cells, purified by lectin affinity chromatography and is present as a mix of multimers as described in Example 7. The gp145 protein contained the following MPER epitope sequence: ALDSWNNLWNWFDIS (SEQ ID NO: 23).
Liposome Preparation Antigens, experimental M13 phage or gp145 protein, were encapsulated in liposome prior to immunization. Liposomes composed of dimyristoyl phosphatidylcholine, dimyristoyl phosphatidylglycerol and cholesterol in molar ratios of 1.8:0.2:1.5 were prepared by dispersion of lyophilized mixtures of lipids at a phospholipid concentration of 50 mM in Dulbecco's PBS with 0.4 g/ml lipid A, either lacking or containing antigen. Liposomes were washed twice in sterile saline to remove the unencapsulated antigen.

Animal Immunizations

Forty female BALB/C mice, 25 g each, were immunized under a protocol approved by the Institutional Laboratory Animal Care and Use Committee. Animals were divided into eight groups of five animals each (Table 9). Mice were immunized intramuscularly four times in alternating caudal thigh muscles at two or three week intervals with $5 \times 10^{11}$ phage or 10 μg gp145 protein each per dose. Blood was collected at two-week intervals starting two weeks prior to the first immunization ending when the animals were euthanized. Blood was incubated at room temperature for 2-3 h, refrigerated overnight at 4° C. then centrifuged. Serum was collected and stored at −20° C. Two weeks after the last boost (week 10) the mice will be euthanized. Blood, spleens, lymph nodes, bone marrows, and livers were obtained and processed from naïve and immunized mice.

TABLE 9

Mouse immunization plan.

| Group# | Immunogen | Immunization (Weeks) | Bleeds (Weeks) 150 ul/mouse/bleed | Euthanasia (collect blood, spleens, lymph nodes, bone marrow and livers) |
|---|---|---|---|---|
| 1 | M13-12D4 | 0, 3, 6, 8 | −2, 0, 2, 4, 6, 8, 10 | Week 10 |
| 2 | M13-12B7 | 0, 3, 6, 8 | −2, 0, 2, 4, 6, 8, 10 | Week 10 |
| 3 | M13-all 5 | 0, 3, 6, 8 | −2, 0, 2, 4, 6, 8, 10 | Week 10 |
| 4 | gp145/M13-all 5 | 0, 3, 6, 8 | −2, 0, 2, 4, 6, 8, 10 | Week 10 |
| 5 | gp145 | 0, 3, 6, 8 | −2, 0, 2, 4, 6, 8, 10 | Week 10 |
| 6 | M13-no insert | 0, 3, 6, 8 | −2, 0, 2, 4, 6, 8, 10 | Week 10 |
| 7 | Naive | 0, 3, 6, 8 | −2, 0, 2, 4, 6, 8, 10 | Week 10 |

IFNγ-Release ELISPOT (Enzyme-Linked Immunosorbent Spot) Assay

Spleen cells secreting IFNγ were analyzed by ELISPOT. Ninety-six-well nitrocellulose-backed MultiScreen-IP sterile plates (Millipore) were coated overnight at 4° C. with 10 μg/ml of anti-gamma interferon (IFNγ) (PBL Interferon Source) in sterile PBS. The wells were blocked with sterile PBS containing 0.5% bovine serum albumin for 30 min at 37° C. and washed with PBS containing 0.025% Tween 20 (wash solution) followed by sterile RPMI-1640 complete medium. Single cell suspensions were prepared from the mouse spleens of each group (five mice/group). Cells ($2 \times 10^6$/well) were plated on anti-IFNγ-coated plates and incubated for 18 h at 37° C. in a humidified $CO_2$ incubator. Cells were incubated with 5 μg/ml acute C gp145 (HIV-1 C06980, Advanced Bioscience Laboratories), gp140 (HIV-1 IIIB, Advanced Bioscience Laboratories), yeast-derived gp41 (Meridian Biosciences) or 10 μg/ml cathepsin degraded, yeast-derived gp41 or no protein. Plates were washed with wash solution followed by distilled water and overlaid with 0.125 μg/ml of biotinylated anti-IFNγ (clone XMG 1.2; BD PharMingen) and incubated at room temperature for 2 h. The plates were then washed and incubated with a 1:1,000 dilution of avidin-conjugated alkaline phosphatase (Vector Laboratories) for 2 h at room temperature. The plates were washed, and bound IFNγ was detected by the addition of 5-bromo-4-chloro-3-indolylphosphate (BCIP)/nitroblue tetrazolium (NBT) (Kirkegaard and Perry Labs). The plates were washed with water, and the individual spots were visualized and counted the next day using a stereo binocular microscope. The average number of spots/number of cells plated was plotted.

Antigen Presentation and Detection of Cytokines from T-Cells by Flow Cytometry

Cells from spleens or lymph nodes from the different groups of mice were stimulated with 5 μg/ml acute C gp145 (HIV-1 C06980, Advanced Bioscience Laboratories), gp140 (HIV-1 IIIB, Advanced Bioscience Laboratories), yeast-derived gp41 (Meridian Biosciences) or 10 μg/ml cathepsin degraded, yeast-derived gp41 or ConA as the postive control for 22 h at 37° C. The cells were incubated with the above-mentioned antigens for 2 h before the addition of brefeldin A (1 mg/ml, Sigma-Aldrich) and monensin (0.07 mg/ml, BD Pharmingen). Cells were incubated for an additional 20 h. Cells were analyzed on an LSR II (BD Immunocytometry Systems) flow cytometer and 500,000 events were collected using FACSDiva software (BD Immunocytometry Systems). Dead cells were excluded using a viability marker and B-cells were excluded. The CD3+ CD4+ and the CD3+ CD8+ T-cells were gated and analyzed for the expression of IL-2, TNF-a, IFN-g and CD107a. The data were analyzed using FlowJo software (Tree Star). Percent positively stained cells per antigen are shown for each group. The black bar represents a two-fold range above the control response, M13—no insert.

Antigen-Specific Serum IgG ELISA

Antigen specific IgG titers were determined by binding ELISA titrations using gp145 and gp41 as targets. Antigens were diluted to 0.25 μg/ml in PBS (pH 7.4), 100 ul per well was added to 96-well microtiter Immunol 2 polystyrene plates. Plates were incubated overnight at 4° C. then washed three times with 300 ul 0.1% PBST (PBS containing 0.1% Tween-20). Serum was titered in 2-fold serial dilutions starting at 1:50 dilution in serum diluent (0.1% PBST containing 5% non-fat milk), and 100 ul each dilution was added to the plate. Plates were incubated at 37° C. for 1 h then washed three times with wash buffer. HRP-labeled anti-mouse IgG antibody diluted to 1:16,000 in serum diluent was added, 100 ul/well. Plates were incubated for 1 h at 37° C. then washed three times with wash buffer. TMB (100 ul, Kirkegaard and Perry Labs) was added, incubated for 30 min at 37° C. and the reaction stopped by adding 100 ul of 1 M phosphoric acid. Plates were read on a spectrophotometer at 410 nm, 570 nm reference filter. Antigen binding titer was determined by calculating the concentration at which binding was detectable above three times background. Two independent assays were performed and the results were averaged.

Surface Plasmon Resonance (SPR) Measurements by Biacore

SPR measurements were conducted with a Biacore T200 using CM5 chips. Peptides were immobilized to the chip surface using the Biacore amine coupling kit (Biacore, AB). All immobilization steps used a flow rate of 10 μl/min and were performed at 25° C. The peptide loading buffer was 20 mM sodium acetate, pH 4.2. The immobilization wizard packaged within the T200 control software was used to immobilize 14700 resonance units (RU) of 10 uM scrambled MPER peptide and 20500 RU of MPER peptide to their respective flow cells. Both peptides had a 10 min contact time during immobilization. The serum samples were diluted 1:50 in Tris buffered saline, pH 7.4 and passed over the chip surface at 30 µl/min for 3 min followed by a 5 min dissociation period. At the end of the 5 min period, a 75 µg/mL solution of sheep anti-mouse IgG(Fc) antibody (The Binding Site) was passed over the flow cells for 2 min at a flow rate of 10 µl/min. After a 70 s dissociation period, the chip surface was regenerated using a 30 second pulse of 50 mM HCl, a 30 second pulse of 100 mM EDTA in 20 mM Tris, pH 7.4, and 30 second pulse of 50% acetic acid followed by a 1 minute injection of Tris-buffered saline, pH 7.4. Non specific binding was subtracted and data analysis was performed using the BIAevaluation 4.1 software. The reported response units for the IgG specific values are the difference between the average value of a 5 second window taken 60 seconds after the end of the anti-IgG injection and the average value of a 5 second window taken 10 seconds before the beginning of the anti-IgG injection.

Pseudovirus Neutralization Assay

TZM-b1 cells were used as assay targets to determine HIV-1 neutralization. BnAb or plasma were titered in 4-fold serial dilutions starting at 25 µg/ml or 1:20 dilution respectively, in growth medium [DMEM with 100 U/ml penicillin, 100 µg/ml streptomycin, 2 mM L-glutamine (Quality Biologics Inc.), and 15% fetal calf serum (Gemini Bio-Products)] and 25 µl added in duplicate to a 96-well flat-bottom black plate. Pseudovirus, diluted in growth medium to a dilution optimized to yield ~150,000 relative luminescence units (RLU), was added in equal volume to each well. The samples were incubated at 37° C. in a humidified 5% $CO_2$ incubator for 1 h. All incubations were under these conditions. TZMbl cells were resuspended at $2\times10^5$ cells/ml in growth medium containing 60 µg/ml DEAE-dextran (Sigma), 50 µl was added to each well. Each plate included wells with cells and pseudovirus (virus control) or cells alone (background control). Plates were incubated for 48 h, and then 100 µl/well of reconstituted Brite Lite Plus (Perkin Elmer) was added. RLU values were measured using a Victor 2 luminometer (Perkin-Elmer). The percent inhibition due to the presence of the antibody was calculated by comparing RLU values from wells containing antibody to well with virus control. Two independent assays were performed and the results were averaged.

PBMC Neutralization Assay

PBMC, collected from HIV-negative donors and cryopreserved, were used as assay targets to determine HIV-1 neutralization. This assay uses replication-competent HIV-1 infectious molecular clones (IMC) containing a Renilla reniformis luciferase (LucR)-expressing HIV-1 reporter gene; viral production is measured with a luminometer (Edmonds, T G et al. Virology 408:1-13 (2010)). Sera were titered in 4-fold serial dilutions starting at 1:20 dilution in IL-2 growth medium [RPMI-1600 with 100 U/ml penicillin, 100 µg/ml streptomycin, 2 mM L-glutamine (Quality Biologics Inc.), 15% fetal calf serum (Gemini Bio-Products), and 20 U/ml recombinant interleukin-2 (Roche Diagnostics)] and 25 µl was added in duplicate to a 96-well round-bottom plate. IMC, diluted in IL-2 growth medium to a dilution optimized to yield ~50,000 RLU, was added in equal volume to each well. The samples were incubated at 37° C. in a humidified 5% $CO_2$ incubator for 1 h. All incubations were under these conditions. PHA/IL-2 stimulated PBMC were resuspended at $2\times10^6$ cells/ml in IL-2 growth medium then 50 µl was added to each well. Each plate included wells with cells and IMC (virus control) or cells alone (background control). Plates were incubated for 24 h, 100 µl of growth medium was added to each well and then plates were incubated for an additional 72 h. Renilla Luciferase Assay System (Promega) was used to quantify luciferase production. Lysis buffer, 50 µl/well, was added and two freeze/thaw cycles were performed, 20 µl/well was transferred to a black, flat-bottom plate and RLU in each well were measured immediately after injection of 100 µl substrate. The percent inhibition due to the presence of the antibody was calculated by comparing RLU values from wells containing antibody to well with virus control. Two independent assays were performed and the results were averaged.

Results

Figure 56:
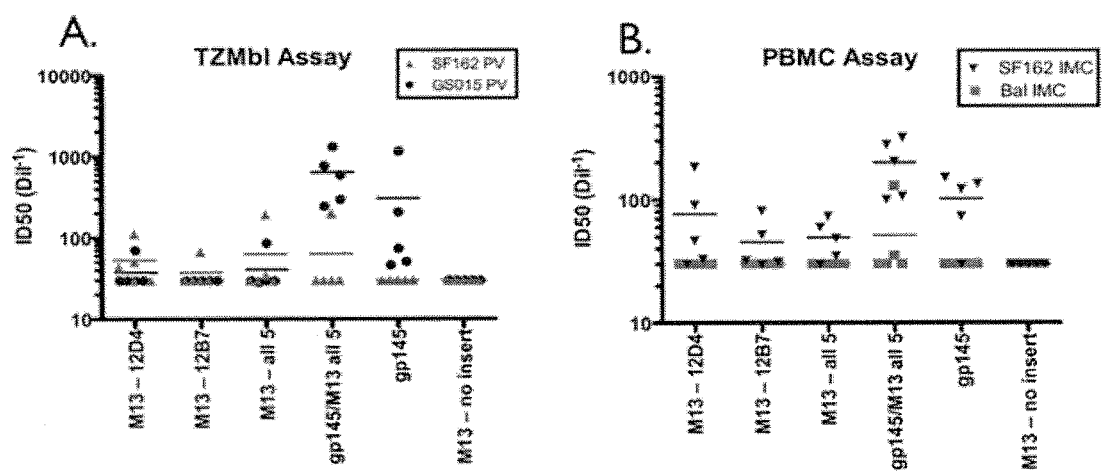

Immunogenicity of the five M13-displayed 4E10 epitopes capable of inhibiting neutralization was evaluated in vivo. Thirty-five female BALB/C mice, seven groups of five animals each, were vaccinated with a single M13-displayed epitope, all five M13-displayed epitopes or all five M13-displayed epitopes in combination with HIV-1 gp145 envelope protein (Table 9). The gp145 envelope protein, from an acute clade C HIV-1 infection, has been shown to elicit neutralizing antibodies in rabbits.

Analysis of Elicited Cellular Immune Response

Cellular immune responses elicited by vaccination were assessed by INFγ-release ELISPOT and intracellular cytokine staining (ICS) assays in both the spleen and lymph node. In these assays HIV-specific responses were measured after stimulation with HIV-1 envelope proteins: gp145, gp140, gp41 or cathepsin degraded gp41. A response two-fold greater than the control group, mice immunized with M13—no insert, was considered a positive response (FIGS. 53 and 54). ICS data was analyzed to determine CD3+CD4+ or CD3+CD8+ T-cell specific responses.

In the INFγ-release ELISPOT assay, a single response was observed in all groups in both the lymph node and the spleen; the M13—all 5 immunized group, stimulated with gp140 in the lymph node and the gp145 immunized group, stimulated with gp145 in the spleen (FIG. 53). Background responses to gp140 were high in the splenic T-cells. IL-2 responses were observed by ICS for all groups against several HIV-1 envelope antigens; TNFα, CD107a and INFγ responses were not detected. Positive IL-2 responses were more frequent in the lymph node than in the spleen, 85% and 48% positive responses, respectively, but were lower in magnitude, 3.9-fold and 4.5-fold above control, respectively. Positive IL-2 responses were more frequent in the CD4+ T-cell compartment than in the CD8+ T-cell. 73% and 60% positive responses, respectively, and were higher in magnitude, 4.5-fold and 3.8-fold above control, respectively (FIG. 54). Mice immunized with liposomes only did not have HIV-1 specific cellular responses.

Analysis of Elicted Antibody Responses

Humoral immune responses were analyzed by IgG binding ELISA, Biacore and by neutralization assays. Binding titers against gp145 and gp140 were determined for all groups (FIG. 55). Animals immunized with gp145 or gp145/M13all 5 produced antibodies with high titers gp145, average of 512000 and 409600 respectively, and gp41, average of 30400 and 43200 respectively; both groups had the highest titers to the gp145 immunizing protein. The other groups did not have detectable binding titers in this assay with the exception of M13—all 5, which had a weak binding titer to gp145, average 1200. Biacore was used to characterize epitope-specific IgG binding to MPER peptide in pooled serum; no binding was observed (data not shown).

Neutralization assays were performed using both TZMbl and PBMC as assay targets. Sera were titered against two neutralization-sensitive HIV-1 strains in both assay platforms and ID50 values were calculated (FIG. 56). Animals immunized with gp145/M13—all 5 had the highest neutralization titers in both the TZMbl and PBMC assays, a 2.1- and 1.9-fold increase respectively over the gp145-immunized group. Animals immunized with a single M13-displayed MPER epitope, M13-12D4 and M13-12B7, or multiple M13-displayed MPER epitopes (M13—all 5), also produced HIV-neutralizing antibodies. All sera were screened against the HIV-2/MPER chimera and a nonspecific viral control, MuLV, no neutralization was observed for either of these viruses.

Example 6

α4β7 Blocking Assay

Materials:
Media: 10% FCS/RPMI/Lglut/PenStrep
Cells: RPMI8866

TABLE 10

Reagents:

| Reagent | Clone# | Mfg | Cat# | Lot# | Working Dil. | Comments |
|---|---|---|---|---|---|---|
| Normal mouse IgG | — | Invtrogen | 10400C | 645253A | 10% | |
| Normal human IgG | — | GenScript | A01006 | A108810 | 10% | Make lyoph, stock to 1 mg/mL H2O |
| Anti-α4blocking MAb | HP2/1 | Beckman Coulter | IM0764 | 21 | 2 ug/well | make lyoph. stock to 0.5 mg/mL H2O |
| Anti-β7-FITC | FIB504 | BioLegend | 321212 | B142196 | 1:10 | |
| Neutravidin-PE | — | Invitrogen | A2660 | 866787 | 1:400 | |
| gp145-AcuteC-biotin | — | V.Polonis | — | LotB | 0.5 ug/well | biotinylated 2X by RF |
| Anti-Env mAbs × 14 | | See Table 12 for list of mAbs tested | | | | rcvd from S. Zolla-Pazner |

Prepare α4β7 Binding Buffer
prepare 1M MnCl2 fresh from powder (1 g MnCl2-4H2O (from Arthos Lab-MW 197.9)+5 mL dH2O
prepare binding buffer per table below
sterile filter solution and store at 4° C.

TABLE 11

| Reagent | Mfr | Cat # | [Final] (mM or %) | [Initial] (M or %) | mL for 500 mL |
|---|---|---|---|---|---|
| HEPES buffer | Gibco | 15830 | 10 | 1 | 5 |
| NaCl | Sigma | 56546 | 150 | 5 | 15 |

TABLE 11-continued

| Reagent | Mfr | Cat # | [Final] (mM or %) | [Initial] (M or %) | mL for 500 mL |
|---|---|---|---|---|---|
| MnCl2 | (commercially available) | | 1 | 1 | 0.5 |
| CaCl2 | Fluka | 21115 | 0.1 | 1 | 0.05 |
| BSA | Sigma | A9576 | 0.5 | 30 | 8.3 |
| NaN3 | Aldrich | 438456 | 0.09 | 10 | 4.5 |
| dH2O | Quality Bio | 351029101 | — | — | 466.6 |

Harvest Cells
collect non-adherent cells and transfer to a 50 ml tube
pellet cells at 200×g for 10' and pour off supernatant
combine all cells into 10 mL media, resuspend virorously to break up clumps and count
adjust volume to 1.0×10⁶ cells/mL media
aliquot 100 uL (100K) cells per well into assay plates (96-well U-bottom polypropylene)
pellet at 200×g for 10'
wash cells 2× with binding buffer

TABLE 12

Samples

| # | Sample ID | Spicificity | [IgG] ug/uL | uL for 10 ug | uL Bndg Bfr | Total uL |
|---|---|---|---|---|---|---|
| A | 1361.100.10.10.1.1 | V2 | 1.52 | 6.6 | 33.4 | 40 |
| B | 1393A.100.10.1.1 | V2 | 2.99 | 3.3 | 36.7 | 40 |
| C | 1357A.100.10.1 | V2 | 0.84 | 11.9 | 28.1 | 40 |
| D | 2158.100.100.10.1.1 | V2 | 5.28 | 1.9 | 38.1 | 40 |
| E | 697-30D.10.1.1 | V2 | 6.44 | 1.6 | 38.4 | 40 |
| F | 830A.10.10.1.1 | V2 | 0.45 | 22.2 | 17.8 | 40 |
| G | 2297.100.1.1 | V2 | 3.01 | 3.3 | 36.7 | 40 |
| H | 447-52D.10.1.1 | V3 | 4.36 | 2.3 | 37.7 | 40 |
| I | 1006-15D.100.1 | V3 | 2.40 | 4.2 | 35.8 | 40 |
| J | 3869.100.10.1.1 | V3 | 5.27 | 1.9 | 38.1 | 40 |
| K | 729-30D.10.10.1.1 | CD4bs | 2.15 | 4.7 | 35.3 | 40 |
| L | 1331-160E.100.10.1 | CD4bs | 1.54 | 6.5 | 33.5 | 40 |
| M | 1570D.10.1.1 | CD4bs | 3.86 | 2.6 | 37.4 | 40 |
| N | 1418(16).10.1 | b19 | 4.75 | 2.1 | 37.9 | 40 |

Preincubate Protein+IgG
add binding buffer to wells according to plate layout and sample calculations
add IgG to the appropriate sample wells according to the sample calculations
add 40 μL binding buffer alone to wells for UNTREATED, POS CTRL and NO IgG CTRL wells
make up stock of protein(s) at 0.025 μg/μL in binding buffer

TABLE 13

| Protein | [stock] ug/uL | # Wells | uL per well | Total Vol | [Final] ug/uL | uL Protein | uL Buffer |
|---|---|---|---|---|---|---|---|
| gp145-AcuteC Lot B2 | 1.0 | 20 | 20 | 400 | 0.025 | 10.0 | 390 | add 20 µL binding buffer to UNTREATED wells
add 20 µL protein to sample wells, POS CTRL and NO IgG CTRL wells (=0.5 µg protein/well)
incubate plate for 60 min at 37° C.
Binding Assay
prepare blocking buffer (10% mouse IgG, 10% human IgG in binding buffer)
add 50 uL/well blocking buffer
add 4 uL (2 ug) anti-α4 blocking mAb to the POS CTRL well
incubate on ice×10 min (do not wash off)
transfer 50 uL protein/IgG complexes to assay plate per layout
incubate on ice×30 min
wash 2× with binding buffer
Staining
prepare staining cocktail

TABLE 14

Figure 57:
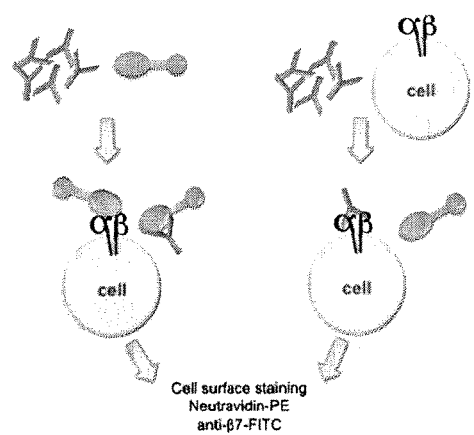

| uL per well | # wells | Total Vol | uL β7-FITC (1:10) | uL NA-PE (1:400) | uL Buffer |
|---|---|---|---|---|---|
| 50 | 20 | 1000 | 100 | 2.5 | 898 | add 50 µL binding buffer to unstained wells
add 50 µL staining cocktail to NO IgG CTRL, POS CTRL and all sample wells
incubate at 4° C. for 30 min
wash 2× with binding buffer
fix with 4% PFA×30-60 min at 4° C.
spin cells down and resuspend in 150 µL binding buffer
store plates at 4° C. until ready to read
Compensation Bead Preparation
prepare 2 wells of compensation beads, wash beads with staining buffer 2×
resuspend beads in 45 uL staining buffer
5 uL CD4-FITC to one well and 5 uL CD4-PE to the other and mix well
incubate at 4° C. for 30 min
wash 2× with staining buffer
resuspend in 200 uL staining buffer A second a4B7 binding inhibition assay is a flow cytometry based assay which can be performed on the RMPI8866 cell line, but is primarily performed on isolated CD4+ and CD8+ T cells cultured to express the active form of the α4β7 heterodimer. A model for this assay is shown in FIG. 57. This assay can be performed as a binding assay to test variants of the HIV-1 env derived from selected acute sequences. The expanded utility of the assay includes the test for functional blocking of the env/α4β7 interaction by monoclonal antibodies or purified serum IgG against either the env protein or the integrin. Selected HIV-1 env protein is generated and biotinylated and pre-incubated with antibody, followed by incubation with the α4β7 expressing cells. Binding is detected by addition of neutravidin-PE and the presence of the α4β7 is confirmed by staining with the non-blocking mAb conjugated to FITC. When testing an anti-integrin antibody, the cells are pre-incubated with the antibody prior to addition of the biotinylated env protein, and detection proceeds as described. Applicants have adapted this method for use with whole env protein as well as biotinylated linear and cyclic peptides. In certain embodiments, the assay is developed to be used with the IMC and VLP constructs.

Figure 58:
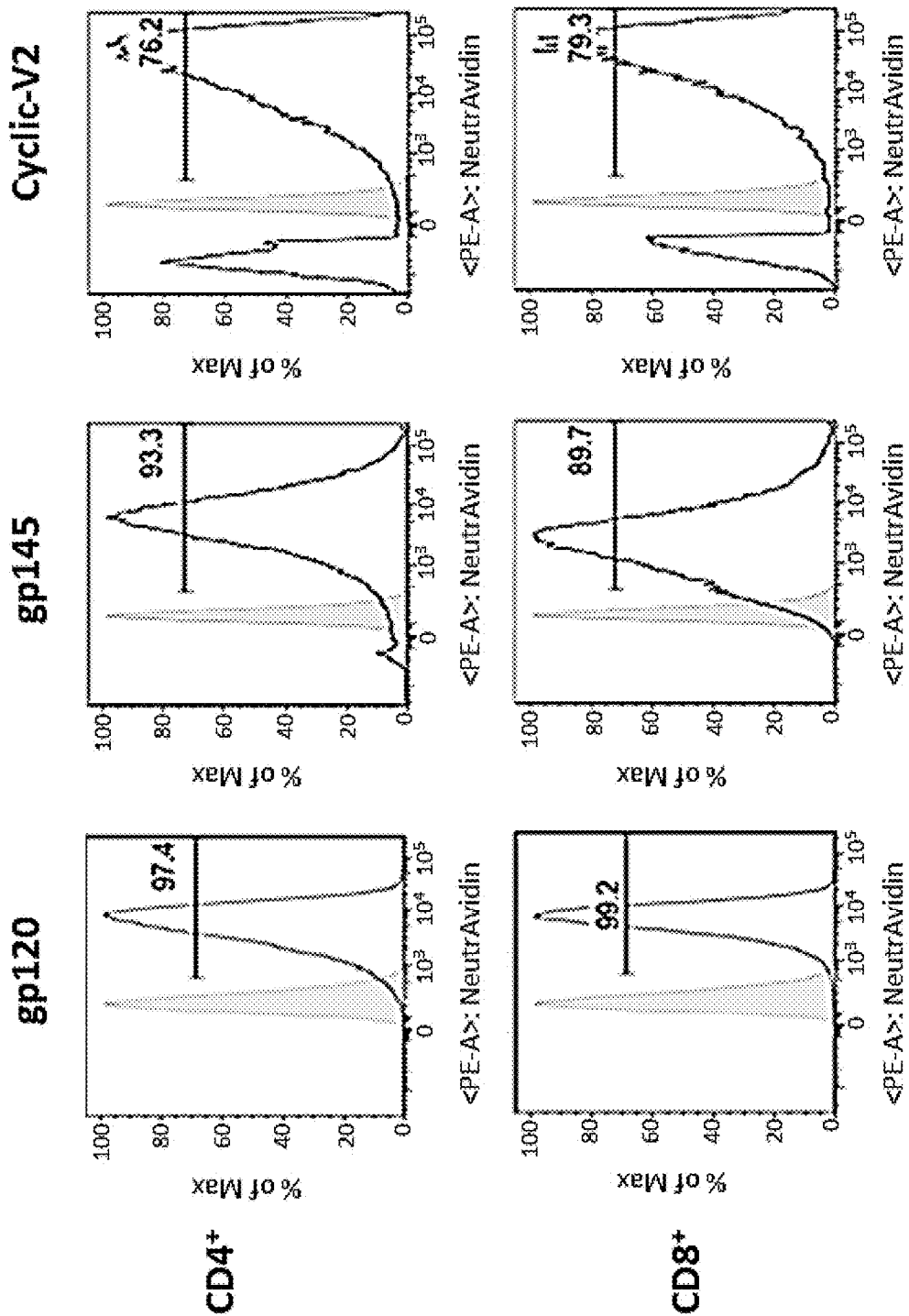

One of the important features of this assay is the ability to use primary T cells expressing the active form of α4β7. To generate these cells, Applicants isolate CD4+ and CD8+ T cells from PBMC by magnetic bead separation. A negative selection protocol is used so the resulting cells are "untouched", purified and bead-free. Following isolation, cells are incubated for 5 days in the presence of anti-CD3/anti-CD28, IL-2 and retinoic acid to induce surface expression of α4β7 (FIG. 58).

Figure 59:
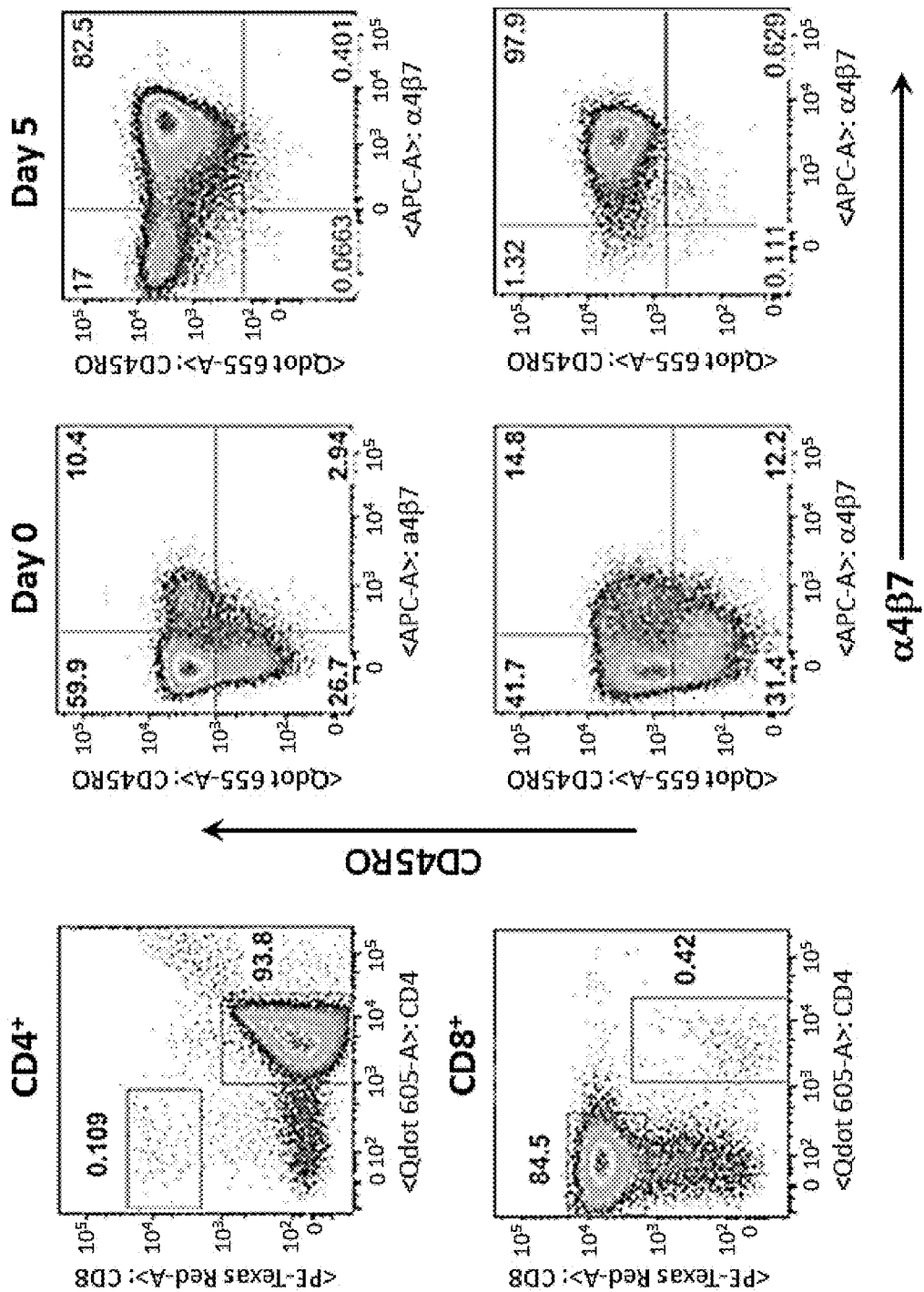

Preliminary experiments during development of this assay were conducted to determine the binding kinetics and overall utility of the assay with a variety of HIV-1 envelope reagents. Recombinant CRF01_AEgp120 and an acute subtype C gp145 (as described above) were biotinylated and bound to α4β7 expressing CD4+ or CD8+ T cells (FIG. 59, left and center panels). A biotinylated cyclic peptide containing the V2 loop of HIV-1 Env derived from CRF01-AE also bound both CD4+α4β7+ and CD8+α4β7+ cells. Similar binding was also seen with the RPMI8866 cell line (data not shown). There was no binding detected with a clade B MN derived gp120 or with a cyclic V2 peptide containing a mutation in the apex of the loop (data not shown).

Figure 60:
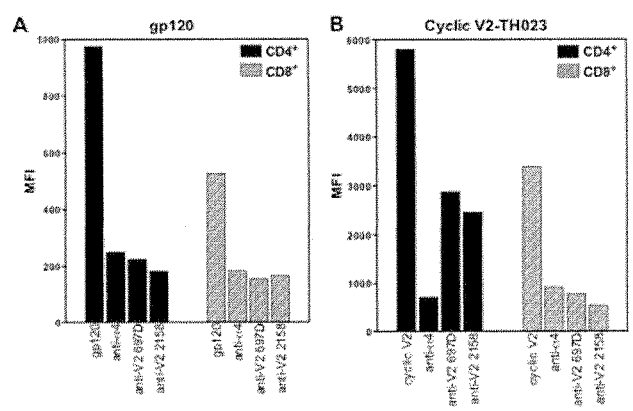

Initial blocking studies were conducted using human anti-V2 monoclonal antibodies (kindly provided by S. Zolla-Pazner) and the CRF01_AE-derived gp120 or cyclic V2 peptide. Both V2-reactive monoclonal antibodies tested, 697-30D and 2158, blocked binding of Env to CD4+α4β7+ and CD8+α4β7+ cells (FIG. 60). As a positive control, cells were pre-incubated with the anti-α4 blocking antibody HP2/1 prior to addition of protein or peptide. Applicants proceeded with these experiments, testing a panel of overlapping linear peptides derived from the V2 loop to delineate the amino acid residues required for this interaction (data not shown).

Methodology

Preparation of α4β7 T Lymphocytes. Cryopreserved PBMC are thawed in complete media and CD4+ or CD8+ T cells are isolated by magnetic bead negative selection. Cells are cultured in the presence of anti-CD3/anti-CD28, IL-2 and retinoic acid for at least 5 days. Polychromatic flow cytometry is used to monitor phenotype, cell viability and expression of active form of α4β7. For some assays, the human B cell lymphoma line RPMI8866 will be used as it highly expresses active form of α4β7.

α4β7 Binding/Blocking Assay. Cells expressing α4β7 are incubated with 2-5 µg biotinylated V2 peptides or HIV-1 envelope glycoprotein for 30 minutes. Following a wash to remove unbound peptide/protein, cells are stained with neutravidin-PE and binding is assessed by flow cytometry. For blocking studies, antibodies are pre-incubated with either the α4β7 expressing cells or with the HIV-1 envelope protein, as appropriate, for 30 minutes prior to addition.

Synthesis of HIV-1 envelope proteins. Acute envelope sequences are selected from subjects in the RV217 acute infection study for synthesis. Sequences are submitted to GeneArt, Inc. for codon optimization and cloning into mammalian expression vectors. Proteins are expressed in CHO cells or HEK293 cells, which provide different glycosylation patterns that may be important for binding assays. Following expression, a portion of each protein is biotinylated for use in α4β7 binding/blocking assays.

Synthesis of biotinylated V2 peptides. Peptides designed by Dr. Tim Cardozo (New York University) are synthesized and biotinylated by Genemed Synthesis Inc. These peptides have been kindly provided to us by Dr. Cardozo.

Example 7

Summary

Data from gel filtration supported the presence of a mixture of different multimer species. However, it was not certain how the globular nature, hydrophobic regions and heavy glycosylation of gp145 affect the resolution of the different multimeric forms in this assay. Therefore, it was difficult to conclude what species are present and in what proportion. In addition, poor resolution in this assay made it difficult to determine the relative quantity of each form. To further analyze the oligomeric froms present in the purified lots of C06980v0c22 gp145, Blue Native PAGE (BN PAGE), and EGS crosslinking, SDS-PAGE was performed using purified proteins. In addition, separation of oligomeric forms was attempted using gel filtration chromatography.

BN Page

Figure 61:
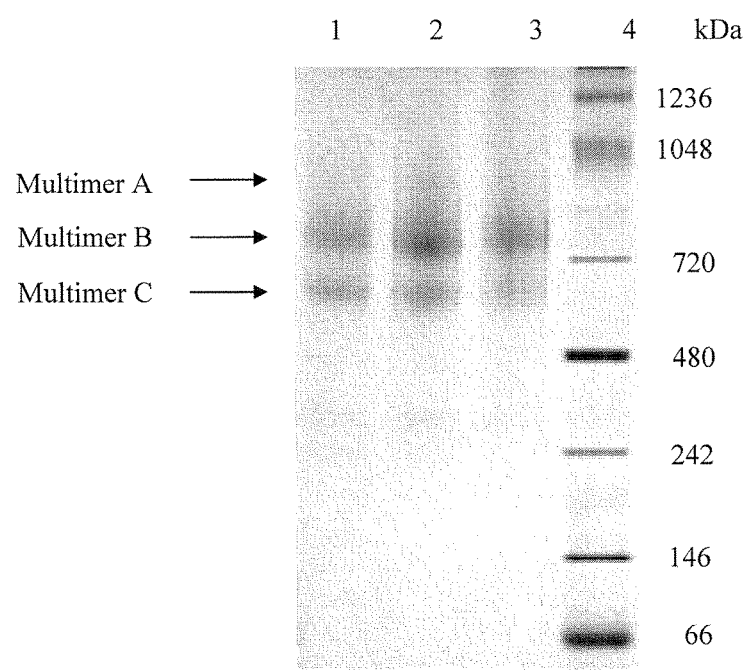

The multimeric composition of purified HIV-1C06980v0c22 gp145 lots 112009, 120710A and 120710B were analyzed using Blue Native PAGE. Purified HIV-1C06980v0c22 gp145 was run on a 4-16% Novex Bis-Tris polyacrylamide gel using Invitrogen's Native PAGE system (FIG. 61). For comparison, Ba-L gp145 and the three clade D gp140 proteins (A07412, 57128, and 57140) described above were also run. Laser densitometry analysis run on the BLUE Native PAGE predicts a mixture of multimeric forms for each protein (Table 15).

Table 15: Laser densitometry prediction of gp140 and gp145 multimer composition

| Clade | Protein | Lot | Apparent Molecular Weight (kDa) | Multimeric Species | Percent composition |
|---|---|---|---|---|---|
| B | Ba-L gp145 | 061308 | >800* | A | 40.3% |
| | | | 691 | B | 21.5% |
| | | | 538 | C | 35.1% |
| | | | 278 | D | 3.1% |
| D | A07412 gp140 | 3-31-05 | >800* | A | 30.5% |
| | | | 733 | B | 32% |
| | | | 574 | C | 37.5% |
| D | 57128 gp140 | 4-13-05 | >800* | A | 21.4% |
| | | | 674 | B | 44.5% |
| | | | 566 | C | 34% |
| D | 57140 gp140 | 4-20-05 | >800* | A | 27.1% |
| | | | 773 | B | 40.6% |
| | | | 659 | C | 32.2% |
| C | C06980v0c22 gp145 | 112009 | >800* | A | 12.8% |
| | | | 767 | B | 52.7% |
| | | | 624 | C | 27.3% |
| | | | 302/244** | D | 7.2% |
| C | C06980v0c22 gp145 | 120710A | >800* | A | 11.4% |
| | | | 751 | B | 61% |
| | | | 621 | C | 22% |
| | | | 308/239** | D | 5.6% |
| C | C06980v0c22 gp145 | 120710B (DTT treated) | >800* | A | 15.1% |
| | | | 770 | B | 59.5% |
| | | | 638 | C | 19.6% |
| | | | 307/239** | D | 5.9% |

*Extremely diffuse band spanning several hundred kDa; difficult to state molecular weight. More than one species may be present in these fractions.
**Doublet with incomplete separation may represent 2 species including some breakdown products.

From Blue Native PAGE, it is clear that the gp140 and gp145 proteins exist as a mixture of various multimers. However, it is not abundantly clear what species are present. If one assumes that monomer is about 140 kDa, then the expected molecular weight of trimer, tetramer, pentamer and hexamer are about 420 kDa, 560 kDa, 700 kDa, and 840 kDa, respectively. However, due to their globular form, hydrophobic regions, and heavy glycosylation, it is suspected that the proteins may not behave in this manner. Accordingly, for this Example, Applicants designated each multimer species as A, B, C or D, with A being the most complex and D the least complex. All C06980v0c22 gp145 lots behave similarly with B as the predominant form along with significant amounts of C and D. DTT treatment of lot 120710B appears to have no significant affect on the multimer composition. A similar trend is seen for the clade D 57140 and 57128 gp140s. The clade D A07412 gp140 is similar, but the C form is slightly greater in quantity than the B form. For the Ba-L gp145, the predominant species are found in a broad, diffuse band corresponding to a likely mixture of high order multimers, classified as the A species. A distinct major C population and a more minor B population are also evident.

EGS Crosslinking/SDS-PAGE

Figure 62:
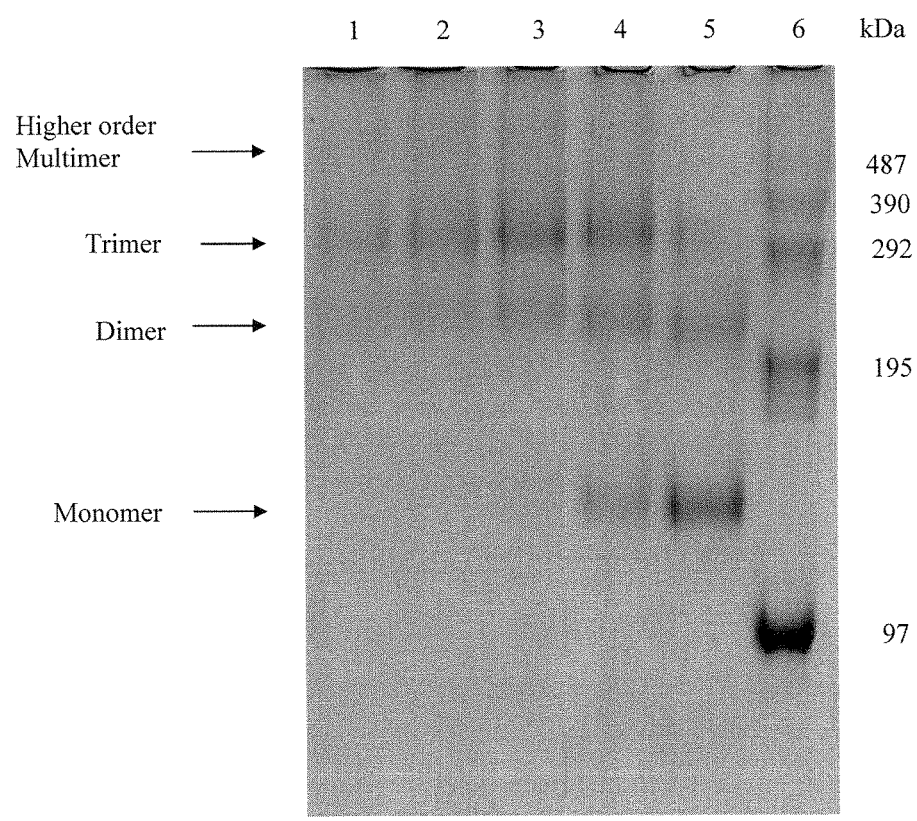
FIG. 62: SDS-PAGE of EGS crosslinked C06980v0c22 gp145 (lot 120710A) under nonreducing conditions. 5 μg of gp145 was treated with 12.5, 5, 1, 0.2 and 0 mM EGS and resolved on a 3-8% NuPAGE Tris Acetate polyacrylamide gel under nonreducing conditions: 12.5 mM EGS (lane 1), 5 mM EGS (lane 2), 1 mM EGS (lane 3), 0.2 mM EGS (lane 4) and 0 mM EGS (lane 5). EGS crosslinked phosphorylase B was run in lane 6 as a molecular weight protein marker.
Figure 63:
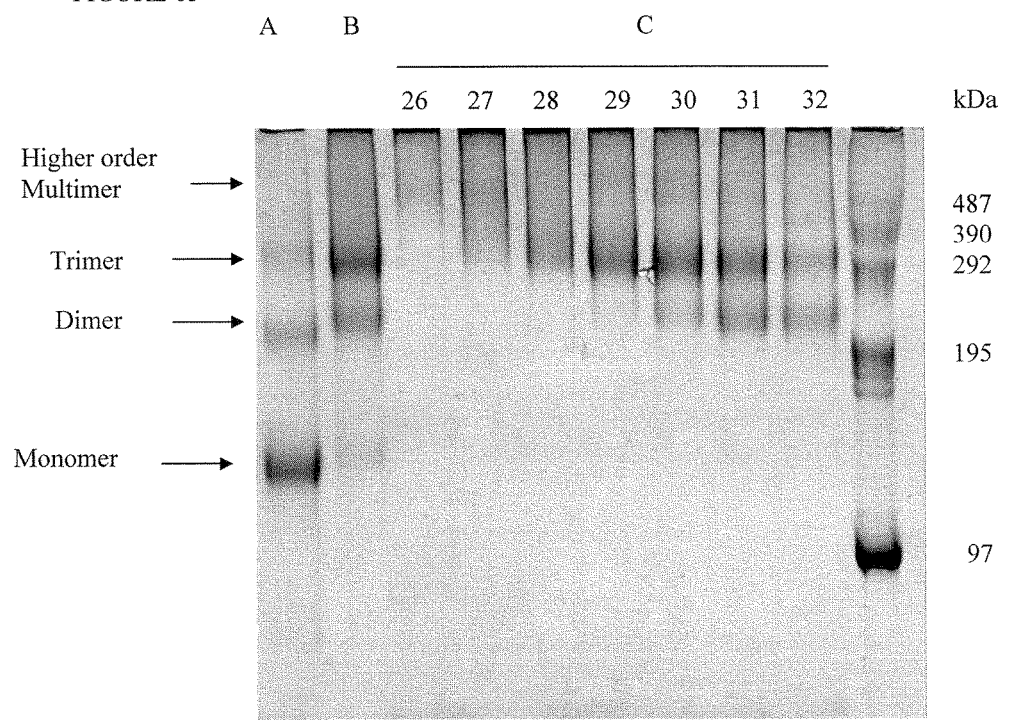
FIG. 63: SDS-PAGE of EGS crosslinked C06980v0c22 gp145 (lot 120710A) purified on Superose 6. 10 μg of gp145 from the column load and eluted fractions was crosslinked with 5 mM EGS. Crosslinked and noncrosslinked gp145 was resolved on a 3-8% NuPAGE Tris Acetate polyacrylamide gel: 5 μg noncrosslinked gp145 column load (A), 10 μg crosslinked gp145 column load (B) and 10 μg crosslinked eluted fractions 26-32 (C). EGS crosslinked phosphorylase B was run as a molecular weight protein marker (D).

C06980v0c22 gp145 gp145 has been further characterized by SDS-PAGE of proteins crosslinked with ethylene glycol bis(succinimidylsuccinate) (EGS) to further characterize the multimeric forms. The data suggests that trimers predominate, but dimers and trace amounts of monomer and higher order multimers are also present. Purified HIV-1$_{C06980v0c22}$ gp145 (lot 120710A) was crosslinked with 0.2, 1, 5 and 12.5 mM EGS and resolved on a 3-8% NuPAGE Tris Acetate polyacrylamide gel (Invitrogen) under reducing and non-reducing conditions and stained with coomassie blue (FIG. 62). Laser densitometry analysis was used to estimate the molecular weights of each gp145 species. When treated with 0.2 mM EGS, gp145 crosslinking is not complete, and three species are evident at 334, 232 and 139 kDa. These correspond well to the predicted molecular weights of trimeric, dimeric and monomeric forms. As EGS concentrations are increased to 5 and 12.5 mM, crosslinking is completed, revealing that trimer is the predominate species. A major dimer species is also present, but monomer makes up only a trace of the total protein. Under nonreducing conditions, a faint band corresponding to a higher order multimer is also evident with the fully crosslinked samples. This reveals that some higher order multimers exist that are held together with disulfide bridges. Multimeric species A, B and C presumably correspond to the higher order multimer, trimer and dimer species as resolved with the EGS crosslinked protein, respectively. Based on Blue Native PAGE results, the major multimer species B and C had apparent molecular weights of 751 and 621 kDa, respectively. These apparent molecular weights were too high to conclude with confidence that they represent trimer and dimer. However, using EGS crosslinking, the apparent molecular weights are more in line with the major forms being trimer or dimer. EGS crosslinking SDS-PAGE is a method used by J. P. Nkolola, et. al. (1) to describe recombinant HIV-1 92UG037.8 gp140 produced in the baculovirus system as trimer. These proteins run at a similar molecular weight as the C06980v0c22 gp145 using a similar EGS crosslinking procedure. The apparent discrepancies in the predicted molecular weights of the gp145 oligomers observed with BN-PAGE and EGS crosslinking SDS-PAGE may be due to how the charge, globular nature, hydrophobic regions and heavy glycosylation of gp145 affect the resolution of the different multimeric forms in these assays. It would seem that BN-PAGE is capable of resolving oligomeric forms in the native state. However, the molecular weights cannot be determined due to proportionate differences in the mobility of gp145 and the molecular weight markers. In EGS-crosslinking SDS-PAGE, oligomers are covalently bound together, but denatured as with a regular SDS-PAGE. Under these conditions, gp145 migrates relative to the standards based on its apparent molecular weight much as it would if not crosslinked.

Dimer and Trimer Purification

Gel filtration chromatography has been investigated as to whether it can be used to isolate the various oligomeric species of gp145. Successful isolation of the various forms would allow for the potential investigation of the antigenicity or immunogenicity of each form.

Gel filtration chromatography using Superose 6 was performed. It is thought that Superose 6 would have potential for separating the high molecular weight gp145 species because of its high molecular weight range; optimal separation of proteins is 5 to 500 kDa. Separation of large proteins often proves to be difficult due to relatively poor resolution of gel filtration resins for high molecular weight proteins, such as the gp145 oligomers. Superose 6 shows some promise for separating the different oligomers. On an analytical Superose 6 PC 3.2/30 (GE Healthcare) column, 25 μl containing 200 μg HIV-1$_{C06980v0c22}$ gp145 lot 120710A was loaded at 0.05 ml/min in PBS, pH 7.2. 50 μl fractions were collected and analyzed by EGS crosslinking/SDS-PAGE (FIG. 63). Although no fractions contained pure trimer or dimer, some enrichment of trimer was evident in certain fractions. Higher order multimers are evident in some fractions. Different column size and conditions could have better resolution and potentially separate out trimer from the higher order multimers and dimers. In further embodiments, optimization of separation conditions may be performed using a Superose 6 column.

REFERENCES

Nkolola, J. P., et al. 2010. Breadth of neutralizing antibodies elicited by stable, homogeneous clade A and clade C HIV-1 gp140 envelope trimers in guinea pigs. J. Virol. 84: 3270-3279.

Having thus described in detail embodiments of the present invention, it is to be understood that the invention defined by the above paragraphs is not to be limited to particular details set forth in the above description as many apparent variations thereof are possible without departing from the spirit or scope of the present invention.

Each patent, patent application, and publication cited or described in the present application is hereby incorporated by reference in its entirety as if each individual patent, patent application, or publication was specifically and individually indicated to be incorporated by reference.

What is claimed is:

1. An isolated peptide comprising a truncated HIV Env protein, wherein the HIV Env protein:
   (i) is mutated in the native gp120/gp41 cleavage site to prevent protease cleavage,
   (ii) comprises the NITER of gp41,
   (iii) is truncated prior to the transmembrane domain; and
   (iv) comprises about 1-10 hydrophilic amino acids at its C-terminus; and
   wherein the peptide comprises an amino acid sequence having 99% or greater identity to the amino acid sequence depicted in SEQ ID NO: 1.

2. The peptide of claim 1, wherein the about 1-10 hydrophilic amino acids are three lysines.

3. The peptide of claim 1, wherein the MPER of gp41 comprises the 4E10 epitope.

4. The peptide of claim 3, wherein the MPER of gp41 comprises the amino acid sequence: L WYIK (SEQ ID NO: 24) at its C-terminus.

5. The peptide of claim 4, wherein the HIV Env protein comprises about 1-10 non-native hydrophilic amino acids C-terminal to and contiguous with the L WYIK (SEQ ID NO: 24) amino acid sequence.

6. The peptide of claim 1, wherein the peptide comprises the amino acid sequence depicted in SEQ ID NO: 1.

7. A composition comprising the peptide of claim 1 and a pharmaceutically acceptable carrier.

8. A method of generating antibodies against HIV in a mammal, comprising administering the composition of claim 7 to the mammal.

9. The method of claim 8, wherein the composition further comprises an adjuvant.

10. A method of conferring immunity against HIV in a mammal, comprising administering the composition of claim 7 to the mammal.

11. The method of claim 10, wherein the composition further comprises an adjuvant.

12. The method of claim 10, comprising administering the composition to the mammal by injection.

13. The method of claim 10, wherein the mammal is selected from the group consisting of: a human, a non-human primate, a dog, a rabbit, a guinea pig, and a mouse.

14. A subunit vaccine comprising the peptide of claim 1.

15. An isolated peptide comprising an amino acid sequence having 99% or greater identity to a-14 the amino acid sequence depicted in SEQ ID NO:3.

16. An isolated peptide comprising the amino acid sequence depicted in SEQ ID NO:3, SEQ ID NO:4, or SEQ ID NO:5.

17. A kit comprising (a) the composition of claim 7 and (b) instructions for administration of the composition to a mammal.

18. An isolated peptide comprising an amino acid sequence having 98% or greater identity to the amino acid sequence depicted in SEQ ID NO:7 or SEQ ID NO:9.

19. The peptide of claim 18, wherein the peptide comprises an amino acid sequence having 99% or greater identity to an amino acid sequence depicted in SEQ ID NO: 7 or SEQ ID NO: 9.

20. The peptide of claim 19, wherein the peptide comprises the amino acid sequence depicted in SEQ ID NO: 7 or SEQ ID NO: 9.

21. The method of claim 11, wherein the adjuvant comprises a liposome formulation.

22. The method of claim 21, wherein the liposome formulation comprises one or more of: dimyristoyl phosphatidylcholine, dimyristoyl phosphatidylglycerol, cholesterol, and phospholipid.

23. The method of claim 22, wherein the liposome formulation comprises phospholipid A.

24. The method of claim 8, wherein the antibodies generated in the mammal are antibodies that compete with the peptide comprising the truncated HIV Env protein for binding integrin α4β7.

25. The isolated peptide of claim 1, wherein the peptide binds integrin α4β7.

* * * * *

SEQUENCE LISTING

```
<160> NUMBER OF SEQ ID NOS: 53

<210> SEQ ID NO 1
<211> LENGTH: 650
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Ser Asn Leu Trp Val Thr Val Tyr Tyr Gly Val Pro Val Trp Arg Glu
1               5                   10                  15

Ala Lys Thr Thr Leu Phe Cys Ala Ser Asp Ala Lys Ala Tyr Glu Arg
            20                  25                  30

Glu Val His Asn Val Trp Ala Thr His Ala Cys Val Pro Thr Asp Pro
        35                  40                  45

Asp Pro Gln Glu Ile Phe Leu Gly Lys Asn Val Thr Glu Lys Phe Asn
    50                  55                  60

Met Trp Lys Asn Tyr Met Val Asp Gln Met His Glu Asp Ile Ile Ser
65                  70                  75                  80

Leu Trp Asp Gln Ser Leu Gln Pro Cys Val Lys Leu Thr Pro Leu Cys
                85                  90                  95

Ile Thr Leu Asn Cys Thr Asp Val Ala His Asn Gly Ser Thr Val Tyr
            100                 105                 110

Asp Asn Asn Ala Thr Val Val Asn Ser Thr Asn Glu Ile Lys Asn Cys
        115                 120                 125

Ser Phe Asn Ile Thr Thr Glu Leu Arg Asp Lys Arg Lys Lys Glu His
    130                 135                 140

Ala Leu Phe Asn Asn Leu Asp Ile Val Gln Leu Asp Gly Asn Ser Ser
145                 150                 155                 160

Leu Tyr Arg Leu Ile Asn Cys Asn Thr Ser Ile Ile Lys Gln Ala Cys
                165                 170                 175

Pro Lys Ile Ser Phe Asp Pro Ile Pro Ile His Tyr Cys Ala Pro Ala
            180                 185                 190

Gly Phe Val Ile Leu Lys Cys Asn Asn Glu Thr Phe Asn Gly Thr Gly
        195                 200                 205

Pro Cys Asn Asn Val Ser Ala Val Gln Cys Thr His Gly Ile Lys Pro
    210                 215                 220

Val Val Ser Thr Gln Leu Leu Leu Asn Gly Ser Leu Ala Lys Gly Glu
225                 230                 235                 240
```

-continued

```
Ile Met Ile Arg Ser Glu Asn Ile Thr Asp Asn Val Lys Thr Ile Ile
                245                 250                 255
Val His Leu Asn Asn Ser Val Glu Ile Val Cys Thr Arg Pro Asn Asn
            260                 265                 270
Asn Thr Arg Lys Ser Ile Arg Ile Gly Pro Gly Gln Thr Phe Tyr Ala
        275                 280                 285
Thr Gly Asp Ile Ile Gly Asp Ile Arg Gln Ala Tyr Cys Ser Ile Asn
    290                 295                 300
Glu Ser Asn Trp Asn Ala Thr Leu Gln Arg Val Ser Lys Lys Leu Ala
305                 310                 315                 320
Glu His Phe Pro Asn Lys Thr Ile Gln Phe Lys Ser Pro Ser Gly Gly
                325                 330                 335
Asp Leu Glu Ile Thr Met His Ser Phe Asn Cys Arg Gly Glu Phe Phe
            340                 345                 350
Tyr Cys Asn Thr Ser Lys Leu Phe Asn Gly Thr Tyr Tyr Pro Asn Gly
        355                 360                 365
Thr Tyr Tyr Pro Asn Gly Thr Asn Ser Thr Leu Ile Ile Pro Cys Arg
    370                 375                 380
Ile Lys Gln Ile Ile Asn Met Trp Gln Gly Val Gly Lys Ala Ile Tyr
385                 390                 395                 400
Ala Ser Pro Ile Ala Gly Asn Ile Thr Cys Arg Ser Asn Ile Thr Gly
                405                 410                 415
Leu Leu Leu Thr Arg Asp Gly Gly Asp Thr Asn Asp Thr Glu Ile Phe
            420                 425                 430
Arg Pro Ala Gly Gly Asp Met Arg Asp Asn Trp Arg Ser Glu Leu Tyr
        435                 440                 445
Lys Tyr Lys Ile Val Glu Ile Lys Pro Leu Gly Val Ala Pro Thr Glu
    450                 455                 460
Ala Lys Ser Arg Val Val Lys Ser Glu Lys Ser Ala Val Thr Ile Gly
465                 470                 475                 480
Ala Val Phe Leu Gly Phe Leu Gly Ala Ala Gly Ser Thr Met Gly Ala
                485                 490                 495
Ala Ser Ile Thr Leu Thr Val Gln Ala Arg Gln Leu Leu Ser Gly Ile
            500                 505                 510
Val Gln Gln Gln Ser Asn Leu Leu Arg Ala Ile Glu Ala Gln Gln His
        515                 520                 525
Met Leu Gln Leu Thr Val Trp Gly Ile Lys Gln Leu Gln Ala Arg Val
    530                 535                 540
Leu Ala Ile Glu Arg Tyr Leu Lys Asp Gln Gln Leu Leu Gly Ile Trp
545                 550                 555                 560
Gly Cys Ser Gly Lys Leu Ile Cys Thr Thr Ala Val Pro Trp Asn Asn
                565                 570                 575
Ser Trp Ser Asn Arg Thr Gln Asp Glu Ile Trp Lys Asn Leu Thr Trp
            580                 585                 590
Met Glu Trp Asp Arg Glu Ile Ser Asn Tyr Thr Asn Thr Ile Tyr Glu
        595                 600                 605
Leu Leu Glu Val Ser Gln Ser Gln Gln Glu Arg Asn Glu Lys Asp Leu
    610                 615                 620
Leu Ala Leu Asp Ser Trp Asn Asn Leu Trp Asn Trp Phe Asp Ile Ser
625                 630                 635                 640
Asn Trp Leu Trp Tyr Ile Lys Lys Lys Lys
                645                 650
```

<210> SEQ ID NO 2
<211> LENGTH: 632
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 2

```
Gly Asn Leu Trp Val Thr Val Tyr Tyr Gly Val Pro Val Trp Lys Glu
1               5                   10                  15

Ala Lys Thr Thr Leu Phe Cys Ala Ser Asp Ala Lys Ala Tyr Glu Lys
            20                  25                  30

Glu Val His Asn Val Trp Ala Thr His Ala Cys Val Pro Thr Asp Pro
        35                  40                  45

Asn Pro Gln Glu Met Val Leu Glu Asn Val Thr Glu Asn Phe Asn Met
    50                  55                  60

Trp Lys Asn Asp Met Val Asp Gln Met His Glu Asp Ile Ile Ser Leu
65                  70                  75                  80

Trp Asp Gln Ser Leu Lys Pro Cys Val Lys Leu Thr Pro Leu Cys Val
                85                  90                  95

Thr Leu Asn Cys Arg Asn Val Thr Asn Ala Thr Asn Asn Thr Tyr Asn
            100                 105                 110

Ser Glu Ile Lys Asn Cys Ser Phe Asn Ile Thr Thr Glu Leu Arg Asp
        115                 120                 125

Lys Lys Lys Lys Val Tyr Ala Leu Phe Tyr Arg Leu Asp Ile Val Pro
    130                 135                 140

Leu Asn Glu Asn Ser Ser Glu Tyr Arg Leu Ile Asn Cys Asn Thr Ser
145                 150                 155                 160

Ala Ile Thr Gln Ala Cys Pro Lys Val Ser Phe Asp Pro Ile Pro Ile
                165                 170                 175

His Tyr Cys Ala Pro Ala Gly Tyr Ala Ile Leu Lys Cys Asn Asn Lys
            180                 185                 190

Thr Phe Asn Gly Thr Gly Pro Cys Asn Asn Val Ser Thr Val Gln Cys
        195                 200                 205

Thr His Gly Ile Lys Pro Val Val Ser Thr Gln Leu Leu Asn Gly
    210                 215                 220

Ser Leu Ala Glu Glu Glu Ile Ile Ile Arg Ser Glu Asn Leu Thr Asn
225                 230                 235                 240

Asn Ala Lys Thr Ile Ile Val His Leu Asn Glu Ser Val Glu Ile Val
                245                 250                 255

Cys Thr Arg Pro Asn Asn Asn Thr Arg Lys Ser Ile Arg Ile Gly Pro
            260                 265                 270

Gly Gln Thr Phe Tyr Ala Thr Gly Asp Ile Ile Gly Asp Ile Arg Gln
        275                 280                 285

Ala His Cys Asn Ile Ser Glu Asp Lys Trp Asn Lys Thr Leu Gln Arg
    290                 295                 300

Val Ser Lys Lys Leu Lys Glu His Phe Pro Asn Lys Thr Ile Lys Phe
305                 310                 315                 320

Glu Pro Ser Ser Gly Gly Asp Leu Glu Ile Thr Thr His Ser Phe Asn
                325                 330                 335

Cys Arg Gly Glu Phe Phe Tyr Cys Asn Thr Ser Lys Leu Phe Asn Ser
            340                 345                 350

Thr Tyr Asn Asn Asn Thr Asn Ser Asn Ser Thr Ile Thr Leu Pro Cys
```

```
                    355                 360                 365
Arg Ile Lys Gln Ile Ile Asn Met Trp Gln Glu Val Gly Arg Ala Met
    370                 375                 380
Tyr Ala Pro Pro Ile Ala Gly Asn Ile Thr Cys Lys Ser Asn Ile Thr
385                 390                 395                 400
Gly Leu Leu Leu Thr Arg Asp Gly Gly Lys Asn Thr Thr Glu Ile
                405                 410                 415
Phe Arg Pro Gly Gly Gly Asp Met Arg Asp Asn Trp Arg Ser Glu Leu
                420                 425                 430
Tyr Lys Tyr Lys Val Val Glu Ile Lys Pro Leu Gly Val Ala Pro Thr
            435                 440                 445
Lys Ala Lys Ser Arg Val Val Glu Arg Glu Lys Arg Ala Val Gly Ile
    450                 455                 460
Gly Ala Val Phe Leu Gly Phe Leu Gly Ala Ala Gly Ser Thr Met Gly
465                 470                 475                 480
Ala Ala Ser Ile Thr Leu Thr Val Gln Ala Arg Gln Leu Leu Ser Gly
                485                 490                 495
Ile Val Gln Gln Gln Ser Asn Leu Leu Arg Ala Ile Glu Ala Gln Gln
                500                 505                 510
His Met Leu Gln Leu Thr Val Trp Gly Ile Lys Gln Leu Gln Thr Arg
            515                 520                 525
Val Leu Ala Ile Glu Arg Tyr Leu Lys Asp Gln Gln Leu Leu Gly Ile
    530                 535                 540
Trp Gly Cys Ser Gly Lys Leu Ile Cys Thr Thr Ala Val Pro Trp Asn
545                 550                 555                 560
Ser Ser Trp Ser Asn Lys Ser Gln Glu Asp Ile Trp Asp Asn Met Thr
                565                 570                 575
Trp Met Gln Trp Asp Arg Glu Ile Ser Asn Tyr Thr Asp Thr Ile Tyr
                580                 585                 590
Arg Leu Leu Glu Asp Ser Gln Asn Gln Gln Glu Lys Asn Glu Lys Asp
            595                 600                 605
Leu Leu Ala Leu Asp Ser Trp Lys Asn Leu Trp Asn Trp Phe Asp Ile
    610                 615                 620
Thr Asn Trp Leu Trp Tyr Ile Lys
625                 630
```

<210> SEQ ID NO 3
<211> LENGTH: 642
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 3

```
Ser Leu Trp Val Thr Val Tyr Tyr Gly Val Pro Val Trp Lys Glu Ala
1               5                   10                  15
Thr Thr Thr Leu Phe Cys Ala Ser Asp Ala Lys Ala His Lys Ala Glu
                20                  25                  30
Ala His Asn Ile Trp Ala Thr His Ala Cys Val Pro Thr Asp Pro Asn
            35                  40                  45
Pro Arg Glu Met Ile Leu Gly Asn Val Thr Glu Asn Phe Asn Met Trp
    50                  55                  60
Lys Asn Asn Met Val Glu Gln Met His Glu Asp Ile Ile Ser Leu Trp
65                  70                  75                  80
```

```
Asp Gln Ser Leu Lys Pro Cys Val Lys Leu Thr Pro Leu Cys Val Thr
                85              90              95
Leu Asn Cys Thr Thr Tyr Trp Asn Gly Thr Leu Gln Gly Asn Glu Thr
            100             105             110
Lys Gly Lys Asn Arg Ser Asp Ile Met Thr Cys Ser Phe Asn Ile Thr
        115             120             125
Thr Glu Ile Arg Asp Lys Lys Gln Glu Thr Ala Leu Phe Tyr Lys
    130             135             140
Leu Asp Val Val Pro Leu Glu Asp Lys Asp Ser Asn Lys Thr Thr Asn
145             150             155             160
Tyr Ser Ser Tyr Arg Leu Ile Asn Cys Asn Thr Ser Val Val Thr Gln
                165             170             175
Ala Cys Pro Lys Val Thr Phe Glu Pro Ile Pro Ile His Tyr Cys Ala
            180             185             190
Pro Ala Gly Phe Ala Ile Leu Lys Cys Asn Asn Lys Thr Phe Asn Gly
        195             200             205
Thr Gly Pro Cys Lys Asn Val Ser Thr Val Gln Cys Thr His Gly Ile
    210             215             220
Arg Pro Val Val Ser Thr Gln Leu Leu Leu Asn Gly Ser Leu Ala Glu
225             230             235             240
Glu Glu Ile Ile Ile Arg Ser Glu Asn Ile Thr Asn Asn Ala Lys Thr
                245             250             255
Ile Ile Val Gln Leu Asn Glu Ser Val Thr Ile Asp Cys Ile Arg Pro
            260             265             270
Asn Asn Asn Thr Arg Lys Ser Ile Arg Ile Gly Pro Gly Gln Ala Leu
        275             280             285
Tyr Thr Thr Asp Ile Ile Gly Asn Ile Arg Gln Ala His Cys Asn Val
    290             295             300
Ser Lys Val Lys Trp Gly Arg Met Leu Lys Arg Val Ala Glu Lys Leu
305             310             315             320
Lys Asp Leu Leu Asn Gln Thr Lys Asn Ile Thr Phe Lys Pro Ser Ser
                325             330             335
Gly Gly Asp Pro Glu Ile Thr Thr His Ser Phe Asn Cys Gly Gly Glu
            340             345             350
Phe Phe Tyr Cys Asn Thr Ser Gly Leu Phe Asn Gly Ser Leu Leu Asn
        355             360             365
Glu Gln Phe Asn Glu Thr Ser Asn Asp Thr Ile Thr Leu Gln Cys Arg
    370             375             380
Ile Lys Gln Ile Ile Asn Met Trp Gln Gly Val Gly Lys Ala Met Tyr
385             390             395             400
Ala Pro Pro Ile Ala Gly Pro Ile Ser Cys Ser Ser Asn Ile Thr Gly
                405             410             415
Leu Leu Leu Thr Arg Asp Gly Gly Asn Thr Gly Asn Asp Ser Glu Ile
            420             425             430
Phe Arg Pro Gly Gly Gly Asp Met Arg Asp Asn Trp Arg Ser Glu Leu
        435             440             445
Tyr Lys Tyr Lys Val Val Arg Ile Glu Pro Met Gly Leu Ala Pro Thr
    450             455             460
Arg Ala Lys Ser Arg Val Val Glu Arg Glu Lys Ser Ala Ile Gly Leu
465             470             475             480
Gly Ala Met Phe Leu Gly Phe Leu Gly Ala Ala Gly Ser Thr Met Gly
                485             490             495
```

```
Ala Ala Ser Leu Thr Leu Thr Val Gln Ala Arg Gln Leu Leu Ser Gly
            500                 505                 510

Ile Val Gln Gln Gln Asn Asn Leu Leu Arg Ala Ile Glu Ala Gln Gln
        515                 520                 525

His Leu Leu Gln Leu Thr Val Trp Gly Ile Lys Gln Leu Gln Ala Arg
    530                 535                 540

Val Leu Ala Met Glu Ser Tyr Leu Lys Asp Gln Gln Leu Leu Gly Ile
545                 550                 555                 560

Trp Gly Cys Ser Gly Lys His Ile Cys Thr Thr Thr Val Pro Trp Asn
                565                 570                 575

Ser Thr Trp Ser Asn Arg Ser Val Glu Glu Ile Trp Asn Asn Met Thr
            580                 585                 590

Trp Met Gln Trp Glu Arg Glu Ile Glu Asn Tyr Thr Gly Leu Ile Tyr
        595                 600                 605

Thr Leu Ile Glu Glu Ser Gln Thr Gln Gln Glu Lys Asn Glu Gln Glu
    610                 615                 620

Leu Leu Gln Leu Asp Lys Trp Ala Ser Leu Trp Asn Trp Phe Ser Ile
625                 630                 635                 640

Thr Lys

<210> SEQ ID NO 4
<211> LENGTH: 642
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Ser Leu Trp Val Thr Val Tyr Tyr Gly Val Pro Val Trp Lys Glu Ala
1               5                   10                  15

Thr Thr Thr Leu Phe Cys Ala Ser Asp Ala Lys Ser Tyr Glu Ala Glu
            20                  25                  30

Ala His Asn Ile Trp Ala Thr His Ala Cys Val Pro Thr Asp Pro Asn
        35                  40                  45

Pro Arg Glu Ile Lys Leu Glu Asn Val Thr Glu Asn Phe Asn Met Trp
    50                  55                  60

Lys Asn Asn Met Val Glu Gln Met His Glu Asp Ile Ile Ser Leu Trp
65                  70                  75                  80

Asp Gln Ser Leu Lys Pro Cys Val Lys Leu Thr Pro Leu Cys Val Ile
                85                  90                  95

Leu Asp Cys Asn Asn Thr Asn Tyr Val Asn Ala Ser Tyr Val Asn Ala
            100                 105                 110

Thr Val Thr Glu Glu Thr Glu Met Lys Asn Cys Ser Phe Asn Ile Thr
        115                 120                 125

Thr Arg Asp Lys Lys Gln Lys Val His Ala Phe Phe Asp Arg Leu Asp
    130                 135                 140

Val Val Pro Ile Asp Lys Asn Asn Lys Ser Tyr Arg Leu Ile Asn Cys
145                 150                 155                 160

Asn Thr Ser Ala Ile Thr Gln Ala Cys Pro Lys Ile Thr Phe Glu Pro
                165                 170                 175

Ile Pro Ile His Tyr Cys Ala Pro Ala Gly Phe Ala Ile Leu Lys Cys
            180                 185                 190

Asn Asp Lys Lys Phe Asn Gly Thr Gly Pro Cys Lys Asn Val Ser Thr
        195                 200                 205
```

```
Val Gln Cys Thr His Gly Ile Lys Pro Val Ser Thr Gln Leu Leu
    210                 215                 220

Leu Asn Gly Ser Leu Ala Glu Glu Ile Ile Arg Ser Glu Asn
225                 230                 235                 240

Leu Thr Asn Asn Ala Lys Thr Ile Ile Val Gln Leu Asn Glu Ser Val
                    245                 250                 255

Pro Ile Thr Cys Ile Arg Pro Asn Asn Asn Thr Arg Gln Ser Thr His
                260                 265                 270

Leu Gly Pro Gly Arg Ala Leu Phe Thr Thr Asn Ile Val Gly Asp Ile
            275                 280                 285

Arg Gln Ala His Cys Asn Ile Ser Gly Glu Lys Trp Asn Lys Thr Leu
        290                 295                 300

Gln Gln Val Ala Lys Lys Leu Arg Gly Leu Phe Asn Gly Ser Thr Thr
305                 310                 315                 320

Met Ile Phe Lys Pro Ser Ser Gly Gly Asp Pro Glu Val Glu His His
                    325                 330                 335

Ser Phe Asn Cys Gly Gly Glu Phe Phe Tyr Cys Asn Thr Ser Gly Leu
                340                 345                 350

Phe Asn Asn Ser Val Trp Ser Asn Asp Thr Ser Ser Ser Asn Asp Thr
            355                 360                 365

Ser Ser Ser Ser Asn Ser Thr Ile Thr Leu Pro Cys Arg Ile Lys Gln
    370                 375                 380

Ile Ile Asn Leu Trp Gln Glu Val Gly Lys Ala Met Tyr Ala Pro Pro
385                 390                 395                 400

Ile Ala Gly Ile Ile Lys Cys Ser Ser Asn Ile Thr Gly Leu Leu Leu
                    405                 410                 415

Gln Arg Asp Gly Gly Asn Asn Asp Ser Arg Thr Asn Thr Asn Glu Ile
                420                 425                 430

Phe Arg Pro Gly Gly Gly Asp Met Arg Asp Asn Trp Arg Ser Glu Leu
            435                 440                 445

Tyr Lys Tyr Lys Val Val Arg Leu Glu Pro Leu Gly Ile Ala Pro Thr
        450                 455                 460

Arg Ala Lys Ser Arg Val Val Glu Arg Glu Lys Ser Ala Ile Gly Leu
465                 470                 475                 480

Gly Ala Met Phe Leu Gly Phe Leu Gly Ala Ala Gly Ser Thr Met Gly
                    485                 490                 495

Ala Ala Ser Met Thr Leu Thr Val Gln Ala Arg Leu Leu Leu Ser Gly
                500                 505                 510

Ile Val Gln Gln Gln Asn Asn Leu Leu Arg Ala Ile Glu Ala Gln Gln
            515                 520                 525

His Leu Leu Gln Leu Thr Val Trp Gly Ile Lys Gln Leu Gln Ala Arg
        530                 535                 540

Val Leu Ala Val Glu Ser Tyr Leu Arg Asp Gln Gln Leu Leu Gly Ile
545                 550                 555                 560

Trp Gly Cys Ser Gly Arg His Ile Cys Thr Thr Ser Val Pro Trp Asn
                    565                 570                 575

Ser Ser Trp Ser Asn Lys Ser Leu Asp Lys Ile Trp Asn Asn Met Thr
                580                 585                 590

Trp Met Glu Trp Glu Lys Glu Ile Glu Asn Tyr Thr Gly Leu Ile Tyr
            595                 600                 605

Ser Leu Ile Glu Glu Ser Gln Thr Gln Gln Arg Asn Glu Gln Glu
        610                 615                 620
```

-continued

```
Leu Leu Gln Leu Asp Gln Met Ala Ser Leu Trp Asn Trp Phe Ser Ile
625                 630                 635                 640

Ser Asn
```

<210> SEQ ID NO 5
<211> LENGTH: 640
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

```
Ser Leu Trp Val Thr Val Tyr Tyr Gly Val Pro Val Trp Lys Glu Ala
1               5                   10                  15

Thr Thr Thr Leu Phe Cys Ala Ser Asp Ala Lys Ala Tyr Lys Ala Glu
                20                  25                  30

Ala His Asn Ile Trp Ala Thr His Ala Cys Val Pro Thr Asp Pro Asn
            35                  40                  45

Pro Gln Glu Ile Val Leu Gly Asn Val Thr Glu Asn Phe Asn Met Trp
    50                  55                  60

Lys Asn Asp Met Val Glu Gln Met His Glu Asp Ile Ile Ser Leu Trp
65                  70                  75                  80

Glu Gln Ser Leu Lys Pro Cys Val Lys Leu Thr Pro Leu Cys Val Thr
                85                  90                  95

Leu Asn Cys Thr Asn Ala Lys Ile Glu Gln Asn Val Thr Val Ala Gly
            100                 105                 110

Met Arg Asn Cys Ser Phe Asn Met Thr Thr Glu Leu Lys Asp Lys Lys
        115                 120                 125

Lys Gln Glu Tyr Ala Leu Phe Tyr Lys Leu Asp Val Val Gln Ile Asp
    130                 135                 140

Asn Ser Ser Thr Asn Thr Asp Tyr Arg Leu Ile Asn Cys Asn Thr Ser
145                 150                 155                 160

Ala Ile Thr Gln Ala Cys Pro Lys Ile Thr Phe Glu Pro Ile Pro Ile
                165                 170                 175

His Tyr Cys Ala Pro Ala Gly Tyr Ala Ile Leu Lys Cys Asn Asn Lys
            180                 185                 190

Thr Phe Asn Gly Met Gly Pro Cys Lys Asn Val Ser Thr Val Gln Cys
        195                 200                 205

Thr His Gly Ile Arg Pro Val Val Ser Thr Gln Leu Leu Leu Asn Gly
    210                 215                 220

Ser Leu Ala Glu Glu Glu Ile Val Ile Arg Ser Glu Asn Leu Thr Asn
225                 230                 235                 240

Asn Ala Lys Ile Ile Ile Val Gln Leu Asn Lys Ser Val Glu Ile Asn
                245                 250                 255

Cys Thr Arg Pro Ser Asn Asn Thr Arg Lys Gly Val His Ile Gly Pro
            260                 265                 270

Gly Gln Ala Ile Tyr Ser Thr Gly Gln Ile Ile Gly Asp Ile Arg Lys
        275                 280                 285

Ala His Cys Asn Ile Ser Arg Lys Glu Trp Asn Ser Thr Leu Gln Gln
    290                 295                 300

Val Thr Lys Lys Leu Gly Ser Leu Phe Asn Thr Thr Lys Ile Ile Phe
305                 310                 315                 320

Asn Ala Ser Ser Gly Gly Asp Pro Glu Ile Thr Thr His Ser Phe Asn
                325                 330                 335
```

Cys Asn Gly Glu Phe Phe Tyr Cys Asn Thr Ala Gly Leu Phe Asn Ser
              340                 345                 350

Thr Trp Asn Arg Thr Asn Ser Glu Trp Ile Asn Ser Lys Trp Thr Asn
          355                 360                 365

Lys Thr Glu Asp Val Asn Ile Thr Leu Gln Cys Arg Ile Lys Gln Ile
      370                 375                 380

Ile Asn Thr Trp Gln Gly Val Gly Lys Ala Met Tyr Ala Pro Pro Val
385                 390                 395                 400

Ser Gly Ile Ile Arg Cys Ser Ser Asn Ile Thr Gly Leu Leu Leu Thr
                405                 410                 415

Arg Asp Gly Gly Gly Ala Asp Asn Asn Arg Gln Asn Glu Ile Phe Arg
            420                 425                 430

Pro Gly Gly Gly Asp Met Arg Asp Asn Trp Arg Ser Glu Leu Tyr Lys
        435                 440                 445

Tyr Lys Val Val Arg Ile Glu Pro Leu Gly Ile Ala Pro Thr Lys Ala
    450                 455                 460

Arg Ser Arg Val Val Glu Arg Glu Lys Ser Ala Ile Gly Leu Gly Ala
465                 470                 475                 480

Leu Phe Leu Gly Phe Leu Gly Thr Ala Gly Ser Pro Met Gly Ala Val
                485                 490                 495

Ser Met Thr Leu Thr Val Gln Ala Arg Gln Val Leu Ser Gly Ile Val
            500                 505                 510

Gln Gln Gln Asn Asn Leu Leu Arg Ala Ile Glu Ala Gln Gln His Leu
        515                 520                 525

Leu Gln Leu Thr Val Trp Gly Ile Lys Gln Leu Gln Ala Arg Ile Leu
    530                 535                 540

Ala Val Glu Ser Tyr Leu Lys Asp Gln Gln Leu Leu Gly Ile Trp Gly
545                 550                 555                 560

Cys Ser Gly Lys His Ile Cys Thr Thr Asn Val Pro Trp Asn Ser Ser
                565                 570                 575

Trp Ser Asn Lys Ser Leu Asp Tyr Ile Trp Lys Asn Met Thr Trp Met
            580                 585                 590

Glu Trp Glu Lys Glu Ile Asp Asn Tyr Thr Glu Leu Ile Tyr Ser Leu
        595                 600                 605

Ile Glu Val Ser Gln Ile Gln Gln Glu Lys Asn Glu Gln Glu Leu Leu
    610                 615                 620

Lys Leu Asp Ser Trp Ala Ser Leu Trp Asn Trp Phe Ser Ile Thr Lys
625                 630                 635                 640

<210> SEQ ID NO 6
<211> LENGTH: 2037
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6
atggatgcaa tgaagagagg gctctgctgt gtgctgctgc tgtgtggagc agtcttcgtt      60
tcggctagcg aggaaaagct gtgggtgacc gtgtactacg gcgtgcccgt gtggaaagag     120
gccaccacca ccctgttctg cgccagcgac gccaaggcct acgacaccga ggtgcacaac     180
gtgtgggcca cccgcgcctg cgtgcccacc gaccccaacc cccaggaagt ggagctggaa     240
aacgtgaccg agaacttcaa catgtggaag aacaacatgg tggagcagat gcacgaggac     300

```
atcatcagcc tgtgggacca gagcctgaag ccctgcgtga agctgacccc cctgtgcgtg      360
accctgaact gcaccgacct gcggaacgcc accaacggca cgacaccaa caccacctcc       420
agcagccggg agatgatggg cggaggggag atgaagaact gcagcttcaa gatcaccacc      480
aacatccggg gcaaggtgca gaaagagtac gccctgttct acgagctgga catcgtgccc      540
atcgacaaca acagcaacaa ccggtacagg ctgatcagct gcaacaccag cgtgatcacc      600
caggcctgcc ccaagatcag cttcgagccc atccccatcc actactgcgc ccctgccggc      660
ttcgccatcc tgaagtgcaa ggacaagaag ttcaacggca agggcccctg cagcaacgtg      720
agcaccgtgc agtgcaccca cggcatccgg cccgtggtgt ccacccagct gctgctgaac      780
ggcagcctgg ccgaggaaga ggtggtgatc agaagcgaga acttcgccga caacgccaag      840
accatcatcg tgcagctgaa cgagagcgtg gagatcaact gcacccggcc caacaacaac      900
acccggaaga gcatccacat cggccctggc agggccctgt acaccaccgg cgagatcatc      960
ggcgacatcc ggcaggccca ctgcaacctg agccgggcca gtggaacga cacccctgaac     1020
aagatcgtga tcaagctgcg ggagcagttc ggcaacaaga ccatcgtgtt caagcacagc     1080
agcggcggag accccgagat cgtgacccac agcttcaact gtggcggcga gttcttctac     1140
tgcaacagca cccagctgtt caacagcacc tggaatgtga ccgaggaaag caacaacacc     1200
gtggagaaca caccatcac cctgccctgc cggatcaagc agatcatcaa tatgtggcag      1260
aaagtgggca gagccatgta cgcccctccc atccggggcc agatccggtg cagcagcaac     1320
atcaccggcc tgctgctgac ccgggacggc ggacccgagg ccaacaagac cgaggtgttc     1380
cggcctggcg gcggagatat gcgggacaac tggcggagcg agctgtacaa gtacaaggtg     1440
gtgaagatcg agcccctggg cgtggccccc accaaggcca agagccgggt ggtgcagcgg     1500
gagaagagcg ccgtgggcat cggcgccgtg tttctgggct cctgggagc cgccggaagc     1560
accatgggag ccgccagcat gaccctgacc gtgcaggccc ggctgctgct gtccggcatc     1620
gtgcagcagc agaacaacct gctgcgggcc attgaggcac agcagcatct gctgcagctg     1680
accgtgtggg gcattaagca gctgcaggcc agggtgctgg ccgtggagag atacctgcgg     1740
gatcagcagc tgctggggat ctgggctgc agcggcaagc tgatctgcac caccgccgtg     1800
ccctggaacg ccagctggtc caacaagagc ctgaacaaaa tctgggacaa catgacctgg     1860
atggaatggg accgcgagat caacaactac accagcatca tctacagcct gatcgaggaa     1920
agccagaacc agcaggaaaa gaacgagcag gaactgctgg aactggacaa gtgggccagc     1980
ctgtggaact ggttcgacat caccgagtgg ctgtggtaca tcaagaagaa gaagtga        2037
```

<210> SEQ ID NO 7
<211> LENGTH: 678
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Met Asp Ala Met Lys Arg Gly Leu Cys Cys Val Leu Leu Leu Cys Gly
1               5                  10                  15

Ala Val Phe Val Ser Ala Ser Glu Glu Lys Leu Trp Val Thr Val Tyr
            20                  25                  30

Tyr Gly Val Pro Val Trp Lys Glu Ala Thr Thr Thr Leu Phe Cys Ala
        35                  40                  45

```
Ser Asp Ala Lys Ala Tyr Asp Thr Glu Val His Asn Val Trp Ala Thr
 50                  55                  60
His Ala Cys Val Pro Thr Asp Pro Asn Pro Gln Glu Val Glu Leu Glu
 65                  70                  75                  80
Asn Val Thr Glu Asn Phe Asn Met Trp Lys Asn Asn Met Val Glu Gln
                     85                  90                  95
Met His Glu Asp Ile Ile Ser Leu Trp Asp Gln Ser Leu Lys Pro Cys
                100                 105                 110
Val Lys Leu Thr Pro Leu Cys Val Thr Leu Asn Cys Thr Asp Leu Arg
            115                 120                 125
Asn Ala Thr Asn Gly Asn Asp Thr Asn Thr Thr Ser Ser Ser Arg Glu
            130                 135                 140
Met Met Gly Gly Gly Glu Met Lys Asn Cys Ser Phe Lys Ile Thr Thr
145                 150                 155                 160
Asn Ile Arg Gly Lys Val Gln Lys Glu Tyr Ala Leu Phe Tyr Glu Leu
                165                 170                 175
Asp Ile Val Pro Ile Asp Asn Ser Asn Asn Arg Tyr Arg Leu Ile
                180                 185                 190
Ser Cys Asn Thr Ser Val Ile Thr Gln Ala Cys Pro Lys Ile Ser Phe
            195                 200                 205
Glu Pro Ile Pro Ile His Tyr Cys Ala Pro Ala Gly Phe Ala Ile Leu
            210                 215                 220
Lys Cys Lys Asp Lys Lys Phe Asn Gly Lys Gly Pro Cys Ser Asn Val
225                 230                 235                 240
Ser Thr Val Gln Cys Thr His Gly Ile Arg Pro Val Val Ser Thr Gln
                245                 250                 255
Leu Leu Leu Asn Gly Ser Leu Ala Glu Glu Val Val Ile Arg Ser
                260                 265                 270
Glu Asn Phe Ala Asp Asn Ala Lys Thr Ile Ile Val Gln Leu Asn Glu
            275                 280                 285
Ser Val Glu Ile Asn Cys Thr Arg Pro Asn Asn Asn Thr Arg Lys Ser
            290                 295                 300
Ile His Ile Gly Pro Gly Arg Ala Leu Tyr Thr Thr Gly Glu Ile Ile
305                 310                 315                 320
Gly Asp Ile Arg Gln Ala His Cys Asn Leu Ser Arg Ala Lys Trp Asn
                325                 330                 335
Asp Thr Leu Asn Lys Ile Val Ile Lys Leu Arg Glu Gln Phe Gly Asn
            340                 345                 350
Lys Thr Ile Val Phe Lys His Ser Ser Gly Gly Asp Pro Glu Ile Val
            355                 360                 365
Thr His Ser Phe Asn Cys Gly Gly Glu Phe Phe Tyr Cys Asn Ser Thr
    370                 375                 380
Gln Leu Phe Asn Ser Thr Trp Asn Val Thr Glu Glu Ser Asn Asn Thr
385                 390                 395                 400
Val Glu Asn Asn Thr Ile Thr Leu Pro Cys Arg Ile Lys Gln Ile Ile
                405                 410                 415
Asn Met Trp Gln Lys Val Gly Arg Ala Met Tyr Ala Pro Pro Ile Arg
            420                 425                 430
Gly Gln Ile Arg Cys Ser Ser Asn Ile Thr Gly Leu Leu Leu Thr Arg
            435                 440                 445
Asp Gly Gly Pro Glu Ala Asn Lys Thr Glu Val Phe Arg Pro Gly Gly
    450                 455                 460
```

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Lys Ala Lys Ser Arg
            485                 490                 495

Val Val Gln Arg Glu Lys Ser Ala Val Gly Ile Gly Ala Val Phe Leu
        500                 505                 510

Gly Phe Leu Gly Ala Ala Gly Ser Thr Met Gly Ala Ala Ser Met Thr
    515                 520                 525

Leu Thr Val Gln Ala Arg Leu Leu Ser Gly Ile Val Gln Gln Gln
530                 535                 540

Asn Asn Leu Leu Arg Ala Ile Glu Ala Gln Gln His Leu Leu Gln Leu
545                 550                 555                 560

Thr Val Trp Gly Ile Lys Gln Leu Gln Ala Arg Val Leu Ala Val Glu
                565                 570                 575

Arg Tyr Leu Arg Asp Gln Gln Leu Leu Gly Ile Trp Gly Cys Ser Gly
            580                 585                 590

Lys Leu Ile Cys Thr Thr Ala Val Pro Trp Asn Ala Ser Trp Ser Asn
        595                 600                 605

Lys Ser Leu Asn Lys Ile Trp Asp Asn Met Thr Trp Met Glu Trp Asp
    610                 615                 620

Arg Glu Ile Asn Asn Tyr Thr Ser Ile Ile Tyr Ser Leu Ile Glu Glu
625                 630                 635                 640

Ser Gln Asn Gln Gln Glu Lys Asn Glu Gln Glu Leu Leu Glu Leu Asp
                645                 650                 655

Lys Trp Ala Ser Leu Trp Asn Trp Phe Asp Ile Thr Glu Trp Leu Trp
            660                 665                 670

Tyr Ile Lys Lys Lys Lys
        675

<210> SEQ ID NO 8
<211> LENGTH: 2046
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 8
atggatgcaa tgaagagagg ctctgctgt tgctgctgc tgtgtggagc agtcttcgtt      60
actaccacag aggctagcga ggaaaagctg tgggtgaccg tgtactacgg cgtgcccgtg    120
tggaaagagg ccaccaccac cctgttctgc gccagcgacg ccaaggccta cgacaccgag    180
gtgcacaacg tgtgggccac ccacgcctgc gtgcccaccg accccaaccc ccaggaagtg    240
gagctggaaa acgtgaccga gaacttcaac atgtggaaga caacatggt ggagcagatg     300 cacgaggaca tcatcagcct gtgggaccag agcctgaagc cctgcgtgaa gctgaccccc    360
ctgtgcgtga ccctgaactg caccgacctg cggaacgcca ccaacggcaa cgacaccaac    420
accacctcca gcagccggga tgatgggc ggaggggaga tgaagaactg cagcttcaag      480
atcaccacca catccggggg caaggtgcag aaagagtacg ccctgttcta cgagctggac    540
atcgtgccca tcgacaacaa cagcaacaac cggtacaggc tgatcagctg caacaccagc    600
gtgatcaccc aggcctgccc caagatcagc ttcgagccca tcccatcca ctactgcgcc    660 cctgccggct tcgccatcct gaagtgcaag gacaagaagt tcaacggcaa gggcccctgc    720
agcaacgtga gcaccgtgca gtgcacccac ggcatccggc ccgtggtgtc cacccagctg    780

```
ctgctgaacg gcagcctggc cgaggaagag gtggtgatca gaagcgagaa cttcgccgac    840
aacgccaaga ccatcatcgt gcagctgaac gagagcgtgg agatcaactg cacccggccc    900
aacaacaaca cccggaagag catccacatc ggccctggca gggccctgta caccaccggc    960
gagatcatcg cgacatccg gcaggccac tgcaacctga gccgggccaa gtggaacgac    1020
accctgaaca agatcgtgat caagctgcgg gagcagttcg caacaagac catcgtgttc    1080 aagcacagca gcggcggaga ccccgagatc gtgacccaca gcttcaactg tggcggcgag    1140
ttcttctact gcaacagcac ccagctgttc aacagcacct ggaatgtgac cgaggaaagc    1200
aacaacaccg tggagaacaa caccatcacc ctgccctgcc ggatcaagca gatcatcaat    1260
atgtggcaga agtgggcag agccatgtac gcccctccca tccggggcca gatccggtgc    1320
agcagcaaca tcaccggcct gctgctgacc cgggacggcg acccgaggc caacaagacc    1380 gaggtgttcc ggcctggcgg cggagatatg cgggacaact ggcggagcga gctgtacaag    1440
tacaaggtgg tgaagatcga gcccctgggc gtggcccca ccaaggccaa gagccgggtg    1500
gtgcagcggg agaagagcgc cgtgggcatc ggcgccgtgt ttctgggctt cctgggagcc    1560 gccgaagca ccatgggagc cgccagcatg accctgaccg tgcaggcccg gctgctgctg    1620
tccggcatcg tgcagcagca gaacaacctg ctgcgggcca ttgaggcaca gcagcatctg    1680
ctgcagctga ccgtgtgggg cattaagcag ctgcaggcca gggtgctggc cgtgagagag    1740
tacctgcggg atcagcagct gctggggatc tggggctgca gcggcaagct gatctgcacc    1800
accgccgtgc cctggaacgc cagctggtcc aacaagagcc tgaacaaaat ctgggacaac    1860
atgacctgga tggaatggga ccgcgagatc aacaactaca ccagcatcat ctacagcctg    1920
atcgaggaaa gccagaacca gcaggaaaag aacgagcagg aactgctgga actggacaag    1980
tgggccagcc tgtggaactg gttcgacatc accgagtggc tgtggtacat caagaagaag    2040
aagtga                                                                2046
```

<210> SEQ ID NO 9
<211> LENGTH: 681
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

```
Met Asp Ala Met Lys Arg Gly Leu Cys Cys Val Leu Leu Cys Gly
1               5                   10                  15

Ala Val Phe Val Thr Thr Thr Glu Ala Ser Glu Glu Lys Leu Trp Val
            20                  25                  30

Thr Val Tyr Gly Val Pro Val Trp Lys Glu Ala Thr Thr Thr Leu
        35                  40                  45

Phe Cys Ala Ser Asp Ala Lys Ala Tyr Asp Thr Glu Val His Asn Val
        50                  55                  60

Trp Ala Thr His Ala Cys Val Pro Thr Asp Pro Asn Pro Gln Glu Val
65                  70                  75                  80

Glu Leu Glu Asn Val Thr Glu Asn Phe Asn Met Trp Lys Asn Asn Met
                85                  90                  95

Val Glu Gln Met His Glu Asp Ile Ile Ser Leu Trp Asp Gln Ser Leu
            100                 105                 110

Lys Pro Cys Val Lys Leu Thr Pro Leu Cys Val Thr Leu Asn Cys Thr
```

```
            115                 120                 125
Asp Leu Arg Asn Ala Thr Asn Gly Asn Asp Thr Asn Thr Thr Ser Ser
            130                 135                 140

Ser Arg Glu Met Met Gly Gly Gly Glu Met Lys Asn Cys Ser Phe Lys
145                 150                 155                 160

Ile Thr Thr Asn Ile Arg Gly Lys Val Gln Lys Glu Tyr Ala Leu Phe
            165                 170                 175

Tyr Glu Leu Asp Ile Val Pro Ile Asp Asn Ser Asn Asn Arg Tyr
            180                 185                 190

Arg Leu Ile Ser Cys Asn Thr Ser Val Ile Thr Gln Ala Cys Pro Lys
            195                 200                 205

Ile Ser Phe Glu Pro Ile Pro Ile His Tyr Cys Ala Pro Ala Gly Phe
210                 215                 220

Ala Ile Leu Lys Cys Lys Asp Lys Lys Phe Asn Gly Lys Gly Pro Cys
225                 230                 235                 240

Ser Asn Val Ser Thr Val Gln Cys Thr His Gly Ile Arg Pro Val Val
            245                 250                 255

Ser Thr Gln Leu Leu Leu Asn Gly Ser Leu Ala Glu Glu Val Val
            260                 265                 270

Ile Arg Ser Glu Asn Phe Ala Asp Asn Ala Lys Thr Ile Ile Val Gln
            275                 280                 285

Leu Asn Glu Ser Val Glu Ile Asn Cys Thr Arg Pro Asn Asn Asn Thr
290                 295                 300

Arg Lys Ser Ile His Ile Gly Pro Gly Arg Ala Leu Tyr Thr Thr Gly
305                 310                 315                 320

Glu Ile Ile Gly Asp Ile Arg Gln Ala His Cys Asn Leu Ser Arg Ala
            325                 330                 335

Lys Trp Asn Asp Thr Leu Asn Lys Ile Val Ile Lys Leu Arg Glu Gln
            340                 345                 350

Phe Gly Asn Lys Thr Ile Val Phe Lys His Ser Ser Gly Gly Asp Pro
            355                 360                 365

Glu Ile Val Thr His Ser Phe Asn Cys Gly Gly Glu Phe Phe Tyr Cys
            370                 375                 380

Asn Ser Thr Gln Leu Phe Asn Ser Thr Trp Asn Val Thr Glu Glu Ser
385                 390                 395                 400

Asn Asn Thr Val Glu Asn Asn Thr Ile Thr Leu Pro Cys Arg Ile Lys
            405                 410                 415

Gln Ile Ile Asn Met Trp Gln Lys Val Gly Arg Ala Met Tyr Ala Pro
            420                 425                 430

Pro Ile Arg Gly Gln Ile Arg Cys Ser Ser Asn Ile Thr Gly Leu Leu
            435                 440                 445

Leu Thr Arg Asp Gly Gly Pro Glu Ala Asn Lys Thr Glu Val Phe Arg
            450                 455                 460

Pro Gly Gly Gly Asp Met Arg Asp Asn Trp Arg Ser Glu Leu Tyr Lys
465                 470                 475                 480

Tyr Lys Val Val Lys Ile Glu Pro Leu Gly Val Ala Pro Thr Lys Ala
            485                 490                 495

Lys Ser Arg Val Val Gln Arg Glu Lys Ser Ala Val Gly Ile Gly Ala
            500                 505                 510

Val Phe Leu Gly Phe Leu Gly Ala Ala Gly Ser Thr Met Gly Ala Ala
            515                 520                 525

Ser Met Thr Leu Thr Val Gln Ala Arg Leu Leu Leu Ser Gly Ile Val
            530                 535                 540
```

| Gln | Gln | Gln | Asn | Asn | Leu | Leu | Arg | Ala | Ile | Glu | Ala | Gln | Gln | His | Leu |
| 545 | | | | 550 | | | | | 555 | | | | | 560 | |

| Leu | Gln | Leu | Thr | Val | Trp | Gly | Ile | Lys | Gln | Leu | Gln | Ala | Arg | Val | Leu |
| | | | | 565 | | | | | 570 | | | | | 575 | |

| Ala | Val | Glu | Arg | Tyr | Leu | Arg | Asp | Gln | Gln | Leu | Leu | Gly | Ile | Trp | Gly |
| | | | 580 | | | | | 585 | | | | | 590 | | |

| Cys | Ser | Gly | Lys | Leu | Ile | Cys | Thr | Thr | Ala | Val | Pro | Trp | Asn | Ala | Ser |
| | | 595 | | | | | 600 | | | | | 605 | | | |

| Trp | Ser | Asn | Lys | Ser | Leu | Asn | Lys | Ile | Trp | Asp | Asn | Met | Thr | Trp | Met |
| 610 | | | | | 615 | | | | | 620 | | | | | |

| Glu | Trp | Asp | Arg | Glu | Ile | Asn | Asn | Tyr | Thr | Ser | Ile | Ile | Tyr | Ser | Leu |
| 625 | | | | 630 | | | | | 635 | | | | | 640 | |

| Ile | Glu | Glu | Ser | Gln | Asn | Gln | Gln | Glu | Lys | Asn | Glu | Gln | Glu | Leu | Leu |
| | | | | 645 | | | | | 650 | | | | | 655 | |

| Glu | Leu | Asp | Lys | Trp | Ala | Ser | Leu | Trp | Asn | Trp | Phe | Asp | Ile | Thr | Glu |
| | | | 660 | | | | | 665 | | | | | 670 | | |

| Trp | Leu | Trp | Tyr | Ile | Lys | Lys | Lys | Lys |
| | | 675 | | | | | 680 | |

<210> SEQ ID NO 10
<211> LENGTH: 2538
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 10

```
atggatgcaa tgaagagagg gctctgctgt gtgctgctgc tgtgtggagc agtcttcgtt      60
actaccacag aggctagcaa cctgtggggtg accgtgtact acggcgtgcc cgtgtggaag     120
gaggccaaga ccaccctgtt ctgcgccagc gacgccaagg cctacgagaa ggaggtgcac     180
aacgtgtggg ccacccacgc ctgcgtgccc accgacccca cccccaggaa gatggagctg     240
cccaacgtga ccgagaactt caacatgtgg aagaacgaca tggtggacca gatgcacgag     300
gacatcatca gcctgtggga ccagagcctg aagccctgcg tgaagctgac ccccctgtgc     360
gtgaccctga actgcaacaa ggtgaacaac accgcagca tcgacaacaa cagcaccgag     420
gaggagatga agaactgcac cttcaacacc accaccgaga tcagggacaa gaagaggacc     480
cagcaggccc tgttctacaa gctggacatc gtgccccctgg caacagcaa cgagagctac     540 aggctgatca actgcaacac cagcaccctg acccaggcct gccccaaggt gaccttcgac     600
cccatcccca tccactactg cgccccagcc ggctacgcca tcctgaagtg caaggacgag     660
aagttcaacg gcaccggccc ctgcaacaac gtgtccaccg tgcagtgcac ccacggcatc     720
aagcccgtgg tgtccaccca gctgctgctg aacggcagcc tggccgagaa ggacatcatc     780
atccgcagcg agaacctgac caacaacgtg aagaccatca tggtgcacct gaacgagagc     840
gtggagatca actgtaccag gcccaacaac aacaccagga gagcatcag gatcggccca     900 ggccagacct tctacgccac cggcggcatc atcggcaaca tcaggcaggc ctactgcacc     960
atcagcaaga acaagtggaa caccaccctg agagagtgg ctaccaagct gaaggagtac    1020
ttcaagaaca ccaccatcca gttcgccccc cactctggcg gcgacctgga gatcaccacc    1080
cacagcttca actgcagggg cgagttcttc tactgcaaca caagccagct gttcaacggg    1140
accagcaccg gcttcagcaa caagagcacc ggcaacgaga cattcaccct gcctgcaga    1200
```

```
atcaagcaga tcatcaacat gtggcaggaa gtgggcaggg ccatgtacgc cccaccaatc    1260
gccgggaaca tcacctgcgt gagcaacatc accggcctgc tgctgaccag ggacggcggg    1320
gacaacaaca caagaaccga gacattccgg ccaggcggcg gagacatgag ggacaactgg    1380
cggagcgagc tgtacaagta caaggtggtg gaggtgaagc ccctgggcgt ggccccaagc    1440
gaagccaggc ggagagtggt ggaacgggag aagagggccg tgggcctggg cgccgtcttt    1500
ctgggattcc tgggggctgc cggatccacc atgggagccg ccagcatcac cctgaccgtg    1560
caggctaggc agctgctgtc cggaatcgtg cagcagcagt ccaacctgct gagggctatc    1620
gaggctcagc agcatatgct ccagctgacc gtgtggggca tcaagcagct gcagaccaag    1680
gtgctggcca tcgagagata tctgcaggac cagcagctgc tcggcatctg ggctgcagc    1740 ggcaagctga tctgcaccac caacgtgccc tggaacagca gctggtccaa caagtccctg    1800
aaggccatct gggacaacat gacctggatg cagtgggaca gagagatcag caactacacc    1860
aacaccatct acaggctgct ggaggacagc cacatccagc aggagaagaa cgagaaggac    1920
ctgctggccc tgaacagctg gaacaacctg tggagctggt tcaacatcac caactggctg    1980
tggtacatcc ggatcttcat catgatcgtg gcggcctga tcggcctgag gatcatcttc    2040
gccatcctgt ccatcgtgaa cagagtgcgc cagggctaca gcccactgag cttccagacc    2100
ctgacaccca accagcgggg cccagacaga ctgggcagga tcgaggagga gggcggcgag    2160
caggacaagg acagatccat caggctggtg aacggcttcc tggccctggc ctgggacgac    2220
ctgagaagcc tgtgcctgtt cagctaccac aggctgaggg acttcatcct gatcgccacc    2280
agggccgtgg aactgctggg gcactccagc ctgaggggcc tgcagagggg ctgggaggcc    2340
ctgaagtacc tgggctccct gggccagtat tggggccagg agctgaagaa gagcgccatc    2400
agactgctgg acatcaccgc catcgccgtg gccgagggca ccgacaggat catcgagttc    2460
atccagagga tctgcagggc catccacaac gtgcccaaca ggatcaggca gggcttcgag    2520
gccgccctgc tgtgatga                                                  2538
```

<210> SEQ ID NO 11
<211> LENGTH: 2535
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11

```
atggatgcaa tgaagagagg gctctgctgt gtgctgctgc tgtgtggagc agtcttcgtt      60
actaccacag aggctagcaa cctgtgggtg accgtgtact acggcgtgcc cgtgtggaag    120
gaggccaaga ccaccctgtt ctgcgccagc gacgccaagg cctacgagaa ggaggtgcac    180
aacgtgtggg ccacccacgc ctgcgtgccc accgacccca accccagga gatggagctg    240 cccaacgtga ccgagaactt caacatgtgg aagaacgaca tggtggacca gatgcacgag    300
gacatcatca gcctgtggga ccagagcctg aagcccctgcg tgaagctgac ccccctgtgc    360
gtgaccctga actgcaacaa ggtgaacaac aaccgcagca tcgacaacaa cagcaccgag    420
gaggagatga agaactgcac cttcaacacc accaccgaga tcagggacaa gaagaggacc    480
cagcaggccc tgttctacaa gctggacatc gtgccctgg caacagcaa cgagagctac    540 aggctgatca actgcaacac cagcaccctg acccaggcct gccccaaggt gaccttcgac    600
```

```
cccatcccca tccactactg cgccccagcc ggctacgcca tcctgaagtg caaggacgag    660
aagttcaacg gcaccggccc ctgcaacaac gtgtccaccg tgcagtgcac ccacggcatc    720
aagcccgtgg tgtccaccca gctgctgctg aacggcagcc tggccgagaa ggacatcatc    780
atccgcagcg agaacctgac caacaacgtg aagaccatca tggtgcacct gaacgagagc    840
gtggagatca actgtaccag gcccaacaac aacaccagga gagcatcag gatcggccca     900 ggccagacct tctacgccac cggcggcatc atcggcaaca tcaggcaggc ctactgcacc    960
atcagcaaga acaagtggaa caccaccctg gagagagtgg ctaccaagct gaaggagtac   1020
ttcaagaaca ccaccatcca gttcgccccc cactctggcg gcgacctgga gatcaccacc   1080
cacagcttca actgcagggg cgagttcttc tactgcaaca aagccagct gttcaacggg    1140 accagcaccg gcttcagcaa caagagcacc ggcaacgaga cattcaccct gccctgcaga   1200
atcaagcaga tcatcaacat gtggcaggaa gtgggcaggg ccatgtacgc cccaccaatc   1260
gccgggaaca tcacctgcgt gagcaacatc accggcctgc tgctgaccag ggacggcggg   1320
gacaacaaca agaaccga gacattccgg ccaggcggcg gagacatgag ggacaactgg    1380
cggagcgagc tgtacaagta caaggtggtg gaggtgaagc cctgggcgt ggccccaagc   1440 gaagccagga gcagagtggt ggaacgggag aagagcgccg tgggcctggg cgccgtcttt   1500
ctgggattcc tgggggctgc cggatccacc atgggagccg ccagcatcac cctgaccgtg   1560
caggctaggc agctgctgtc cggaatcgtg cagcagcagt ccaacctgct gagggctatc   1620
gaggctcagc agcatatgct ccagctgacc gtgtggggca tcaagcagct gcagaccaag   1680
gtgctggcca tcgagagata tctgcaggac cagcagctgc tcggcatctg gggctgcagc   1740
ggcaagctga tctgcaccac caacgtgccc tggaacagca gctggtccaa caagtccctg   1800
aaggccatct gggacaacat gacctggatg cagtgggaca gagagatcag caactacacc   1860
aacaccatct acaggctgct ggaggacagc cacatccagc aggagaagaa cgagaaggac   1920
ctgctggccc tgaacagctg gaacaacctg tggagctggt tcaacatcac caactggctg   1980
tggtacatcc ggatcttcat catgatcgtg ggcggcctga tcggcctgag gatcatcttc   2040
gccatcctgt ccatcgtgaa cagagtgcgc cagggctaca gcccactgag cttccagacc   2100
ctgacaccca accagcgggg cccagacaga ctgggcagga tcgaggagga gggcggcgag   2160
caggacaagg acagatccat caggctggtg aacggcttcc tggccctggc ctgggacgac   2220
ctgagaagcc tgtgcctgtt cagctaccac aggctgaggg acttcatcct gatcgccacc   2280
agggccgtgg aactgctggg gcactccagc ctgaggggcc tgcagagggg ctgggaggcc   2340
ctgaagtacc tgggctccct gggccagtat tggggccagg agctgaagaa gagcgccatc   2400
agactgctgg acatcaccgc catcgccgtg gccgagggca ccgacaggat catcgagttc   2460
atccagagga tctgcagggc catccacaac gtgcccaaca ggatcaggca gggcttcgag   2520
gccgccctgc tgtga                                                   2535
```

<210> SEQ ID NO 12
<211> LENGTH: 2517
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 12

```
atggatgcaa tgaagagagg gctctgctgt gtgctgctgc tgtgtggagc agtcttcgtt    60
```

```
actaccacag aggctagcaa cctgtgggtg accgtgtact acggcgtgcc cgtgtggaga    120
gaggccaaga ccaccctgtt ctgcgccagc gacgccaagg cctacgaaaa ggaggtgcac    180
aacgtgtggg ccacccacgc ctgcgtgccc accgaccccg accccagga gatggtgctg     240
aagaacgtga ccgagaactt caacatgtgg aagaacgaca tggtggagca gatgcacgag    300
gacatcatca gcctgtggga ccagagcctg aagccctgcg tgaagctgac ccccctgtgc    360
gtgaccctga cctgcaccaa cgtgaacgcc accgacaacg tgacctacaa ggagaagatg    420
gagggcgaga tcaagaactg cagcttcaac atcaccaccg agatcaggga caagaagagg    480
aaggtccacg ccctgttcta caggctggac gtggtgcagc tgaacaacag caacgagtac    540
atcctgatca actgcaacac cagcgccatc acccaggcct gccccaaggt gtccttcgac    600
cccatcccca tccactactg cgccccagcc ggctacgcca tcctgaagtg caacgacaag    660
cccttcaacg gcaccggccc atgccacaac gtgtctaccg tgcagtgcac ccacggcatc    720
aagcccgtga tcagcaccca gctgctgctg aacggcagcc tggccgagaa ggaggtgatc    780
atccgcttcg agaacctgac cgacaacgcc aagaccatca tcgtgcagct gaaccagagc    840
atcgagatca gtgcatcag gcccaacaac aacaccagag agagcatcag gatcggccca    900
ggccaggcct tctacgccac cagggacatc atcggcgaca tcagaagggc ctactgcacc    960
atcgagacag agaggtggaa ggagacactg gcaacgtca cagagaagct gaaggagtac     1020
ttccccaaca ccaacatcag ctttgctccc tcctctggcg gggacctgga gatcaccacc    1080
cacagcttca actgcagggg cgagttcttc tacagaaaca ccagcaagct gttcaacaac    1140
aacgacaccg agaacaacct gaccatcacc ctgccctgca gaatcaagca gatcgtgaac    1200
atgtggcagg gcgtgggcag ggccatgtac gccccaccca tcgagggcaa catcacctgc    1260
aagtccaaca tcaccggcct gctgctgacc agagacggcg gcaacggcac agagaggaac    1320
gagacattca ggccaggcgg cggagacatg aggaacaact ggcggagcga gctgtacaag    1380
tacaaggtgg tggagatcaa gcccctgggg atcgccccaa ccggcgccaa gagaagagtg    1440
gtggagagag agaagagggc cgtcggcatg ggcgccgtgt ttctgggctt cctgggagcc    1500
gccggaagca ccatgggagc cgccagcctg accctgacag tgcaggccag acaggtgctg    1560
tccgggatcg tgcagcagca gagcaacctg ctgagagcta tcgaggctca gcagcacatg    1620
ctgcagctga ccgtgtgggg catcaagcag ctgcagacca gggtgctggc catcgagaga    1680
tacctgaaag atcagcagct gctcggcctc tggggctgca gcggcaagct gatctgcacc    1740
acagccgtgc catggaatag cagctggtcc aacaagagcg agatcgacat ctggaacaac    1800
atgacctgga tgcagtggga cagagagatc agcaactaca ccaacaccat ctacagactg    1860
ctggaggaca gccagaccca gcaggagaag aacgagaagg acctgctggc cctggacagc    1920
tggaagaacc tgtggaactg gtttaacatc accaagtggc tgtggtacat caagatcttc    1980
atcatcatcg gggcggcct gatcggcctg aggatcatct tcgccgtgct gtccatcgtg    2040
aacagagtgc gccagggta cagcccactg agcttccaga ccctgatccc cagccccaga    2100
ggccccgaca gctgggcag gatcgaggag gagggcggcg agcaggacaa gggcagatcc    2160
gtgaggctgg tgaacggctt cctggccctg gcctgggacg acctgagaag cctgtgcctg    2220
ttcagctatc accagctgag ggacttcatc ctgatcgtgg ccagagccgt gggcctgctg    2280
ggcaggtcca gcctgagggg cctgcagaga ggctgggaga tcctgaagta cctgggcggg    2340
ctggtgcagt actggggcct ggagctgaag aagagcgccg tgagcctgtt cgacacaatc    2400
```

|  |  |
|---|---|
| gccatcgccg tgaccgaggg caccgacagg atcatcgagc tgatccagag gtcctgcaga | 2460 |
| gccatcagga acgtgcccac caggatcagg cagggcttcg aggccgccct gcagtga | 2517 |

<210> SEQ ID NO 13
<211> LENGTH: 2517
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13

|  |  |
|---|---|
| atggatgcaa tgaagagagg gctctgctgt gtgctgctgc tgtgtggagc agtcttcgtt | 60 |
| actaccacag aggctagcaa cctgtgggtg accgtgtact acggcgtgcc cgtgtggaga | 120 |
| gaggccaaga ccaccctgtt ctgcgccagc gacgccaagg cctacgaaaa ggaggtgcac | 180 |
| aacgtgtggg ccacccacgc ctgcgtgccc accgaccccg accccagga gatggtgctg | 240 |
| aagaacgtga ccgagaactt caacatgtgg aagaacgaca tggtggagca gatgcacgag | 300 |
| gacatcatca gcctgtggga ccagagcctg aagcccgcg tgaagctgac ccccctgtgc | 360 |
| gtgaccctga cctgcaccaa cgtgaacgcc accgacaacg tgacctacaa ggagaagatg | 420 |
| gagggcgaga tcaagaactg cagcttcaac atcaccaccg agatcaggga caagaagagg | 480 |
| aaggtccacg ccctgttcta caggctggac gtggtgcagc tgaacaacag caacgagtac | 540 |
| atcctgatca actgcaacac cagcgccatc acccaggcct gccccaaggt gtccttcgac | 600 |
| cccatcccca tccactactg cgccccagcc ggctacgcca tcctgaagtg caacgacaag | 660 |
| cccttcaacg gcaccggccc atgccacaac gtgtctaccg tgcagtgcac ccacggcatc | 720 |
| aagcccgtga tcagcaccca gctgctgctg aacggcagcc tggccgagaa ggaggtgatc | 780 |
| atccgcttcg agaacctgac cgacaacgcc aagaccatca tcgtgcagct gaaccagagc | 840 |
| atcgagatca gtgcatcag gcccaacaac aacaccagag agagcatcag gatcggccca | 900 |
| ggccaggcct tctacgccac cagggacatc atcggcgaca tcagaagggc ctactgcacc | 960 |
| atcgagacag agaggtggaa ggagacactg gcaacgtca cagagaagct gaaggagtac | 1020 |
| ttccccaaca ccaacatcag ctttgctccc tcctctggcg gggacctgga gatcaccacc | 1080 |
| cacagcttca actgcagggg cgagttcttc tacagaaaca ccagcaagct gttcaacaac | 1140 |
| aacgacaccg agaacaacct gaccatcacc ctgccctgca gaatcaagca gatcgtgaac | 1200 |
| atgtggcagg gcgtgggcag ggccatgtac gccccaccca tcgagggcaa catcacctgc | 1260 |
| aagtccaaca tcaccggcct gctgctgacc agagacggcg gcaacggcac agagaggaac | 1320 |
| gagacattca ggccaggcgg cggagacatg aggaacaact ggcggagcga gctgtacaag | 1380 |
| tacaaggtgg tggagatcaa gcccctgggg atcgccccaa ccggcgccaa gagcagagtg | 1440 |
| gtggagagag agaagagcgc cgtcggcatg ggcgccgtgt ttctgggctt cctgggagcc | 1500 |
| gccggaagca ccatgggagc cgccagcctg accctgacag tgcaggccag acaggtgctg | 1560 |
| tccgggatcg tgcagcagca gagcaacctg ctgagagcta tcgaggctca gcagcacatg | 1620 |
| ctgcagctga ccgtgtgggg catcaagcag ctgcagacca gggtgctggc catcgagaga | 1680 |
| tacctgaaag atcagcagct gctcggcctc tggggctgca gcggcaagct gatctgcacc | 1740 |
| acagccgtgc catggaatag cagctggtcc aacaagagcg agatcgacat ctggaacaac | 1800 |
| atgacctgga tgcagtggga cagagagatc agcaactaca ccaacaccat ctacagactg | 1860 |
| ctggaggaca gccagaccca gcaggagaag aacgagaagg acctgctggc cctggacagc | 1920 |

| | |
|---|---|
| tggaagaacc tgtggaactg gtttaacatc accaagtggc tgtggtacat caagatcttc | 1980 |
| atcatcatcg tgggcggcct gatcggcctg aggatcatct tcgccgtgct gtccatcgtg | 2040 |
| aacagagtgc gccaggggta cagcccactg agcttccaga ccctgatccc cagccccaga | 2100 |
| ggcccccgaca agctgggcag gatcgaggag gagggcggcg agcaggacaa gggcagatcc | 2160 |
| gtgaggctgg tgaacggctt cctggccctg gcctgggacg acctgagaag cctgtgcctg | 2220 |
| ttcagctatc accagctgag ggacttcatc ctgatcgtgg ccagagccgt gggcctgctg | 2280 |
| ggcaggtcca gcctgagggg cctgcagaga ggctgggaga tcctgaagta cctgggcggg | 2340 |
| ctggtgcagt actggggcct ggagctgaag aagagcgccg tgagcctgtt cgacacaatc | 2400 |
| gccatcgccg tgaccgaggg caccgacagg atcatcgagc tgatccagag gtcctgcaga | 2460 |
| gccatcagga acgtgcccac caggatcagg cagggcttcg aggccgccct gcagtga | 2517 |

<210> SEQ ID NO 14
<211> LENGTH: 2559
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 14

| | |
|---|---|
| atggatgcaa tgaagagagg gctctgctgt gtgctgctgc tgtgtggagc agtcttcgtt | 60 |
| actaccacag aggctagcaa cctgtgggtg accgtgtact acggcgtgcc cgtgtggaga | 120 |
| gaggccaaga ccaccctgtt ctgcgccagc gacgccaagg cctacgagag ggaggtgcac | 180 |
| aacgtgtggg ccacccacgc ctgcgtgccc accgaccccg acccacagga aatctttctg | 240 |
| ggcaagaacg tgaccgagaa gttcaacatg tgggagaact acatggtgga ccagatgcac | 300 |
| gaggacatca tcagcctgtg ggaccagagc ctgcagccct gcgtgaagct gaccccctg | 360 |
| tgcatcaccc tgaactgcac cgacttcacc gcccacaacg gcagcaccgt gtacgacaac | 420 |
| aacgccaccg ccaacagcac caacgagatc aagaactgca gcttcaacat catctccgag | 480 |
| ctgagggaca gaggaagaa ggagaacgcc ctgttcaaca acctggacat cgtgcagctg | 540 |
| gacggcaact ccagcctgta cagactgatc aactgcaaca ccagcatcat caagcaggcc | 600 |
| tgtcccaaga tcagcttcga ccccatcccc atccactact gcgccccagc cggcttcgtg | 660 |
| atcctgacct gcaacaacga cattcaac ggcaccggcc catgcaacaa cgtgtccgct | 720 |
| gtgcagtgta cccacgggat caagcccgtg gtgtccaccc agctgctgct gaacggcagc | 780 |
| ctggccaagg gcgagatcat gatcagaagc gagaacatca ccaacaacgt gaagaccatc | 840 |
| atcgtgcact tcaacaagag cgtggagatc gtgtgcacca ggcccaacaa caccaccagg | 900 |
| aagagcatca ggatcggccc aggccagacc ttctacgcca ccggcgacat catcggcgac | 960 |
| atccggcagg cctactgcag catcaacgag agcaactgga acatcaccct gcagagggtg | 1020 |
| tccaagaagc tggccgagca cttccccaac agaaccatcc agttcgagag ccctctggc | 1080 |
| ggcgacctgg agatcaccat gcacagcttc aactgcaggg gcgagttctt ctactgcaac | 1140 |
| acatccaagc tgttcaagag cacctaccac cccaacggca cctacaacct gaacggcaca | 1200 |
| aacagcaccc tgatcatccc atgcaggatc aagcagatca tcaacatgtg gcagggcgtg | 1260 |
| ggcaaggcca tctacgccag cccaatcgcc ggcagcatca cctgcagaag caacatcacc | 1320 |
| ggcctgctgc tgaccaggga cggcggcgac accaacgaca ccgagatctt caggcccacc | 1380 |

```
ggcggagaca tgagggacaa ctggcggagc gagctgtaca agtacaagat cgtggagatc    1440
aagcccctgg gcgtggctcc aaccgaggcc aagagaaggg tggtgaagag agagaagagg    1500
gccgtcacca tcggcgccgt gtttctgggc ttcctgggag ccgccggaag caccatggga    1560
gccgcctcca tcaccctgac cgtgcaggcc aggcagctgc tgtccgggat cgtgcagcag    1620
cagagcaacc tgctgcgggc catcgaagct cagcagcaca tgctgcagct ggcagtctgg    1680
ggcatcaagc agctgcaggc cagagtgctg gccatcgaga gataccctgaa ggatcagcag    1740 ctgctcggca tctggggctg cagcggcaag ctgatctgca ccaccgccgt gccctggaac    1800
aacagctggt ccaacaggac ccaggacgag atctggaaga acctgacctg gatggagtgg    1860
gacagagaga tcagcaacta caccaacaca atctacgagc tgctggaggt gtcccagagc    1920
cagcaggaga ggaacgagaa ggacctgctg gccctggaca gctggaacaa cctgtggaac    1980
tggttcgaca tcagcaactg gctgtggtac atcaagatct tcatcatgat cgtgggcggc    2040
ctgatcggcc tgaggatcat cttcgccgtg ctgtccatcg tgaacagagt gcggcagggc    2100
tacagccccc tgagcttcca gaccctgatc cccaaccaga gagagcccga caggcccggc    2160
aggatcgagg aggagggcgg cgagcaggac aaggatagat ctatcagact ggtgtccggc    2220
ttcctggccc tggcctggga cgacctgaga agcctgtgca tcttcctgta ccaccacctg    2280
agggacctga tcctgatcgc cgctagagcc acagagctgc tggggaggtc cagcctgagg    2340
ggcctgcaga gaggctggga ggccctgaag tacctgggca gcctggtgca gtactgggggc    2400 ctggagatca agaagagcgc catcaacctg ctggacacaa tcgccatcgc cgtggccgag    2460
ggcaccgaca ggatcatcga gatcgtgcag agggcctgta gggccgtgct gaacatcctg    2520
agaaggatcc ggcagggcct ggaggctgcc ctgcagtga                           2559
```

<210> SEQ ID NO 15
<211> LENGTH: 2561
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 15

```
atggatgcaa tgaagagagg gctctgctgt gtgctgctgc tgtgtggagc agtcttcgtt      60
actaccacag aggctagcaa cctgtggggtg accgtgtact acggcgtgcc cgtgtggaga    120
gaggccaaga ccaccctgtt ctgcgccagc gacgccaagg cctacgagag ggaggtgcac    180
aacgtgtggg ccacccacgc ctgcgtgccc accgaccccg acccacagga aatctttctg    240
ggcaagaacg tgaccgagaa gttcaacatg tgggagaact acatggtgga ccagatgcac    300
gaggacatca tcagcctgtg ggaccagagc ctgcagccct gcgtgaagct gacccccctg    360
tgcatcaccc tgaactgcac cgacttcacc gcccacaacg gcagcaccgt gtacgacaac    420
aacgccaccg ccaacagcac caacgagatc aagaactgca gcttcaacat catctccgag    480
ctgagggaca gaggaagaa ggagaacgcc ctgttcaaca cctggacat cgtgcagctg    540 gacggcaact ccagcctgta cagactgatc aactgcaaca ccagcatcat caagcaggcc    600
tgtcccaaga tcagcttcga ccccatcccc atccactact gcgccccagc cggcttcgtg    660
atcctgacct gcaacaacga cacattcaac ggcaccggcc catgcaacaa cgtgtccgct    720
gtgcagtgta cccacgggat caagcccgtg gtgtccaccc agctgctgct gaacggcagc    780
ctggccaagg gcgagatcat gatcagaagc gagaacatca ccaacaacgt gaagaccatc    840
```

```
atcgtgcact tcaacaagag cgtggagatc gtgtgcacca ggcccaacaa caacaccagg      900
aagagcatca ggatcggccc aggccagacc ttctacgcca ccggcgacat catcggcgac      960
atccggcagg cctactgcag catcaacgag agcaactgga acatcaccct gcagagggtg     1020
tccaagaagc tggccgagca cttccccaac agaaccatcc agttcgagag ccctctggc      1080 ggcgacctgg agatcaccat gcacagcttc aactgcaggg gcgagttctt ctactgcaac     1140
acatccaagc tgttcaagag cacctaccac cccaacggca cctacaacct gaacggcaca     1200
aacagcaccc tgatcatccc atgcaggatc aagcagatca tcaacatgtg gcagggcgtg     1260
ggcaaggcca tctacgccag cccaatcgcc ggcagcatca cctgcagaag caacatcacc     1320
ggcctgctgc tgaccaggga cggcggcgac accaacgaca ccgagatctt caggcccacc     1380
ggcggagaca tgagggacaa ctggcggagc gagctgtaca agtacaagat cgtggagatc     1440
aagcccctgg gcgtggctcc aaccgaggcc aagagcaggg tggtgaagag cgagaagagc     1500
gccgtcacca tcggcgccgt gtttctgggc ttcctgggag ccgccggaag caccatggga     1560
gccgcctcca tcaccctgac cgtgcaggcc aggcagctgc tgtccgggat cgtgcagcag     1620
cagagcaacc tgctgcgggc catcgaagct cagcagcaca tgctgcagct ggcagtctgg     1680
ggcatcaagc agctgcaggc cagagtgctg gccatcgaga gatacctgaa ggatcagcag     1740
ctgctcggca tctggggctg cagcggcaag ctgatctgca ccaccgccgt gccctggaac     1800
aacagctggt ccaacaggac ccaggacgag atctggaaga acctgacctg gatggagtgg     1860
gacagagaga tcagcaacta caccaacaca atctacgagc tgctggaggt gtcccagagc     1920
cagcaggaga ggaacgagaa ggacctgctg gccctggaca gctggaacaa cctgtggaac     1980
tggttcgaca tcagcaactg gctgtggtac atcaagatct tcatcatgat cgtgggcggc     2040
ctgatcggcc tgaggatcat cttcgccgtg ctgtccatcg tgaacagagt gcggcagggc     2100
tacagccccc tgagcttcca gaccctgatc cccaaccaga gagagcccga caggcccggc     2160
aggatcgagg aggagggcgg cgagcaggac aaggatagat ctatcagact ggtgtccggc     2220
ttcctggccc tggcctggga cgacctgaga agcctgtgca tcttcctgta ccaccacctg     2280
agggacctga tcctgatcgc cgctagagcc acagagctgc tggggaggtc cagcctgagg     2340
ggcctgcaga gaggctggga ggccctgaag tacctgggca gcctggtgca gtactggggc     2400
ctggagatca gaagagcgc catcaacctg ctggacacaa tcgccatcgc cgtggccgag      2460
ggcaccgaca ggatcatcga gatcgtgcag agggcctgta gggccgtgct gaacatcctg     2520
agaaggatcc ggcagggcct ggaggctgcc ctgcagtgat g                          2561
```

<210> SEQ ID NO 16
<211> LENGTH: 2562
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 16

```
atggatgcaa tgaagagagg gctctgctgt gtgctgctgc tgtgtggagc agtcttcgtt       60
actaccacag aggctagcaa cctgtgggtg accgtgtact acggcgtgcc cgtgtggaga      120
gaggccaaga ccaccctgtt ctgcgccagc gacgccaagg cctacgagcg ggaggtgcac      180
aacgtgtggg ccacccacgc ctgcgtgccc accgaccccg accctcagga aatcttcctg      240
```

```
ggcaagaacg tgaccgagaa gttcaacatg tggaagaact acatggtgga ccagatgcac      300
gaggacatca tcagcctgtg ggaccagagc ctgcagccct gcgtgaagct gaccccctg       360
tgcatcaccc tgaactgcac cgacgtgacc gcccacaacg gcagcaccgt gtacgacaac      420
aacgccaccg tggtgaacag caccaacgag atcaagaact gcagcttcaa catcaccacc      480
gagctgaggg acaagaggaa gaaggagcac gccctgttca caacctggga catcgtgcag     540
ctggacggca acagctccct gtacagactg atcaactgca caccagcat catcaagcag      600
gcctgcccca agatcagctt cgaccccatc cccatccact actgcgcccc agccggcttc     660
gtgatcctga gtgcaacaa cgagacattc aacggcaccg cccctgtaa caacgtgtcc       720
gctgtgcagt gcacccacgg catcaagccc gtggtgtcca cccagctgct gctgaacggc      780
agcctggcca gggcgagat catgatcaga agcgagaaca tcaccgacaa cgtgaagacc      840
atcatcgtgc acctgaacaa cagcgtggag atcgtgtgca ccaggcccaa caacaacacc      900
aggaagagca tcaggatcgg cccaggccaa accttctacg ccaccggcga catcatcggc      960
gacatccggc aggcctactg cagcatcaac gagagcaact ggaacgccac cctgcagagg     1020
gtgtccaaga gctggccga gcacttcccc aacaagacca tccagttcaa gagcccctct     1080
ggcggcgacc tggagatcac catgcacagc ttcaactgca ggggcgagtt cttctactgc      1140
aacacatcca gctgtttaa cgggacctac tacccaaacg gcacatacta cccaaacggg      1200
accaacagca ccctgatcat cccatgcagg atcaagcaga tcatcaacat gtggcagggc     1260
gtgggcaagg ccatctacgc cagcccaatc gccggcaaca tcacctgccg gtccaacatc      1320
accgcctgc tgctgaccag ggacggcggc gacaccaacg acaccgagat cttcaggcca      1380
gccggcggag acatgaggga caactggcgg agcgagctgt acaagtacaa gatcgtggag      1440
atcaagcccc tgggcgtggc tccaaccgag gccaagagaa gggtggtgaa gagagagaag     1500
agggccgtca ccatcggcgc cgtgtttctg ggcttcctgg gagccgccgg aagcaccatg     1560
ggagccgcct ccatcaccct gaccgtgcag gccaggcagc tgctgtccgg gatcgtgcag     1620
cagcagagca acctgctgag agccattgag gctcagcagc acatgctgca gctgacagtg      1680
tggggcatca agcagctgca ggccagagtg ctggccatcg agagatacct gaaggatcag      1740
cagctgctcg gcatctgggg ctgcagcggc aagctgatct gcaccaccgc cgtgccctgg      1800
aacaactcct ggtccaacag gacccaggac gagatctgga gaaccctgac ctggatggag      1860
tgggacagag agatcagcaa ctacaccaac accatctacg agctgctgga ggtgtcccag      1920
agccagcagg agaggaacga gaaggacctg ctggccctgg atagctggaa caacctgtgg      1980
aactggttcg acatcagcaa ctggctgtgg tacatcaaga tcttcatcat gatcgtgggc     2040
ggcctgatcg gcctgaggat catcttcgcc gtgctgtcca tcgtgaacag agtgcggcag     2100
ggctacagcc ccctgagctt ccagaccctg atccccaacc agagagagcc cgacaggccc     2160
ggcaggatcg aggaggaggg cggcgagcag gacaaggaca gatccatcag gctggtgtcc      2220
ggcttcctgg ccctggcctg ggacgacctg agaagcctgt gcatcttcct gtaccaccac      2280
ctgagggact tcatcctgat cgccgccagg gccacagagc tgctggggag gtccagcctg     2340
aggggcctgc agagaggctg ggaggccctg aagtacctgg gcagcctggt gcagtactgg      2400
ggcctggaga tcaagaagag cgccatcaac ctgctggaca caatcgccat cgccgtggcc      2460
gagggcaccg acaggatcat cgagatcgtg cagagggcct gtagggccgt gctgaacatc      2520
cccagaagga tcagacaggg gctggaggct gccctgcagt ga                          2562
```

<210> SEQ ID NO 17
<211> LENGTH: 2562
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 17

| | |
|---|---:|
| atggatgcaa tgaagagagg gctctgctgt gtgctgctgc tgtgtggagc agtcttcgtt | 60 |
| actaccacag aggctagcaa cctgtgggtg accgtgtact acggcgtgcc cgtgtggaga | 120 |
| gaggccaaga ccaccctgtt ctgcgccagc gacgccaagg cctacgagcg ggaggtgcac | 180 |
| aacgtgtggg ccacccacgc ctgcgtgccc accgaccccg accctcagga aatcttcctg | 240 |
| ggcaagaacg tgaccgagaa gttcaacatg tggaagaact acatggtgga ccagatgcac | 300 |
| gaggacatca tcagcctgtg ggaccagagc ctgcagccct gcgtgaagct gacccccctg | 360 |
| tgcatcaccc tgaactgcac cgacgtgacc gcccacaacg gcagcaccgt gtacgacaac | 420 |
| aacgccaccg tggtgaacag caccaacgag atcaagaact gcagcttcaa catcaccacc | 480 |
| gagctgaggg acaagaggaa gaaggagcac gcccctgttca caacctgga catcgtgcag | 540 |
| ctggacggca acagctccct gtacagactg atcaactgca caccagcat catcaagcag | 600 |
| gcctgcccca gatcagctt cgaccccatc cccatccact actgcgcccc agccggcttc | 660 |
| gtgatcctga agtgcaacaa cgagacattc aacggcaccg gcccctgtaa caacgtgtcc | 720 |
| gctgtgcagt gcacccacgg catcaagccc gtggtgtcca cccagctgct gctgaacggc | 780 |
| agcctggcca agggcgagat catgatcaga agcgagaaca tcaccgacaa cgtgaagacc | 840 |
| atcatcgtgc acctgaacaa cagcgtggag atcgtgtgca ccaggcccaa caacaacacc | 900 |
| aggaagagca tcaggatcgg cccaggccag accttctacg ccaccggcga catcatcggc | 960 |
| gacatccggc aggcctactg cagcatcaac gagagcaact ggaacgccac cctgcagagg | 1020 |
| gtgtccaaga gctggccga gcacttcccc aacaagacca tccagttcaa gagcccctct | 1080 |
| ggcggcgacc tggagatcac catgcacagc ttcaactgca ggggcgagtt cttctactgc | 1140 |
| aacacatcca gctgttttaa cgggacctac tacccaaacg gcatactac cccaaacggg | 1200 |
| accaacagca ccctgatcat ccccatgcag atcaagcaga tcatcaacat gtggcagggc | 1260 |
| gtgggcaagg ccatctacgc cagcccaatc gccggcaaca tcacctgccg gtccaacatc | 1320 |
| accggcctgc tgctgaccag ggacggcggc gacaccaacg acaccgagat cttcaggcca | 1380 |
| gccggcggag acatgaggga caactggcgg agcgagctgt acaagtacaa gatcgtggag | 1440 |
| atcaagcccc tgggcgtggc tccaaccgag gccaagagca gggtggtgaa gagcgagaag | 1500 |
| agcgccgtca ccatcggcgc cgtgtttctg ggcttcctgg gagccgccgg aagcaccatg | 1560 |
| ggagccgcct ccatcacccct gaccgtgcag gccaggcagc tgctgtccgg gatcgtgcag | 1620 |
| cagcagagca acctgctgag agccattgag gctcagcagc acatgctgca gctgacagtg | 1680 |
| tggggcatca agcagctgca ggccagagtg ctggccatcg agagatacct gaaggatcag | 1740 |
| cagctgctcg gcatctgggg ctgcagcggc aagctgatct gcaccaccgc cgtgccctgg | 1800 |
| aacaactcct ggtccaacag gacccaggac gagatctgga gaacctgac ctggatggag | 1860 |
| tgggacagag agatcagcaa ctacaccaac accatctacg agctgctgga ggtgtcccag | 1920 |
| agccagcagg agaggaacga gaaggacctg ctggccctgg atagctggaa caacctgtgg | 1980 |
| aactggttcg acatcagcaa ctggctgtgg tacatcaaga tcttcatcat gatcgtgggc | 2040 |

```
ggcctgatcg gcctgaggat catcttcgcc gtgctgtcca tcgtgaacag agtgcggcag    2100
ggctacagcc ccctgagctt ccagaccctg atccccaacc agagagagcc cgacaggccc    2160
ggcaggatcg aggaggaggg cggcgagcag gacaaggaca gatccatcag gctggtgtcc    2220
ggcttcctgg ccctggcctg ggacgacctg agaagcctgt gcatcttcct gtaccaccac    2280
ctgagggact tcatcctgat cgccgccagg gccacagagc tgctggggag gtccagcctg    2340
aggggcctgc agagaggctg ggaggccctg aagtacctgg gcagcctggt gcagtactgg    2400
ggcctggaga tcaagaagag cgccatcaac ctgctggaca caatcgccat cgccgtggcc    2460
gagggcaccg acaggatcat cgagatcgtg cagagggcct gtagggccgt gctgaacatc    2520
cccagaagga tcagacaggg gctggaggct gccctgcagt ga                       2562

<210> SEQ ID NO 18
<211> LENGTH: 5930
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
tggcacatgg ccaatgcata tcgatctata cattgaatca atattggcaa ttagccatat      60
tagtcattgg ttatatagca taaatcaata ttggctattg gccattgcat acgttgtatc     120
tatatcataa tatgtacatt tatattggct catgtccaat atgaccgcca tgttgacatt     180
gattattgac tagttattaa tagtaatcaa ttacggggtc attagttcat agcccatata     240
tggagttccg cgttacataa cttacggtaa atggcccgcc tggctgaccg cccaacgacc     300
cccgcccatt gacgtcaata atgacgtatg ttcccatagt aacgccaata gggactttcc     360
attgacgtca atgggtggag tatttacggt aaactgccca cttggcagta catcaagtgt     420
atcatatgcc aagtccgccc cctattgacg tcaatgacgg taaatggccc gcctggcatt     480
atgcccagta catgacctta cgggactttc ctacttggca gtacatctac gtattagtca     540
tcgctattac catggtgatg cggttttggc agtacaccaa tgggcgtgga tagcggtttg     600
actcacgggg atttccaagt ctccacccca ttgacgtcaa tgggagtttg ttttggcacc     660
aaaatcaacg ggactttcca aaatgtcgta taaccccgcc ccgttgacgc aaatgggcg     720 gtaggcgtgt acggtgggag gtctatataa gcagagctcg tttagtgaac cgtcagatcg     780
cctggagacg ccatccacgc tgttttgacc tccatagaag acaccgggac cgatccagcc     840
tccgcggccg ggaacggtgc attggaacgc ggattccccg tgccaagagt gacgtaagta     900
ccgcctatag actctatagg cacccccctt ggctcttat gcatgctata ctgtttttgg     960
cttggggcct atacccccc gcttccttat gctataggtg atggtatagc ttagcctata    1020
ggtgtgggtt attgaccatt attgaccact cccctattgg tgacgatact ttccattact    1080
aatccataac atgctctttt gccacaacta tctctattgg ctatatgcca atactctgtc    1140
cttcagagac tgacacggac tctgtatttt tacaggatgg ggtcccattt attatttaca    1200
aattcacata tacaacaacg ccgtcccccg tgcccgcagt ttttattaaa catagcgtgg    1260
gatctccacg cgaatctcgg gtacgtgttc cggacatggg ctcttctccg gtagcggcgg    1320
agcttccaca tccgagccct ggtcccatgc ctccagcggc tcatggtcgc tcggcagctc    1380
cttgctccta acagtggagg ccagacttag gcacagcaca atgcccacca ccaccagtgt    1440
gccgcacaag gccgtggcgg tagggtatgt gtctgaaaat gagctcggag attgggctcg    1500
```

```
caccgctgac gcagatggaa gacttaaggc agcggcagaa gaagatgcag gcagctgagt    1560
tgttgtattc tgataagagt cagaggtaac tcccgttgcg gtgctgttaa cggtggaggg    1620
cagtgtagtc tgagcagtac tcgttgctgc cgcgcgcgcc accagacata atagctgaca    1680
gactaacaga ctgttccttt ccatgggtct tttctgcagt caccgtccat ttaaatacgc    1740
gtgccaccat ggatgcaatg aagagagggc tctgctgtgt gctgctgctg tgtggagcag    1800
tcttcgttac taccacagag gctagcgggg atatcggcgc cgaattcgga tccactagta    1860
gatctctcga gaacggccgc cagtgtgctg gaattaattc gctgtctgcg agggccagct    1920
gttggggtga gtactccctc tcaaaagcgg gcatgacttc tgcgctaaga ttgtcagttt    1980
ccaaaaacga ggaggatttg atattcacct ggcccgcggt gatgcctttg agggtggccg    2040
cgtccatctg gtcagaaaag acaatctttt tgttgtcaag cttgaggtgt ggcaggcttg    2100
agatctggcc atacacttga gtgacaatga catccacttt gcctttctct ccacaggtgt    2160
ccactcccag gtccaactgc aggtcgagca tgcatctagg gcggccaatt ccgcccctct    2220 ccctccccc  ccctaacgt tactggccga agccgcttgg aataaggccg gtgtgcgttt    2280
gtctatatgt tattttccac catattgccg tcttttggca atgtgagggc ccggaaacct    2340
ggccctgtct tcttgacgag cattcctagg gtctttccc ctctcgccaa aggaatgcaa    2400
ggtctgttga atgtcgtgaa ggaagcagtt cctctggaag cttcttgaag acaaacaacg    2460
tctgtagcga ccctttgcag gcagcggaac cccccacctg gcgacaggtg cctctgcggc    2520
caaaagccac gtgtataaga tacacctgca aaggcggcac aaccccagtg ccacgttgtg    2580
agttggatag ttgtggaaag agtcaaatgg ctctcctcaa gcgtattcaa caaggggctg    2640
aaggatgccc agaaggtacc ccattgtatg ggatctgatc tggggcctcg gtgcacatgc    2700
tttacatgtg tttagtcgag gttaaaaaaa cgtctaggcc ccccgaacca cggggacgtg    2760
gttttccttt gaaaaacacg atgataagct tgccacaacc cacaaggaga cgaccttcca    2820
tgaccgagta caagcccacg gtgcgcctcg ccacccgcga cgacgtcccc cgggccgtac    2880
gcaccctcgc cgccgcgttc gccgactacc ccgccacgcg ccacaccgtg gacccggacc    2940
gccacatcga gcgggtcacc gagctgcaag aactcttcct cacgcgcgtc gggctcgaca    3000
tcggcaaggt gtgggtcgcg gacgacggcg ctgcggtggc ggtctggacc acgccggaga    3060
gcgtcgaagc gggggcggtg ttcgccgaga tcggcccgcg catggccgag ttgagcggtt    3120
cccggctggc cgcgcagcaa cagatggaag gcctcctggc tccgcaccgg cccaaggagc    3180
ccgcgtggtt cctggccacc gtcggcgtct cgcccgacca ccagggcaag ggtctgggca    3240
gcgccgtcgt gctccccgga gtggaggcgg ccgagcgcgc cggggtgccc gccttcctgg    3300
agacctccgc gccccgcaac ctccccttct acgagcggct cggcttcacc gtcaccgccg    3360
acgtcgaggt gcccgaagga ccgcgcacct ggtgcatgac ccgcaagccc ggtgcctgac    3420
gcccgcccca cgacccgcag cgcccgaccg aaaggagcgc acgacccat ggctccgacc    3480 gaagccaccc ggggcggccc cgccgacccc gcacccgccc ccgaggccca ccgacgtcga    3540
cctcgagggc gcgccgctga tcagcctcga ctgtgccttc tagttgccag ccatctgttg    3600
tttgcccctc cccgtgcct  tccttgaccc tggaaggtgc cactcccact gtcctttcct    3660
aataaaatga ggaaattgca tcgcattgtc tgagtaggtg tcattctatt ctgggggtg    3720 gggtggggca ggacagcaag ggggaggatt ggaagacaa  tagcaggcat gctgggatg    3780 cggtgggctc tatggcttct gcggccgcag cttggcgtaa tcatggtcat agctgtttcc    3840
```

```
tgtgtgaaat tgttatccgc tcacaattcc acacaacata cgagccggaa gcataaagtg    3900
taaagcctgg ggtgcctaat gagtgagcta actcacatta attgcgttgc gctcactgcc    3960
cgctttccag tcgggaaacc tgtcgtgcca gctgcattaa tgaatcggcc aacgcgcggg    4020
gagaggcggt ttgcgtattg ggcgctcttc cgcttcctcg ctcactgact cgctgcgctc    4080
ggtcgttcgg ctgcggcgag cggtatcagc tcactcaaag gcggtaatac ggttatccac    4140
agaatcaggg gataacgcag gaaagaacat gtgagcaaaa ggccagcaaa aggccaggaa    4200
ccgtaaaaag gccgcgttgc tggcgttttt ccataggctc cgcccccctg acgagcatca    4260
caaaaatcga cgctcaagtc agaggtggcg aaacccgaca ggactataaa gataccaggc    4320
gtttccccct ggaagctccc tcgtgcgctc tcctgttccg accctgccgc ttaccggata    4380
cctgtccgcc tttctccctt cgggaagcgt ggcgctttct catagctcac gctgtaggta    4440
tctcagttcg gtgtaggtcg ttcgctccaa gctgggctgt gtgcacgaac cccccgttca    4500
gcccgaccgc tgcgccttat ccggtaacta tcgtcttgag tccaacccgg taagacacga    4560
cttatcgcca ctggcagcag ccactggtaa caggattagc agagcgaggt atgtaggcgg    4620
tgctacagag ttcttgaagt ggtggcctaa ctacggctac actagaagaa cagtatttgg    4680
tatctgcgct ctgctgaagc cagttacctt cggaaaaaga gttggtagct cttgatccgg    4740
caaacaaacc accgctggta gcggtggttt ttttgtttgc aagcagcaga ttacgcgcag    4800
aaaaaaagga tctcaagaag atcctttgat cttttctacg gggtctgacg ctcagtggaa    4860
cgaaaactca cgttaaggga ttttggtcat gagattatca aaaaggatct tcacctagat    4920
ccttttaaat taaaaatgaa gttttaaatc aatctaaagt atatatgagt aaacttggtc    4980
tgacagttag aaaaactcat cgagcatcaa atgaaactgc aatttattca tatcaggatt    5040
atcaatacca tatttttgaa aaagccgttt ctgtaatgaa ggagaaaact caccgaggca    5100
gttccatagg atggcaagat cctggtatcg gtctgcgatt ccgactcgtc aacatcaat    5160 acaacctatt aatttcccct cgtcaaaaat aaggttatca agtgagaaat caccatgagt    5220
gacgactgaa tccggtgaga atggcaaaag cttatgcatt tctttccaga cttgttcaac    5280
aggccagcca ttacgctcgt catcaaaatc actcgcatca accaaaccgt tattcattcg    5340
tgattgcgcc tgagcgagac gaaatacgcg atcgctgtta aaaggacaat acaaacagg    5400 aatcgaatgc aaccggcgca ggaacactgc cagcgcatca acaatatttt cacctgaatc    5460
aggatattct tctaatacct ggaatgctgt tttcccgggg atcgcagtgg tgagtaacca    5520
tgcatcatca ggagtacgga taaaatgctt gatggtcgga agaggcataa attccgtcag    5580
ccagtttagt ctgaccatct catctgtaac atcattggca acgctacctt tgccatgttt    5640
cagaaacaac tctggcgcat cgggcttccc atacaatcga tagattgtcg cacctgattg    5700
cccgacatta tcgcgagccc atttataccc atataaatca gcatccatgt tggaatttaa    5760
tcgcggcctt gagcaagacg tttcccgttg aatatggctc atactcttcc ttttcaata    5820 ttattgaagc atttatcagg gttattgtct catgagcgga tacatatttg aatgtattta    5880
gaaaaataaa caaatagggg ttccgcgcac atttccccga aaagtgccac    5930
```

<210> SEQ ID NO 19
<211> LENGTH: 7866
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 19

```
tggcacatgg ccaatgcata tcgatctata cattgaatca atattggcaa ttagccatat      60
tagtcattgg ttatatagca taaatcaata ttggctattg ccattgcat acgttgtatc      120
tatatcataa tatgtacatt tatattggct catgtccaat atgaccgcca tgttgacatt     180
gattattgac tagttattaa tagtaatcaa ttacggggtc attagttcat agcccatata     240
tggagttccg cgttacataa cttacggtaa atggcccgcc tggctgaccg cccaacgacc     300
cccgcccatt gacgtcaata atgacgtatg ttcccatagt aacgccaata gggactttcc     360
attgacgtca atgggtggag tatttacggt aaactgccca cttggcagta catcaagtgt     420
atcatatgcc aagtccgccc cctattgacg tcaatgacgg taaatggccc gcctggcatt     480
atgcccagta catgacctta cgggactttc ctacttggca gtacatctac gtattagtca     540
tcgctattac catggtgatg cggttttggc agtacaccaa tgggcgtgga tagcggtttg     600
actcacgggg atttccaagt ctccacccca ttgacgtcaa tgggagtttg ttttggcacc     660
aaaatcaacg ggactttcca aaatgtcgta ataaccccgc cccgttgacg caaatgggcg     720
gtaggcgtgt acggtgggag gtctatataa gcagagctcg tttagtgaac cgtcagatcg     780
cctggagacg ccatccacgc tgttttgacc tccatagaag acaccgggac cgatccagcc     840
tccgcggccg ggaacggtgc attggaacgc ggattcccg tgccaagagt gacgtaagta      900
ccgcctatag actctatagg cacaccctt tggctcttat gcatgctata ctgttttgg       960
cttggggcct atacaccccc gcttccttat gctataggtg atggtatagc ttagcctata    1020
ggtgtgggtt attgaccatt attgaccact cccctattgg tgacgatact ttccattact    1080
aatccataac atggctcttt gccacaacta tctctattgg ctatatgcca atactctgtc    1140
cttcagagac tgacacggac tctgtatttt tacaggatgg ggtcccatt attatttaca     1200
aattcacata tacaacaacg ccgtcccccg tgcccgcagt ttttattaaa catagcgtgg    1260
gatctccacg cgaatctcgg gtacgtgttc cggacatggg ctcttctccg gtagcggcgg    1320
agcttccaca tccgagccct ggtcccatgc ctccagcggc tcatggtcgc tcggcagctc    1380
cttgctccta acagtggagg ccagacttag gcacagcaca atgcccacca ccaccagtgt    1440
gccgcacaag gccgtggcgg tagggtatgt gtctgaaaat gagctcggag attgggctcg    1500
caccgctgac gcagatggaa gacttaaggc agcggcagaa gaagatgcag gcagctgagt    1560
tgttgtattc tgataagagt cagaggtaac tcccgttgcg gtgctgttaa cggtggaggg    1620
cagtgtagtc tgagcagtac tcgttgctgc cgcgcgcgcc accagacata atagctgaca    1680
gactaacaga ctgttccttt ccatgggtct tttctgcagt caccgtccat ttaaatacgc    1740
gtgccaccat ggatgcaatg aagagagggc tctgctgtgt gctgctgctg tgtggagcag    1800
tcttcgttac taccacagag gctagcaacc tgtgggtgac cgtgtactac ggcgtgcccg    1860
tgtggagaga ggccaagacc accctgttct gcgccagcga cgccaaggcc tacgagcggg    1920
aggtgcacaa cgtgtgggcc acccacgcct gcgtgcccac cgaccccgac cctcaggaaa    1980
tcttcctggg caagaacgtg accgagaagt caacatgtgt gaagaactac atggtggacc    2040
agatgcacga ggacatcatc agcctgtggg accagagcct gcagccctgc gtgaagctga    2100
cccccctgtg catcacccct aactgcaccg acgtgaccgc ccacaacggc agcaccgtgt    2160
acgacaacaa cgccaccgtg gtgaacagca ccaacgagat caagaactgc agcttcaaca    2220
tcaccaccga gctgagggac aagagggaag aggagcacgc cctgttcaac aacctggaca    2280
```

```
tcgtgcagct ggacggcaac agctccctgt acagactgat caactgcaac accagcatca      2340
tcaagcaggc ctgccccaag atcagcttcg accccatccc catccactac tgcgcccag       2400 ccggcttcgt gatcctgaag tgcaacaacg agacattcaa cggcaccggc ccctgtaaca     2460
acgtgtccgc tgtgcagtgc acccacggca tcaagcccgt ggtgtccacc cagctgctgc     2520
tgaacggcag cctggccaag ggcgagatca tgatcagaag cgagaacatc accgacaacg     2580
tgaagaccat catcgtgcac ctgaacaaca gcgtggagat cgtgtgcacc aggcccaaca     2640
acaacaccag gaagagcatc aggatcggcc caggccagac cttctacgcc accggcgaca     2700
tcatcggcga catccggcag gcctactgca gcatcaacga gagcaactgg aacgccaccc     2760
tgcagagggt gtccaagaag ctggccgagc acttccccaa caagaccatc cagttcaaga     2820
gcccctctgg cggcgacctg gagatcacca tgcacagctt caactgcagg ggcgagttct     2880
tctactgcaa cacatccaag ctgtttaacg ggacctacta cccaaacggc acatactacc     2940
caaacgggac caacagcacc ctgatcatcc catgcaggat caagcagatc atcaacatgt     3000
ggcagggcgt gggcaaggcc atctacgcca gcccaatcgc cggcaacatc acctgccggt     3060
ccaacatcac cggcctgctg ctgaccaggg acggcggcga caccaacgac accgagatct     3120
tcaggccagc cggcggagac atgagggaca actggcggag cgagctgtac aagtacaaga     3180
tcgtggagat caagcccctg ggcgtggctc aaccgaggc caagagcagg gtggtgaaga     3240
gcgagaagag cgccgtcacc atcggcgccg tgtttctggg cttcctggga gccgccggaa     3300
gcaccatggg agccgcctcc atcaccctga ccgtgcaggc caggcagctg ctgtccggga     3360
tcgtgcagca gcagagcaac ctgctgagag ccattgaggc tcagcagcac atgctgcagc     3420
tgacagtgtg gggcatcaag cagctgcagg ccagagtgct ggccatcgag agatacctga     3480
aggatcagca gctgctcggc atctgggggct gcagcggcaa gctgatctgc accaccgccg     3540
tgccctggaa caactcctgg tccaacagga cccaggacga gatctggaag aacctgacct     3600
ggatggagtg ggacagagag atcagcaact acaccaacac catctacgag ctgctggagg     3660
tgtcccagag ccagcaggag aggaacgaga aggacctgct ggccctggat agctggaaca     3720
acctgtggaa ctggttcgac atcagcaact ggctgtggta catcaagaag aagaagtgaa     3780
ttcggatcca ctagtagatc tctcgagaac ggccgccagt gtgctggaat taattcgctg     3840
tctgcgaggg ccagctgttg gggtgagtac tccctctcaa aagcgggcat gacttctgcg     3900
ctaagattgt cagtttccaa aaacgaggag gatttgatat tcacctggcc cgcggtgatg     3960
cctttgaggg tggccgcgtc catctggtca gaaaagacaa tcttttttgtt gtcaagcttg     4020 aggtgtggca ggcttgagat ctggccatac acttgagtga caatgacatc cactttgcct     4080
ttctctccac aggtgtccac tcccaggtcc aactgcaggt cgagcatgca tctagggcgg     4140
ccaattccgc ccctctccct ccccccccc taacgttact ggccgaagcc gcttggaata     4200
aggccggtgt gcgtttgtct atatgttatt ttccaccata ttgccgtctt ttggcaatgt     4260
gagggcccgg aaacctggcc ctgtcttctt gacgagcatt cctaggggtc tttcccctct     4320
cgccaaagga atgcaaggtc tgttgaatgt cgtgaaggaa gcagttcctc tggaagcttc     4380
ttgaagacaa caacgtctg tagcgaccct ttgcaggcag cggaaccccc cacctggcga     4440
caggtgcctc tgcggccaaa agccacgtgt ataagataca cctgcaaagg cggcacaacc     4500
ccagtgccac gttgtgagtt ggatagttgt ggaaagagtc aaatggctct cctcaagcgt     4560
attcaacaag ggctgaagg atgcccagaa ggtaccccat tgtatgggat ctgatctggg     4620
gcctcggtgc acatgcttta catgtgttta gtcgaggtta aaaaaacgtc taggccccc      4680
```

-continued

```
gaaccacggg gacgtggttt tcctttgaaa aacacgatga taagcttgcc acaacccaca    4740
aggagacgac cttccatgac cgagtacaag cccacggtgc gcctcgccac ccgcgacgac    4800
gtcccccggg ccgtacgcac cctcgccgcc gcgttcgccg actacccccgc cacgcgccac    4860 accgtggacc cggaccgcca catcgagcgg gtcaccgagc tgcaagaact cttcctcacg    4920
cgcgtcgggc tcgacatcgg caaggtgtgg gtcgcggacg acggcgctgc ggtggcggtc    4980
tggaccacgc cggagagcgt cgaagcgggg gcggtgttcg ccgagatcgg cccgcgcatg    5040
gccgagttga gcggttcccg gctggccgcg cagcaacaga tggaaggcct cctggctccg    5100
caccggccca aggagcccgc gtggttcctg gccaccgtcg gcgtctcgcc cgaccaccag    5160
ggcaagggtc tgggcagcgc cgtcgtgctc cccggagtgg aggcggccga gcgcgccggg    5220
gtgcccgcct tcctggagac ctcccgcgccc cgcaacctcc ccttctacga gcggctcggc    5280
ttcaccgtca ccgccgacgt cgaggtgccc gaaggaccgc gcacctggtg catgacccgc    5340
aagcccggtg cctgacgccc gccccacgac ccgcagcgcc cgaccgaaag gagcgcacga    5400
ccccatggct ccgaccgaag ccacccgggg cggcccccgcc gaccccgcac ccgcccccga    5460
ggcccaccga cgtcgacctc gagggcgcgc cgctgatcag cctcgactgt gccttctagt    5520
tgccagccat ctgttgtttg cccctccccc gtgccttcct tgaccctgga aggtgccact    5580
cccactgtcc tttcctaata aaatgaggaa attgcatcgc attgtctgag taggtgtcat    5640
tctattctgg ggggtggggt ggggcaggac agcaaggggg aggattggga agacaatagc    5700
aggcatgctg gggatgcggt gggctctatg gcttctgcgg ccgcagcttg gcgtaatcat    5760
ggtcatagct gtttcctgtg tgaaattgtt atccgctcac aattccacac aacatacgag    5820
ccggaagcat aaagtgtaaa gcctggggtg cctaatgagt gagctaactc acattaattg    5880
cgttgcgctc actgcccgct ttccagtcgg gaaacctgtc gtgccagctg cattaatgaa    5940
tcggccaacg cgcggggaga ggcggtttgc gtattgggcg ctcttccgct tcctcgctca    6000
ctgactcgct gcgctcggtc gttcggctgc ggcgagcggt atcagctcac tcaaaggcgg    6060
taatacggtt atccacagaa tcaggggata acgcaggaaa gaacatgtga gcaaaaggcc    6120
agcaaaaggc caggaaccgt aaaaaggccg cgttgctggc gtttttccat aggctccgcc    6180
cccctgacga gcatcacaaa aatcgacgct caagtcagag gtggcgaaac ccgacaggac    6240
tataaagata ccaggcgttt ccccctggaa gctccctcgt gcgctctcct gttccgaccc    6300
tgccgcttac cggatacctg tccgcctttc tcccttcggg aagcgtggcg ctttctcata    6360
gctcacgctg taggtatctc agttcggtgt aggtcgttcg ctccaagctg ggctgtgtgc    6420
acgaaccccc cgttcagccc gaccgctgcg ccttatccgg taactatcgt cttgagtcca    6480
acccggtaag acacgactta tcgccactgg cagcagccac tggtaacagg attagcagag    6540
cgaggtatgt aggcggtgct acagagttct tgaagtggtg gcctaactac ggctacacta    6600
gaagaacagt atttggtatc tgcgctctgc tgaagccagt taccttcgga aaaagagttg    6660
gtagctcttg atccggcaaa caaaccaccg ctggtagcgg tggttttttt gtttgcaagc    6720
agcagattac gcgcagaaaa aaaggatctc aagaagatcc tttgatcttt tctacggggt    6780
ctgacgctca gtggaacgaa aactcacgtt aagggatttt ggtcatgaga ttatcaaaaa    6840
ggatcttcac ctagatcctt ttaaattaaa aatgaagttt taaatcaatc taaagtatat    6900
atgagtaaac ttggtctgac agttagaaaa actcatcgag catcaaatga actgcaatt    6960 tattcatatc aggattatca ataccatatt tttgaaaaag ccgtttctgt aatgaaggag    7020
```

-continued

```
aaaactcacc gaggcagttc cataggatgg caagatcctg gtatcggtct gcgattccga    7080
ctcgtccaac atcaatacaa cctattaatt tcccctcgtc aaaaataagg ttatcaagtg    7140
agaaatcacc atgagtgacg actgaatccg gtgagaatgg caaaagctta tgcatttctt    7200
tccagacttg ttcaacaggc cagccattac gctcgtcatc aaaatcactc gcatcaacca    7260
aaccgttatt cattcgtgat tgcgcctgag cgagacgaaa tacgcgatcg ctgttaaaag    7320
gacaattaca aacaggaatc gaatgcaacc ggcgcaggaa cactgccagc gcatcaacaa    7380
tattttcacc tgaatcagga tattcttcta atacctggaa tgctgttttc ccggggatcg    7440
cagtggtgag taaccatgca tcatcaggag tacggataaa atgcttgatg gtcggaagag    7500
gcataaattc cgtcagccag tttagtctga ccatctcatc tgtaacatca ttggcaacgc    7560
tacctttgcc atgtttcaga aacaactctg gcgcatcggg cttcccatac aatcgataga    7620
ttgtcgcacc tgattgcccg acattatcgc gagcccattt atcccatat aaatcagcat     7680 ccatgttgga atttaatcgc ggccttgagc aagacgtttc ccgttgaata tggctcatac    7740
tcttcctttt tcaatattat tgaagcattt atcagggtta ttgtctcatg agcggataca    7800
tatttgaatg tatttagaaa aataaacaaa tagggggttcc gcgcacattt ccccgaaaag   7860
tgccac                                                              7866
```

<210> SEQ ID NO 20
<211> LENGTH: 2035
<212> TYPE: DNA
<213> ORGANISM: Artificial Sequence
<220> FEATURE:
<221> NAME/KEY: source
<223> OTHER INFORMATION: /note="Description of Artificial Sequence:
   Synthetic polynucleotide"
<220> FEATURE:
<221> NAME/KEY: CDS
<222> LOCATION: (1)..(2028)

<400> SEQUENCE: 20

```
atg gat gca atg aag aga ggg ctc tgc tgt gtg ctg ctg ctg tgt gga    48
Met Asp Ala Met Lys Arg Gly Leu Cys Cys Val Leu Leu Leu Cys Gly
1               5                   10                  15 gca gtc ttc gtt act acc aca gag gct agc aac ctg tgg gtg acc gtg    96
Ala Val Phe Val Thr Thr Thr Glu Ala Ser Asn Leu Trp Val Thr Val
            20                  25                  30 tac tac ggc gtg ccc gtg tgg aga gag gcc aag acc acc ctg ttc tgc   144
Tyr Tyr Gly Val Pro Val Trp Arg Glu Ala Lys Thr Thr Leu Phe Cys
        35                  40                  45 gcc agc gac gcc aag gcc tac gag cgg gag gtg cac aac gtg tgg gcc   192
Ala Ser Asp Ala Lys Ala Tyr Glu Arg Glu Val His Asn Val Trp Ala
    50                  55                  60 acc cac gcc tgc gtg ccc acc gac ccc gac cct cag gaa atc ttc ctg   240
Thr His Ala Cys Val Pro Thr Asp Pro Asp Pro Gln Glu Ile Phe Leu
65                  70                  75                  80 ggc aag aac gtg acc gag aag ttc aac atg tgg aag aac tac atg gtg   288
Gly Lys Asn Val Thr Glu Lys Phe Asn Met Trp Lys Asn Tyr Met Val
                85                  90                  95 gac cag atg cac gag gac atc atc agc ctg tgg gac cag agc ctg cag   336
Asp Gln Met His Glu Asp Ile Ile Ser Leu Trp Asp Gln Ser Leu Gln
            100                 105                 110 ccc tgc gtg aag ctg acc ccc ctg tgc atc acc ctg aac tgc acc gac   384
Pro Cys Val Lys Leu Thr Pro Leu Cys Ile Thr Leu Asn Cys Thr Asp
        115                 120                 125 gtg acc gcc cac aac ggc agc acc gtg tac gac aac aac gcc acc gtg   432
Val Thr Ala His Asn Gly Ser Thr Val Tyr Asp Asn Asn Ala Thr Val
```

```
                    130                 135                 140
gtg aac agc acc aac gag atc aag aac tgc agc ttc aac atc acc acc      480
Val Asn Ser Thr Asn Glu Ile Lys Asn Cys Ser Phe Asn Ile Thr Thr
145                 150                 155                 160 gag ctg agg gac aag agg aag aag gag cac gcc ctg ttc aac aac ctg      528
Glu Leu Arg Asp Lys Arg Lys Lys Glu His Ala Leu Phe Asn Asn Leu
                165                 170                 175 gac atc gtg cag ctg gac ggc aac agc tcc ctg tac aga ctg atc aac      576
Asp Ile Val Gln Leu Asp Gly Asn Ser Ser Leu Tyr Arg Leu Ile Asn
            180                 185                 190 tgc aac acc agc atc atc aag cag gcc tgc ccc aag atc agc ttc gac      624
Cys Asn Thr Ser Ile Ile Lys Gln Ala Cys Pro Lys Ile Ser Phe Asp
        195                 200                 205 ccc atc ccc atc cac tac tgc gcc cca gcc ggc ttc gtg atc ctg aag      672
Pro Ile Pro Ile His Tyr Cys Ala Pro Ala Gly Phe Val Ile Leu Lys
    210                 215                 220 tgc aac aac gag aca ttc aac ggc acc ggc ccc tgt aac aac gtg tcc      720
Cys Asn Asn Glu Thr Phe Asn Gly Thr Gly Pro Cys Asn Asn Val Ser
225                 230                 235                 240 gct gtg cag tgc acc cac ggc atc aag ccc gtg gtg tcc acc cag ctg      768
Ala Val Gln Cys Thr His Gly Ile Lys Pro Val Val Ser Thr Gln Leu
                245                 250                 255 ctg ctg aac ggc agc ctg gcc aag ggc gag atc atg atc aga agc gag      816
Leu Leu Asn Gly Ser Leu Ala Lys Gly Glu Ile Met Ile Arg Ser Glu
            260                 265                 270 aac atc acc gac aac gtg aag acc atc atc gtg cac ctg aac aac agc      864
Asn Ile Thr Asp Asn Val Lys Thr Ile Ile Val His Leu Asn Asn Ser
        275                 280                 285 gtg gag atc gtg tgc acc agg ccc aac aac aac acc agg aag agc atc      912
Val Glu Ile Val Cys Thr Arg Pro Asn Asn Asn Thr Arg Lys Ser Ile
    290                 295                 300 agg atc ggc cca ggc cag acc ttc tac gcc acc ggc gac atc atc ggc      960
Arg Ile Gly Pro Gly Gln Thr Phe Tyr Ala Thr Gly Asp Ile Ile Gly
305                 310                 315                 320 gac atc cgg cag gcc tac tgc agc atc aac gag agc aac tgg aac gcc     1008
Asp Ile Arg Gln Ala Tyr Cys Ser Ile Asn Glu Ser Asn Trp Asn Ala
                325                 330                 335 acc ctg cag agg gtg tcc aag aag ctg gcc gag cac ttc ccc aac aag     1056
Thr Leu Gln Arg Val Ser Lys Lys Leu Ala Glu His Phe Pro Asn Lys
            340                 345                 350 acc atc cag ttc aag agc ccc tct ggc ggc gac ctg gag atc acc atg     1104
Thr Ile Gln Phe Lys Ser Pro Ser Gly Gly Asp Leu Glu Ile Thr Met
        355                 360                 365 cac agc ttc aac tgc agg ggc gag ttc ttc tac tgc aac aca tcc aag     1152
His Ser Phe Asn Cys Arg Gly Glu Phe Phe Tyr Cys Asn Thr Ser Lys
    370                 375                 380 ctg ttt aac ggg acc tac tac cca aac ggc aca tac tac cca aac ggg     1200
Leu Phe Asn Gly Thr Tyr Tyr Pro Asn Gly Thr Tyr Tyr Pro Asn Gly
385                 390                 395                 400 acc aac agc acc ctg atc atc cca tgc agg atc aag cag atc atc aac     1248
Thr Asn Ser Thr Leu Ile Ile Pro Cys Arg Ile Lys Gln Ile Ile Asn
                405                 410                 415 atg tgg cag ggc gtg ggc aag gcc atc tac gcc agc cca atc gcc ggc     1296
Met Trp Gln Gly Val Gly Lys Ala Ile Tyr Ala Ser Pro Ile Ala Gly
            420                 425                 430 aac atc acc tgc cgg tcc aac atc acc ggc ctg ctg ctg acc agg gac     1344
Asn Ile Thr Cys Arg Ser Asn Ile Thr Gly Leu Leu Leu Thr Arg Asp
        435                 440                 445 ggc ggc gac acc aac gac acc gag atc ttc agg cca gcc ggc gga gac     1392
```

```
Gly Gly Asp Thr Asn Asp Thr Glu Ile Phe Arg Pro Ala Gly Gly Asp
        450                 455                 460 atg agg gac aac tgg cgg agc gag ctg tac aag tac aag atc gtg gag      1440
Met Arg Asp Asn Trp Arg Ser Glu Leu Tyr Lys Tyr Lys Ile Val Glu
465                 470                 475                 480 atc aag ccc ctg ggc gtg gct cca acc gag gcc aag agc agg gtg gtg      1488
Ile Lys Pro Leu Gly Val Ala Pro Thr Glu Ala Lys Ser Arg Val Val
                485                 490                 495 aag agc gag aag agc gcc gtc acc atc ggc gcc gtg ttt ctg ggc ttc      1536
Lys Ser Glu Lys Ser Ala Val Thr Ile Gly Ala Val Phe Leu Gly Phe
            500                 505                 510 ctg gga gcc gcc gga agc acc atg gga gcc gcc tcc atc acc ctg acc      1584
Leu Gly Ala Ala Gly Ser Thr Met Gly Ala Ala Ser Ile Thr Leu Thr
        515                 520                 525 gtg cag gcc agg cag ctg ctg tcc ggg atc gtg cag cag cag agc aac      1632
Val Gln Ala Arg Gln Leu Leu Ser Gly Ile Val Gln Gln Gln Ser Asn
    530                 535                 540 ctg ctg aga gcc att gag gct cag cag cac atg ctg cag ctg aca gtg      1680
Leu Leu Arg Ala Ile Glu Ala Gln Gln His Met Leu Gln Leu Thr Val
545                 550                 555                 560 tgg ggc atc aag cag ctg cag gcc aga gtg ctg gcc atc gag aga tac      1728
Trp Gly Ile Lys Gln Leu Gln Ala Arg Val Leu Ala Ile Glu Arg Tyr
                565                 570                 575 ctg aag gat cag cag ctg ctc ggc atc tgg ggc tgc agc ggc aag ctg      1776
Leu Lys Asp Gln Gln Leu Leu Gly Ile Trp Gly Cys Ser Gly Lys Leu
            580                 585                 590 atc tgc acc acc gcc gtg ccc tgg aac aac tcc tgg tcc aac agg acc      1824
Ile Cys Thr Thr Ala Val Pro Trp Asn Asn Ser Trp Ser Asn Arg Thr
        595                 600                 605 cag gac gag atc tgg aag aac ctg acc tgg atg gag tgg gac aga gag      1872
Gln Asp Glu Ile Trp Lys Asn Leu Thr Trp Met Glu Trp Asp Arg Glu
    610                 615                 620 atc agc aac tac acc aac acc atc tac gag ctg ctg gag gtg tcc cag      1920
Ile Ser Asn Tyr Thr Asn Thr Ile Tyr Glu Leu Leu Glu Val Ser Gln
625                 630                 635                 640 agc cag cag gag agg aac gag aag gac ctg ctg gcc ctg gat agc tgg      1968
Ser Gln Gln Glu Arg Asn Glu Lys Asp Leu Leu Ala Leu Asp Ser Trp
                645                 650                 655 aac aac ctg tgg aac tgg ttc gac atc agc aac tgg ctg tgg tac atc      2016
Asn Asn Leu Trp Asn Trp Phe Asp Ile Ser Asn Trp Leu Trp Tyr Ile
            660                 665                 670 aag aag aag aag tgaattc                                              2035
Lys Lys Lys Lys
        675

<210> SEQ ID NO 21
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Met Asp Ala Met Lys Arg Gly Leu Cys Cys Val Leu Leu Leu Cys Gly
1               5                   10                  15

Ala Val Phe Val Ser Ala Ser
            20

<210> SEQ ID NO 22
```

```
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Met Asp Ala Met Lys Arg Gly Leu Cys Cys Val Leu Leu Leu Cys Gly
1               5                   10                  15

Ala Val Phe Val Thr Thr Thr Glu Ala Ser
            20                  25

<210> SEQ ID NO 23
<211> LENGTH: 15
<212> TYPE: PRT
<213> ORGANISM: Human immunodeficiency virus

<400> SEQUENCE: 23

Ala Leu Asp Ser Trp Asn Asn Leu Trp Asn Trp Phe Asp Ile Ser
1               5                   10                  15

<210> SEQ ID NO 24
<211> LENGTH: 5
<212> TYPE: PRT
<213> ORGANISM: Human immunodeficiency virus

<400> SEQUENCE: 24

Leu Trp Tyr Ile Lys
1               5

<210> SEQ ID NO 25
<211> LENGTH: 25
<212> TYPE: PRT
<213> ORGANISM: Human immunodeficiency virus

<400> SEQUENCE: 25

Glu Leu Leu Ala Leu Asp Ser Trp Asn Asn Leu Trp Asn Trp Phe Asp
1               5                   10                  15

Ile Ser Asn Trp Leu Trp Tyr Ile Lys
            20                  25

<210> SEQ ID NO 26
<211> LENGTH: 25
<212> TYPE: PRT
<213> ORGANISM: Human immunodeficiency virus

<400> SEQUENCE: 26

Asp Leu Leu Ala Leu Asp Ser Trp Lys Asn Leu Trp Asn Trp Phe Asp
1               5                   10                  15

Ile Thr Asn Trp Leu Trp Tyr Ile Lys
            20                  25

<210> SEQ ID NO 27
<211> LENGTH: 6
<212> TYPE: PRT
<213> ORGANISM: Human immunodeficiency virus

<400> SEQUENCE: 27

Ala Leu Asp Ser Trp Asn
1               5

<210> SEQ ID NO 28
```

```
<211> LENGTH: 6
<212> TYPE: PRT
<213> ORGANISM: Human immunodeficiency virus

<400> SEQUENCE: 28

Glu Leu Asp Lys Trp Ala
1               5

<210> SEQ ID NO 29
<211> LENGTH: 17
<212> TYPE: PRT
<213> ORGANISM: Human immunodeficiency virus

<400> SEQUENCE: 29

Glu Lys Asn Glu Gln Glu Leu Leu Glu Leu Asp Lys Trp Ala Ser Leu
1               5                   10                  15

Trp

<210> SEQ ID NO 30
<211> LENGTH: 6
<212> TYPE: PRT
<213> ORGANISM: Human immunodeficiency virus

<400> SEQUENCE: 30

Asn Trp Phe Asp Ile Ser
1               5

<210> SEQ ID NO 31
<211> LENGTH: 6
<212> TYPE: PRT
<213> ORGANISM: Human immunodeficiency virus

<400> SEQUENCE: 31

Asn Trp Phe Asp Ile Thr
1               5

<210> SEQ ID NO 32
<211> LENGTH: 676
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Met Asp Ala Met Lys Arg Gly Leu Cys Cys Val Leu Leu Leu Cys Gly
1               5                   10                  15

Ala Val Phe Val Thr Thr Thr Glu Ala Ser Asn Leu Trp Val Thr Val
                20                  25                  30

Tyr Tyr Gly Val Pro Val Trp Arg Glu Ala Lys Thr Thr Leu Phe Cys
            35                  40                  45

Ala Ser Asp Ala Lys Ala Tyr Glu Arg Glu Val His Asn Val Trp Ala
        50                  55                  60

Thr His Ala Cys Val Pro Thr Asp Pro Asp Pro Gln Glu Ile Phe Leu
65                  70                  75                  80

Gly Lys Asn Val Thr Glu Lys Phe Asn Met Trp Lys Asn Tyr Met Val
                85                  90                  95

Asp Gln Met His Glu Asp Ile Ile Ser Leu Trp Asp Gln Ser Leu Gln
                100                 105                 110

Pro Cys Val Lys Leu Thr Pro Leu Cys Ile Thr Leu Asn Cys Thr Asp
            115                 120                 125
```

```
Val Thr Ala His Asn Gly Ser Thr Val Tyr Asp Asn Asn Ala Thr Val
    130                 135                 140
Val Asn Ser Thr Asn Glu Ile Lys Asn Cys Ser Phe Asn Ile Thr Thr
145                 150                 155                 160
Glu Leu Arg Asp Lys Arg Lys Lys Glu His Ala Leu Phe Asn Asn Leu
                165                 170                 175
Asp Ile Val Gln Leu Asp Gly Asn Ser Ser Leu Tyr Arg Leu Ile Asn
                180                 185                 190
Cys Asn Thr Ser Ile Ile Lys Gln Ala Cys Pro Lys Ile Ser Phe Asp
            195                 200                 205
Pro Ile Pro Ile His Tyr Cys Ala Pro Ala Gly Phe Val Ile Leu Lys
    210                 215                 220
Cys Asn Asn Glu Thr Phe Asn Gly Thr Gly Pro Cys Asn Asn Val Ser
225                 230                 235                 240
Ala Val Gln Cys Thr His Gly Ile Lys Pro Val Val Ser Thr Gln Leu
                245                 250                 255
Leu Leu Asn Gly Ser Leu Ala Lys Gly Glu Ile Met Ile Arg Ser Glu
            260                 265                 270
Asn Ile Thr Asp Asn Val Lys Thr Ile Ile Val His Leu Asn Asn Ser
            275                 280                 285
Val Glu Ile Val Cys Thr Arg Pro Asn Asn Asn Thr Arg Lys Ser Ile
    290                 295                 300
Arg Ile Gly Pro Gly Gln Thr Phe Tyr Ala Thr Gly Asp Ile Ile Gly
305                 310                 315                 320
Asp Ile Arg Gln Ala Tyr Cys Ser Ile Asn Glu Ser Asn Trp Asn Ala
                325                 330                 335
Thr Leu Gln Arg Val Ser Lys Lys Leu Ala Glu His Phe Pro Asn Lys
                340                 345                 350
Thr Ile Gln Phe Lys Ser Pro Ser Gly Gly Asp Leu Glu Ile Thr Met
            355                 360                 365
His Ser Phe Asn Cys Arg Gly Glu Phe Phe Tyr Cys Asn Thr Ser Lys
    370                 375                 380
Leu Phe Asn Gly Thr Tyr Tyr Pro Asn Gly Thr Tyr Tyr Pro Asn Gly
385                 390                 395                 400
Thr Asn Ser Thr Leu Ile Ile Pro Cys Arg Ile Lys Gln Ile Ile Asn
                405                 410                 415
Met Trp Gln Gly Val Gly Lys Ala Ile Tyr Ala Ser Pro Ile Ala Gly
            420                 425                 430
Asn Ile Thr Cys Arg Ser Asn Ile Thr Gly Leu Leu Leu Thr Arg Asp
        435                 440                 445
Gly Gly Asp Thr Asn Asp Thr Glu Ile Phe Arg Pro Ala Gly Gly Asp
450                 455                 460
Met Arg Asp Asn Trp Arg Ser Glu Leu Tyr Lys Tyr Lys Ile Val Glu
465                 470                 475                 480
Ile Lys Pro Leu Gly Val Ala Pro Thr Glu Ala Lys Ser Arg Val Val
                485                 490                 495
Lys Ser Glu Lys Ser Ala Val Thr Ile Gly Ala Val Phe Leu Gly Phe
            500                 505                 510
Leu Gly Ala Ala Gly Ser Thr Met Gly Ala Ala Ser Ile Thr Leu Thr
        515                 520                 525
Val Gln Ala Arg Gln Leu Leu Ser Gly Ile Val Gln Gln Ser Asn
    530                 535                 540
```

```
Leu Leu Arg Ala Ile Glu Ala Gln Gln His Met Leu Gln Leu Thr Val
545                 550                 555                 560

Trp Gly Ile Lys Gln Leu Gln Ala Arg Val Leu Ala Ile Glu Arg Tyr
            565                 570                 575

Leu Lys Asp Gln Gln Leu Leu Gly Ile Trp Gly Cys Ser Gly Lys Leu
        580                 585                 590

Ile Cys Thr Thr Ala Val Pro Trp Asn Asn Ser Trp Ser Asn Arg Thr
        595                 600                 605

Gln Asp Glu Ile Trp Lys Asn Leu Thr Trp Met Glu Trp Asp Arg Glu
610                 615                 620

Ile Ser Asn Tyr Thr Asn Thr Ile Tyr Glu Leu Leu Glu Val Ser Gln
625                 630                 635                 640

Ser Gln Gln Glu Arg Asn Glu Lys Asp Leu Leu Ala Leu Asp Ser Trp
            645                 650                 655

Asn Asn Leu Trp Asn Trp Phe Asp Ile Ser Asn Trp Leu Trp Tyr Ile
        660                 665                 670

Lys Lys Lys Lys
        675

<210> SEQ ID NO 33
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
atggatgcaa tgaagagagg gctctgctgt gtgctgctgc tgtgtggagc agtcttcgtt      60
tcggctagc                                                              69

<210> SEQ ID NO 34
<211> LENGTH: 78
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
atggatgcaa tgaagagagg gctctgctgt gtgctgctgc tgtgtggagc agtcttcgtt      60
actaccacag aggctagc                                                    78

<210> SEQ ID NO 35
<211> LENGTH: 819
<212> TYPE: PRT
<213> ORGANISM: Human immunodeficiency virus

<400> SEQUENCE: 35

Ser Asn Leu Trp Val Thr Val Tyr Tyr Gly Val Pro Val Trp Lys Glu
1               5                   10                  15

Ala Lys Thr Thr Leu Phe Cys Ala Ser Asp Ala Lys Ala Tyr Glu Lys
            20                  25                  30

Glu Val His Asn Val Trp Ala Thr His Ala Cys Val Pro Thr Asp Pro
        35                  40                  45

Asn Pro Gln Glu Met Glu Leu Pro Asn Val Thr Glu Asn Phe Asn Met
    50                  55                  60
```

-continued

Trp Lys Asn Asp Met Val Asp Gln Met His Glu Asp Ile Ile Ser Leu
 65                  70                  75                  80

Trp Asp Gln Ser Leu Lys Pro Cys Val Lys Leu Thr Pro Leu Cys Val
                 85                  90                  95

Thr Leu Asn Cys Asn Lys Val Asn Asn Asn Arg Ser Ile Asp Asn Asn
            100                 105                 110

Ser Thr Glu Glu Met Lys Asn Cys Thr Phe Asn Thr Thr Thr Glu
        115                 120                 125

Ile Arg Asp Lys Lys Arg Thr Gln Gln Ala Leu Phe Tyr Lys Leu Asp
    130                 135                 140

Ile Val Pro Leu Gly Asn Ser Asn Glu Ser Tyr Arg Leu Ile Asn Cys
145                 150                 155                 160

Asn Thr Ser Thr Leu Thr Gln Ala Cys Pro Lys Val Thr Phe Asp Pro
                165                 170                 175

Ile Pro Ile His Tyr Cys Ala Pro Ala Gly Tyr Ala Ile Leu Lys Cys
            180                 185                 190

Lys Asp Glu Lys Phe Asn Gly Thr Gly Pro Cys Asn Asn Val Ser Thr
        195                 200                 205

Val Gln Cys Thr His Gly Ile Lys Pro Val Val Ser Thr Gln Leu Leu
    210                 215                 220

Leu Asn Gly Ser Leu Ala Glu Lys Asp Ile Ile Ile Arg Ser Glu Asn
225                 230                 235                 240

Leu Thr Asn Asn Val Lys Thr Ile Met Val His Leu Asn Glu Ser Val
                245                 250                 255

Glu Ile Asn Cys Thr Arg Pro Asn Asn Asn Thr Arg Lys Ser Ile Arg
            260                 265                 270

Ile Gly Pro Gly Gln Thr Phe Tyr Ala Thr Gly Gly Ile Ile Gly Asn
        275                 280                 285

Ile Arg Gln Ala Tyr Cys Thr Ile Ser Lys Asn Lys Trp Asn Thr Thr
    290                 295                 300

Leu Glu Arg Val Ala Thr Lys Leu Lys Glu Tyr Phe Lys Asn Thr Thr
305                 310                 315                 320

Ile Gln Phe Ala Pro His Ser Gly Gly Asp Leu Glu Ile Thr Thr His
                325                 330                 335

Ser Phe Asn Cys Arg Gly Glu Phe Phe Tyr Cys Asn Thr Ser Gln Leu
            340                 345                 350

Phe Asn Gly Thr Ser Thr Gly Phe Ser Asn Lys Ser Thr Gly Asn Glu
        355                 360                 365

Thr Phe Thr Leu Pro Cys Arg Ile Lys Gln Ile Ile Asn Met Trp Gln
    370                 375                 380

Glu Val Gly Arg Ala Met Tyr Ala Pro Pro Ile Ala Gly Asn Ile Thr
385                 390                 395                 400

Cys Val Ser Asn Ile Thr Gly Leu Leu Leu Thr Arg Asp Gly Gly Asp
                405                 410                 415

Asn Asn Thr Arg Thr Glu Thr Phe Arg Pro Gly Gly Gly Asp Met Arg
            420                 425                 430

Asp Asn Trp Arg Ser Glu Leu Tyr Lys Tyr Lys Val Val Glu Val Lys
        435                 440                 445

Pro Leu Gly Val Ala Pro Ser Glu Ala Arg Arg Val Val Glu Arg
    450                 455                 460

Glu Lys Arg Ala Val Gly Leu Gly Ala Val Phe Leu Gly Phe Leu Gly
465                 470                 475                 480

Ala Ala Gly Ser Thr Met Gly Ala Ala Ser Ile Thr Leu Thr Val Gln

```
            485                 490                 495
Ala Arg Gln Leu Leu Ser Gly Ile Val Gln Gln Ser Asn Leu Leu
            500                 505                 510

Arg Ala Ile Glu Ala Gln Gln His Met Leu Gln Leu Thr Val Trp Gly
        515                 520                 525

Ile Lys Gln Leu Gln Thr Lys Val Leu Ala Ile Glu Arg Tyr Leu Gln
        530                 535                 540

Asp Gln Gln Leu Leu Gly Ile Trp Gly Cys Ser Gly Lys Leu Ile Cys
545                 550                 555                 560

Thr Thr Asn Val Pro Trp Asn Ser Ser Trp Ser Asn Lys Ser Leu Lys
                565                 570                 575

Ala Ile Trp Asp Asn Met Thr Trp Met Gln Trp Asp Arg Glu Ile Ser
            580                 585                 590

Asn Tyr Thr Asn Thr Ile Tyr Arg Leu Leu Glu Asp Ser His Ile Gln
        595                 600                 605

Gln Glu Lys Asn Glu Lys Asp Leu Leu Ala Leu Asn Ser Trp Asn Asn
    610                 615                 620

Leu Trp Ser Trp Phe Asn Ile Thr Asn Trp Leu Trp Tyr Ile Arg Ile
625                 630                 635                 640

Phe Ile Met Ile Val Gly Gly Leu Ile Gly Leu Arg Ile Phe Ala
                645                 650                 655

Ile Leu Ser Ile Val Asn Arg Val Arg Gln Gly Tyr Ser Pro Leu Ser
            660                 665                 670

Phe Gln Thr Leu Thr Pro Asn Gln Arg Gly Pro Asp Arg Leu Gly Arg
        675                 680                 685

Ile Glu Glu Glu Gly Gly Glu Gln Asp Lys Asp Arg Ser Ile Arg Leu
    690                 695                 700

Val Asn Gly Phe Leu Ala Leu Ala Trp Asp Asp Leu Arg Ser Leu Cys
705                 710                 715                 720

Leu Phe Ser Tyr His Arg Leu Arg Asp Phe Ile Leu Ile Ala Thr Arg
                725                 730                 735

Ala Val Glu Leu Leu Gly His Ser Ser Leu Arg Gly Leu Gln Arg Gly
            740                 745                 750

Trp Glu Ala Leu Lys Tyr Leu Gly Ser Leu Gly Gln Tyr Trp Gly Gln
        755                 760                 765

Glu Leu Lys Lys Ser Ala Ile Arg Leu Leu Asp Ile Thr Ala Ile Ala
    770                 775                 780

Val Ala Glu Gly Thr Asp Arg Ile Ile Glu Phe Ile Gln Arg Ile Cys
785                 790                 795                 800

Arg Ala Ile His Asn Val Pro Asn Arg Ile Arg Gln Gly Phe Glu Ala
                805                 810                 815

Ala Leu Leu

<210> SEQ ID NO 36
<211> LENGTH: 819
<212> TYPE: PRT
<213> ORGANISM: Human immunodeficiency virus

<400> SEQUENCE: 36

Ser Asn Leu Trp Val Thr Val Tyr Tyr Gly Val Pro Val Trp Lys Glu
1               5                   10                  15

Ala Lys Thr Thr Leu Phe Cys Ala Ser Asp Ala Lys Ala Tyr Glu Lys
            20                  25                  30

Glu Val His Asn Val Trp Ala Thr His Ala Cys Val Pro Thr Asp Pro
```

```
                 35                  40                  45
Asn Pro Gln Glu Met Glu Leu Pro Asn Val Thr Glu Asn Phe Asn Met
 50                  55                  60

Trp Lys Asn Asp Met Val Asp Gln Met His Glu Asp Ile Ile Ser Leu
 65                  70                  75                  80

Trp Asp Gln Ser Leu Lys Pro Cys Val Lys Leu Thr Pro Leu Cys Val
                 85                  90                  95

Thr Leu Asn Cys Asn Lys Val Asn Asn Arg Ser Ile Asp Asn Asn
                100                 105                 110

Ser Thr Glu Glu Glu Met Lys Asn Cys Thr Phe Asn Thr Thr Glu
                115                 120                 125

Ile Arg Asp Lys Lys Arg Thr Gln Gln Ala Leu Phe Tyr Lys Leu Asp
                130                 135                 140

Ile Val Pro Leu Gly Asn Ser Asn Glu Ser Tyr Arg Leu Ile Asn Cys
145                 150                 155                 160

Asn Thr Ser Thr Leu Thr Gln Ala Cys Pro Lys Val Thr Phe Asp Pro
                165                 170                 175

Ile Pro Ile His Tyr Cys Ala Pro Ala Gly Tyr Ala Ile Leu Lys Cys
                180                 185                 190

Lys Asp Glu Lys Phe Asn Gly Thr Gly Pro Cys Asn Asn Val Ser Thr
                195                 200                 205

Val Gln Cys Thr His Gly Ile Lys Pro Val Val Ser Thr Gln Leu Leu
                210                 215                 220

Leu Asn Gly Ser Leu Ala Glu Lys Asp Ile Ile Ile Arg Ser Glu Asn
225                 230                 235                 240

Leu Thr Asn Asn Val Lys Thr Ile Met Val His Leu Asn Glu Ser Val
                245                 250                 255

Glu Ile Asn Cys Thr Arg Pro Asn Asn Asn Thr Arg Lys Ser Ile Arg
                260                 265                 270

Ile Gly Pro Gly Gln Thr Phe Tyr Ala Thr Gly Gly Ile Ile Gly Asn
                275                 280                 285

Ile Arg Gln Ala Tyr Cys Thr Ile Ser Lys Asn Lys Trp Asn Thr Thr
                290                 295                 300

Leu Glu Arg Val Ala Thr Lys Leu Lys Glu Tyr Phe Lys Asn Thr Thr
305                 310                 315                 320

Ile Gln Phe Ala Pro His Ser Gly Gly Asp Leu Glu Ile Thr Thr His
                325                 330                 335

Ser Phe Asn Cys Arg Gly Glu Phe Phe Tyr Cys Asn Thr Ser Gln Leu
                340                 345                 350

Phe Asn Gly Thr Ser Thr Gly Phe Ser Asn Lys Ser Thr Gly Asn Glu
                355                 360                 365

Thr Phe Thr Leu Pro Cys Arg Ile Lys Gln Ile Ile Asn Met Trp Gln
                370                 375                 380

Glu Val Gly Arg Ala Met Tyr Ala Pro Pro Ile Ala Gly Asn Ile Thr
385                 390                 395                 400

Cys Val Ser Asn Ile Thr Gly Leu Leu Leu Thr Arg Asp Gly Gly Asp
                405                 410                 415

Asn Asn Thr Arg Thr Glu Thr Phe Arg Pro Gly Gly Gly Asp Met Arg
                420                 425                 430

Asp Asn Trp Arg Ser Glu Leu Tyr Lys Tyr Lys Val Val Glu Val Lys
                435                 440                 445

Pro Leu Gly Val Ala Pro Ser Glu Ala Arg Ser Arg Val Val Glu Arg
450                 455                 460
```

Glu Lys Ser Ala Val Gly Leu Gly Ala Val Phe Leu Gly Phe Leu Gly
465                 470                 475                 480

Ala Ala Gly Ser Thr Met Gly Ala Ala Ser Ile Thr Leu Thr Val Gln
                485                 490                 495

Ala Arg Gln Leu Leu Ser Gly Ile Val Gln Gln Ser Asn Leu Leu
            500                 505                 510

Arg Ala Ile Glu Ala Gln Gln His Met Leu Gln Leu Thr Val Trp Gly
            515                 520                 525

Ile Lys Gln Leu Gln Thr Lys Val Leu Ala Ile Glu Arg Tyr Leu Gln
530                 535                 540

Asp Gln Gln Leu Leu Gly Ile Trp Gly Cys Ser Gly Lys Leu Ile Cys
545                 550                 555                 560

Thr Thr Asn Val Pro Trp Asn Ser Ser Trp Ser Asn Lys Ser Leu Lys
                565                 570                 575

Ala Ile Trp Asp Asn Met Thr Trp Met Gln Trp Asp Arg Glu Ile Ser
            580                 585                 590

Asn Tyr Thr Asn Thr Ile Tyr Arg Leu Leu Glu Asp Ser His Ile Gln
            595                 600                 605

Gln Glu Lys Asn Glu Lys Asp Leu Leu Ala Leu Asn Ser Trp Asn Asn
610                 615                 620

Leu Trp Ser Trp Phe Asn Ile Thr Asn Trp Leu Trp Tyr Ile Arg Ile
625                 630                 635                 640

Phe Ile Met Ile Val Gly Gly Leu Ile Gly Leu Arg Ile Ile Phe Ala
                645                 650                 655

Ile Leu Ser Ile Val Asn Arg Val Arg Gln Gly Tyr Ser Pro Leu Ser
            660                 665                 670

Phe Gln Thr Leu Thr Pro Asn Gln Arg Gly Pro Asp Arg Leu Gly Arg
            675                 680                 685

Ile Glu Glu Glu Gly Gly Glu Gln Asp Lys Asp Arg Ser Ile Arg Leu
            690                 695                 700

Val Asn Gly Phe Leu Ala Leu Ala Trp Asp Asp Leu Arg Ser Leu Cys
705                 710                 715                 720

Leu Phe Ser Tyr His Arg Leu Arg Asp Phe Ile Leu Ile Ala Thr Arg
                725                 730                 735

Ala Val Glu Leu Leu Gly His Ser Ser Leu Arg Gly Leu Gln Arg Gly
            740                 745                 750

Trp Glu Ala Leu Lys Tyr Leu Gly Ser Leu Gly Gln Tyr Trp Gly Gln
            755                 760                 765

Glu Leu Lys Lys Ser Ala Ile Arg Leu Leu Asp Ile Thr Ala Ile Ala
            770                 775                 780

Val Ala Glu Gly Thr Asp Arg Ile Ile Glu Phe Ile Gln Arg Ile Cys
785                 790                 795                 800

Arg Ala Ile His Asn Val Pro Asn Arg Ile Arg Gln Gly Phe Glu Ala
                805                 810                 815

Ala Leu Leu

<210> SEQ ID NO 37
<211> LENGTH: 813
<212> TYPE: PRT
<213> ORGANISM: Human immunodeficiency virus

<400> SEQUENCE: 37

Ser Asn Leu Trp Val Thr Val Tyr Tyr Gly Val Pro Val Trp Arg Glu
1               5                   10                  15

```
Ala Lys Thr Thr Leu Phe Cys Ala Ser Asp Ala Lys Ala Tyr Glu Lys
            20                  25                  30

Glu Val His Asn Val Trp Ala Thr His Ala Cys Val Pro Thr Asp Pro
        35                  40                  45

Asp Pro Gln Glu Met Val Leu Lys Asn Val Thr Glu Asn Phe Asn Met
50                  55                  60

Trp Lys Asn Asp Met Val Glu Gln Met His Glu Asp Ile Ile Ser Leu
65                  70                  75                  80

Trp Asp Gln Ser Leu Lys Pro Cys Val Lys Leu Thr Pro Leu Cys Val
                85                  90                  95

Thr Leu Thr Cys Thr Asn Val Asn Ala Thr Asp Asn Val Thr Tyr Lys
            100                 105                 110

Glu Lys Met Glu Gly Glu Ile Lys Asn Cys Ser Phe Asn Ile Thr Thr
        115                 120                 125

Glu Ile Arg Asp Lys Lys Arg Lys Val His Ala Leu Phe Tyr Arg Leu
130                 135                 140

Asp Val Val Gln Leu Asn Asn Ser Asn Glu Tyr Ile Leu Ile Asn Cys
145                 150                 155                 160

Asn Thr Ser Ala Ile Thr Gln Ala Cys Pro Lys Val Ser Phe Asp Pro
            165                 170                 175

Ile Pro Ile His Tyr Cys Ala Pro Ala Gly Tyr Ala Ile Leu Lys Cys
        180                 185                 190

Asn Asp Lys Pro Phe Asn Gly Thr Gly Pro Cys His Asn Val Ser Thr
        195                 200                 205

Val Gln Cys Thr His Gly Ile Lys Pro Val Ile Ser Thr Gln Leu Leu
    210                 215                 220

Leu Asn Gly Ser Leu Ala Glu Lys Glu Val Ile Ile Arg Phe Glu Asn
225                 230                 235                 240

Leu Thr Asp Asn Ala Lys Thr Ile Ile Val Gln Leu Asn Gln Ser Ile
            245                 250                 255

Glu Ile Lys Cys Ile Arg Pro Asn Asn Asn Thr Arg Glu Ser Ile Arg
            260                 265                 270

Ile Gly Pro Gly Gln Ala Phe Tyr Ala Thr Arg Asp Ile Ile Gly Asp
        275                 280                 285

Ile Arg Arg Ala Tyr Cys Thr Ile Glu Thr Glu Arg Trp Lys Glu Thr
        290                 295                 300

Leu Gly Asn Val Thr Glu Lys Leu Lys Glu Tyr Phe Pro Asn Thr Asn
305                 310                 315                 320

Ile Ser Phe Ala Pro Ser Ser Gly Gly Asp Leu Glu Ile Thr Thr His
            325                 330                 335

Ser Phe Asn Cys Arg Gly Glu Phe Phe Tyr Arg Asn Thr Ser Lys Leu
        340                 345                 350

Phe Asn Asn Asn Asp Thr Glu Asn Asn Leu Thr Ile Thr Leu Pro Cys
        355                 360                 365

Arg Ile Lys Gln Ile Val Asn Met Trp Gln Gly Val Gly Arg Ala Met
        370                 375                 380

Tyr Ala Pro Pro Ile Glu Gly Asn Ile Thr Cys Lys Ser Asn Ile Thr
385                 390                 395                 400

Gly Leu Leu Leu Thr Arg Asp Gly Gly Asn Gly Thr Glu Arg Asn Glu
            405                 410                 415

Thr Phe Arg Pro Gly Gly Gly Asp Met Arg Asn Asn Trp Arg Ser Glu
        420                 425                 430
```

```
Leu Tyr Lys Tyr Lys Val Val Glu Ile Lys Pro Leu Gly Ile Ala Pro
            435                 440                 445

Thr Gly Ala Lys Arg Arg Val Val Glu Arg Glu Lys Arg Ala Val Gly
450                 455                 460

Met Gly Ala Val Phe Leu Gly Phe Leu Gly Ala Ala Gly Ser Thr Met
465                 470                 475                 480

Gly Ala Ala Ser Leu Thr Leu Thr Val Gln Ala Arg Gln Val Leu Ser
            485                 490                 495

Gly Ile Val Gln Gln Ser Asn Leu Leu Arg Ala Ile Glu Ala Gln
            500                 505                 510

Gln His Met Leu Gln Leu Thr Val Trp Gly Ile Lys Gln Leu Gln Thr
            515                 520                 525

Arg Val Leu Ala Ile Glu Arg Tyr Leu Lys Asp Gln Gln Leu Leu Gly
530                 535                 540

Leu Trp Gly Cys Ser Gly Lys Leu Ile Cys Thr Thr Ala Val Pro Trp
545                 550                 555                 560

Asn Ser Ser Trp Ser Asn Lys Ser Glu Ile Asp Ile Trp Asn Asn Met
            565                 570                 575

Thr Trp Met Gln Trp Asp Arg Glu Ile Ser Asn Tyr Thr Asn Thr Ile
            580                 585                 590

Tyr Arg Leu Leu Glu Asp Ser Gln Thr Gln Gln Glu Lys Asn Glu Lys
            595                 600                 605

Asp Leu Leu Ala Leu Asp Ser Trp Lys Asn Leu Trp Asn Trp Phe Asn
            610                 615                 620

Ile Thr Lys Trp Leu Trp Tyr Ile Lys Ile Phe Ile Ile Val Gly
625                 630                 635                 640

Gly Leu Ile Gly Leu Arg Ile Ile Phe Ala Val Leu Ser Ile Val Asn
            645                 650                 655

Arg Val Arg Gln Gly Tyr Ser Pro Leu Ser Phe Gln Thr Leu Ile Pro
            660                 665                 670

Ser Pro Arg Gly Pro Asp Lys Leu Gly Arg Ile Glu Glu Glu Gly Gly
            675                 680                 685

Glu Gln Asp Lys Gly Arg Ser Val Arg Leu Val Asn Gly Phe Leu Ala
            690                 695                 700

Leu Ala Trp Asp Asp Leu Arg Ser Leu Cys Leu Phe Ser Tyr His Gln
705                 710                 715                 720

Leu Arg Asp Phe Ile Leu Ile Val Ala Arg Ala Val Gly Leu Leu Gly
                725                 730                 735

Arg Ser Ser Leu Arg Gly Leu Gln Arg Gly Trp Glu Ile Leu Lys Tyr
            740                 745                 750

Leu Gly Gly Leu Val Gln Tyr Trp Gly Leu Glu Leu Lys Lys Ser Ala
            755                 760                 765

Val Ser Leu Phe Asp Thr Ile Ala Ile Ala Val Thr Glu Gly Thr Asp
770                 775                 780

Arg Ile Ile Glu Leu Ile Gln Arg Ser Cys Arg Ala Ile Arg Asn Val
785                 790                 795                 800

Pro Thr Arg Ile Arg Gln Gly Phe Glu Ala Ala Leu Gln
                805                 810
```

<210> SEQ ID NO 38
<211> LENGTH: 813
<212> TYPE: PRT
<213> ORGANISM: Human immunodeficiency virus

<400> SEQUENCE: 38

-continued

```
Ser Asn Leu Trp Val Thr Val Tyr Tyr Gly Val Pro Val Trp Arg Glu
1               5                   10                  15

Ala Lys Thr Thr Leu Phe Cys Ala Ser Asp Ala Lys Ala Tyr Glu Lys
                20                  25                  30

Glu Val His Asn Val Trp Ala Thr His Ala Cys Val Pro Thr Asp Pro
            35                  40                  45

Asp Pro Gln Glu Met Val Leu Lys Asn Val Thr Glu Asn Phe Asn Met
50                  55                  60

Trp Lys Asn Asp Met Val Gln Met His Glu Asp Ile Ile Ser Leu
65                  70                  75                  80

Trp Asp Gln Ser Leu Lys Pro Cys Val Lys Leu Thr Pro Leu Cys Val
                85                  90                  95

Thr Leu Thr Cys Thr Asn Val Asn Ala Thr Asp Asn Val Thr Tyr Lys
                100                 105                 110

Glu Lys Met Glu Gly Glu Ile Lys Asn Cys Ser Phe Asn Ile Thr Thr
            115                 120                 125

Glu Ile Arg Asp Lys Lys Arg Lys Val His Ala Leu Phe Tyr Arg Leu
        130                 135                 140

Asp Val Val Gln Leu Asn Asn Ser Asn Glu Tyr Ile Leu Ile Asn Cys
145                 150                 155                 160

Asn Thr Ser Ala Ile Thr Gln Ala Cys Pro Lys Val Ser Phe Asp Pro
                165                 170                 175

Ile Pro Ile His Tyr Cys Ala Pro Ala Gly Tyr Ala Ile Leu Lys Cys
                180                 185                 190

Asn Asp Lys Pro Phe Asn Gly Thr Gly Pro Cys His Asn Val Ser Thr
            195                 200                 205

Val Gln Cys Thr His Gly Ile Lys Pro Val Ile Ser Thr Gln Leu Leu
        210                 215                 220

Leu Asn Gly Ser Leu Ala Glu Lys Glu Val Ile Ile Arg Phe Glu Asn
225                 230                 235                 240

Leu Thr Asp Asn Ala Lys Thr Ile Ile Val Gln Leu Asn Gln Ser Ile
                245                 250                 255

Glu Ile Lys Cys Ile Arg Pro Asn Asn Asn Thr Arg Glu Ser Ile Arg
                260                 265                 270

Ile Gly Pro Gly Gln Ala Phe Tyr Ala Thr Arg Asp Ile Ile Gly Asp
            275                 280                 285

Ile Arg Arg Ala Tyr Cys Thr Ile Glu Thr Glu Arg Trp Lys Glu Thr
        290                 295                 300

Leu Gly Asn Val Thr Glu Lys Leu Lys Glu Tyr Phe Pro Asn Thr Asn
305                 310                 315                 320

Ile Ser Phe Ala Pro Ser Ser Gly Gly Asp Leu Glu Ile Thr Thr His
                325                 330                 335

Ser Phe Asn Cys Arg Gly Glu Phe Phe Tyr Arg Asn Thr Ser Lys Leu
                340                 345                 350

Phe Asn Asn Asn Asp Thr Glu Asn Leu Thr Ile Thr Leu Pro Cys
            355                 360                 365

Arg Ile Lys Gln Ile Val Asn Met Trp Gln Gly Val Gly Arg Ala Met
        370                 375                 380

Tyr Ala Pro Pro Ile Glu Gly Asn Ile Thr Cys Lys Ser Asn Ile Thr
385                 390                 395                 400

Gly Leu Leu Leu Thr Arg Asp Gly Gly Asn Gly Thr Glu Arg Asn Glu
                405                 410                 415
```

-continued

Thr Phe Arg Pro Gly Gly Asp Met Arg Asn Asn Trp Arg Ser Glu
            420                 425                 430

Leu Tyr Lys Tyr Lys Val Val Glu Ile Lys Pro Leu Gly Ile Ala Pro
        435                 440                 445

Thr Gly Ala Lys Ser Arg Val Val Glu Arg Glu Lys Ser Ala Val Gly
    450                 455                 460

Met Gly Ala Val Phe Leu Gly Phe Leu Gly Ala Ala Gly Ser Thr Met
465                 470                 475                 480

Gly Ala Ala Ser Leu Thr Leu Thr Val Gln Ala Arg Gln Val Leu Ser
                485                 490                 495

Gly Ile Val Gln Gln Gln Ser Asn Leu Leu Arg Ala Ile Glu Ala Gln
            500                 505                 510

Gln His Met Leu Gln Leu Thr Val Trp Gly Ile Lys Gln Leu Gln Thr
        515                 520                 525

Arg Val Leu Ala Ile Glu Arg Tyr Leu Lys Asp Gln Gln Leu Leu Gly
    530                 535                 540

Leu Trp Gly Cys Ser Gly Lys Leu Ile Cys Thr Thr Ala Val Pro Trp
545                 550                 555                 560

Asn Ser Ser Trp Ser Asn Lys Ser Glu Ile Asp Ile Trp Asn Asn Met
                565                 570                 575

Thr Trp Met Gln Trp Asp Arg Glu Ile Ser Asn Tyr Thr Asn Thr Ile
            580                 585                 590

Tyr Arg Leu Leu Glu Asp Ser Gln Thr Gln Glu Lys Asn Glu Lys
        595                 600                 605

Asp Leu Leu Ala Leu Asp Ser Trp Lys Asn Leu Trp Asn Trp Phe Asn
    610                 615                 620

Ile Thr Lys Trp Leu Trp Tyr Ile Lys Ile Phe Ile Ile Ile Val Gly
625                 630                 635                 640

Gly Leu Ile Gly Leu Arg Ile Ile Phe Ala Val Leu Ser Ile Val Asn
                645                 650                 655

Arg Val Arg Gln Gly Tyr Ser Pro Leu Ser Phe Gln Thr Leu Ile Pro
            660                 665                 670

Ser Pro Arg Gly Pro Asp Lys Leu Gly Arg Ile Glu Glu Glu Gly Gly
        675                 680                 685

Glu Gln Asp Lys Gly Arg Ser Val Arg Leu Val Asn Gly Phe Leu Ala
    690                 695                 700

Leu Ala Trp Asp Asp Leu Arg Ser Leu Cys Leu Phe Ser Tyr His Gln
705                 710                 715                 720

Leu Arg Asp Phe Ile Leu Ile Val Ala Arg Ala Val Gly Leu Leu Gly
                725                 730                 735

Arg Ser Ser Leu Arg Gly Leu Gln Arg Gly Trp Glu Ile Leu Lys Tyr
            740                 745                 750

Leu Gly Gly Leu Val Gln Tyr Trp Gly Leu Glu Leu Lys Lys Ser Ala
        755                 760                 765

Val Ser Leu Phe Asp Thr Ile Ala Ile Ala Val Thr Glu Gly Thr Asp
    770                 775                 780

Arg Ile Ile Glu Leu Ile Gln Arg Ser Cys Arg Ala Ile Arg Asn Val
785                 790                 795                 800

Pro Thr Arg Ile Arg Gln Gly Phe Glu Ala Ala Leu Gln
                805                 810

<210> SEQ ID NO 39
<211> LENGTH: 827
<212> TYPE: PRT

<213> ORGANISM: Human immunodeficiency virus

<400> SEQUENCE: 39

```
Ser Asn Leu Trp Val Thr Val Tyr Tyr Gly Val Pro Val Trp Arg Glu
1               5                   10                  15

Ala Lys Thr Thr Leu Phe Cys Ala Ser Asp Ala Lys Ala Tyr Glu Arg
            20                  25                  30

Glu Val His Asn Val Trp Ala Thr His Ala Cys Val Pro Thr Asp Pro
        35                  40                  45

Asp Pro Gln Glu Ile Phe Leu Gly Lys Asn Val Thr Glu Lys Phe Asn
    50                  55                  60

Met Trp Glu Asn Tyr Met Val Asp Gln Met His Glu Asp Ile Ile Ser
65                  70                  75                  80

Leu Trp Asp Gln Ser Leu Gln Pro Cys Val Lys Leu Thr Pro Leu Cys
                85                  90                  95

Ile Thr Leu Asn Cys Thr Asp Phe Thr Ala His Asn Gly Ser Thr Val
            100                 105                 110

Tyr Asp Asn Asn Ala Thr Ala Asn Ser Thr Asn Glu Ile Lys Asn Cys
        115                 120                 125

Ser Phe Asn Ile Ile Ser Glu Leu Arg Asp Lys Arg Lys Lys Glu Asn
    130                 135                 140

Ala Leu Phe Asn Asn Leu Asp Ile Val Gln Leu Asp Gly Asn Ser Ser
145                 150                 155                 160

Leu Tyr Arg Leu Ile Asn Cys Asn Thr Ser Ile Ile Lys Gln Ala Cys
                165                 170                 175

Pro Lys Ile Ser Phe Asp Pro Ile Pro Ile His Tyr Cys Ala Pro Ala
            180                 185                 190

Gly Phe Val Ile Leu Thr Cys Asn Asn Glu Thr Phe Asn Gly Thr Gly
        195                 200                 205

Pro Cys Asn Asn Val Ser Ala Val Gln Cys Thr His Gly Ile Lys Pro
    210                 215                 220

Val Val Ser Thr Gln Leu Leu Leu Asn Gly Ser Leu Ala Lys Gly Glu
225                 230                 235                 240

Ile Met Ile Arg Ser Glu Asn Ile Thr Asn Asn Val Lys Thr Ile Ile
                245                 250                 255

Val His Phe Asn Lys Ser Val Glu Ile Val Cys Thr Arg Pro Asn Asn
            260                 265                 270

Asn Thr Arg Lys Ser Ile Arg Ile Gly Pro Gly Gln Thr Phe Tyr Ala
        275                 280                 285

Thr Gly Asp Ile Ile Gly Asp Ile Arg Gln Ala Tyr Cys Ser Ile Asn
    290                 295                 300

Glu Ser Asn Trp Asn Ile Thr Leu Gln Arg Val Ser Lys Lys Leu Ala
305                 310                 315                 320

Glu His Phe Pro Asn Arg Thr Ile Gln Phe Glu Ser Pro Ser Gly Gly
                325                 330                 335

Asp Leu Glu Ile Thr Met His Ser Phe Asn Cys Arg Gly Glu Phe Phe
            340                 345                 350

Tyr Cys Asn Thr Ser Lys Leu Phe Lys Ser Thr Tyr His Pro Asn Gly
        355                 360                 365

Thr Tyr Asn Leu Asn Gly Thr Asn Ser Thr Leu Ile Ile Pro Cys Arg
    370                 375                 380

Ile Lys Gln Ile Ile Asn Met Trp Gln Gly Val Gly Lys Ala Ile Tyr
385                 390                 395                 400
```

```
Ala Ser Pro Ile Ala Gly Ser Ile Thr Cys Arg Ser Asn Ile Thr Gly
                405                 410                 415

Leu Leu Leu Thr Arg Asp Gly Asp Thr Asn Asp Thr Glu Ile Phe
        420                 425                 430

Arg Pro Thr Gly Gly Asp Met Arg Asp Asn Trp Arg Ser Glu Leu Tyr
            435                 440                 445

Lys Tyr Lys Ile Val Glu Ile Lys Pro Leu Gly Val Ala Pro Thr Glu
        450                 455                 460

Ala Lys Arg Arg Val Val Lys Arg Glu Lys Arg Ala Val Thr Ile Gly
465                 470                 475                 480

Ala Val Phe Leu Gly Phe Leu Gly Ala Ala Gly Ser Thr Met Gly Ala
                485                 490                 495

Ala Ser Ile Thr Leu Thr Val Gln Ala Arg Gln Leu Leu Ser Gly Ile
            500                 505                 510

Val Gln Gln Gln Ser Asn Leu Leu Arg Ala Ile Glu Ala Gln Gln His
        515                 520                 525

Met Leu Gln Leu Ala Val Trp Gly Ile Lys Gln Leu Gln Ala Arg Val
    530                 535                 540

Leu Ala Ile Glu Arg Tyr Leu Lys Asp Gln Gln Leu Leu Gly Ile Trp
545                 550                 555                 560

Gly Cys Ser Gly Lys Leu Ile Cys Thr Thr Ala Val Pro Trp Asn Asn
                565                 570                 575

Ser Trp Ser Asn Arg Thr Gln Asp Glu Ile Trp Lys Asn Leu Thr Trp
            580                 585                 590

Met Glu Trp Asp Arg Glu Ile Ser Asn Tyr Thr Asn Thr Ile Tyr Glu
        595                 600                 605

Leu Leu Glu Val Ser Gln Ser Gln Gln Glu Arg Asn Glu Lys Asp Leu
    610                 615                 620

Leu Ala Leu Asp Ser Trp Asn Asn Leu Trp Asn Trp Phe Asp Ile Ser
625                 630                 635                 640

Asn Trp Leu Trp Tyr Ile Lys Ile Phe Ile Met Ile Val Gly Gly Leu
                645                 650                 655

Ile Gly Leu Arg Ile Ile Phe Ala Val Leu Ser Ile Val Asn Arg Val
            660                 665                 670

Arg Gln Gly Tyr Ser Pro Leu Ser Phe Gln Thr Leu Ile Pro Asn Gln
        675                 680                 685

Arg Glu Pro Asp Arg Pro Gly Arg Ile Glu Glu Gly Gly Glu Gln
    690                 695                 700

Asp Lys Asp Arg Ser Ile Arg Leu Val Ser Gly Phe Leu Ala Leu Ala
705                 710                 715                 720

Trp Asp Asp Leu Arg Ser Leu Cys Ile Phe Leu Tyr His His Leu Arg
                725                 730                 735

Asp Leu Ile Leu Ile Ala Ala Arg Ala Thr Glu Leu Leu Gly Arg Ser
            740                 745                 750

Ser Leu Arg Gly Leu Gln Arg Gly Trp Glu Ala Leu Lys Tyr Leu Gly
        755                 760                 765

Ser Leu Val Gln Tyr Trp Gly Leu Glu Ile Lys Lys Ser Ala Ile Asn
    770                 775                 780

Leu Leu Asp Thr Ile Ala Ile Ala Val Ala Glu Gly Thr Asp Arg Ile
785                 790                 795                 800

Ile Glu Ile Val Gln Arg Ala Cys Arg Ala Val Leu Asn Ile Leu Arg
                805                 810                 815

Arg Ile Arg Gln Gly Leu Glu Ala Ala Leu Gln
```

<210> SEQ ID NO 40
<211> LENGTH: 827
<212> TYPE: PRT
<213> ORGANISM: Human immunodeficiency virus

<400> SEQUENCE: 40

| | | | | | | | | | | | | | | |
|---|---|---|---|---|---|---|---|---|---|---|---|---|---|---|
| Ser | Asn | Leu | Trp | Val | Thr | Val | Tyr | Tyr | Gly | Val | Pro | Val | Trp | Arg | Glu |
| 1 | | | | 5 | | | | | 10 | | | | | 15 | |
| Ala | Lys | Thr | Thr | Leu | Phe | Cys | Ala | Ser | Asp | Ala | Lys | Ala | Tyr | Glu | Arg |
| | | | 20 | | | | | 25 | | | | | 30 | | |
| Glu | Val | His | Asn | Val | Trp | Ala | Thr | His | Ala | Cys | Val | Pro | Thr | Asp | Pro |
| | | | 35 | | | | | 40 | | | | | 45 | | |
| Asp | Pro | Gln | Glu | Ile | Phe | Leu | Gly | Lys | Asn | Val | Thr | Glu | Lys | Phe | Asn |
| | 50 | | | | | 55 | | | | | 60 | | | | |
| Met | Trp | Glu | Asn | Tyr | Met | Val | Asp | Gln | Met | His | Glu | Asp | Ile | Ile | Ser |
| 65 | | | | | 70 | | | | | 75 | | | | | 80 |
| Leu | Trp | Asp | Gln | Ser | Leu | Gln | Pro | Cys | Val | Lys | Leu | Thr | Pro | Leu | Cys |
| | | | | 85 | | | | | 90 | | | | | 95 | |
| Ile | Thr | Leu | Asn | Cys | Thr | Asp | Phe | Thr | Ala | His | Asn | Gly | Ser | Thr | Val |
| | | | 100 | | | | | 105 | | | | | 110 | | |
| Tyr | Asp | Asn | Asn | Ala | Thr | Ala | Asn | Ser | Thr | Asn | Glu | Ile | Lys | Asn | Cys |
| | | | 115 | | | | | 120 | | | | | 125 | | |
| Ser | Phe | Asn | Ile | Ile | Ser | Glu | Leu | Arg | Asp | Lys | Arg | Lys | Lys | Glu | Asn |
| | 130 | | | | | 135 | | | | | 140 | | | | |
| Ala | Leu | Phe | Asn | Asn | Leu | Asp | Ile | Val | Gln | Leu | Asp | Gly | Asn | Ser | Ser |
| 145 | | | | | 150 | | | | | 155 | | | | | 160 |
| Leu | Tyr | Arg | Leu | Ile | Asn | Cys | Asn | Thr | Ser | Ile | Ile | Lys | Gln | Ala | Cys |
| | | | | 165 | | | | | 170 | | | | | 175 | |
| Pro | Lys | Ile | Ser | Phe | Asp | Pro | Ile | Pro | Ile | His | Tyr | Cys | Ala | Pro | Ala |
| | | | 180 | | | | | 185 | | | | | 190 | | |
| Gly | Phe | Val | Ile | Leu | Thr | Cys | Asn | Asn | Glu | Thr | Phe | Asn | Gly | Thr | Gly |
| | | | 195 | | | | | 200 | | | | | 205 | | |
| Pro | Cys | Asn | Asn | Val | Ser | Ala | Val | Gln | Cys | Thr | His | Gly | Ile | Lys | Pro |
| | 210 | | | | | 215 | | | | | 220 | | | | |
| Val | Val | Ser | Thr | Gln | Leu | Leu | Leu | Asn | Gly | Ser | Leu | Ala | Lys | Gly | Glu |
| 225 | | | | | 230 | | | | | 235 | | | | | 240 |
| Ile | Met | Ile | Arg | Ser | Glu | Asn | Ile | Thr | Asn | Asn | Val | Lys | Thr | Ile | Ile |
| | | | | 245 | | | | | 250 | | | | | 255 | |
| Val | His | Phe | Asn | Lys | Ser | Val | Glu | Ile | Val | Cys | Thr | Arg | Pro | Asn | Asn |
| | | | 260 | | | | | 265 | | | | | 270 | | |
| Asn | Thr | Arg | Lys | Ser | Ile | Arg | Ile | Gly | Pro | Gly | Gln | Thr | Phe | Tyr | Ala |
| | | | 275 | | | | | 280 | | | | | 285 | | |
| Thr | Gly | Asp | Ile | Ile | Gly | Asp | Ile | Arg | Gln | Ala | Tyr | Cys | Ser | Ile | Asn |
| | 290 | | | | | 295 | | | | | 300 | | | | |
| Glu | Ser | Asn | Trp | Asn | Ile | Thr | Leu | Gln | Arg | Val | Ser | Lys | Lys | Leu | Ala |
| 305 | | | | | 310 | | | | | 315 | | | | | 320 |
| Glu | His | Phe | Pro | Asn | Arg | Thr | Ile | Gln | Phe | Glu | Ser | Pro | Ser | Gly | Gly |
| | | | | 325 | | | | | 330 | | | | | 335 | |
| Asp | Leu | Glu | Ile | Thr | Met | His | Ser | Phe | Asn | Cys | Arg | Gly | Glu | Phe | Phe |
| | | | 340 | | | | | 345 | | | | | 350 | | |
| Tyr | Cys | Asn | Thr | Ser | Lys | Leu | Phe | Lys | Ser | Thr | Tyr | His | Pro | Asn | Gly |
| | | | 355 | | | | | 360 | | | | | 365 | | |

```
Thr Tyr Asn Leu Asn Gly Thr Asn Ser Thr Leu Ile Ile Pro Cys Arg
    370                 375                 380

Ile Lys Gln Ile Ile Asn Met Trp Gln Gly Val Gly Lys Ala Ile Tyr
385                 390                 395                 400

Ala Ser Pro Ile Ala Gly Ser Ile Thr Cys Arg Ser Asn Ile Thr Gly
                405                 410                 415

Leu Leu Leu Thr Arg Asp Gly Gly Asp Thr Asn Asp Thr Glu Ile Phe
            420                 425                 430

Arg Pro Thr Gly Gly Asp Met Arg Asp Asn Trp Arg Ser Glu Leu Tyr
        435                 440                 445

Lys Tyr Lys Ile Val Glu Ile Lys Pro Leu Gly Val Ala Pro Thr Glu
    450                 455                 460

Ala Lys Ser Arg Val Val Lys Ser Glu Lys Ser Ala Val Thr Ile Gly
465                 470                 475                 480

Ala Val Phe Leu Gly Phe Leu Gly Ala Ala Gly Ser Thr Met Gly Ala
                485                 490                 495

Ala Ser Ile Thr Leu Thr Val Gln Ala Arg Gln Leu Leu Ser Gly Ile
            500                 505                 510

Val Gln Gln Gln Ser Asn Leu Leu Arg Ala Ile Glu Ala Gln Gln His
        515                 520                 525

Met Leu Gln Leu Ala Val Trp Gly Ile Lys Gln Leu Gln Ala Arg Val
    530                 535                 540

Leu Ala Ile Glu Arg Tyr Leu Lys Asp Gln Gln Leu Leu Gly Ile Trp
545                 550                 555                 560

Gly Cys Ser Gly Lys Leu Ile Cys Thr Thr Ala Val Pro Trp Asn Asn
                565                 570                 575

Ser Trp Ser Asn Arg Thr Gln Asp Glu Ile Trp Lys Asn Leu Thr Trp
            580                 585                 590

Met Glu Trp Asp Arg Glu Ile Ser Asn Tyr Thr Asn Thr Ile Tyr Glu
        595                 600                 605

Leu Leu Glu Val Ser Gln Ser Gln Gln Glu Arg Asn Glu Lys Asp Leu
    610                 615                 620

Leu Ala Leu Asp Ser Trp Asn Asn Leu Trp Asn Trp Phe Asp Ile Ser
625                 630                 635                 640

Asn Trp Leu Trp Tyr Ile Lys Ile Phe Ile Met Ile Val Gly Gly Leu
                645                 650                 655

Ile Gly Leu Arg Ile Ile Phe Ala Val Leu Ser Ile Val Asn Arg Val
            660                 665                 670

Arg Gln Gly Tyr Ser Pro Leu Ser Phe Gln Thr Leu Ile Pro Asn Gln
        675                 680                 685

Arg Glu Pro Asp Arg Pro Gly Arg Ile Glu Glu Gly Gly Glu Gln
    690                 695                 700

Asp Lys Asp Arg Ser Ile Arg Leu Val Ser Gly Phe Leu Ala Leu Ala
705                 710                 715                 720

Trp Asp Asp Leu Arg Ser Leu Cys Ile Phe Leu Tyr His His Leu Arg
                725                 730                 735

Asp Leu Ile Leu Ile Ala Ala Arg Ala Thr Glu Leu Leu Gly Arg Ser
            740                 745                 750

Ser Leu Arg Gly Leu Gln Arg Gly Trp Glu Ala Leu Lys Tyr Leu Gly
        755                 760                 765

Ser Leu Val Gln Tyr Trp Gly Leu Glu Ile Lys Lys Ser Ala Ile Asn
    770                 775                 780

Leu Leu Asp Thr Ile Ala Ile Ala Val Ala Glu Gly Thr Asp Arg Ile
```

```
                785                 790                 795                 800
Ile Glu Ile Val Gln Arg Ala Cys Arg Ala Val Leu Asn Ile Leu Arg
                        805                 810                 815

Arg Ile Arg Gln Gly Leu Glu Ala Ala Leu Gln
                820                 825

<210> SEQ ID NO 41
<211> LENGTH: 828
<212> TYPE: PRT
<213> ORGANISM: Human immunodeficiency virus

<400> SEQUENCE: 41

Ser Asn Leu Trp Val Thr Val Tyr Tyr Gly Val Pro Val Trp Arg Glu
1               5                   10                  15

Ala Lys Thr Thr Leu Phe Cys Ala Ser Asp Ala Lys Ala Tyr Glu Arg
                20                  25                  30

Glu Val His Asn Val Trp Ala Thr His Ala Cys Val Pro Thr Asp Pro
            35                  40                  45

Asp Pro Gln Glu Ile Phe Leu Gly Lys Asn Val Thr Glu Lys Phe Asn
        50                  55                  60

Met Trp Lys Asn Tyr Met Val Asp Gln Met His Glu Asp Ile Ile Ser
65                  70                  75                  80

Leu Trp Asp Gln Ser Leu Gln Pro Cys Val Lys Leu Thr Pro Leu Cys
                85                  90                  95

Ile Thr Leu Asn Cys Thr Asp Val Thr Ala His Asn Gly Ser Thr Val
                100                 105                 110

Tyr Asp Asn Asn Ala Thr Val Val Asn Ser Thr Asn Glu Ile Lys Asn
            115                 120                 125

Cys Ser Phe Asn Ile Thr Thr Glu Leu Arg Asp Lys Arg Lys Lys Glu
        130                 135                 140

His Ala Leu Phe Asn Asn Leu Asp Ile Val Gln Leu Asp Gly Asn Ser
145                 150                 155                 160

Ser Leu Tyr Arg Leu Ile Asn Cys Asn Thr Ser Ile Ile Lys Gln Ala
                165                 170                 175

Cys Pro Lys Ile Ser Phe Asp Pro Ile Pro Ile His Tyr Cys Ala Pro
                180                 185                 190

Ala Gly Phe Val Ile Leu Lys Cys Asn Asn Glu Thr Phe Asn Gly Thr
            195                 200                 205

Gly Pro Cys Asn Asn Val Ser Ala Val Gln Cys Thr His Gly Ile Lys
        210                 215                 220

Pro Val Val Ser Thr Gln Leu Leu Leu Asn Gly Ser Leu Ala Lys Gly
225                 230                 235                 240

Glu Ile Met Ile Arg Ser Glu Asn Ile Thr Asp Asn Val Lys Thr Ile
                245                 250                 255

Ile Val His Leu Asn Asn Ser Val Glu Ile Val Cys Thr Arg Pro Asn
                260                 265                 270

Asn Asn Thr Arg Lys Ser Ile Arg Ile Gly Pro Gly Gln Thr Phe Tyr
            275                 280                 285

Ala Thr Gly Asp Ile Ile Gly Asp Ile Arg Gln Ala Tyr Cys Ser Ile
        290                 295                 300

Asn Glu Ser Asn Trp Asn Ala Thr Leu Gln Arg Val Ser Lys Lys Leu
305                 310                 315                 320

Ala Glu His Phe Pro Asn Lys Thr Ile Gln Phe Lys Ser Pro Ser Gly
                325                 330                 335
```

-continued

```
Gly Asp Leu Glu Ile Thr Met His Ser Phe Asn Cys Arg Gly Phe
            340                 345                 350

Phe Tyr Cys Asn Thr Ser Lys Leu Phe Asn Gly Thr Tyr Tyr Pro Asn
            355                 360                 365

Gly Thr Tyr Tyr Pro Asn Gly Thr Asn Ser Thr Leu Ile Ile Pro Cys
    370                 375                 380

Arg Ile Lys Gln Ile Ile Asn Met Trp Gln Gly Val Gly Lys Ala Ile
385                 390                 395                 400

Tyr Ala Ser Pro Ile Ala Gly Asn Ile Thr Cys Arg Ser Asn Ile Thr
                405                 410                 415

Gly Leu Leu Leu Thr Arg Asp Gly Gly Asp Thr Asn Asp Thr Glu Ile
            420                 425                 430

Phe Arg Pro Ala Gly Gly Asp Met Arg Asp Asn Trp Arg Ser Glu Leu
        435                 440                 445

Tyr Lys Tyr Lys Ile Val Glu Ile Lys Pro Leu Gly Val Ala Pro Thr
    450                 455                 460

Glu Ala Lys Arg Arg Val Val Lys Arg Glu Lys Arg Ala Val Thr Ile
465                 470                 475                 480

Gly Ala Val Phe Leu Gly Phe Leu Gly Ala Ala Gly Ser Thr Met Gly
                485                 490                 495

Ala Ala Ser Ile Thr Leu Thr Val Gln Ala Arg Gln Leu Leu Ser Gly
            500                 505                 510

Ile Val Gln Gln Gln Ser Asn Leu Leu Arg Ala Ile Glu Ala Gln Gln
        515                 520                 525

His Met Leu Gln Leu Thr Val Trp Gly Ile Lys Gln Leu Gln Ala Arg
    530                 535                 540

Val Leu Ala Ile Glu Arg Tyr Leu Lys Asp Gln Gln Leu Leu Gly Ile
545                 550                 555                 560

Trp Gly Cys Ser Gly Lys Leu Ile Cys Thr Thr Ala Val Pro Trp Asn
                565                 570                 575

Asn Ser Trp Ser Asn Arg Thr Gln Asp Glu Ile Trp Lys Asn Leu Thr
            580                 585                 590

Trp Met Glu Trp Asp Arg Glu Ile Ser Asn Tyr Thr Asn Thr Ile Tyr
        595                 600                 605

Glu Leu Leu Glu Val Ser Gln Ser Gln Gln Glu Arg Asn Glu Lys Asp
    610                 615                 620

Leu Leu Ala Leu Asp Ser Trp Asn Asn Leu Trp Asn Trp Phe Asp Ile
625                 630                 635                 640

Ser Asn Trp Leu Trp Tyr Ile Lys Ile Phe Ile Met Ile Val Gly Gly
                645                 650                 655

Leu Ile Gly Leu Arg Ile Ile Phe Ala Val Leu Ser Ile Val Asn Arg
            660                 665                 670

Val Arg Gln Gly Tyr Ser Pro Leu Ser Phe Gln Thr Leu Ile Pro Asn
        675                 680                 685

Gln Arg Glu Pro Asp Arg Pro Gly Arg Ile Glu Glu Glu Gly Gly Glu
    690                 695                 700

Gln Asp Lys Asp Arg Ser Ile Arg Leu Val Ser Gly Phe Leu Ala Leu
705                 710                 715                 720

Ala Trp Asp Asp Leu Arg Ser Leu Cys Ile Phe Leu Tyr His His Leu
                725                 730                 735

Arg Asp Phe Ile Leu Ile Ala Ala Arg Ala Thr Glu Leu Leu Gly Arg
            740                 745                 750

Ser Ser Leu Arg Gly Leu Gln Arg Gly Trp Glu Ala Leu Lys Tyr Leu
```

```
                    755                 760                 765
Gly Ser Leu Val Gln Tyr Trp Gly Leu Glu Ile Lys Lys Ser Ala Ile
770                 775                 780

Asn Leu Leu Asp Thr Ile Ala Ile Ala Val Ala Glu Gly Thr Asp Arg
785                 790                 795                 800

Ile Ile Glu Ile Val Gln Arg Ala Cys Arg Ala Val Leu Asn Ile Pro
                    805                 810                 815

Arg Arg Ile Arg Gln Gly Leu Glu Ala Ala Leu Gln
                820                 825

<210> SEQ ID NO 42
<211> LENGTH: 828
<212> TYPE: PRT
<213> ORGANISM: Human immunodeficiency virus

<400> SEQUENCE: 42

Ser Asn Leu Trp Val Thr Val Tyr Tyr Gly Val Pro Val Trp Arg Glu
1               5                   10                  15

Ala Lys Thr Thr Leu Phe Cys Ala Ser Asp Ala Lys Ala Tyr Glu Arg
                20                  25                  30

Glu Val His Asn Val Trp Ala Thr His Ala Cys Val Pro Thr Asp Pro
            35                  40                  45

Asp Pro Gln Glu Ile Phe Leu Gly Lys Asn Val Thr Glu Lys Phe Asn
50                  55                  60

Met Trp Lys Asn Tyr Met Val Asp Gln Met His Glu Asp Ile Ile Ser
65              70                  75                  80

Leu Trp Asp Gln Ser Leu Gln Pro Cys Val Lys Leu Thr Pro Leu Cys
                85                  90                  95

Ile Thr Leu Asn Cys Thr Asp Val Thr Ala His Asn Gly Ser Thr Val
            100                 105                 110

Tyr Asp Asn Asn Ala Thr Val Val Asn Ser Thr Asn Glu Ile Lys Asn
        115                 120                 125

Cys Ser Phe Asn Ile Thr Thr Glu Leu Arg Asp Lys Arg Lys Lys Glu
130                 135                 140

His Ala Leu Phe Asn Asn Leu Asp Ile Val Gln Leu Asp Gly Asn Ser
145                 150                 155                 160

Ser Leu Tyr Arg Leu Ile Asn Cys Asn Thr Ser Ile Ile Lys Gln Ala
                165                 170                 175

Cys Pro Lys Ile Ser Phe Asp Pro Ile Pro Ile His Tyr Cys Ala Pro
            180                 185                 190

Ala Gly Phe Val Ile Leu Lys Cys Asn Asn Glu Thr Phe Asn Gly Thr
        195                 200                 205

Gly Pro Cys Asn Asn Val Ser Ala Val Gln Cys Thr His Gly Ile Lys
210                 215                 220

Pro Val Val Ser Thr Gln Leu Leu Leu Asn Gly Ser Leu Ala Lys Gly
225                 230                 235                 240

Glu Ile Met Ile Arg Ser Glu Asn Ile Thr Asp Asn Val Lys Thr Ile
                245                 250                 255

Ile Val His Leu Asn Asn Ser Val Glu Ile Val Cys Thr Arg Pro Asn
            260                 265                 270

Asn Asn Thr Arg Lys Ser Ile Arg Ile Gly Pro Gly Gln Thr Phe Tyr
        275                 280                 285

Ala Thr Gly Asp Ile Ile Gly Asp Ile Arg Gln Ala Tyr Cys Ser Ile
290                 295                 300
```

-continued

```
Asn Glu Ser Asn Trp Asn Ala Thr Leu Gln Arg Val Ser Lys Lys Leu
305                 310                 315                 320
Ala Glu His Phe Pro Asn Lys Thr Ile Gln Phe Lys Ser Pro Ser Gly
            325                 330                 335
Gly Asp Leu Glu Ile Thr Met His Ser Phe Asn Cys Arg Gly Glu Phe
            340                 345                 350
Phe Tyr Cys Asn Thr Ser Lys Leu Phe Asn Gly Thr Tyr Tyr Pro Asn
        355                 360                 365
Gly Thr Tyr Tyr Pro Asn Gly Thr Asn Ser Thr Leu Ile Ile Pro Cys
        370                 375                 380
Arg Ile Lys Gln Ile Ile Asn Met Trp Gln Gly Val Gly Lys Ala Ile
385                 390                 395                 400
Tyr Ala Ser Pro Ile Ala Gly Asn Ile Thr Cys Arg Ser Asn Ile Thr
                405                 410                 415
Gly Leu Leu Leu Thr Arg Asp Gly Gly Asp Thr Asn Asp Thr Glu Ile
                420                 425                 430
Phe Arg Pro Ala Gly Gly Asp Met Arg Asp Asn Trp Arg Ser Glu Leu
        435                 440                 445
Tyr Lys Tyr Lys Ile Val Glu Ile Lys Pro Leu Gly Val Ala Pro Thr
    450                 455                 460
Glu Ala Lys Ser Arg Val Val Lys Ser Glu Lys Ser Ala Val Thr Ile
465                 470                 475                 480
Gly Ala Val Phe Leu Gly Phe Leu Gly Ala Ala Gly Ser Thr Met Gly
                485                 490                 495
Ala Ala Ser Ile Thr Leu Thr Val Gln Ala Arg Gln Leu Leu Ser Gly
                500                 505                 510
Ile Val Gln Gln Gln Ser Asn Leu Leu Arg Ala Ile Glu Ala Gln Gln
                515                 520                 525
His Met Leu Gln Leu Thr Val Trp Gly Ile Lys Gln Leu Gln Ala Arg
        530                 535                 540
Val Leu Ala Ile Glu Arg Tyr Leu Lys Asp Gln Gln Leu Leu Gly Ile
545                 550                 555                 560
Trp Gly Cys Ser Gly Lys Leu Ile Cys Thr Thr Ala Val Pro Trp Asn
                565                 570                 575
Asn Ser Trp Ser Asn Arg Thr Gln Asp Glu Ile Trp Lys Asn Leu Thr
            580                 585                 590
Trp Met Glu Trp Asp Arg Glu Ile Ser Asn Tyr Thr Asn Thr Ile Tyr
            595                 600                 605
Glu Leu Leu Glu Val Ser Gln Ser Gln Gln Glu Arg Asn Glu Lys Asp
        610                 615                 620
Leu Leu Ala Leu Asp Ser Trp Asn Asn Leu Trp Asn Trp Phe Asp Ile
625                 630                 635                 640
Ser Asn Trp Leu Trp Tyr Ile Lys Ile Phe Ile Met Ile Val Gly Gly
                645                 650                 655
Leu Ile Gly Leu Arg Ile Ile Phe Ala Val Leu Ser Ile Val Asn Arg
                660                 665                 670
Val Arg Gln Gly Tyr Ser Pro Leu Ser Phe Gln Thr Leu Ile Pro Asn
        675                 680                 685
Gln Arg Glu Pro Asp Arg Pro Gly Arg Ile Glu Glu Glu Gly Gly Glu
        690                 695                 700
Gln Asp Lys Asp Arg Ser Ile Arg Leu Val Ser Gly Phe Leu Ala Leu
705                 710                 715                 720
Ala Trp Asp Asp Leu Arg Ser Leu Cys Ile Phe Leu Tyr His His Leu
```

```
                    725                 730                 735
Arg Asp Phe Ile Leu Ile Ala Ala Arg Ala Thr Glu Leu Leu Gly Arg
                740                 745                 750

Ser Ser Leu Arg Gly Leu Gln Arg Gly Trp Glu Ala Leu Lys Tyr Leu
            755                 760                 765

Gly Ser Leu Val Gln Tyr Trp Gly Leu Glu Ile Lys Lys Ser Ala Ile
        770                 775                 780

Asn Leu Leu Asp Thr Ile Ala Ile Ala Val Ala Glu Gly Thr Asp Arg
785                 790                 795                 800

Ile Ile Glu Ile Val Gln Arg Ala Cys Arg Ala Val Leu Asn Ile Pro
                805                 810                 815

Arg Arg Ile Arg Gln Gly Leu Glu Ala Ala Leu Gln
                820                 825

<210> SEQ ID NO 43
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Glu Leu Leu Ala Leu Asp Ser Trp Asn Asn Leu Trp Asn Trp Phe Asp
1               5                   10                  15

Ile Ser Asn Trp Leu Trp Tyr Ile Lys Lys Lys Lys
            20                  25

<210> SEQ ID NO 44
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Ile Phe Ile Met Ile Val Gly Gly Leu
1               5

<210> SEQ ID NO 45
<211> LENGTH: 6
<212> TYPE: PRT
<213> ORGANISM: Human immunodeficiency virus

<400> SEQUENCE: 45

Trp Leu Trp Tyr Ile Lys
1               5

<210> SEQ ID NO 46
<211> LENGTH: 5
<212> TYPE: PRT
<213> ORGANISM: Human immunodeficiency virus

<400> SEQUENCE: 46

Ser Leu Trp Val Thr
1               5

<210> SEQ ID NO 47
<211> LENGTH: 5
<212> TYPE: PRT
```

```
<213> ORGANISM: Human immunodeficiency virus

<400> SEQUENCE: 47

Phe Ser Ile Thr Lys
1               5

<210> SEQ ID NO 48
<211> LENGTH: 12
<212> TYPE: PRT
<213> ORGANISM: Human immunodeficiency virus

<400> SEQUENCE: 48

Arg Ala Lys Arg Arg Val Val Glu Arg Glu Lys Arg
1               5                   10

<210> SEQ ID NO 49
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Arg Ala Lys Ser Arg Val Val Glu Arg Glu Lys Ser
1               5                   10

<210> SEQ ID NO 50
<211> LENGTH: 5
<212> TYPE: PRT
<213> ORGANISM: Human immunodeficiency virus

<400> SEQUENCE: 50

Phe Ser Ile Ser Asn
1               5

<210> SEQ ID NO 51
<211> LENGTH: 12
<212> TYPE: PRT
<213> ORGANISM: Human immunodeficiency virus

<400> SEQUENCE: 51

Lys Ala Arg Arg Arg Val Val Glu Arg Glu Lys Arg
1               5                   10

<210> SEQ ID NO 52
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Lys Ala Arg Ser Arg Val Val Glu Arg Glu Lys Ser
1               5                   10

<210> SEQ ID NO 53
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 53

Leu Glu Leu Asp Lys Trp Ala Ser Leu Trp Asn Trp Phe Asp Ile Thr
1               5                   10                  15

Asn Trp Leu Trp Tyr Ile Lys
            20
```